United States Patent
Schlake et al.

(10) Patent No.: US 12,258,567 B2
(45) Date of Patent: Mar. 25, 2025

(54) ARTIFICIAL NUCLEIC ACID MOLECULES

(71) Applicant: CureVac SE, Tübingen (DE)

(72) Inventors: Thomas Schlake, Gundelfingen (DE); Stefanie Grund, Stuttgart (DE)

(73) Assignee: CureVac SE, Tübingen (DE)

( * ) Notice: Subject to any disclaimer, the term of this patent is extended or adjusted under 35 U.S.C. 154(b) by 217 days.

(21) Appl. No.: 15/755,739

(22) PCT Filed: Aug. 22, 2016

(86) PCT No.: PCT/EP2016/001417
§ 371 (c)(1),
(2) Date: Feb. 27, 2018

(87) PCT Pub. No.: WO2017/036580
PCT Pub. Date: Mar. 9, 2017

(65) Prior Publication Data
US 2018/0237786 A1    Aug. 23, 2018

(30) Foreign Application Priority Data
Aug. 28, 2015 (WO) ............... PCT/EP2015/001755

(51) Int. Cl.
*C07H 21/02* (2006.01)
*C07H 21/04* (2006.01)
*C12N 15/67* (2006.01)
*A01K 67/00* (2006.01)

(52) U.S. Cl.
CPC .................................. *C12N 15/67* (2013.01)

(58) Field of Classification Search
CPC .................................................... C12N 15/67
See application file for complete search history.

(56) References Cited

U.S. PATENT DOCUMENTS

| | | | |
|---|---|---|---|
| 9,061,059 B2 * | 6/2015 | Chakraborty | C07K 16/40 |
| 2005/0032730 A1 | 2/2005 | Von der Mulbe et al. | |
| 2005/0059624 A1 | 3/2005 | Hoerr et al. | |
| 2005/0196754 A1 * | 9/2005 | Drmanac | C07K 14/47 |
| | | | 435/6.11 |
| 2005/0250723 A1 | 11/2005 | Hoerr et al. | |
| 2006/0188490 A1 | 8/2006 | Hoerr et al. | |
| 2008/0025944 A1 | 1/2008 | Hoerr et al. | |
| 2008/0220983 A1 * | 9/2008 | Trinklein | C12N 15/1086 |
| | | | 506/10 |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2012/0021043 A1 | 1/2012 | Kramps et al. | |
| 2012/0258046 A1 | 10/2012 | Mutzke | |
| 2013/0129754 A1 | 5/2013 | Thess et al. | |
| 2013/0142818 A1 | 6/2013 | Baumhof et al. | |
| 2013/0259879 A1 | 10/2013 | Baumhof et al. | |
| 2013/0280283 A1 | 10/2013 | Lorenz et al. | |
| 2013/0295043 A1 | 11/2013 | Kallen et al. | |
| 2013/0336998 A1 | 12/2013 | Kallen et al. | |
| 2015/0037326 A1 | 2/2015 | Butler-Ransohoff et al. | |
| 2015/0050302 A1 | 2/2015 | Thess | |
| 2015/0057340 A1 | 2/2015 | Thess et al. | |
| 2015/0093413 A1 | 4/2015 | Thess et al. | |
| 2015/0118183 A1 | 4/2015 | Baumhof | |
| 2015/0118264 A1 | 4/2015 | Baumhof et al. | |
| 2015/0165006 A1 | 6/2015 | Thess et al. | |
| 2015/0184195 A1 | 7/2015 | Thess et al. | |
| 2015/0218554 A1 | 8/2015 | Thess | |
| 2015/0306249 A1 | 10/2015 | Baumhof et al. | |
| 2015/0320847 A1 | 11/2015 | Thess et al. | |
| 2016/0130345 A1 | 5/2016 | Fotin-Mleczek et al. | |

(Continued)

FOREIGN PATENT DOCUMENTS

| | | |
|---|---|---|
| WO | WO 2002/098443 | 12/2002 |
| WO | WO 2012/019630 | 2/2012 |

(Continued)

OTHER PUBLICATIONS

Bernasconi et al. Quantitative profiling of housekeeping and Epstein-Barr virus gene transcription in Burkitt lymphoma cell lines using an oligonucleotide microarray. Virology Journal 3:43 doi: 10.1186/1743-422X-3-43, 15 pages, (Year: 2006).*

Kriegova et al. PSMB2 and RPL32 are suitable denominators to normalize gene expression profiles in bronchoalveolar cells. BMC Molecular Biology 9:69 doi: 10.1186/1471-2199-9-69, 14 pages, (Year: 2008).*

International Preliminary Report on Patentability issued in corresponding PCT Application No. PCT/EP2016/001417, mailed on Mar. 6, 2018.

International Search Report and Written Opinion issued in corresponding PCT Application No. PCT/EP2016/001417, mailed on Nov. 14, 2016.

(Continued)

*Primary Examiner* — Quang Nguyen
(74) *Attorney, Agent, or Firm* — Parker Highlander PLLC

(57) ABSTRACT

The invention relates to an artificial nucleic acid molecule comprising at least one open reading frame and at least one 3'-untranslated region element (3'-UTR element) and/or at least one 5'-untranslated region element (5'-UTR element), wherein the artificial nucleic acid molecule is characterized by high translation efficiency. The translation efficiency is contributed, at least in part, by the 5'-UTR element or the 3'-UTR element, or both of the 5'-UTR element and the 3'-UTR element. The invention further relates to the use of such an artificial nucleic acid molecule in gene therapy and/or genetic vaccination. Furthermore novel 3'-UTR elements and 5'-UTR elements are provided.

Figure 8:
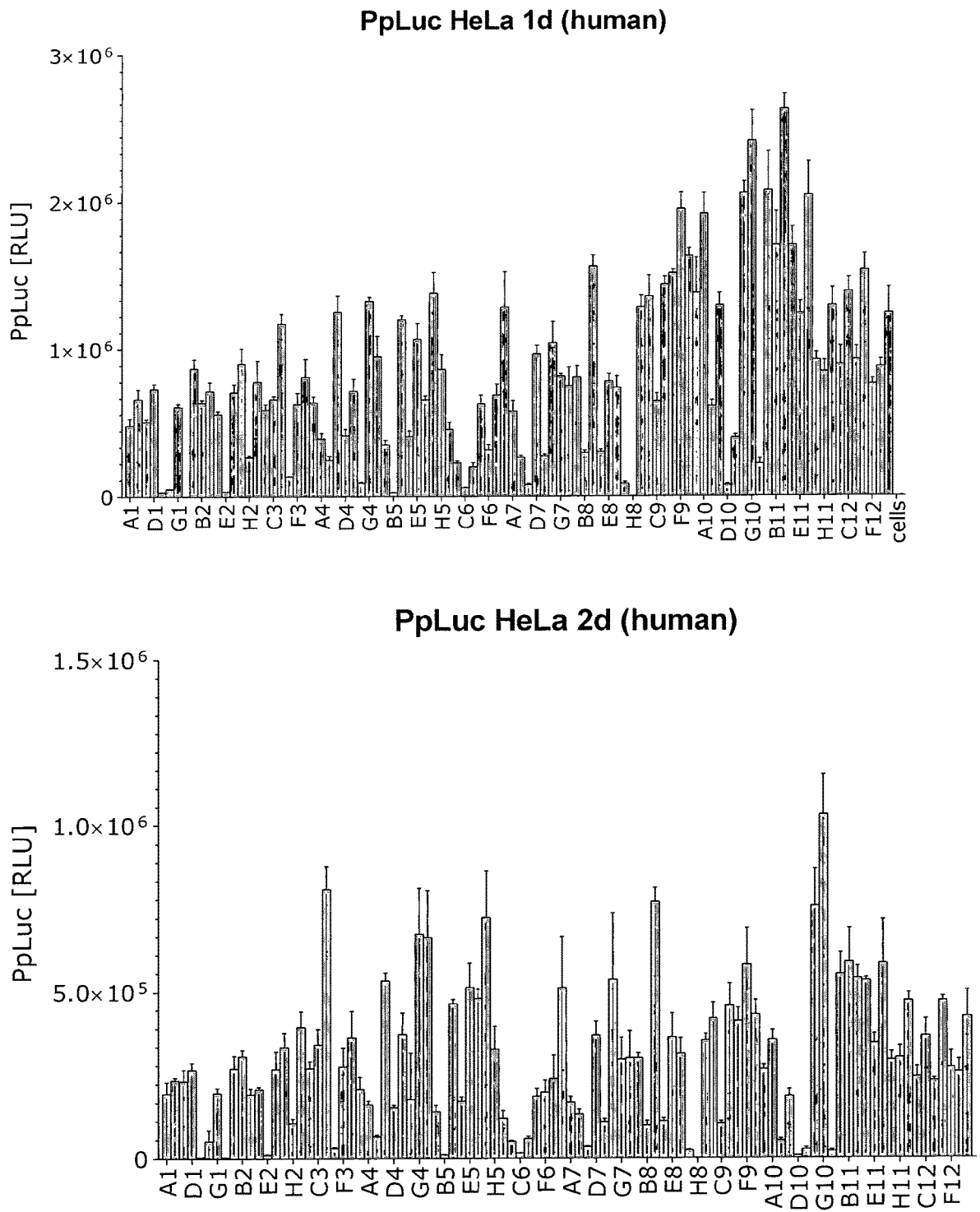

18 Claims, 11 Drawing Sheets
Specification includes a Sequence Listing.

(56) References Cited

U.S. PATENT DOCUMENTS

| | | |
|---|---|---|
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mülbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |

FOREIGN PATENT DOCUMENTS

| | | |
|---|---|---|
| WO | WO 2014/164253 | 10/2014 |
| WO | WO 2016/107877 | 7/2016 |
| WO | WO 2016/165825 | 10/2016 |
| WO | WO 2016/165831 | 10/2016 |
| WO | WO 2016/174227 | 11/2016 |
| WO | WO 2016/174271 | 11/2016 |
| WO | WO 2016/184575 | 11/2016 |
| WO | WO 2016/184576 | 11/2016 |
| WO | WO 2016/193206 | 12/2016 |
| WO | WO 2016/193226 | 12/2016 |
| WO | WO 2016/203025 | 12/2016 |
| WO | WO 2017/001058 | 1/2017 |
| WO | WO 2017/009376 | 1/2017 |
| WO | WO 2017/021546 | 2/2017 |
| WO | WO 2017/025120 | 2/2017 |
| WO | WO 2017/025447 | 2/2017 |
| WO | WO 2017/064146 | 4/2017 |
| WO | WO 2017/081110 | 5/2017 |

OTHER PUBLICATIONS

Database DDBJ/EMBL/GenBank [online], Accession No. BC002570.1, URL=<https://www.ncbi.nlm.nih.gov/nuccore/BC002570.1/>, retrieved Jul. 20, 2020, Strausberg, R.L. et al., Definition: *Homo sapiens* proteasome (prosome, macropain) subunit, beta type, 3, mRNA (cDNA clone IMAGE:3140974), uploaded Oct. 27, 2008.

Kochetov et al., "Translational enhancers for plant gene engineering," *Vavilov Journal of Genetics and Breeding*, 18(4):610-617, 2014. (Russian with English abstract).

Quimisse et al., "Contribution of consensus 5'-untranslated region to the translational efficiency of heterologous genes in plant cells," *RUDN Journal of Agronomy and Animal Industries*, 3:56-68, 2015. (Russian with English abstract).

Volkova et al., "Estimation of translational importance of mammalian mRNA nucleotide sequence characteristics based on ribosome profiling data," *Vavilov Journal of Genetics and Breeding*, 20(6):779-786, 2016. (Russian with English abstract).

Wilkie et al., "Regulation of mRNA translation by 5'-and 3'-UTR-binding factors," *Trends in Biochemical Sciences*, 28(4):182-188, 2003.

* cited by examiner

Fig. 1A: 32L4 - PpLuc(GC) - albumin7- A64 - C30 - hSL

SEQ ID NO: 205

GGGGCGCUGCCUACGGAGGUGGCAGCCAUCUCCUUCUCGGCAUCAAGCUUGAGG*AUGGAG
GACGCCAAGAACAUCAAGAAGGGCCCGGCGCCCUUCUACCCGCUGGAGGACGGGACCGCC
GGCGAGCAGCUCCACAAGGCCAUGAAGCGGUACGCCCUGGUGCCGGGCACGAUCGCCUUC
ACCGACGCCCACAUCGAGGUCGACAUCACCUACGCGGAGUACUUCGAGAUGAGCGUGCGC
CUGGCCGAGGCCAUGAAGCGGUACGGCCUGAACACCAACCACCGGAUCGUGGUGUGCUCG
GAGAACAGCCUGCAGUUCUUCAUGCCGGUGCUGGGCGCCCUCUUCAUCGGCGUGGCCGUC
GCCCCGGCGAACGACAUCUACAACGAGCGGGAGCUGCUGAACAGCAUGGGGAUCAGCCAG
CCGACCGUGGUGUUCGUGAGCAAGAAGGGCCUGCAGAAGAUCCUGAACGUGCAGAAGAAG
CUGCCCAUCAUCCAGAAGAUCAUCAUCAUGGACAGCAAGACCGACUACCAGGGCUUCCAG
UCGAUGUACACGUUCGUGACCAGCCACCUCCCGCCGGGCUUCAACGAGUACGACUUCGUC
CCGGAGAGCUUCGACCGGGACAAGACCAUCGCCCUGAUCAUGAACAGCAGCGGCAGCACC
GGCCUGCCGAAGGGGGUGGCCCUGCCGCACCGGACCGCCUGCGUGCGCUUCUCGCACGCC
CGGGACCCCAUCUUCGGCAACCAGAUCAUCCCGGACACCGCCAUCCUGAGCGUGGUGCCG
UUCCACCACGGCUUCGGCAUGUUCACGACCCUGGGCUACCUCAUCUGCGGCUUCCGGGUG
GUCCUGAUGUACCGGUUCGAGGAGGAGCUGUUCCUGCGGAGCCUGCAGGACUACAAGAUC
CAGAGCGCGCUGCUCGUGCCGACCCUGUUCAGCUUCUUCGCCAAGAGCACCCUGAUCGAC
AAGUACGACCUGUCGAACCUGCACGAGAUCGCCAGCGGGGGCGCCCCGCUGAGCAAGGAG
GUGGGCGAGGCCGUGGCCAAGCGGUUCCACCUCCCGGGCAUCCGCCAGGGCUACGGCCUG
ACCGAGACCACGAGCGCGAUCCUGAUCACCCCCGAGGGGGACGACAAGCCGGGCGCCGUG
GGCAAGGUGGUCCCGUUCUUCGAGGCCAAGGUGGUGGACCUGGACACCGGCAAGACCCUG
GGCGUGAACCAGCGGGGCGAGCUGUGCGUGCGGGGGCCGAUGAUCAUGAGCGGCUACGUG
AACAACCCGGAGGCCACCAACGCCCUCAUCGACAAGGACGGCUGGCUGCACAGCGGCGAC
AUCGCCUACUGGGACGAGGACGAGCACUUCUUCAUCGUCGACCGGCUGAAGUCGCUGAUC
AAGUACAAGGGCUACCAGGUGGCGCCGGCCGAGCUGGAGAGCAUCCUGCUCCAGCACCCC
AACAUCUUCGACGCCGGCGUGGCCGGGCUGCCGGACGACGACGCCGGCGAGCUGCCGGCC
GCGGUGGUGGUGCUGGAGCACGGCAAGACCAUGACGGAGAAGGAGAUCGUCGACUACGUG
GCCAGCCAGGUGACCACCGCCAAGAAGCUGCGGGGCGGCGUGGUGUUCGUGGACGAGGUC
CCGAAGGGCCUGACCGGGAAGCUCGACGCCCGGAAGAUCCGCGAGAUCCUGAUCAAGGCC
AAGAAGGGCGGCAAGAUCGCCGUGUAAGACUAGU*CAUCACAUUUAAAAGCAUCUCAGCC
UACCAUGAGAAUAAGAGAAAGAAAAUGAAGAUCAAUAGCUUAUUCAUCUCUUUUUCUUUU
UCGUUGGUGUAAAGCCAACACCCUGUCUAAAAAACAUAAAUUUCUUUAAUCAUUUUGCCU
CUUUUCUCUGUGCUUCAAUUAAUAAAAAAUGGAAAGAACCU**AGAUCUAAAAAAAAAAAA
AAAAAAAAAAAAAAAAAAAAAAAAAAAAAAAAAAAAAAAAAAAAAAAAAUGCAUCCCC
CCCCCCCCCCCCCCCCCCCCCCCCAAAGGCUCUUUUCAGAGCCACCAGAAUU

Fig. 1A

Fig. 1B: Artificial nucleic acid (SEQ ID NO: 210).

[5'-UTR corresponding to SEQ ID NO: 1] - PpLuc(GC) - albumin7– A64 - C30 – hSL

GGGGAAACAGUGUGGGGCCUAGAGCGCUGGGUGGGCGCGUUCUGCGGCCUGAGCAGGGAC
GGGUAGUGAAGCGGUUACGCCCCUUCUUCGCGUCUUGGCGGGAGCCUGACGCCCCGCUUC
UCCCCUAACGAGGUGUCCCACCGGCGCCCGCCGAGGCCUAGGCCUCCGCAGCCGCCCUCC
GUCUCCUCAGCCCCGACGCUGCGCCUUGGGCCUUGUGCGCAUUUUUUUCGGGGGAAAACU
GAGGCUCGGAGUGCGAAAGUCAGCCGAGGUCGCCCCGCCCAGGACAGAGAAGGGCUGUGG
UCGGCUGAUCCGCGGCAUUCCCGGGAAGCUUGAGGAUGGAGGACGCCAAGAACAUCAAGA
AGGGCCCGGCGCCCUUCUACCGCUGGAGGACGGGACCGCCGGCGAGCAGCUCCACAAGG
CCAUGAAGCGGUACGCCCUGGUGCCGGGCACGAUCGCCUUCACCGACGCCCACAUCGAGG
UCGACAUCACCUACGCGGAGUACUUCGAGAUGAGCGUGCGCCUGGCCGAGGCCAUGAAGC
GGUACGGCCUGAACACCAACCACCGGAUCGUGGUGUGCUCGGAGAACAGCCUGCAGUUCU
UCAUGCCGGUGCUGGGCGCCCUCUUCAUCGGCGUGGCCGUCGCCCCGGCGAACGACAUCU
ACAACGAGCGGGAGCUGCUGAACAGCAUGGGGAUCAGCCAGCCGACCGUGGUGUUCGUGA
GCAAGAAGGGCCUGCAGAAGAUCCUGAACGUGCAGAAGAAGCUGCCCAUCAUCCAGAAGA
UCAUCAUCAUGGACAGCAAGACCGACUACCAGGGCUUCCAGUCGAUGUACACGUUCGUGA
CCAGCCACCUCCCGCCGGGCUUCAACGAGUACGACUUCGUCCCGGAGAGCUUCGACCGGG
ACAAGACCAUCGCCCUGAUCAUGAACAGCAGCGGCAGCACCGGCCUGCCGAAGGGGGUGG
CCCUGCCGCACCGGACCGCCUGCGUGCGCUUCUCGCACGCCCGGGACCCCAUCUUCGGCA
ACCAGAUCAUCCCGGACACCGCCAUCCUGAGCGUGGUGCCGUUCCACCACGGCUUCGGCA
UGUUCACGACCCUGGGCUACCUCAUCUGCGGCUUCCGGGUGGUCCUGAUGUACCGGUUCG
AGGAGGAGCUGUUCCUGCGGAGCCUGCAGGACUACAAGAUCCAGAGCGCGCUGCUCGUGC
CGACCCUGUUCAGCUUCUUCGCCAAGAGCACCCUGAUCGACAAGUACGACCUGUCGAACC
UGCACGAGAUCGCCAGCGGGGGCGCCCCGCUGAGCAAGGAGGUGGGCGAGGCCGUGGCCA
AGCGGUUCCACCUCCCGGGCAUCCGCCAGGGCUACGGCCUGACCGAGACCACGAGCGCGA
UCCUGAUCACCCCGAGGGGGACGACAAGCCGGGCGCCGUGGGCAAGGUGGUCCCGUUCU
UCGAGGCCAAGGUGGUGGACCUGGACACCGGCAAGACCCUGGGCGUGAACCAGCGGGGCG
AGCUGUGCGUGCGGGGCCGAUGAUCAUGAGCGGCUACGUGAACAACCCGGAGGCCACCA
ACGCCCUCAUCGACAAGGACGGCUGGCUGCACAGCGGCGACAUCGCCUACUGGGACGAGG
ACGAGCACUUCUUCAUCGUCGACCGGCUGAAGUCGCUGAUCAAGUACAAGGGCUACCAGG
UGGCGCCGGCCGAGCUGGAGAGCAUCCUGCUCCAGCACCCCAACAUCUUCGACGCCGGCG
UGGCCGGGCUGCCGGACGACGACGCCGGCGAGCUGCCGGCCGCGGUGGUGGUGCUGGAGC
ACGGCAAGACCAUGACGGAGAAGGAGAUCGUCGACUACGUGGCCAGCCAGGUGACCACCG
CCAAGAAGCUGCGGGGCGGCGUGGUGUUCGUGGACGAGGUCCCGAAGGGCCUGACCGGGA
AGCUCGACGCCCGGAAGAUCCGCGAGAUCCUGAUCAAGGCCAAGAAGGGCGGCAAGAUCG
CCGUGUAAGACUAGUG<ins>CAUCACAUUUAAAAGCAUCUCAGCCUACCAUGAGAAUAAGAGAA</ins>
<ins>AGAAAAUGAAGAUCAAUAGCUUAUUCAUCUCUUUUUCUUUUUCGUUGGUGUAAAGCCAAC</ins>
<ins>ACCCUGUCUAAAAAACAUAAAUUUCUUUAAUCAUUUUGCCUCUUUUCUCUGUGCUUCAAU</ins>
<ins>UAAUAAAAAAUGGAAAGAACCU</ins>AGAUCUAAAAAAAAAAAAAAAAAAAAAAAAAAAAAAAA
AAAAAAAAAAAAAAAAAAAAAAAAAAAAAAAAAAUGCAUCCCCCCCCCCCCCCCCCCCCC
CCCCCCCCAAAGGCUCUUUUCAGAGCCACCAGAAU
U

Fig. 1B

Fig. 1C: Artificial nucleic acid (SEQ ID NO: 211).

32L4 - PpLuc(GC) - [3'-UTR corresponding to SEQ ID NO: 1] – A64 – C30 – hSL

GGGGCGCUGCCUACGGAGGUGGCAGCCAUCUCCUUCUCGGCAUCAAGCUUGAGG
*AUGGAGGACGCCAAGAACAUCAAGAAGGGCCCGGCGCCCUUCUACCCGCUGGAG
GACGGGACCGCCGGCGAGCAGCUCCACAAGGCCAUGAAGCGGUACGCCCUGGUG
CCGGGCACGAUCGCCUUCACCGACGCCCACAUCGAGGUCGACAUCACCUACGCG
GAGUACUUCGAGAUGAGCGUGCGCCUGGCCGAGGCCAUGAAGCGGUACGGCCUG
AACACCAACCACCGGAUCGUGGUGUGCUCGGAGAACAGCCUGCAGUUCUUCAUG
CCGGUGCUGGGCGCCCUCUUCAUCGGCGUGGCCGUCGCCCCGGCGAACGACAUC
UACAACGAGCGGGAGCUGCUGAACAGCAUGGGGAUCAGCCAGCCGACCGUGGUG
UUCGUGAGCAAGAAGGGCCUGCAGAAGAUCCUGAACGUGCAGAAGAAGCUGCCC
AUCAUCCAGAAGAUCAUCAUCAUGGACAGCAAGACCGACUACCAGGGCUUCCAG
UCGAUGUACACGUUCGUGACCAGCCACCUCCCGCCGGGCUUCAACGAGUACGAC
UUCGUCCCGGAGAGCUUCGACCGGGACAAGACCAUCGCCCUGAUCAUGAACAGC
AGCGGCAGCACCGGCCUGCCGAAGGGGGUGGCCCUGCCGCACCGGACCGCCUGC
GUGCGCUUCUCGCACGCCCGGGACCCCAUCUUCGGCAACCAGAUCAUCCCGGAC
ACCGCCAUCCUGAGCGUGGUGCCGUUCCACCACGGCUUCGGCAUGUUCACGACC
CUGGGCUACCUCAUCUGCGGCUUCCGGGUGGUCCUGAUGUACCGGUUCGAGGAG
GAGCUGUUCCUGCGGAGCCUGCAGGACUACAAGAUCCAGAGCGCGCUGCUCGUG
CCGACCCUGUUCAGCUUCUUCGCCAAGAGCACCCUGAUCGACAAGUACGACCUG
UCGAACCUGCACGAGAUCGCCAGCGGGGCGCCCCGCUGAGCAAGGAGGUGGGC
GAGGCCGUGGCCAAGCGGUUCCACCUCCCGGGCAUCCGCCAGGGCUACGGCCUG
ACCGAGACCACGAGCGCGAUCCUGAUCACCCCGAGGGGGACGACAAGCCGGGC
GCCGUGGGCAAGGUGGUCCCGUUCUUCGAGGCCAAGGUGGUGGACCUGGACACC
GGCAAGACCCUGGGCGUGAACCAGCGGGGCGAGCUGUGCGUGCGGGGCCGAUG
AUCAUGAGCGGCUACGUGAACAACCCGGAGGCCACCAACGCCCUCAUCGACAAG
GACGGCUGGCUGCACAGCGGCGACAUCGCCUACUGGGACGAGGACGAGCACUUC
UUCAUCGUCGACCGGCUGAAGUCGCUGAUCAAGUACAAGGGCUACCAGGUGGCG
CCGGCCGAGCUGGAGAGCAUCCUGCUCCAGCACCCCAACAUCUUCGACGCCGGC
GUGGCCGGGCUGCCGGACGACGACGCCGGCGAGCUGCCGGCCGCGGUGGUGGUG
CUGGAGCACGGCAAGACCAUGACGGAGAAGGAGAUCGUCGACUACGUGGCCAGC
CAGGUGACCACCGCCAAGAAGCUGCGGGGCGGCGUGGUGUUCGUGGACGAGGUC
CCGAAGGGCCUGACCGGGAAGCUCGACGCCCGGAAGAUCCGCGAGAUCCUGAUC
AAGGCCAAGAAGGGCGGCAAGAUCGCCGUGUAAGACUAGU*<u>CGCCGCCGCCGCCG
CCGCCGGAGCCUGUCGCCGUCCUGUCCCCAGCCUGCUUGUGUCCCGUGAGGUUG
UCAAUAAACCUGCCCUCGGGCUGCCGCCUCCC</u>AGAUCUAAAAAAAAAAAAAAAA
AAAAAAAAAAAAAAAAAAAAAAAAAAAAAAAAAAAAAAAAAAAAAAAUGCAUC
CCCCCCCCCCCCCCCCCCCCCCCCCCCCAAAGGCUCUUUUCAGAGCCACCAG
AAUU

Fig. 1C

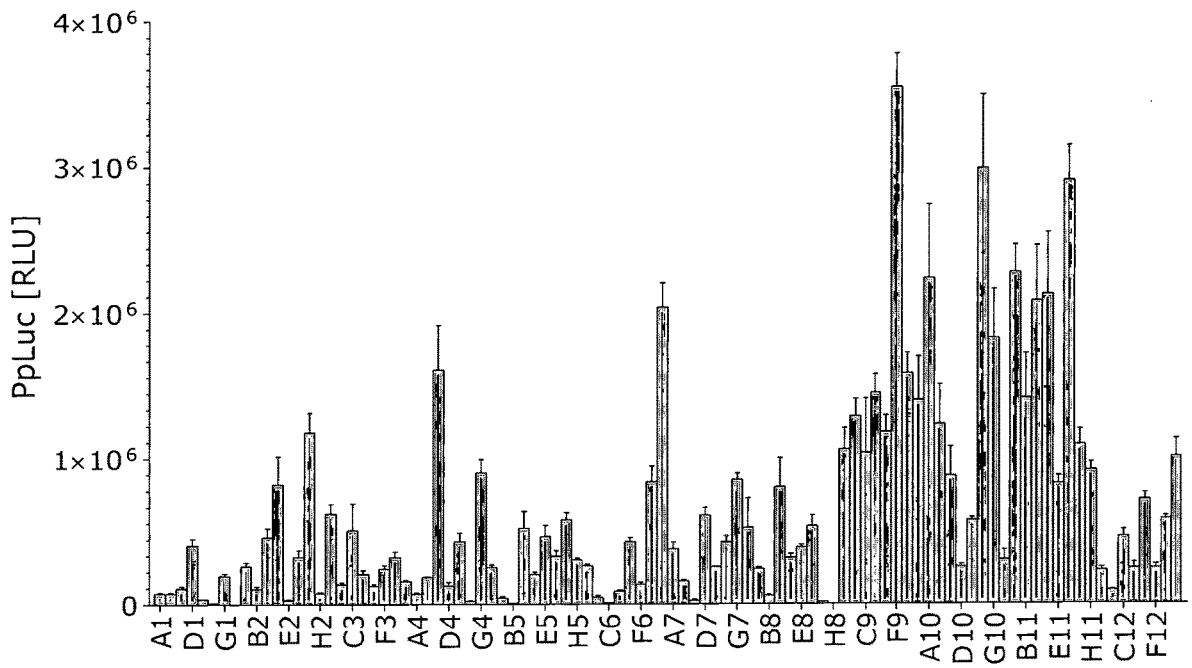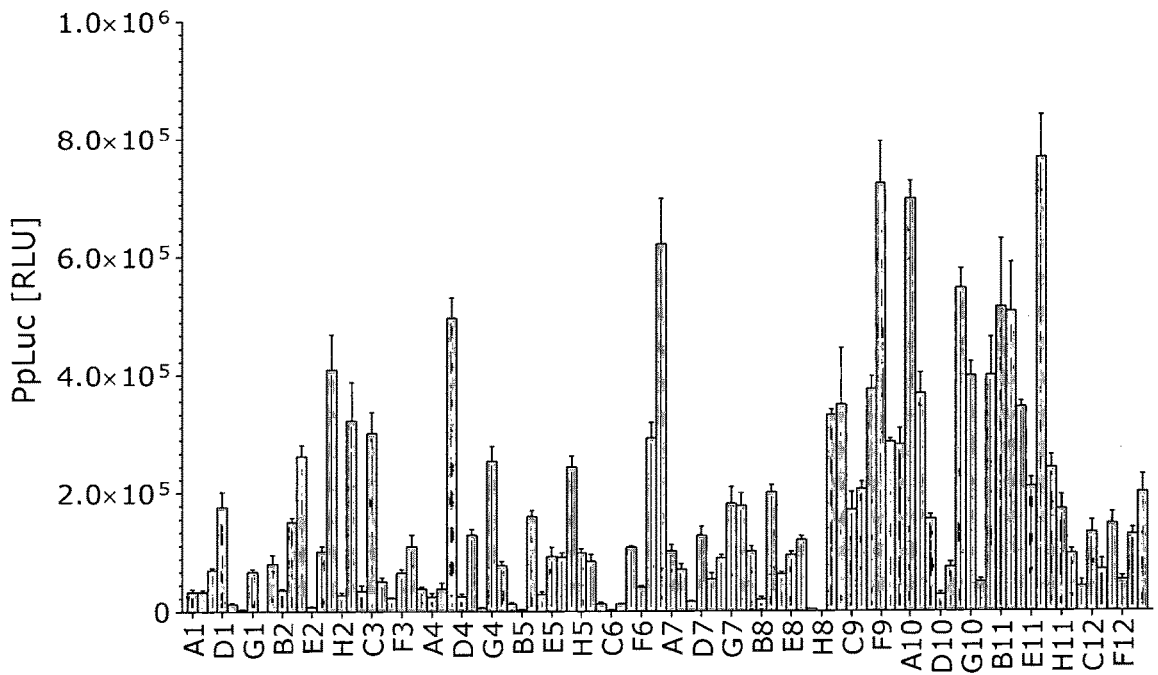
Fig. 2

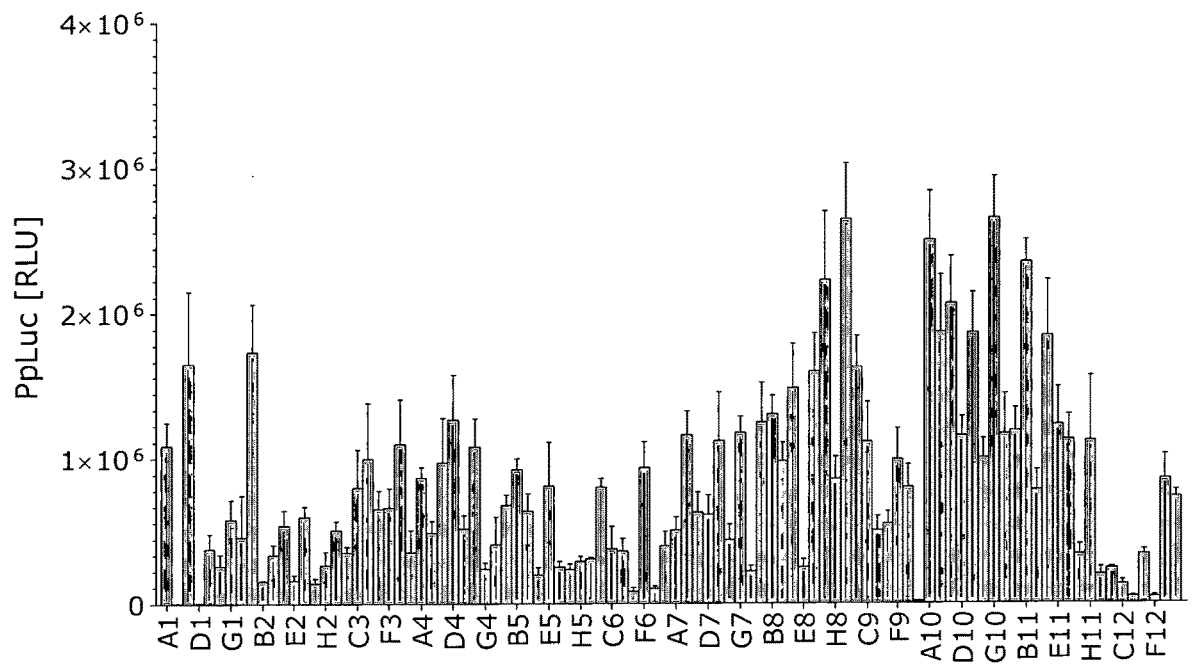
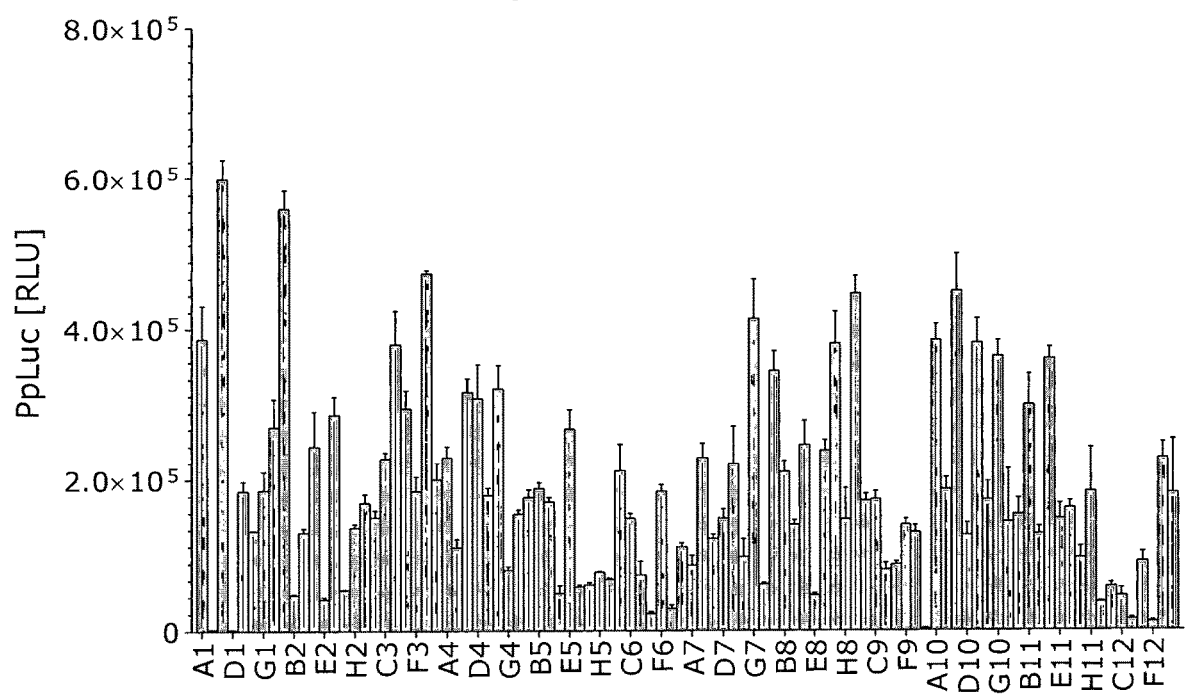
Fig. 3

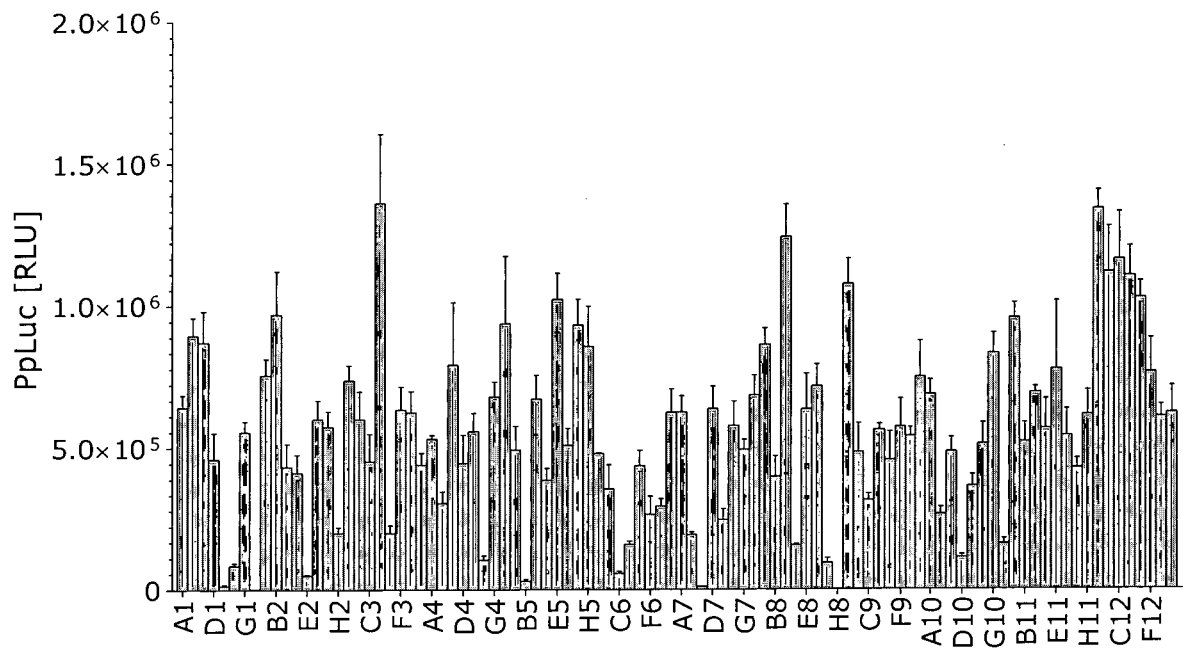
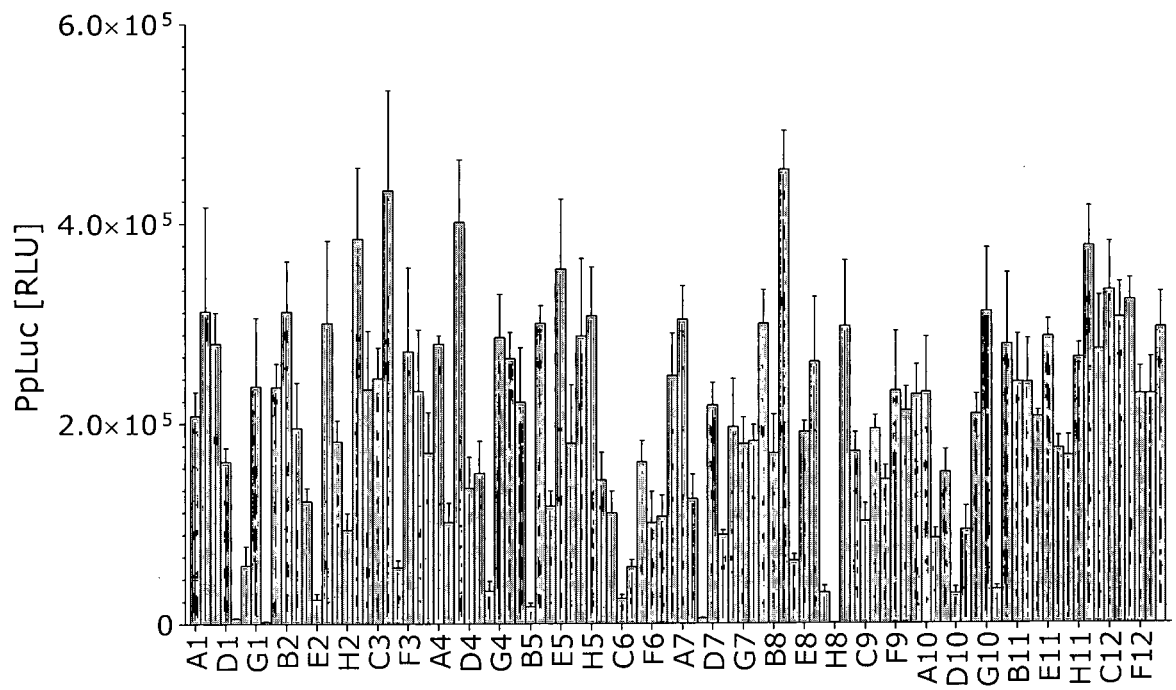
Fig. 4

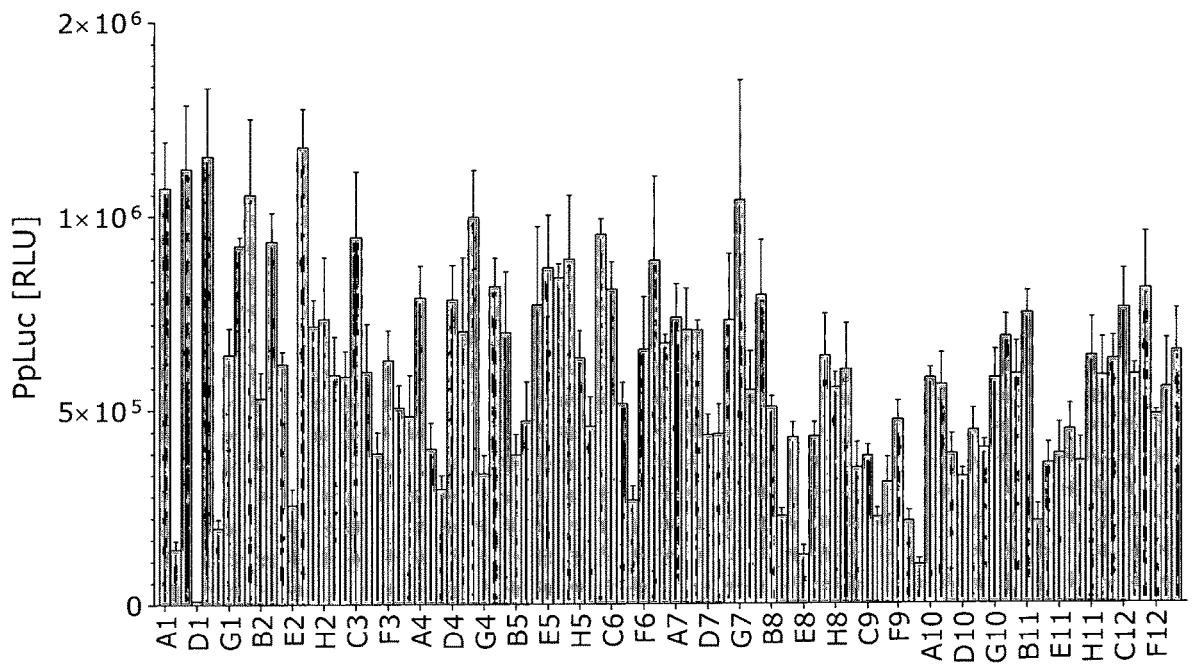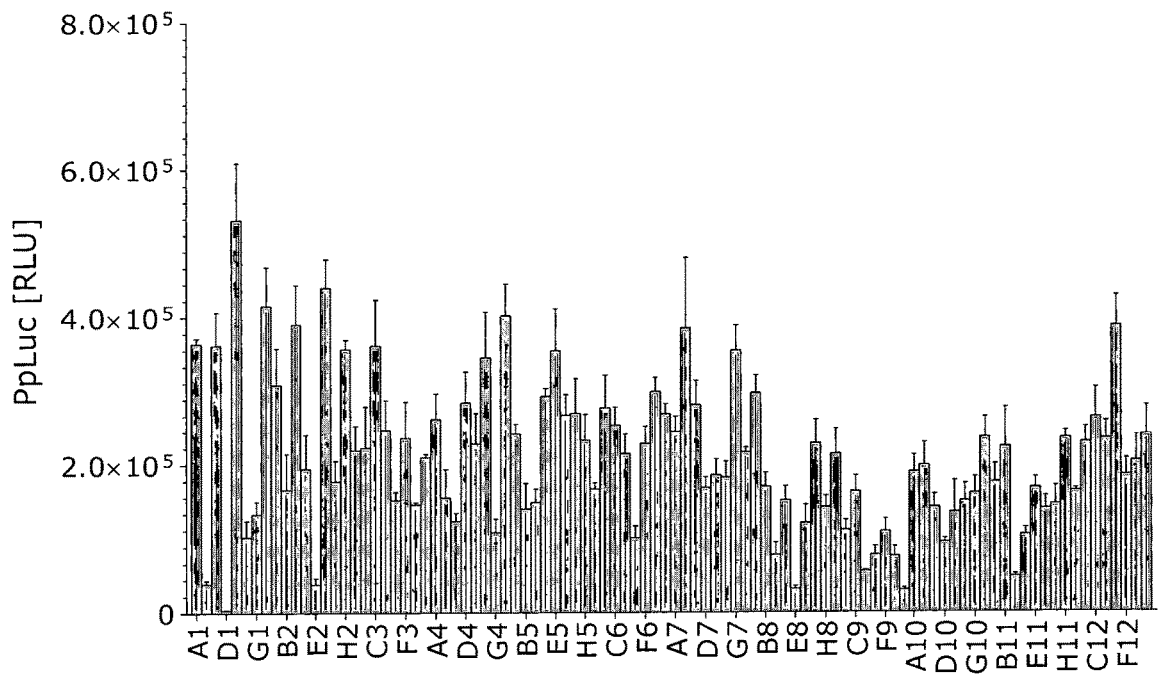
Fig. 5

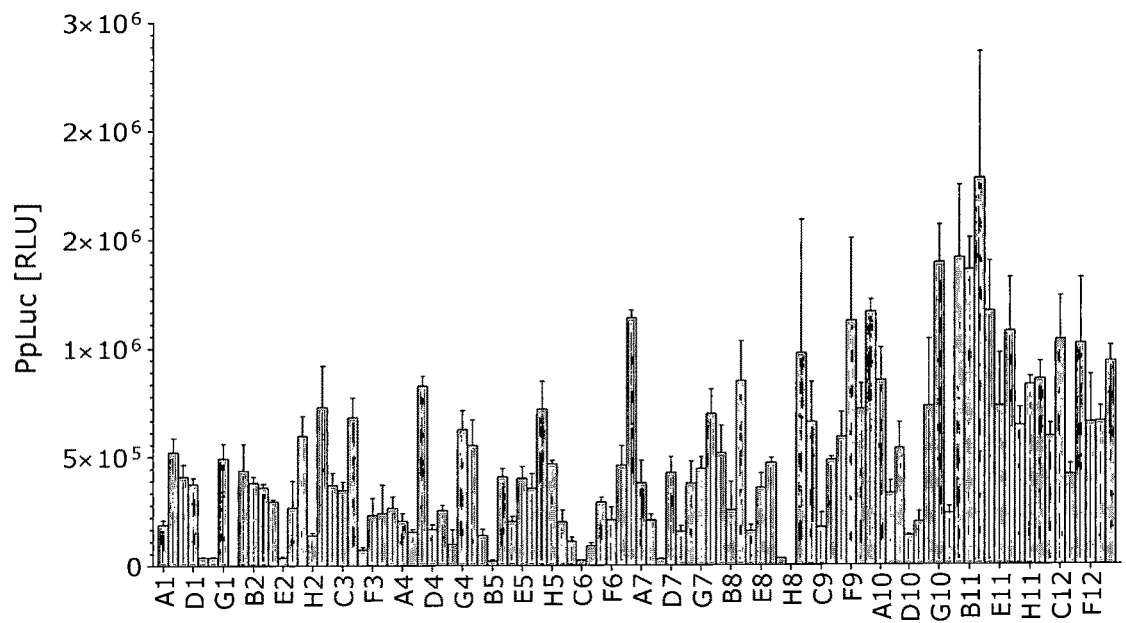
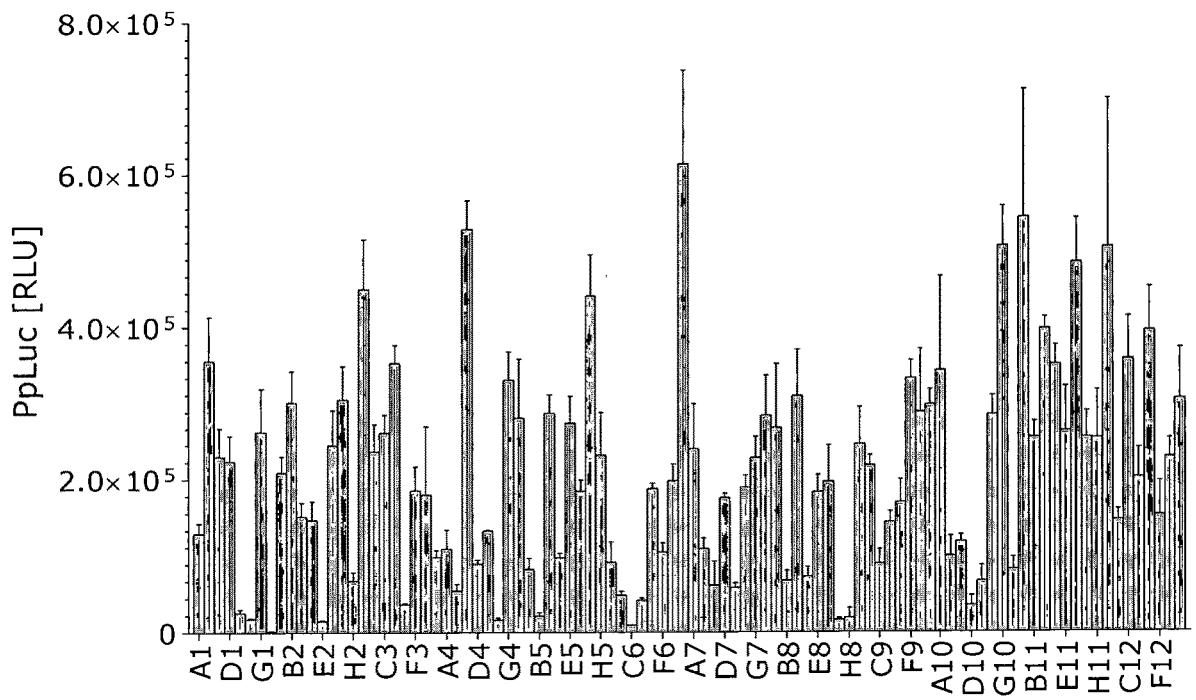
Fig. 6

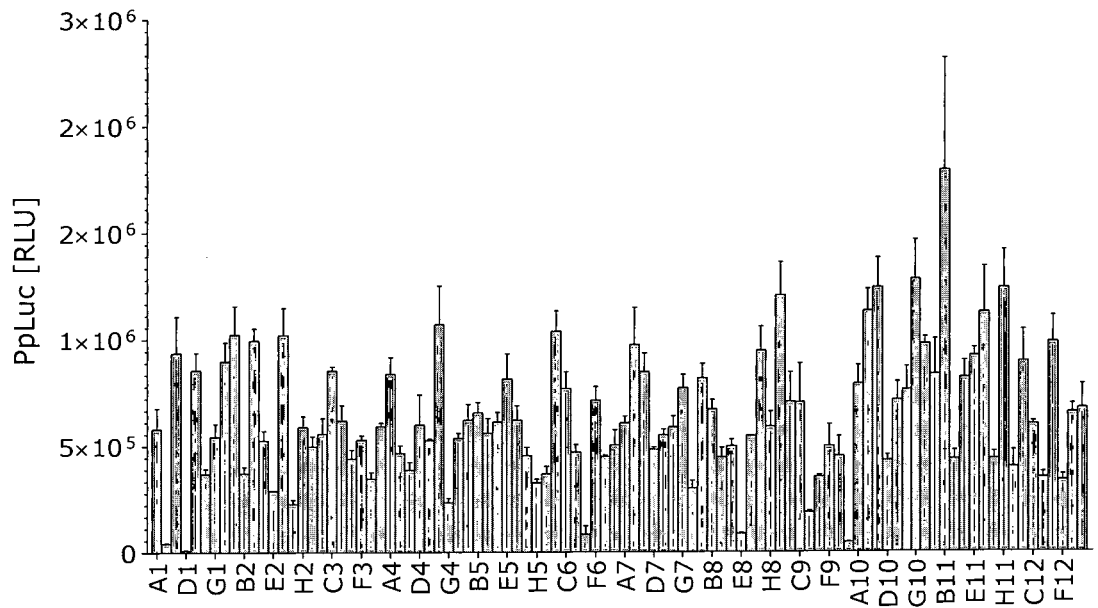
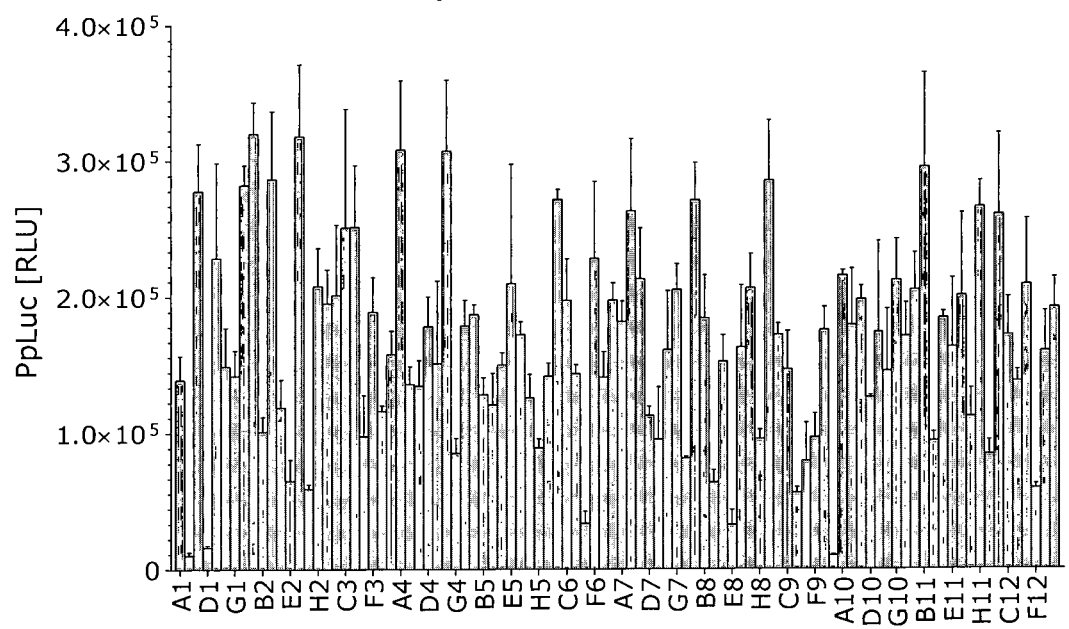
Fig. 7

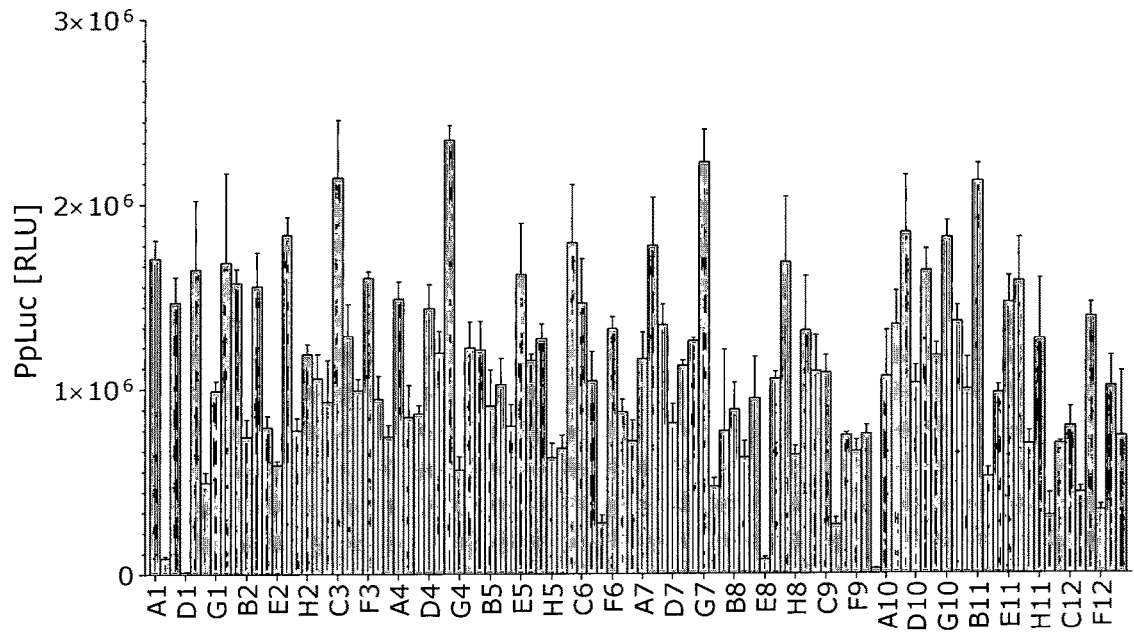
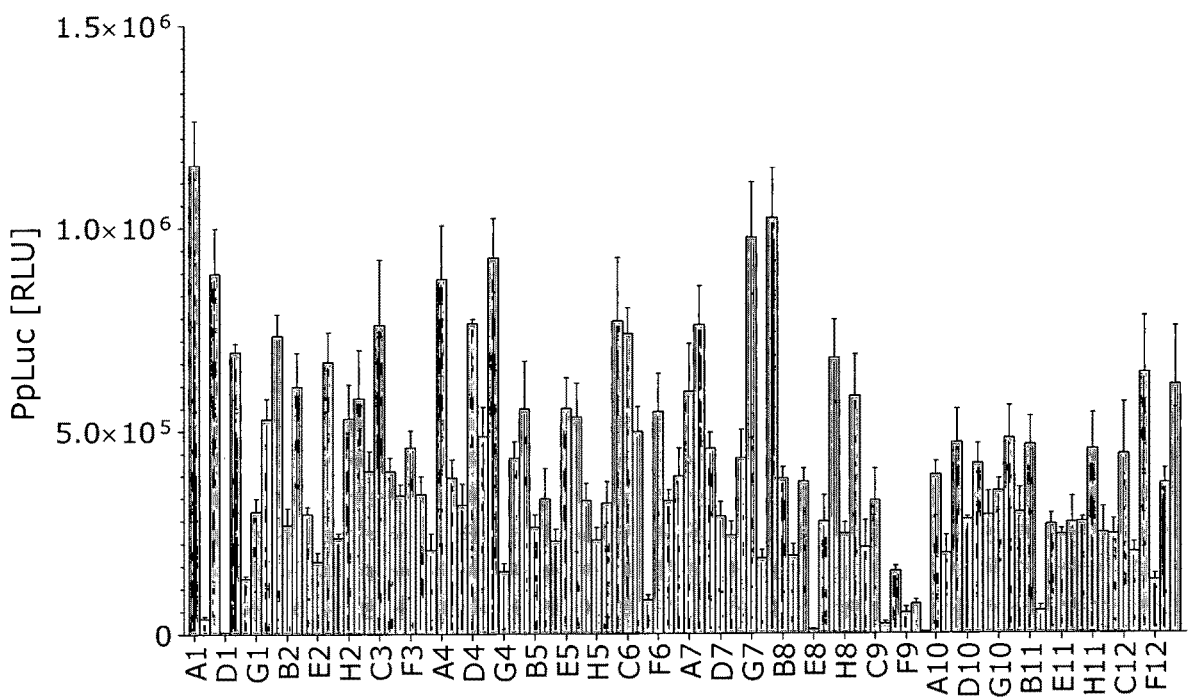
Fig. 9

ARTIFICIAL NUCLEIC ACID MOLECULES

This application is a national phase application under 35 U.S.C. § 371 of International Application No. PCT/EP2016/001417, filed Aug. 22, 2016, which claims benefit of International Application No. PCT/EP2015/001755, filed Aug. 28, 2015, the entire contents of each of which are hereby incorporated by reference.

The invention relates to artificial nucleic acid molecules comprising an open reading frame, a 3'-untranslated region element (3'-UTR element) and/or a 5'-untranslated region element (5'-UTR element) and optionally a poly(A) sequence and/or a polyadenylation-signal. The invention relates further to a vector comprising a 3'-UTR element and/or a 5'-UTR element, to a cell comprising the artificial nucleic acid molecule or the vector, to a pharmaceutical composition comprising the artificial nucleic acid molecule or the vector and to a kit comprising the artificial nucleic acid molecule, the vector and/or the pharmaceutical composition, preferably for use in the field of gene therapy and/or genetic vaccination.

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent early onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to misregulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product. However, misregulation of transcription or translation may also occur, if mutations affect genes encoding proteins which are involved in the transcriptional or translational machinery of the cell. Such mutations may lead to pathological up- or down-regulation of genes which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows evoking a desired immune response to selected antigens, such as characteristic components of bacterial surfaces, viral particles, tumour antigens or the like. Generally, vaccination is one of the pivotal achievements of modern medicine. However, effective vaccines are currently available only for a limited number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumor antigen in vivo. Genetic vaccines are expressed upon administration to a patient after uptake by target cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information. Alternatively, genetic vaccination or gene therapy may also comprise methods which include isolation of specific body cells from a patient to be treated, subsequent in ex vivo transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting mutagenic events such as in loss of function of the impaired genes. As a further risk, the undesired generation of anti-DNA antibodies has emerged. Another drawback is the limited expression level of the encoded peptide or protein that is achievable upon DNA administration because the DNA must enter the nucleus in order to be transcribed before the resulting mRNA can be translated. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

Typically, RNA degradation contributes to the regulation of the RNA half-life time. That effect was considered and proven to fine tune the regulation of eukaryotic gene expression (Friedel et al., 2009. Conserved principles of mammalian transcriptional regulation revealed by RNA half-life, Nucleic Acid Research 37(17): 1-12). Accordingly, each naturally occurring mRNA has its individual half-life depending on the gene from which the mRNA is derived and in which cell type it is expressed. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half-life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that it is usually desired that the product encoded by the RNA sequence accumulates in vivo. On the other hand, the RNA has to maintain its structural and functional integrity when prepared for a suitable dosage form, in the course of its storage, and when administered. Thus, efforts were made to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the coding region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'-UTR) and/or at their 3'-end (3'-UTR) as well as other structural features, such as a 5'-cap structure or a 3'-poly(A) tail. Both, 5'-UTR and 3'-UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenosine nucleotides added to the 3'-end of the transcribed mRNA. It may comprise up to about 400 adenosine nucleotides. It was found that the length of such a 3'-poly(A) tail is a potentially critical element for the stability of the individual mRNA.

Also, it was shown that the 3'-UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'-UTR of α-globin mRNA is apparently involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

An interesting regulatory function has further been demonstrated for the UTRs in ribosomal protein mRNAs: while the 5'-UTR of ribosomal protein mRNAs controls the growth-associated translation of the mRNA, the stringency of that regulation is conferred by the respective 3'-UTR in ribosomal protein mRNAs (Ledda et al., Effect of the 3'-UTR length on the translational regulation of 5'-terminal oligopyrimidine mRNAs, Gene, Vol. 344, 2005, p. 213-220). This mechanism contributes to the specific expression pattern of ribosomal proteins, which are typically transcribed in a constant manner so that some ribosomal protein mRNAs such as ribosomal protein S9 or ribosomal protein L32 are referred to as housekeeping genes (Janovick-Guretzky et al., Housekeeping Gene Expression in Bovine Liver is Affected by Physiological State, Feed Intake, and Dietary Treatment, J. Dairy Sci., Vol. 90, 2007, p. 2246-2252). The growth-associated expression pattern of ribosomal proteins is thus mainly due to regulation on the level of translation.

WO 2014/164253 A1 describes some specific nucleic acid molecules having 5'-UTRs and/or 3'-UTRs, without detailing on translation efficiency of such molecules.

Irrespective of factors influencing mRNA stability, effective translation of the administered nucleic acid molecules by the target cells or tissue is crucial for any approach using nucleic acid molecules for gene therapy or genetic vaccination. As can be seen from the examples cited above, along with the regulation of stability, also translation of the majority of mRNAs is regulated by structural features like UTRs, 5'-cap and 3'-poly(A) tail. In this context, it has been reported that the length of the poly(A) tail may play an important role for translation efficiency as well. Stabilizing 3'-elements, however, may also have an attenuating effect on translation.

It is the object of the invention to provide nucleic acid molecules which may be suitable for application in gene therapy and/or genetic vaccination. Particularly, it is the object of the invention to provide an mRNA species which is stabilized against preterm degradation or decay without exhibiting significant functional loss in translation efficiency. It is also an object of the invention to provide an artificial nucleic acid molecule, preferably an mRNA, which is characterized by high translation efficiency. One particular object of the invention is the provision of an mRNA, wherein the efficiency of translation (ribosomal production of the respective encoded protein) is enhanced, e.g. with reference to a reference nucleic acid molecule (reference mRNA). Another object of the present invention is to provide nucleic acid molecules coding for such a superior mRNA species which may be amenable for use in gene therapy and/or genetic vaccination. It is a further object of the present invention to provide a pharmaceutical composition for use in gene therapy and/or genetic vaccination. In summary, it is the object of the present invention to provide improved nucleic acid species which overcome the above discussed disadvantages of the prior art by a cost-effective and straight-forward approach.

The object underlying the present invention is solved by the claimed subject matter. In particular, the present inventors identified UTR elements (5'-UTR elements and 3'-UTR elements) which provide high translation efficiency. It is a common aspect of preferred nucleic acid molecules of this invention that they are all characterized by a translation efficiency which is higher than the translation efficiency of previously known nucleic acid molecules. An assay for determining high translation efficiency, with reference to a reference nucleic acid molecule, is also provided.

The present invention was made with support from the US Government under Agreement No. HR0011-11-3-0001 awarded by DARPA. The US Government has certain rights in the invention.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells. In the sense of the present invention an antigen may be the product of translation of a provided nucleic acid molecule, preferably an mRNA as defined herein. In this context, also fragments, variants and derivatives of peptides and proteins comprising at least one epitope are understood as antigens. In the context of the present invention, tumour antigens and pathogenic antigens as defined herein are particularly preferred.

In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild-type sequence by at least one nucleotide. The term "wild-type" may be understood as a sequence occurring in nature. When any particular "artificial nucleic acid molecule" is described herein to be "based on" any particular wild-type nucleic acid molecule, then said artificial nucleic acid molecule differs from said wild-type nucleic acid molecule by at least one nucleotide. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA that typically may have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein which is positively charged under physiological conditions, particularly under physiological conditions in vivo. A "cationic peptide or protein" may contain at least one positively charged amino acid, or more than one positively charged amino acid, e.g. selected from Arg, His, Lys or Orn. Accordingly, "polycationic" components are also within the scope exhibiting more than one positive charge under the conditions given.

5'-cap: A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5'-cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

DNA: DNA is the usual abbreviation for deoxy-ribo-nucleic acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA sequence. DNA may be single stranded or double stranded. In the double stranded form, the nucleotides of the first strand typically hybridize with the nucleotides of the second strand, e.g. by A/T-base-pairing and G/C-base-pairing.

Epitope: (also called "antigen determinant") can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 5%, 10%, 20%, preferably at least 30%, more preferably at least 40%, more preferably at least 50%, even more preferably at least 60%, even more preferably at least 70%, and most preferably at least 80% of the total (i.e. full-length) molecule from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG), at its 5'-end and a subsequent region which usually exhibits a length which is a multiple of 3 nucleotides. Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "protein coding region".

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein A protein typically comprises one or more peptides or polypeptides. A protein is typically folded into 3-dimensional form, which may be required for to protein to exert its biological function.

Poly(A) sequence: A poly(A) sequence, also called poly (A) tail or 3'-poly(A) tail, is typically understood to be a sequence of adenosine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides. A poly(A) sequence is typically located at the 3'end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation: Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

Restriction site: A restriction site, also termed restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA. mRNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. Typically, transcription of DNA usually results in the so-called premature RNA which has to be processed into so-called messenger-RNA, usually abbreviated as mRNA. Processing of the premature RNA, e.g. in eukaryotic organisms, comprises a variety of different post-transcriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino-acid sequence of a particular peptide or protein. Typically, a mature mRNA comprises a 5'-cap, a 5'-UTR, an open reading frame, a 3'-UTR and a poly(A) sequence. Aside from messenger RNA, several non-coding types of RNA exist which may be involved in regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Translation efficiency (or efficiency of translation): This term, as used herein, typically relates to a property of a nucleic acid molecule (e.g. mRNA) comprising an open reading frame (ORF). Translation efficiency is experimentally quantifiable. Translation efficiency is typically measured by determining the quantity of protein translated from the ORF. For experimental quantification of translation efficiency, the ORF preferably encodes a reporter protein or any other protein that can be quantified. However, without wishing to be bound to a particular theory, it is understood that high translation efficiency is typically provided by a specific UTR element (a specific 5'-UTR element or a specific 3'-UTR element). Thus, within the context of the present invention, the term translation efficiency is particularly used in relation to nucleic acid molecules which, in addition to the ORF, comprise at least one 5'-UTR element and/or at least one 3'-UTR element, preferably as defined herein. While for the purposes of experimental quantification of translation efficiency, the ORF suitably encodes a reporter protein or any other protein that can be quantified, the present invention is not limited to such purposes; consequently, the at least one 5'-UTR element and/or at least one 3'-UTR element of the invention (which provides high translation efficiency) can be comprised in a nucleic acid molecule comprising an ORF, which does not encode a reporter protein.

Translation efficiency is a relative term. Thus, the translation efficiency of various, e.g. two or more, nucleic acid molecules can be determined and compared, e.g. by experimental quantification of protein encoded by the ORF. This can be done under standardized conditions, e.g. in a standardized assay as described herein. Thus, translation efficiency determined under standardized conditions is an objective feature. Preferably, the translation efficiency of two nucleic acid molecules is determined and compared. The first of said two nucleic acid molecules can be referred to as "subject nucleic acid molecule" or "subject construct", and the second of said two nucleic acid molecules can be referred to as "reference nucleic acid molecule" or "reference construct". The subject nucleic acid molecule can be an artificial nucleic acid molecule according to the present invention. For this purpose, reference nucleic acid molecule and subject nucleic acid molecule share the same ORF (identical nucleic acid sequence); and preferably the nucleic acid sequence of the subject nucleic acid molecule is identical to the nucleic acid sequence of the reference nucleic acid molecule, with the exception of the UTR element that is tested, i.e. either the 5'-UTR element or the 3'-UTR element; in other words, subject nucleic acid molecule and reference nucleic acid molecule preferably differ from each other only in that either the 5'-UTR element or the 3'-UTR element has a different nucleic acid sequence; so that the 5'-UTR element or the 3'-UTR element is the sole structural feature, which distinguishes the subject nucleic acid molecule from the reference nucleic acid molecule.

In the assay described herein, subject nucleic acid molecule and reference nucleic acid molecule are transfected into mammalian cells, and translation efficiency is determined.

When the translation efficiency of the subject nucleic acid molecule is higher than the translation efficiency of the reference nucleic acid molecule, then the subject nucleic acid molecule is said to be characterized by high translation efficiency. In this instance, the 5'-UTR element or the 3'-UTR element which distinguishes the subject nucleic acid molecule from the reference nucleic acid molecule is said to provide high translation efficiency (to the subject nucleic acid molecule). In other words, the high translation efficiency is said to be "provided" by the specific 5'-UTR element or the 3'-UTR element which is present in the subject nucleic acid molecule but not in the reference nucleic acid molecule; and the subject nucleic acid molecule (or artificial nucleic acid molecule) which comprises such 5'-UTR or 3'-UTR and at least one ORF is said to "be characterized by" high translation efficiency.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector which allows the convenient storage of a nucleic acid molecule, for example, of an mRNA molecule. Thus, the vector may comprise a sequence corresponding, e.g., to a desired mRNA sequence or a part thereof, such as a sequence corresponding to the open reading frame and the 3'-UTR and/or the 5'-UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA polymerase promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule.

Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

3'-untranslated region (3'-UTR): Generally, the term "3'-UTR" refers to a part of the artificial nucleic acid molecule, which is located 3' (i.e. "downstream") of an open reading frame and which is not translated into protein. Typically, a 3'-UTR is the part of an mRNA which is located between the protein coding region (open reading frame (ORF) or coding sequence (CDS)) and the poly(A) sequence of the mRNA. In the context of the invention, the term 3'-UTR may also comprise elements, which are not encoded in the template, from which an RNA is transcribed, but which are added after transcription during maturation, e.g. a poly(A) sequence. A 3'-UTR of the mRNA is not translated into an amino acid sequence. The 3'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5' capping, splicing the pre-mature mRNA to excise optional introns and modifications of the 3'-end, such as polyadenylation of the 3'-end of the pre-mature mRNA and optional endo-/or exonuclease cleavages etc. In the context of the present invention, a 3'-UTR corresponds to the sequence of a mature mRNA which is located between the stop codon of the protein coding region, preferably immediately 3' to the stop codon of the protein coding region, and the poly(A) sequence of the mRNA. The term "corresponds to" means that the 3'-UTR sequence may be an RNA sequence, such as in the mRNA sequence used for defining the 3'-UTR sequence, or a DNA sequence which corresponds to such RNA sequence. In the context of the present invention, the term "a 3'-UTR of a gene", is the sequence which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence (both sense and antisense strand and both mature and immature) of the 3'-UTR. Preferably, the 3'UTRs have a length of more than 20, 30, 40 or 50 nucleotides.

5'-untranslated region (5'-UTR): Generally, the term "5'-UTR" refers to a part of the artificial nucleic acid molecule, which is located 5' (i.e. "upstream") of an open reading frame and which is not translated into protein. A 5'-UTR is typically understood to be a particular section of messenger RNA (mRNA), which is located 5' of the open reading frame of the mRNA. Typically, the 5'-UTR starts with the transcriptional start site and ends one nucleotide before the start codon of the open reading frame. Preferably, the 5'UTRs have a length of more than 20, 30, 40 or 50 nucleotides. The 5'-UTR may comprise elements for controlling gene expression, also called regulatory elements. Such regulatory elements may be, for example, ribosomal binding sites. The 5'-UTR may be posttranscriptionally modified, for example by addition of a 5'-CAP. A 5'-UTR of the mRNA is not translated into an amino acid sequence. The 5'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5' capping, splicing the pre-mature mRNA to excise optional introns and modifications of the 3'-end, such as polyadenylation of the 3'-end of the pre-mature mRNA and optional endo-/or exonuclease cleavages etc. In the context of the present invention, a 5'-UTR corresponds to the sequence of a mature mRNA which is located between the start codon and, for example, the 5'-CAP. Preferably, the 5'-UTR corresponds to the sequence which extends from a nucleotide located 3' to the 5'-CAP, more preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence which corresponds to such RNA sequence. In the context of the present invention, the term "a 5'-UTR of a gene" is the sequence which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence (both sense and antisense strand and both mature and immature) of the 5'-UTR.

5'Terminal Oligopyrimidine Tract (TOP): The 5' terminal oligopyrimidine tract (TOP) is typically a stretch of pyrimidine nucleotides located in the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5' terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5' end with a cytosine nucleotide. In TOP genes and TOP mRNAs, the TOP-motif preferably starts at its 5' end with the transcriptional start site and ends one nucleotide 5' to the first purin residue in said gene or mRNA. A TOP motif in the sense of the present invention is preferably located at the 5'end of a sequence which represents a 5'-UTR or at the 5'end of a sequence which codes for a 5'-UTR. Thus, preferably, a stretch of 3 or more pyrimidine nucleotides is called "TOP motif" in the sense of the present invention if this stretch is located at the 5'end of a respective sequence, such as the artificial nucleic acid molecule, the 5'-UTR element of the artificial nucleic acid molecule, or the nucleic acid sequence which is derived from the 5'-UTR of a TOP gene as described herein. In other words, a stretch of 3 or more pyrimidine nucleotides, which is not located at the 5'-end of a 5'-UTR or a 5'-UTR element but anywhere within a 5'-UTR or a 5'-UTR element, is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-CAP to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary between 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363 of the patent application WO2013/143700, whose disclosure is incorporated herewith by reference. In this context a particularly preferred fragment of a 5'-UTR of a TOP gene is a 5'-UTR of a TOP gene lacking the 5'TOP motif. The terms "5'-UTR of a TOP gene" or "5'-TOP UTR" preferably refer to the 5'-UTR of a naturally occurring TOP gene. A preferred example is represented by SEQ ID NO: 208 (5'-UTR of human ribosomal protein Large 32 lacking the 5' terminal oligopyrimidine tract); corresponding to SEQ ID NO. 1368 of the patent application WO2013/143700).

Wild-type. e.g. wild-type nucleic acid molecule: The term "wild-type" may be understood as a sequence occurring in nature. A wild-type nucleic molecule may typically be understood to be a nucleic acid molecule, e.g. a DNA or an RNA, that occurs naturally. In other words, an artificial nucleic acid molecule may be understood as a natural nucleic acid molecule. Such nucleic acid molecule may be natural due to its individual sequence (which occurs naturally) and/or due to other modifications, e.g. structural modifications of nucleotides which occur naturally. A wild-type nucleic acid molecule may be a DNA molecule, an RNA molecule or a hybrid-molecule comprising DNA and RNA portions. Herein, the term "wild-type" refers to any sequence as long as it occurs in nature, reflection in publically accessible sequence collections such as GenBank is not required. The National Institute of Health (NIH) provides a publically accessible, annotated collection of publicly available nucleotide sequences ("GenBank", accessible through the NCBI Entrez retrieval system: http//www.ncbi.nlm.nih-.gov), (Nucleic Acids Research, 2013; 41(D1):D36-42), including publicly available wild-type sequences. Each GenBank record is assigned a unique constant identifier called an accession number and appears on the ACCESSION line of a GenBank record; and changes to the sequence data are tracked by an integer extension of the accession number which appears on the VERSION line of the GenBank record. Further, the term "wild-type nucleic acid molecule" is not restricted to mean "one single molecule" but is, typically, understood to comprise an ensemble of identical molecules. Accordingly, it may relate to a plurality of identical molecules contained in an aliquot.

DETAILED DESCRIPTION

The invention relates to an artificial nucleic acid molecule comprising at least one open reading frame and at least one 3'-untranslated region element (3'-UTR element) and/or at least one 5'-untranslated region element (5'-UTR element), wherein said artificial nucleic acid molecule is characterized by high translation efficiency. The translation efficiency is contributed, at least in part, by the 5'-UTR element or the 3'-UTR element, or both of the 5'-UTR element and the 3'-UTR element. The invention further relates to the use of such an artificial nucleic acid molecule in gene therapy and/or genetic vaccination. Furthermore, novel 3'-UTR elements and 5'-UTR elements are provided.

In a first aspect, the present invention relates to an artificial nucleic acid molecule comprising
 a. at least one open reading frame (ORF); and
 b. at least one 3'-untranslated region element (3'-UTR element) and/or at least one 5'-untranslated region element (5'-UTR element), wherein said artificial nucleic acid molecule is characterized by high translation efficiency.

For example, the artificial nucleic acid molecule of the invention may differ from other (e.g. wild-type or artificial) nucleic acid molecules in that at least one 3'-UTR element (preferably one 3'-UTR element) is replaced by at least one nonidentical 3'-UTR element (preferably one 3'-UTR element) or in that at least one 5'-UTR element (preferably one 5'-UTR element) is replaced by at least one nonidentical 5'-UTR element (preferably one 5'-UTR element).

In general, replacing one (or least one) 3'-UTR element or replacing one (or least one) 5'-UTR element (in a starting nucleic acid molecule or reference nucleic acid molecule) generally means that a sequence of at least some nucleotides of said 3'-UTR element or of said 5'-UTR element is replaced by a nonidentical nucleic acid sequence. Preferably, when replacing a 5'-UTR element, a continuous sequence of nucleotides of the 5'-UTR element is replaced by a nonidentical continuous sequence (element) of nucleotides; and when replacing a 3'-UTR element, a continuous sequence of nucleotides of the 3'-UTR element is replaced by a nonidentical continuous sequence (element) of nucleotides. The continuous sequence of nucleotides of the original (replaced) element and of the replacing element can each be independently of any lengths, such as from 1 to more than 500 nucleotides, 20 to 500 nucleotides, 40 to 400 nucleotides, 60 to 300 nucleotides, 80 to 200 nucleotides or 100 to 150 nucleotides. When a (5'- or 3'-) UTR element is replaced, this does not necessarily mean that all nucleotides located 5' of the start codon or all nucleotides located 3' of the stop codon are replaced. In preferred embodiments, a continuous sequence, which is a subset of all the nucleotides located 5' of the start codon or a subset of all nucleotides located 3' of the stop codon, respectively, is replaced. Examples thereof are shown in FIGS. 1B (5') and 1C (3'). It is possible to exactly replace a known 5'-UTR element, or a known 3'-UTR element, present in the staring sequence or reference sequence. For example, when a (e.g. reference) nucleic acid comprises a 5'-UTR element corresponding to the sequence according to SEQ ID NO: 208; the artificial nucleic acid molecule of the present invention can be made by replacing exactly the entire continuous sequence according to SEQ ID NO: 208 by a nonidentical continuous 5'-UTR element according to the present invention, i.e. a 5'-UTR element which provides high translation efficiency. Alternatively, it is possible that a known UTR element is not replaced exactly, e.g. a continuous nucleic acid sequence comprising additional nucleotides, i.e. in addition to the known UTR element, is replaced, or e.g. only a fraction (usually a major fraction, i.e. 90% of length or more) of a known UTR element is replaced. While these possibilities have been illustrated here for the case of 5'-UTR elements, the same possibilities also exist for 3'-UTR elements. In other words, the replaced UTR element need not necessarily be confined by the exact boundaries of a known UTR element. These possibilities are illustrated further, by means of example, in FIG. 1B and FIG. 1C, respectively, each in comparison with FIG. 1A. Likewise, the replacing UTR element need not necessarily be confined by the exact boundaries of a known UTR element.

Preferably, the artificial nucleic acid molecule according to the present invention does not comprise a 3'-UTR (element) and/or a 5'-UTR (element) of ribosomal protein S6, of RPL36AL, of rps16 or of ribosomal protein L9. More preferably, the artificial nucleic acid molecule according to the present invention does not comprise a 3'-UTR (element) and/or a 5'-UTR (element) of ribosomal protein S6, of RPL36AL, of rps16 or of ribosomal protein L9 and the open reading frame of the artificial nucleic acid molecule according to the present invention does not code for a GFP protein. Even more preferably, the artificial nucleic acid molecule according to the present invention does not comprise a 3'-UTR (element) and/or a 5'-UTR (element) of ribosomal protein S6, of RPL36AL, of rps16 or of ribosomal protein L9 and the open reading frame of the artificial nucleic acid molecule according to the present invention does not code for a reporter protein, e.g., selected from the group consisting of globin proteins (particularly beta-globin), luciferase protein, GFP proteins, glucuronidase proteins (particularly beta-glucuronidase) or variants thereof, for example, variants exhibiting at least 70% sequence identity to a globin protein, a luciferase protein, a GFP protein, or a glucuronidase protein.

The term "3'-UTR element" refers to a nucleic acid sequence which comprises or consists of a nucleic acid sequence that is derived from a 3'-UTR or from a variant or a fragment of a 3'-UTR. A "3'-UTR element" preferably refers to a nucleic acid sequence which is comprised by a 3'-UTR of an artificial nucleic acid sequence, such as an artificial mRNA.

Accordingly, in the sense of the present invention, preferably, a 3'-UTR element may be comprised by the 3'-UTR of an mRNA, preferably of an artificial mRNA, or a 3'-UTR element may be comprised by the 3'-UTR of the respective transcription template. Preferably, a 3'-UTR element is a nucleic acid sequence which corresponds to the 3'-UTR of an mRNA, preferably to the 3'-UTR of an artificial mRNA, such as an mRNA obtained by transcription of a genetically engineered vector construct. Preferably, a 3'-UTR element in the sense of the present invention functions as a 3'-UTR or codes for a nucleotide sequence that fulfils the function of a 3'-UTR.

Accordingly, the term "5'-UTR element" refers to a nucleic acid sequence which comprises or consists of a nucleic acid sequence that is derived from a 5'-UTR or from a variant or a fragment of a 5'-UTR. A "5'-UTR element" preferably refers to a nucleic acid sequence which is comprised by a 5'-UTR of an artificial nucleic acid sequence, such as an artificial mRNA. Accordingly, in the sense of the present invention, preferably, a 5'-UTR element may be comprised by the 5'-UTR of an mRNA, preferably of an artificial mRNA, or a 5'-UTR element may be comprised by the 5'-UTR of the respective transcription template. Preferably, a 5'-UTR element is a nucleic acid sequence which corresponds to the 5'-UTR of an mRNA, preferably to the 5'-UTR of an artificial mRNA, such as an mRNA obtained by transcription of a genetically engineered vector construct. Preferably, a 5'-UTR element in the sense of the present invention functions as a 5'-UTR or codes for a nucleotide sequence that fulfils the function of a 5'-UTR.

The 3'-UTR element and/or the 5'-UTR element in the artificial nucleic acid molecule according to the present invention provides high translation efficiency to said artificial nucleic acid molecule. Thus, the artificial nucleic acid molecule according to the present invention may in particular comprise:

- a 3'-UTR element which provides high translation efficiency to said artificial nucleic acid molecule,
- a 5'-UTR element which provides high translation efficiency to said artificial nucleic acid molecule,
- a 3'-UTR element which provides high translation efficiency to said artificial nucleic acid molecule and a 5'-UTR element which provides high translation efficiency to said artificial nucleic acid molecule.

Preferably, the artificial nucleic acid molecule according to the present invention comprises a 3'-UTR element which provides high translation efficiency to said artificial nucleic acid molecule and/or a 5'-UTR element which provides high translation efficiency to said artificial nucleic acid molecule.

Preferably, the artificial nucleic acid molecule according to the present invention comprises at least one 3'-UTR element and at least one 5'-UTR element, i.e. at least one 3'-UTR element which provides high translation efficiency to said artificial nucleic acid molecule and at least one 5'-UTR element which provides high translation efficiency to said artificial nucleic acid molecule.

As described in detail below, said at least one 3'-UTR element which provides high translation efficiency to said artificial nucleic acid molecule or said at least one 5'-UTR element which provides high translation efficiency to said artificial nucleic acid molecule can be selected from naturally occurring (preferably heterologous) 3'-UTR elements and 5'-UTR elements (together naturally occurring UTR elements or wild-type UTR elements), and from artificial 3'-UTR elements and artificial 5'-UTR elements (together artificial UTR elements). Wild-type UTR elements can be selected from the group comprising wild-type UTR elements published in the literature and in publically accessible databases, such as GenBank (NCBI), and wild-type UTR elements not previously published. The latter can be identified by sequencing mRNas found in cells, preferably mammalian cells. Using this approach, the present inventors identified several wild-type UTR elements not previously published, and UTR elements of this type are provided in the present invention. The term artificial UTR element is not particularly limited and can refer to any nucleic acid sequence not found in nature, i.e. nonidentical to a wild-type UTR element. In preferred embodiments, however, the artificial UTR element used in the present invention is a nucleic acid sequence which shows a certain degree of sequence identity to a wild-type UTR element, such as 10 to 99.9%, 20 to 99%, 30 to 98%, 40 to 97%, 50 to 96%, 60 to 95%, 70 to 90%. In preferred embodiments, artificial UTR used in the present invention is identical to a wild-type UTR except that one, or two, or three, or four, or five, or more than five nucleotides have been substituted by the same number of nucleotides (e.g. one nucleotide being substituted by one nucleotide). Preferably, substitution of one nucleotide is a substitution by the respective complementary nucleotide. Preferred artificial UTR elements correspond to wild-type UTR elements, except that (i) some or all ATG triplets in a wild-type 5'-UTR element (if present) are converted to the triplet TAG; and/or (ii) selected cleavage site(s) for a particular restriction enzyme in a wild-type 5'-UTR element or in a in a wild-type 3'-UTR element (if present) are eliminated by substituting one nucleotide within the cleavage site for said specific restriction enzyme by the complementary nucleotide, thereby removing the cleavage sites for said specific restriction enzyme. The latter is usually desired when a (e.g. wild-type) UTR element comprises a cleavage site for said specific restriction enzyme, and when said particular restriction enzyme is (planned to be) used in subsequent cloning steps. Since such internal cleavage of 5'-UTR elements and 3'-UTR elements is undesired, an artificial UTR element can be generated in which the restriction cleavage site for said specific restriction enzyme is eliminated. Such substitution can be done by any suitable method known to the person skilled in the art, e.g. use of modified primers by PCR.

Optionally, the artificial nucleic acid molecule according to the present invention comprises at least one 3'-UTR element and at least one 5'-UTR element, i.e. at least one 3'-UTR element which prolongs and/or increases protein production from said artificial nucleic acid molecule and at least one 5'-UTR element which prolongs and/or increases protein production from said artificial nucleic acid molecule.

Protein Production: Assay for Determining Whether Protein Production is Prolonged and/or Increased "Prolonging and/or increasing protein production from said artificial nucleic acid molecule" in general refers to the amount of protein produced from the artificial nucleic acid molecule according to the present invention with the respective 3'-UTR element and/or the 5'-UTR element in comparison to the amount of protein produced from a respective reference nucleic acid lacking a 3'-UTR and/or a 5'-UTR or comprising a reference 3'-UTR and/or a reference 5'-UTR, such as a 3'-UTR and/or a 5'-UTR naturally occurring in combination with the ORF.

In particular, the at least one 3'-UTR element and/or the 5'-UTR element of the artificial nucleic acid molecule according to the present invention prolongs protein production from the artificial nucleic acid molecule according to the present invention, e.g. from an mRNA according to the present invention, compared to a respective nucleic acid lacking a 3'-UTR and/or 5'-UTR or comprising a reference 3'-UTR and/or 5'-UTR, such as a 3'- and/or 5'-UTR naturally occurring in combination with the ORF.

In particular, the at least one 3'-UTR element and/or 5'-UTR element of the artificial nucleic acid molecule according to the present invention increases protein production, in particular the protein expression and/or total protein production, from the artificial nucleic acid molecule according to the present invention, e.g. from an mRNA according to the present invention, compared to a respective nucleic acid lacking a 3'- and/or 5'-UTR or comprising a reference 3'- and/or 5'-UTR, such as a 3'- and/or 5'-UTR naturally occurring in combination with the ORF.

Preferably, the at least one 3'-UTR element and/or the at least one 5'-UTR element of the artificial nucleic acid molecule according to the present invention do not negatively influence translational efficiency of a nucleic acid compared to the translational efficiency of a respective nucleic acid lacking a 3'-UTR and/or a 5'-UTR or comprising a reference 3'-UTR and/or a reference 5'-UTR, such as a 3'-UTR and/or a 5'-UTR naturally occurring in combination with the ORF. Alternatively, the translation efficiency is enhanced by the 3'-UTR and/or a 5'-UTR in comparison to the translation efficiency of the protein encoded by the respective ORF in its natural context.

The term "respective nucleic acid molecule" or "reference nucleic acid molecule" as used herein means that—apart from the different 3'-UTRs and/or 5'-UTRs—the reference nucleic acid molecule is comparable, preferably identical, to the artificial nucleic acid molecule of the invention comprising the 3'-UTR element and/or the 5'-UTR element.

In order to assess the protein production in vivo or in vitro as defined herein (i.e. in vitro referring to ("living") cells and/or tissue, including tissue of a living subject; cells include in particular cell lines, primary cells, cells in tissue or subjects, preferred are mammalian cells, e.g. human cells and mouse cells and particularly preferred are the human cell lines HeLa, HEPG2 and U-937 and the mouse cell lines NIH3T3, JAWSII and L929, furthermore primary cells are particularly preferred, in particular preferred embodiments human dermal fibroblasts (HDF) by the inventive artificial nucleic acid molecule, the expression of the encoded protein is determined following injection/transfection of the inventive artificial nucleic acid molecule into target cells/tissue and compared to the protein expression induced by the reference nucleic acid. Quantitative methods for determining protein expression are known in the art (e.g. Western-Blot, FACS, ELISA, mass spectrometry). Particularly useful in this context is the determination of the expression of reporter proteins like luciferase, Green fluorescent protein (GFP), or secreted alkaline phosphatase (SEAP). Thus, an artificial nucleic acid according to the invention or a reference nucleic acid is introduced into the target tissue or cell, e.g. via transfection or injection, preferably in a mammalian expression system, such as in mammalian cells, e.g. in HDF, L929, HepG2 and/or Hela cells. Several hours or several days (e.g. 6, 12, 24, 48 or 72 hours) post initiation of expression or post introduction of the nucleic acid molecule, a target cell sample is collected and measured via FACS and/or lysed. Afterwards the lysates can be used to detect the expressed protein (and thus determine the efficiency of protein expression) using several methods, e.g. Western-Blot, FACS, ELISA, mass spectrometry or by fluorescence or luminescence measurement.

Therefore, if the protein expression from an artificial nucleic acid molecule according to the invention is compared to the protein expression from a reference nucleic acid molecule at a specific point in time (e.g. 6, 12, 24, 48 or 72 hours post initiation of expression or post introduction of the nucleic acid molecule), both nucleic acid molecules are introduced separately into target tissue/cells, a sample from the tissue/cells is collected after a specific point in time, protein lysates are prepared according to the particular protocol adjusted to the particular detection method (e.g. Western Blot, ELISA, fluorescence or luminescence measurement, etc. as known in the art) and the protein is detected by the chosen detection method. As an alternative to the measurement of expressed protein amounts in cell lysates—or, in addition to the measurement of protein amounts in cell lysates prior to lysis of the collected cells or using an aliquot in parallel—protein amounts may also be determined by using FACS analysis.

The term "prolonging protein production" from an artificial nucleic acid molecule such as an artificial mRNA preferably means that the protein production from the artificial nucleic acid molecule such as the artificial mRNA is prolonged compared to the protein production from a reference nucleic acid molecule such as a reference mRNA, e.g. comprising a reference 3'- and/or 5'-UTR or lacking a 3'- and/or 5'-UTR, preferably in a mammalian expression system, such as in HDF, L929, HEP2G or HeLa cells. Thus, protein produced from the artificial nucleic acid molecule such as the artificial mRNA is observable for a longer period of time than what may be seen for a protein produced from a reference nucleic acid molecule. In other words, the amount of protein produced from the artificial nucleic acid molecule such as the artificial mRNA measured at a later point in time, e.g. 48 hours or 72 hours after transfection, is larger than the amount of protein produced from a reference nucleic acid molecule such as a reference mRNA at a corresponding later point in time. Such a "later point in time" may be, for example, any time beyond 24 hours post initiation of expression, such as post transfection of the nucleic acid molecule, e.g. 36, 48, 60, 72, 96 hours post initiation of expression, i.e. after transfection. Moreover, for the same nucleic acid, the amount of protein produced at a later point in time may be normalized to the amount produced an earlier (reference) point in time, for example the amount of protein at a later point in time may be expressed as percentage of the amount of protein at 24 h after transfection.

Preferably, this effect of prolonging protein production is determined by (i) measuring protein amounts, e.g. obtained by expression of an encoded reporter protein such as luciferase, preferably in a mammalian expression system such as in HDF, L929, HEP2G or HeLa cells, over time, (ii) determining the amount of protein observed at a "reference" point in time $t_1$, for example $t_1=24$ h after transfection, and setting this protein amount to 100%, (iii) determining the amount of protein observed at one or more later points in time $t_2$, $t_3$, etc., for example $t_2=48$ h and $t_3=72$ h after transfection, and calculating the relative amount of protein observed at a later point in time as a percentage of the protein amount at a point in time $t_1$. For example, a protein which is expressed at $t_1$ in an amount of "80", at $t_2$ in an amount of "20", and at $t_3$ in an amount of "10", the relative amount of protein at $t_2$ would be 25%, and at $t_3$ 12.5%. These relative amounts at a later point in time may then be compared in a step (iv) to relative protein amounts for the corresponding points in time for a nucleic acid molecule lacking a 3'- and/or 5'-UTR, respectively, or comprising a reference 3'- and/or 5'-UTR, respectively. By comparing the relative protein amount produced from the artificial nucleic acid molecule according to the present invention to the relative protein amount produced from the reference nucleic acid molecule, i.e. the nucleic acid molecule lacking a 3'- and/or 5'-UTR, respectively, or comprising a reference 3'- and/or 5'-UTR, respectively, a factor may be determined by which the protein production from the artificial nucleic acid molecule according to the present invention is prolonged compared to the protein production from the reference nucleic acid molecule.

Preferably, the at least one 3'- and/or 5'-UTR element in the artificial nucleic acid molecule according to the invention prolongs protein production from said artificial nucleic acid molecule at least 1.2 fold, preferably at least 1.5 fold, more preferably at least 2 fold, even more preferably at least 2.5 fold, compared to the protein production from a reference nucleic acid molecule lacking 3'- and/or 5'-UTR, respectively, or comprising a reference 3'- and/or 5'-UTR, respectively. In other words, the (relative) amount of protein produced from the artificial nucleic acid molecule according to the invention at a certain later point in time as described above is increased by a factor of at least 1.2, preferably at least 1.5, more preferably at least 2, even more preferably at least 2.5, compared to the (relative) amount of protein produced from a reference nucleic acid molecule, which is e.g. lacking a 3'- and/or 5'-UTR, respectively, or comprising a reference 3'- and/or 5'-UTR, respectively, for the same later point in time.

Alternatively, the effect of prolonging protein production may also be determined by (i) measuring protein amounts, e.g. obtained by expression of an encoded reporter protein such as luciferase, preferably in a mammalian expression system such as in HDF, L929, HEP2G or HeLa cells, over time, (ii) determining the point in time at which the protein amount undercuts the amount of protein observed, e.g., at 1, 2, 3, 4, 5, or 6 hours post initiation of expression, e.g. 1, 2, 3, 4, 5, or 6 hours post transfection of the artificial nucleic acid molecule, and (iii) comparing the point in time at which the protein amount undercuts the protein amount observed at 1, 2, 3, 4, 5, or 6 hours post initiation of expression to said point in time determined for a nucleic acid molecule lacking a 3'- and/or 5'-UTR, respectively, or comprising a reference 3'- and/or 5'-UTR, respectively.

For example, the protein production from the artificial nucleic acid molecule such as the artificial mRNA—in an amount which is at least the amount observed in the initial phase of expression, such as 1, 2, 3, 4, 5, or 6 hours post initiation of expression, such as post transfection of the nucleic acid molecule—is prolonged by at least about 5 hours, preferably by at least about 10 hours, more preferably by at least about 24 hours compared to the protein production from a reference nucleic acid molecule, such as a reference mRNA, in a mammalian expression system, such as in mammalian cells, e.g. in HDF, L929, HEP2G or HeLa cells. Thus, the artificial nucleic acid molecule according to the present invention preferably allows for prolonged protein production in an amount which is at least the amount observed in the initial phase of expression, such as 1, 2, 3, 4, 5, or 6 hours post initiation of expression, such as post transfection, by at least about 5 hours, preferably by at least about 10 hours, more preferably by at least about 24 hours compared to a reference nucleic acid molecule lacking a 3'- and/or 5'-UTR, respectively, or comprising a reference 3'- and/or 5'-UTR, respectively.

In preferred embodiments, the period of protein production from the artificial nucleic acid molecule according to the present invention is extended at least 1.2 fold, preferably at least 1.5 fold, more preferably at least 2 fold, even more preferably at least 2.5 fold, compared to the protein production from a reference nucleic acid molecule lacking a 3'- and/or 5'-UTR, respectively, or comprising a reference 3'- and/or 5'-UTR, respectively.

Preferably, this prolonging effect on protein production is achieved, while the total amount of protein produced from the artificial nucleic acid molecule according to the present invention, e.g. within a time span of 48 or 72 hours, corresponds at least to the amount of protein produced from a reference nucleic acid molecule lacking a 3'- and/or 5'-UTR, respectively, or comprising a reference 3'- and/or 5'-UTR, respectively, such as a 3'-UTR and/or 5'-UTR naturally occurring with the ORF of the artificial nucleic acid molecule. Thus, the present invention provides an artificial nucleic acid molecule which allows for prolonged protein production in a mammalian expression system, such as in mammalian cells, e.g. in HDF, L929, HEP2G or HeLa cells, as specified above, wherein the total amount of protein produced from said artificial nucleic acid molecule, e.g. within a time span of 48 or 72 hours, is at least the total amount of protein produced, e.g. within said time span, from a reference nucleic acid molecule lacking a 3'- and/or 5'-UTR, respectively, or comprising a reference 3'- and/or 5'-UTR, respectively, such as a 3'- and/or 5'-UTR naturally occurring with the ORF of the artificial nucleic acid molecule.

Moreover, the term "prolonged protein expression" also includes "stabilized protein expression", whereby "stabilized protein expression" preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, an mRNA comprising a reference 3'- and/or 5'-UTR, respectively, or lacking a 3'- and/or 5'-UTR, respectively.

Accordingly, the level of protein production, e.g. in a mammalian system, from the artificial nucleic acid molecule comprising a 3'- and/or 5'-UTR element according to the present invention, e.g. from an mRNA according to the present invention, preferably does not drop to the extent observed for a reference nucleic acid molecule, such as a reference mRNA as described above. To assess to which extent the protein production from a specific nucleic acid molecule drops, for example, the amount of a protein (encoded by the respective ORF) observed 24 hours after initiation of expression, e.g. 24 hours post transfection of the artificial nucleic acid molecule according to the present invention into a cell, such as a mammalian cell, may be compared to the amount of protein observed 48 hours after initiation of expression, e.g. 48 hours post transfection. Thus, the ratio of the amount of protein encoded by the ORF of the artificial nucleic acid molecule according to the present invention, such as the amount of a reporter protein, e.g., luciferase, observed at a later point in time, e.g. 48 hours, post initiation of expression, e.g. post transfection, to the amount of protein observed at an earlier point in time, e.g. 24 hours, post initiation of expression, e.g. post transfection, is preferably higher than the corresponding ratio (including the same points in time) for a reference nucleic acid molecule comprising a reference 3'- and/or 5'-UTR, respectively, or lacking a 3'- and/or 5'-UTR, respectively.

Preferably, the ratio of the amount of protein encoded by the ORF of the artificial nucleic acid molecule according to the present invention, such as the amount of a reporter protein, e.g., luciferase, observed at a later point in time, e.g. 48 hours, post initiation of expression, e.g. post transfection, to the amount of protein observed at an earlier point in time, e.g. 24 hours, post initiation of expression, e.g. post transfection, is preferably at least 0.2, more preferably at least about 0.3, even more preferably at least about 0.4, even more preferably at least about 0.5, and particularly preferably at least about 0.7. For a respective reference nucleic acid molecule, e.g. an mRNA comprising a reference 3'- and/or 5'-UTR, respectively, or lacking a 3'- and/or 5'-UTR, respectively, said ratio may be, for example between about 0.05 and about 0.35.

Thus, the present invention provides an artificial nucleic acid molecule comprising an ORF and a 3'- and/or 5'-UTR element as described above, wherein the ratio of the protein amount, e.g. the amount of luciferase, observed 48 hours after initiation of expression to the protein amount observed 24 hours after initiation of expression, preferably in a mammalian expression system, such as in mammalian cells, e.g. in HDF cells or in HeLa cells, is preferably at least 0.2, more preferably at least about 0.3, more preferably at least about 0.4, even more preferably at least about 0.5, even more preferably at least about 0.6, and particularly preferably at least about 0.7. Thereby, preferably the total amount of protein produced from said artificial nucleic acid molecule, e.g. within a time span of 48 hours, corresponds at least to the total amount of protein produced, e.g. within said time span, from a reference nucleic acid molecule lacking a 3'- and/or 5'-UTR, respectively, or comprising a reference 3'- and/or 5'-UTR, respectively, such as a 3'-UTR and/or 5'-UTR naturally occurring with the ORF of the artificial nucleic acid molecule.

Preferably, the present invention provides an artificial nucleic acid molecule comprising an ORF and a 3'-UTR element and/or a 5'-UTR element as described above, wherein the ratio of the protein amount, e.g. the amount of luciferase, observed 72 hours after initiation of expression to the protein amount observed 24 hours after initiation of expression, preferably in a mammalian expression system, such as in mammalian cells, e.g. in HeLa cells or HDF cells, is preferably above about 0.05, more preferably above about 0.1, more preferably above about 0.2, even more preferably above about 0.3, wherein preferably the total amount of protein produced from said artificial nucleic acid molecule, e.g. within a time span of 72 hours, is at least the total amount of protein produced, e.g. within said time span, from a reference nucleic acid molecule lacking a 3'- and/or 5'-UTR, respectively, or comprising a reference 3'- and/or 5'-UTR, respectively, such as a 3'- and/or 5'-UTR naturally occurring with the ORF of the artificial nucleic acid molecule.

"Increased protein expression" or "enhanced protein expression" in the context of the present invention preferably means an increased/enhanced protein expression at one point in time after initiation of expression or an increased/enhanced total amount of expressed protein compared to the expression induced by a reference nucleic acid molecule. Thus, the protein level observed at a certain point in time after initiation of expression, e.g. after transfection, of the artificial nucleic acid molecule according to the present invention, e.g. after transfection of an mRNA according to the present invention, for example, 6, 12, 24, 48 or 72 hours post transfection, is preferably higher than the protein level observed at the same point in time after initiation of expression, e.g. after transfection, of a reference nucleic acid molecule, such as a reference mRNA comprising a reference 3'- and/or 5'-UTR, respectively, or lacking a 3'- and/or 5'-UTR, respectively. In a preferred embodiment, the maximum amount of protein (as determined e.g. by protein activity or mass) expressed from the artificial nucleic acid molecule is increased with respect to the protein amount expressed from a reference nucleic acid comprising a reference 3'- and/or 5'-UTR, respectively, or lacking a 3'- and/or 5'-UTR, respectively. Peak expression levels are preferably reached within 48 hours, more preferably within 24 hours and even more preferably within 12 hours after, for instance, transfection.

Preferably, the term "increased total protein production" or "enhanced total protein production" from an artificial nucleic acid molecule according to the invention refers to an increased/enhanced protein production over a time span, in which protein is produced from an artificial nucleic acid molecule, e.g. 48 hours or 72 hours, preferably in a mammalian expression system, such as in mammalian cells, e.g. in HDF, L929, HEP2G or HeLa cells in comparison to a reference nucleic acid molecule lacking a 3'- and/or 5'-UTR, respectively, or comprising a reference 3'- and/or 5'-UTR, respectively. According to a preferred embodiment, the cumulative amount of protein expressed over time is increased when using the artificial nucleic acid molecule according to the invention.

The total amount of protein for a specific time period may be determined by (i) collecting tissue or cells at several points in time after introduction of the artificial nucleic acid molecule (e.g. 6, 12, 24, 48 and 72 hours post initiation of expression or post introduction of the nucleic acid molecule), and the protein amount per point in time can be determined as explained above. In order to calculate the cumulative protein amount, a mathematical method of determining the total amount of protein can be used, e.g. the area under the curve (AUC) can be determined according to the following formula:

$$AUC = \int_a^b f(x)\,d(x)$$

In order to calculate the area under the curve for total amount of protein, the integral of the equation of the expression curve from each end point (a and b) is calculated.

Thus, "total protein production" preferably refers to the area under the curve (AUC) representing protein production over time.

Preferably, the at least one 3'- or 5'-UTR element according to the present invention increases protein production from said artificial nucleic acid molecule at least 1.5 fold, preferably at least 2 fold, more preferably at least 2.5 fold, compared to the protein production from a reference nucleic acid molecule lacking a 3'- and/or 5'-UTR, respectively. In other words, the total amount of protein produced from in the artificial nucleic acid molecule according to the invention at a certain point in time, e.g. 48 hours or 72 hours post initiation of expression, e.g. post transfection, is increased by a factor of at least 1.5, preferably at least 2, more preferably at least 2.5, compared to the (relative) amount of protein produced from a reference nucleic acid molecule, which is e.g. lacking a 3'- and/or 5'-UTR, respectively, or comprising a reference 3'- and/or 5'-UTR, respectively, for the corresponding later point in time.

The mRNA and/or protein production prolonging effect and efficiency and/or the protein production increasing effect and efficiency of the variants, fragments and/or variant fragments of the 3'-UTR and/or the 5'-UTR as well as the mRNA and/or protein production prolonging effect and efficiency and/or the protein production increasing effect and efficiency of the at least one 3'-UTR element and/or the at least one 5'-UTR element of the artificial nucleic acid molecule according to the present invention may be determined by any method suitable for this purpose known to skilled person.

For example, artificial mRNA molecules may be generated comprising a coding sequence/open reading frame (ORF) for a reporter protein, such as luciferase, and a 3'-UTR element according to the present invention, i.e. which prolongs and/or increases protein production from said artificial mRNA molecule. In addition such an inventive mRNA molecule may further comprise a 5'-UTR element according to the present invention, i.e. which prolongs and/or increases protein production from said artificial mRNA molecule, no 5'-UTR element or a 5'-UTR element which is not according to the present invention, e.g. a reference 5'-UTR. Accordingly, artificial mRNA molecules may be generated comprising a coding sequence/open reading frame (ORF) for a reporter protein, such as luciferase, and a 5'-UTR element according to the present invention, i.e. which prolongs and/or increases protein production from said artificial mRNA molecule. In addition such an inventive mRNA molecule may further comprise a 3'-UTR element according to the present invention, i.e. which prolongs and/or increases protein production from said artificial mRNA molecule, no 3'-UTR element or a 3'-UTR element which is not according to the present invention, e.g. a reference 3'-UTR.

According to the present invention mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be lipofected into mammalian cells, such as HeLa cells or HDF cells, and samples may be analyzed certain points in time after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample points in time may be determined by quantitative PCR methods. The quantities of reporter protein encoded by the respective mRNAs may be determined, e.g., by Western Blot, ELISA assays, FACS analysis or reporter assays such as luciferase assays depending on the reporter protein used. The effect of stabilizing protein expression and/or prolonging protein expression may be, for example, analyzed by determining the ratio of the protein level observed 48 hours post transfection and the protein level observed 24 hours post transfection. The closer said value is to 1, the more stable the protein expression is within this time period. Such measurements may of course also be performed at 72 or more hours and the ratio of the protein level observed 72 hours post transfection and the protein level observed 24 hours post transfection may be determined to determine stability of protein expression.

Translation Efficiency: Assay for Determining Translation Efficiency

As described in detail above, translation efficiency is a property of a nucleic acid molecule (e.g. mRNA) comprising an open reading frame (ORF) and is typically provided by a specific UTR element (a specific 5'-UTR element or a specific 3'-UTR element) comprised in the nucleic acid molecule. Translation efficiency is typically measured by means of the quantity of protein translated from the ORF. In this regard, the present invention provides general methods as well as a specific assay. The translation efficiency of various, e.g. two or more, nucleic acid molecules can be compared, e.g. by experimental quantification of protein encoded by the ORF.

In general, in order to assess translation efficiency, cell-based methods are employed. Translation efficiency is experimentally tested in vivo or in vitro as defined herein (i.e. in vitro referring to ("living") cells and/or tissue, including tissue of a living subject; cells include in particular cell lines, primary cells, cells in tissue or subjects, preferred are mammalian cells, e.g. human cells and mouse cells and particularly preferred are the human cell lines HeLa, HEPG2 and U-937 and the mouse cell lines NIH3T3, JAWSII and L929, furthermore primary cells are particularly preferred, in particular preferred embodiments human dermal fibroblasts (HDF) by the inventive artificial nucleic acid molecule, the expression of the encoded protein is determined following injection/transfection of the inventive artificial nucleic acid molecule into target cells/tissue and compared to the protein expression induced by the reference nucleic acid. Quantitative methods for determining protein expression are known in the art (e.g. Western-Blot, FACS, ELISA, mass spectrometry). Particularly useful in this context is the determination of the expression of reporter proteins like luciferase, Green fluorescent protein (GFP), or secreted alkaline phosphatase (SEAP). Thus, an artificial nucleic acid according to the invention or a reference nucleic acid is introduced into the target tissue or cell, e.g. via transfection or injection, preferably in a mammalian expression system, such as in mammalian cells, e.g. in HDF, L929, HepG2 and/or Hela cells. Several hours or several days (e.g. 6, 12, 24, 48 or 72 hours) post initiation of expression or post introduction of the nucleic acid molecule, a target cell sample is collected and measured via FACS and/or lysed. Afterwards the lysates can be used to detect the expressed protein (and thus determine the translation efficiency) using several methods, e.g. Western-Blot, FACS, ELISA, mass spectrometry or by fluorescence or luminescence measurement.

Therefore, if the protein expression from an artificial nucleic acid molecule according to the invention is compared to the protein expression from a reference nucleic acid molecule at a specific point in time (e.g. 6, 12, 24, 48 or 72 hours post initiation of expression or post introduction of the nucleic acid molecule), both nucleic acid molecules are introduced separately into target tissue/cells, a sample from the tissue/cells is collected after a specific point in time, protein lysates are prepared according to the particular protocol adjusted to the particular detection method (e.g. Western Blot, ELISA, fluorescence or luminescence measurement, etc. as known in the art) and the protein is detected by the chosen detection method. As an alternative to the measurement of expressed protein amounts in cell lysates—or, in addition to the measurement of protein amounts in cell lysates prior to lysis of the collected cells or using an aliquot in parallel—protein amounts may also be determined by using FACS analysis.

Other general aspects correspond to aspects described above in relation to protein production, unless the context dictates otherwise.

Preferably, the high translation efficiency is provided to the artificial nucleic acid molecule of the present invention by the at least one 3'-untranslated region element (3'-UTR element) and/or the at least one 5'-untranslated region element (5'-UTR element). "provided by" means that in the absence of the at least one 3'-untranslated region element (3'-UTR element) and/or the at least one 5'-untranslated region element (5'-UTR element), the translation efficiency is not high, as defined herein.

The term "high translation efficiency" can be used to compare the translation efficiency of an artificial nucleic acid molecule of the present invention to a reference nucleic acid molecule. The term "reference nucleic acid molecule" as used herein means that—apart from the different 3'-UTRs and/or 5'-UTRs—the reference nucleic acid molecule is comparable, preferably identical, to the artificial nucleic acid molecule of the invention comprising the 3'-UTR element and/or the 5'-UTR element. Thus, the translation efficiency of the artificial nucleic acid molecule can be compared to the translation efficiency of a reference nucleic acid molecule. A respective method for comparing the translation efficiency is provided herein.

All aspects described above in relation to determination of protein production apply to the method for comparing the translation efficiency as well, unless the context dictates otherwise. Since the method for comparing translation efficiency involves the comparison of two nucleic acid molecules, two parallel experiments are carried out, the only difference between these experiments being the nature of the nucleic acid molecule. In other words, all other conditions, such as e.g. growth medium, temperature, pH, are identical between the experiments. The skilled person will routinely chose appropriate conditions based on the common general knowledge and the guidance given herein, provided that identical conditions are chosen for both parallel experiments. Typically, one of the parallel experiments relates to a reference nucleic acid molecule (which may be wild-type or artificial), and the other one relates to an artificial nucleic acid molecule (also termed subject nucleic acid molecule. This method allows for comparing whether the subject nucleic acid molecule is characterized by high translation efficiency; i.e. whether it is an artificial nucleic acid molecule according to the present invention. Particular aspects of the method for comparing the translation efficiency are the following:

In this method, the reference nucleic acid molecule comprises at least one open reading frame (ORF), which is identical to the at least one open reading frame (ORF) of the artificial nucleic acid molecule; and the reference nucleic acid molecule does not comprise at least one 3'-untranslated region element (3'-UTR element) of the artificial nucleic acid molecule and/or at least one 5'-untranslated region element (5'-UTR element) of the artificial nucleic acid molecule. The translation efficiency of the artificial nucleic acid molecule and the translation efficiency of the reference nucleic acid molecule are compared by a method comprising the steps:
(i) transfecting mammalian cells with the artificial nucleic acid molecule and measuring expressed amounts of the protein encoded by the ORF of the artificial nucleic acid molecule at a certain point in time after transfection (e.g. 24 or 48 h),
(ii) transfecting mammalian cells with the reference nucleic acid molecule and measuring expressed amounts of the protein encoded by the ORF of the reference nucleic acid molecule at the same point in time after transfection,
(iii) calculating the ratio of the amount of protein expressed from the artificial nucleic acid molecule to the amount of protein expressed from the reference nucleic acid molecule,
wherein the ratio calculated in (iii) is ≥1, preferably >1.

Thus, by comparing the relative protein amount produced from the subject nucleic acid molecule according to the present invention to the relative protein amount produced from the reference nucleic acid molecule, a factor may be determined by which the translation efficiency of the artificial nucleic acid molecule according to the present invention is increased compared to the translation efficiency of the reference nucleic acid molecule.

"after transfection" is used to refer to the point in time at which the cells have been transfected with the subject nucleic acid molecule and the reference nucleic acid molecule.

Preferably, the at least one 3'- and/or 5'-UTR element in the artificial nucleic acid molecule according to the invention increases translation efficiency of said artificial nucleic acid molecule at least 1.2 fold, preferably at least 1.5 fold, more preferably at least 2 fold, even more preferably at least 2.5 fold, compared to the protein production from a reference nucleic acid molecule comprising a reference 3'- and/or 5'-UTR, respectively (i.e. the ratio calculated in (iii) is at least 1.2, preferably at least 1.5, more preferably at least 2, even more preferably at least 2.5). In other words, the translation efficiency is increased by a factor of at least 1.2, preferably at least 1.5, more preferably at least 2, even more preferably at least 2.5, compared to the translation efficiency of a reference nucleic acid molecule, for the same point in time.

The high translation efficiency is conferred by the 5'-UTR or by the 3'-UTR by which the subject nucleic acid molecule differs from the reference nucleic acid molecule.

In a preferred embodiment of the method for comparing the translation efficiency according to the present invention, (i) the reference nucleic acid molecule comprises at a 3'-UTR element which is not present in the artificial nucleic acid molecule, or (ii) the reference nucleic acid molecule comprises a 5'-UTR element which is not present in the artificial nucleic acid molecule. In more preferred embodiments, (i) the reference nucleic acid molecule comprises at a 3'-UTR element which is derived from a 3'-UTR of an albumin gene, preferably a 3'-UTR corresponding to the sequence according to SEQ ID NO: 207, or (ii) the reference nucleic acid molecule comprises a 5'-UTR element which is derived from a 5'-UTR of a TOP gene, preferably a 5'-UTR of human ribosomal protein Large 32 lacking the 5' terminal oligopyrimidine tract, preferably a 5'-UTR corresponding to the sequence according to SEQ ID NO: 208.

In an alternative preferred embodiment, (i) the reference nucleic acid molecule does not comprise any 3'-untranslated region element (3'-UTR element), or (ii) the reference nucleic acid molecule does not comprise any 5'-untranslated region element (5'-UTR element).

In a preferred embodiment, the cells used in the step of transfection of the artificial nucleic acid molecule and the reference nucleic acid molecule are mammalian cells, preferably selected from the group of HDF, L929, HEP2G and HeLa cells. It can further be preferred that the method is carried out in parallel in more than one type of mammalian cells, such as in parallel in a combination of any two, preferably any three, more preferably all four of the above cell lines. When the method is carried out in parallel in more than one type of mammalian cells, then a subject nucleic acid molecule can be considered to be characterized by high translation efficiency when the ratio calculated in step (iii) is ≥1, preferably >1, in at least one type of mammalian cells used. However, it is preferred that a subject nucleic acid molecule is considered to be characterized by high translation efficiency when the ratio calculated in step (iii) is ≥1, preferably >1, in at least two types, such as at least three types, such as four types, of mammalian cells used.

The expressed amounts of the protein encoded by the ORF of the artificial nucleic acid molecule and the reference nucleic acid molecule are measured at a certain point in time after transfection (e.g. 12 h, 24 h, 36 h, 48 h or 72 h). Preferably the expressed amounts of the protein encoded by the ORF are measured 24 h after transfection.

The present invention also provides a specific preferred reference construct that can be used in the method of the present invention. It is particularly preferred that the reference nucleic acid molecule is an mRNA of SEQ ID NO: 205 (FIG. 1A). In this case, it is further preferable that the reference nucleic acid molecule differs from the artificial nucleic acid molecule only in that the at least one 3'-UTR element is replaced by at least one other 3'-UTR element (preferably one 3'-UTR element) or in that at least one 5'-UTR element is replaced by at least one other 5'-UTR element (preferably one 5'-UTR element). In either case, this allows for directly testing whether said other 3'-UTR element or other 5'-UTR element, respectively, provides high translation efficiency.

It is particularly preferred that the method of determining translation efficiency is further characterized as follows:
(a) in the step of transfection, the cells are mammalian cells which are selected from the group of HDF, L929, HEP2G and HeLa cells; and
(b) the point in time for measuring is 24 h after transfection; and
(c) the reference nucleic acid molecule is an mRNA of SEQ ID NO: 205 (FIG. 1A); and preferably, (d) the reference nucleic acid molecule differs from the artificial nucleic acid molecule only in that (i) the at least one 3'-UTR element (preferably one 3'-UTR element) is replaced by at least one other 3'-UTR element (preferably one 3'-UTR element), or (ii) the at least one 5'-UTR element (preferably one 5'-UTR element)) is replaced by at least one other 5'-UTR element (preferably one 5'-UTR element); in other words, the subject nucleic acid molecule is identical to the reference nucleic acid molecule, except that at least one 5'-UTR element differs from the 5'-UTR shown in FIG. 1A, or that the at least one 3'-UTR element differs from the 3'-UTR shown in FIG. 1A. An example of 5'-UTR element replacement is shown in FIG. 1B; an example of 3'-UTR element replacement is shown in FIG. 1C.

When all of (a) to (d) are fulfilled, the method is also referred to as "standardized assay for determining translation efficiency", or simply "assay for determining translation efficiency". It is particularly preferred that an artificial nucleic acid molecule of the invention is characterized by high translation efficiency as determinable by this standard assay for determining translation efficiency. This standard assay allows for the straightforward identification of particularly advantageous artificial nucleic acid molecules.

The standard assay was used in Example 3 of the present invention. Thereby, the present inventors found that a group of new artificial nucleic acids shares the advantageous feature of high translation efficiency, i.e. higher than the translation efficiency of the reference nucleic acid molecule of FIG. 1A, see Example 3.5. This is a very surprising and advantageous finding, particularly from the background that said reference nucleic acid molecule comprises a 3'-UTR element which is derived from a 3'-UTR of an albumin gene (a 3'-UTR corresponding to the DNA sequence according to SEQ ID NO: 207), and a 5'-UTR element which is derived from a 5'-UTR of a TOP gene, particularly a 5'-UTR of human ribosomal protein Large 32 lacking the 5' terminal oligopyrimidine tract (a 5'-UTR corresponding to the DNA sequence according to SEQ ID NO: 208). Such 3'-UTR elements and 5'-UTR elements are known to be advantageous in the context of protein translation in a cell (for a 3'-UTR derived from an albumin gene, see WO2013/143700; for a 5'-TOP-UTR, see WO2013/143700). The present invention provides a further improvement.

In some embodiments, the ORF of the artificial nucleic acid molecule encodes a protein that can be quantified, preferably a reporter protein. These embodiments are very suitable in the method for comparing the translation efficiency according to the present invention. In other embodiments, the ORF of the artificial nucleic acid molecule does not encode a protein that can be quantified, preferably a reporter protein. For example, when a particular 5'-UTR or a 3'-UTR has been determined by the method of the invention, using an ORF of the artificial nucleic acid molecule encodes a protein that can be quantified, to provide high translation efficiency, said 5'-UTR or a 3'-UTR can be recombined with any ORF. For example, while in the standardized assay for determining translation efficiency the ORF encodes a reporter protein, artificial nucleic acids of the present invention are not limited to the ORF used in the standardized assay.

These methods can also be used iteratively; i.e. an artificial nucleic acid molecule, which has been determined by the method herein to be characterized by high translation efficiency, can itself be used as "reference construct" for a subsequent round of the method herein. This enables testing whether yet further artificial nucleic acid molecule is characterized by even higher translation efficiency (or whether a UTR comprised in the further artificial nucleic acid molecule provides even higher translation efficiency). This enables the identification of even further improved artificial nucleic acid molecules and UTRs.

Stable mRNA

In some embodiments, the at least one 3'-UTR element and/or the at least one 5'-UTR element in the artificial nucleic acid molecule according to the present invention, is derived from a stable mRNA. Thereby, "derived" from a stable mRNA means that the at least one 3'-UTR element and/or the at least one 5'-UTR element shares at least 50%, preferably at least 60%, preferably at least 70%, more preferably at least 75%, more preferably at least 80%, more preferably at least 85%, even more preferably at least 90%/o, even more preferably at least 95%, and particularly preferably at least 98% sequence identity with a 3'-UTR element and/or a 5'-UTR element of a stable mRNA. Preferably, the stable mRNA is a naturally occurring mRNA and, thus, a 3'-UTR element and/or a 5'-UTR element of a stable mRNA refers to a 3'-UTR and/or a 5'-UTR, or fragments or variants thereof, of naturally occurring mRNA. Moreover, a 3'-UTR element and/or a 5'-UTR element derived from a stable mRNA preferably also refers to a 3'-UTR element and/or a 5'-UTR element, which is modified in comparison to a naturally occurring 3'-UTR element and/or 5'-UTR element, e.g. in order to increase RNA stability even further and/or to prolong and/or increase protein production. It goes without saying that such modifications are preferred, which do not impair RNA stability, e.g. in comparison to a naturally occurring (non-modified) 3'-UTR element and/or 5'-UTR element. In particular, the term mRNA as used herein refers to an mRNA molecule, however, it may also refer to an mRNA species as defined herein.

Preferably, the stability of mRNA, i.e. mRNA decay and/or half-life, is assessed under standard conditions, for example standard conditions (standard medium, incubation, etc.) for a certain cell line used.

The term "stable mRNA" as used herein refers in general to an mRNA having a slow mRNA decay. Thus, a "stable mRNA" has typically a long half-life. The half-life of an mRNA is the the time required for degrading 50% of the in vivo or in vitro existing mRNA molecules. Accordingly, stability of mRNA is usually assessed in vivo or in vitro. Thereby, in vitro refers in particular to ("living") cells and/or tissue, including tissue of a living subject. Cells include in particular cell lines, primary cells, cells in tissue or subjects. In specific embodiments cell types allowing cell culture may be suitable for the present invention. Particularly preferred are mammalian cells, e.g. human cells and mouse cells. In particularly preferred embodiments the human cell lines HeLa, HEPG2 and U-937 and the mouse cell lines NIH3T3, JAWSII and L929 are used. Furthermore primary cells are particularly preferred, in particular preferred embodiments human dermal fibroblasts (HDF) may be used. Alternatively also a tissue of a subject may be used.

Preferably, the half-life of a "stable mRNA" is at least 5 h, at least 6 h, at least 7 h, at least 8 h, at least 9 h, at least 10 h, at least 11 h, at least 12 h, at least 13 h, at least 14 h, and/or at least 15 h. The half-life of an mRNA of interest may be determined by different methods known to the person skilled in the art. Typically, the half-life of an mRNA of interest is determined by determining the decay constant, whereby usually an ideal in vivo (or in vitro as defined above) situation is assumed, in which transcription of the mRNA of interest can be "turned off" completely (or at least to an undetectable level). In such an ideal situation it is usually assumed that mRNA decay follows first-order kinetics. Accordingly, the decay of an mRNA may usually be described by the following equation:

$$A(t)=A_0 * e^{-\lambda t}$$

with $A_0$ being the amount (or concentration) of the mRNA of interest at time 0, i.e. before the decay starts, A(t) being the amount (or concentration) of the mRNA of interest at a time t during decay and λ being the decay constant. Thus, if the amount (or concentration) of the mRNA of interest at time 0 ($A_0$) and the amount (or concentration) of the mRNA of interest at a certain time t during the decay process (A(t) and t) are known, the decay constant λ may be calculated. Based on the decay constant λ, the half-life $t_{1/2}$ can be calculated by the following equation:

$$t_{1/2}=\ln 2/\lambda.$$

since per definition A(t)/A0=1/2 at $t_{1/2}$. Thus, to assess the half-life of an mRNA of interest, usually the amount or concentration of the mRNA is determined during the RNA decay process in vivo (or in vitro as defined above).

To determine the amount or concentration of mRNA during the RNA decay process in vivo (or in vitro as defined above), various methods may be used, which are known to the skilled person. Non-limiting examples of such methods include general inhibition of transcription, e.g. with a transcription inhibitor such as actinomycin D, use of inducible promoters to specifically promote transient transcription, e.g. c-fos serum-inducible promoter system and Tet-off regulatory promoter system, and kinetic labelling techniques, e.g. pulse labelling, for example by 4-thiouridine (4sU), 5-Ethynyluridine (EU) or 5'-bromo-uridine (BrU). Further details and preferred embodiments regarding how to determine the amount or concentration of mRNA during the RNA decay are outlined below, in the context of a method for identifying a 3'-UTR element and/or the at least one 5'-UTR element according to the present invention. The respective description and preferred embodiments of how to determine the amount or concentration of mRNA during the RNA decay apply here as well.

Preferably, a "stable mRNA" in the sense of the present invention has a slower mRNA decay compared to average mRNA, preferably assessed in vivo (or in vitro as defined above). For example, "average mRNA decay" may be assessed by investigating mRNA decay of a plurality of mRNA species, preferably 100, at least 300, at least 500, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, at least 19000, at least 20000, at least 21000, at least 22000, at least 23000, at least 24000, at least 25000, at least 26000, at least 27000, at least 28000, at least 29000, at least 30000 mRNA species. It is particularly preferred that the whole transcriptome is assessed, or as many mRNA species of the transcriptome as possible. This may be achieved, for example, by using a micro array providing whole transcript coverage.

An "mRNA species", as used herein, corresponds to a genomic transcription unit, i.e. usually to a gene. Thus, within one "mRNA species" different transcripts may occur, for example, due to mRNA processing. For example, an mRNA species may be represented by a spot on a microarray. Accordingly, a microarray provides an advantageous tool to determine the amount of a plurality of mRNA species, e.g. at a certain point in time during mRNA decay. However, also other techniques known to the skilled person, e.g. RNA-seq, quantitative PCR etc. may be used.

In the present invention it is particularly preferred that a stable mRNA is characterized by an mRNA decay wherein the ratio of the amount of said mRNA at a second point in time to the amount of said mRNA at a first point in time is at least 0.5 (50%), at least 0.6 (60%), at least 0.7 (70%), at least 0.75 (75%), at least 0.8 (80%), at least 0.85 (85%), at least 0.9 (90%), or at least 0.95 (95%). Thereby, the second point in time is later in the decay process than the first point in time.

Preferably, the first point in time is selected such that only mRNA undergoing a decay process is considered, i.e. emerging mRNA—e.g. in ongoing transcription—is avoided. For example, if kinetic labelling techniques, e.g. pulse labelling, are used, the first point in time is preferably selected such that the incorporation of the label into mRNA is completed, i.e. no ongoing incorporation of the label into mRNA occurs. Thus, if kinetic labelling is used, the first point in time may be at least 10 min, at least 20 min, at least 30 min, at least 40 min, at least 50 min, at least 60 min, at least 70 min, at least 80 min, or at least 90 min after the end of the experimental labelling procedure, e.g. after the end of the incubation of cells with the label.

For example, the first point in time may be preferably from 0 to 6 h after the stop of transcription (e.g. by a transcriptional inhibitor), stop of promoter induction in case of inducible promoters or after stop of pulse or label supply, e.g. after end of labelling. More preferably, the first point in time may be 30 min to 5 h, even more preferably 1 h to 4 h and particularly preferably about 3 h after the stop of transcription (e.g. by a transcriptional inhibitor), stop of promoter induction in case of inducible promoters or after stop of pulse or label supply, e.g. after end of labelling.

Preferably, the second point in time is selected as late as possible during the mRNA decay process. However, if a plurality of mRNA species is considered, the second point in time is preferably selected such that still a considerable amount of the plurality of mRNA species, preferably at least 10% of the mRNA species, is present in a detectable amount, i.e. in an amount higher than 0. Preferably, the second point in time is at least 5 h, at least 6 h, at least 7 h, at least 8 h, at least 9 h, at least 10 h, at least 11 h, at least 12 h, at least 13 h, at least 14 h, or at least 15 h after the end of transcription or the end of the experimental labelling procedure.

Thus, the time span between the first point in time and the second point in time is preferably as large as possible within the above described limits. Therefore, the time span between the first point in time and the second point in time is preferably at least 4 h, at least 5 h, at least 6 h, at least 7 h, at least 8 h, at least 9 h, at least 10 h, at least 11 h, or at least 12 h.

Moreover, it is possible that the at least one 3'-UTR element and/or the at least one 5'-UTR element in the artificial nucleic acid molecule according to the present invention is identified by a method for identifying a 3'-UTR element and/or a 5'-UTR element according to the present invention as described herein. It is particularly preferred that the at least one 3'-UTR element and/or the at least one 5'-UTR element in the artificial nucleic acid molecule according to the present invention, is identified by a method for identifying a 3'-UTR element and/or a 5'-UTR element, which provides high translation efficiency to an artificial nucleic acid molecule, as described herein.

Preferred Embodiments of the Artificial Nucleic Acid Molecule of the Present Invention Preferably, the at least one 3'-UTR element and/or the at least one 5'-UTR element in the artificial nucleic acid molecule according to the present invention comprises or consists of a nucleic acid sequence which is derived from the 3'-UTR and/or the 5'-UTR of a eukaryotic protein coding gene, preferably from the 3'-UTR and/or the 5'-UTR of a vertebrate protein coding gene, more preferably from the 3'-UTR and/or the 5'-UTR of a mammalian protein coding gene, e.g. from mouse and human protein coding genes, even more preferably from the 3'-UTR and/or the 5'-UTR of a primate or rodent protein coding gene, in particular the 3'-UTR and/or the 5'-UTR of a human or murine protein coding gene.

In general, it is understood that the at least one 3'-UTR element in the artificial nucleic acid molecule according to the present invention comprises or consists of a nucleic acid sequence which is preferably derived from a naturally (in nature) occurring 3'-UTR, whereas the at least one 5'-UTR element in the artificial nucleic acid molecule according to the present invention comprises or consists of a nucleic acid sequence which is preferably derived from a naturally (in nature) occurring 5'-UTR.

Preferably, the at least one open reading frame is heterologous to the at least one 3'-UTR element and/or to the at least one 5'-UTR element. The term "heterologous" in this context means that two sequence elements comprised by the artificial nucleic acid molecule, such as the open reading frame and the 3'-UTR element and/or the open reading frame and the 5'-UTR element, do not occur naturally (in nature) in this combination. They are typically recombinant. Preferably, the 3'-UTR element and/or the 5'-UTR element are/is derived from a different gene than the open reading frame. For example, the ORF may be derived from a different gene than the 3'-UTR element and/or to the at least one 5'-UTR element, e.g. encoding a different protein or the same protein but of a different species etc. I.e. the open reading frame is derived from a gene which is distinct from the gene from which the 3'-UTR element and/or to the at least one 5'-UTR element is derived. In a preferred embodiment, the ORF does not encode a human or plant (e.g., *Arabidopsis*) ribosomal protein, preferably does not encode human ribosomal protein S6 (RPS6), human ribosomal protein L36a-like (RPL36AL) or *Arabidopsis* ribosomal protein S16 (RPS16). In a further preferred embodiment, the open reading frame (ORF) does not encode ribosomal protein S6 (RPS6), ribosomal protein L36a-like (RPL36AL) or ribosomal protein S16 (RPS16).

In specific embodiments it is preferred that the open reading frame does not code for a reporter protein, e.g., selected from the group consisting of globin proteins (particularly beta-globin), luciferase protein, GFP proteins or variants thereof, for example, variants exhibiting at least 70% sequence identity to a globin protein, a luciferase protein, or a GFP protein. Thereby, it is particularly preferred that the open reading frame does not code for a GFP protein. It is also particularly preferred that the open reading frame (ORF) does not encode a reporter gene or is not derived from a reporter gene, wherein the reporter gene is preferably not selected from group consisting of globin proteins (particularly beta-globin), luciferase protein, beta-glucuronidase (GUS) and GFP proteins or variants thereof, preferably not selected from EGFP, or variants of any of the above genes, typically exhibiting at least 70% sequence identity to any of these reporter genes, preferably a globin protein, a luciferase protein, or a GFP protein.

Even more preferably, the 3'-UTR element and/or the 5'-UTR element is heterologous to any other element comprised in the artificial nucleic acid as defined herein. For example, if the artificial nucleic acid according to the invention comprises a 3'-UTR element from a given gene, it does preferably not comprise any other nucleic acid sequence, in particular no functional nucleic acid sequence (e.g. coding or regulatory sequence element) from the same gene, including its regulatory sequences at the 5' and 3' terminus of the gene's ORF. Accordingly, for example, if the artificial nucleic acid according to the invention comprises a 5'-UTR element from a given gene, it does preferably not comprise any other nucleic acid sequence, in particular no functional nucleic acid sequence (e.g. coding or regulatory sequence element) from the same gene, including its regulatory sequences at the 5' and 3' terminus of the gene's ORF.

Moreover, it is preferred that the artificial nucleic acid according to the present invention comprises at least one open reading frame, at least one 3'-UTR (element) and at least one 5'-UTR (element), whereby either the at least one 3'-UTR (element) is a 3'-UTR element according to the present invention and/or the at least one 5'-UTR (element) is a 5'-UTR element according to the present invention. In such a preferred artificial nucleic acid according to the present invention, which comprises at least one open reading frame, at least one 3'-UTR (element) and at least one 5'-UTR (element), it is particularly preferred that each of the at least one open reading frame, the at least one 3'-UTR (element) and the at least one 5'-UTR (element) are heterologous, i.e. neither the at least one 3'-UTR (element) and the at least one 5'-UTR (element) nor the open reading frame and the 3'-UTR (element) or the 5'-UTR (element), respectively, are occurring naturally (in nature) in this combination. This means that the artificial nucleic acid molecule comprises an ORF, a 3'-UTR (element) and a 5'-UTR (element), all of which are heterologous to each other, e.g. they are recombinant as each of them is derived from different genes (and their 5' and 3' UTR's). In another preferred embodiment, the 3'-UTR (element) is not derived from a 3'-UTR (element) of a viral gene or is not of viral origin.

Preferably, the at least one 3'-UTR element and/or to the at least one 5'-UTR element is functionally linked to the ORF. This means preferably that the 3'-UTR element and/or to the at least one 5'-UTR element is associated with the ORF such that it may exert a function, such as an enhancing or stabilizing function on the expression of the encoded peptide or protein or a stabilizing function on the artificial nucleic acid molecule. Preferably, the ORF and the 3'-UTR element are associated in 5'→3' direction and/or the 5'-UTR element and the ORF are associated in 5'→3' direction. Thus, preferably, the artificial nucleic acid molecule comprises in general the structure 5'-[5'-UTR element]-(optional)-linker-ORF-(optional)-linker-[3'-UTR element]-3', wherein the artificial nucleic acid molecule may comprise only a 5'-UTR element and no 3'-UTR element, only a 3'-UTR element and no 5'-UTR element, or both, a 3'-UTR element and a 5'-UTR element. Furthermore, the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the at least one 3'-UTR element and/or the at least one 5'-UTR element comprises or consists of a nucleic acid sequence which is derived from the 3'-UTR and/or the 5'-UTR of a transcript of a gene selected from the group consisting of ZNF460, TGM2, IL7R, BGN, TK1, RAB3B, CBX6, FZD2, COL8A1, NDUFS7, PHGDH, PLK2, TSPO, PTGS1, FBXO32, NID2, ATP5D, EXOSC4, NOL9, UBB4B, VPS18, ORMDL2, FSCN1, TMEM33, TUBA4A, EMP3, TMEM201, CRIP2, BRAT1, SERPINH1, CD9, DPYSL2, CDK9, TFRC, PSMB3 5'-UTR, FASN, PSMB6, PRSS56, KPNA6, SFT2D2, PARD6B, LPP, SPARC, SCAND1, VASN, SLC26A1, LCLAT1, FBXL18, SLC35F6, RAB3D, MAP1B, VMA21, CYBA, SEZ6L2, PCOLCE, VTN, ALDH16A1, RAVER1, KPNA6, SERINC5, JUP, CPN2, CRIP2, EPT1, PNPO, SSSCA1, POLR2L, LIN7C, UQCR10, PYCRL, AMN, MAP1S, NDUFS7, PHGDH, TSPO, ATP5D, EXOSC4, TUBB4B, TUBA4A, EMP3, CRIP2, BRAT1, CD9, CDK9, PSMB3, PSMB6, PRSS56, SCAND1, AMN, CYBA, PCOLCE, MAP1S, VTN, ALDH16A1 (all preferably human) and Dpysl2, Ccnd1, Acox2, Cbx6, Ubc, Ldlr, Nudt22, Pcyox11, Ankrd1, Tmem37, Tspyl4, Slc7a3, Cst6, Aacs, Nosip, Itga7, Ccnd2, Ebp, Sf3b5, Fasn, Hmgcsl, Osr1, Lmnb1, Vma21, Kif20a, Cdca8, Slc7a1, Ubqln2, Prps2, Shmt2, Aurkb, Fignl1, Cad, Anln, Slfn9, Ncaph, Pole, Uhrf1, Gja1, Fam64a, Kif2c, Tspan10, Scand1, Gpr84, Fads3, Cers6, Cxcr4, Gprc5c, Fen1, Cspg4, Mrp134, Comtd1, Armc6, Emr4, Atp5d, 1110001J03Rik, Csf2ra, Aarsd1, Kif22, Cth, Tpgs1, Ccl17, Alkbh7, Ms4a8a, Acox2, Ubc, Slpi, Pcyox11, Igf2bp1, Tmem37, Slc7a3, Cst6, Ebp, Sf3b5, Plk1, Cdca8, Kif22, Cad, Cth, Pole, Kif2c, Scand1, Gpr84, Tpgs1, Ccl17, Alkbh7, Ms4a8a, Mrp134, Comtd1, Armc6, Atp5d, 1110001J03Rik, Nudt22, Aarsd1 (all preferably mouse).

Preferably, the at least one 3'-UTR element and/or the at least one 5'-UTR element of the artificial nucleic acid molecule according to the present invention comprises or consists of a "functional fragment", a "functional variant" or a "functional fragment of a variant" of the 3'-UTR and/or the 5'-UTR of a transcript of a gene.

Preferably, the at least one 5'-UTR element comprises a nucleic acid sequence which is derived from the 5'-UTR of a transcript of a gene selected from the group consisting of ZNF460-5'-UTR, TGM2-5'-UTR, IL7R-5'-UTR, BGN-5'-UTR, TK1-5'-UTR, RAB3B-5'-UTR, CBX6-5'-UTR, FZD2-5'-UTR, COL8A1-5'-UTR, NDUFS7-5'-UTR, PHGDH-5'-UTR, PLK2-5'-UTR, TSPO-5'-UTR, PTGS1-5'-UTR, FBXO32-5'-UTR, NID2-5'-UTR, ATP5D-5'-UTR, EXOSC4-5'-UTR, NOL9-5'-UTR, UBB4B-5'-UTR, VPS18-5'-UTR, ORMDL2-5'-UTR, FSCN1-5'-UTR, TMEM33-5'-UTR, TUBA4A-5'-UTR, EMP3-5'-UTR, TMEM201-5'-UTR, CRIP2-5'-UTR, BRAT1-5'-UTR, SERPINH1-5'-UTR, CD9-5'-UTR, DPYSL2-5'-UTR, CDK9-5'-UTR, TFRC-5'-UTR, PSMB3 5'-UTR, FASN-5'-UTR, PSMB6-5'-UTR, PRSS56-5'-UTR, KPNA6-5'-UTR, SFT2D2-5'-UTR, PARD6B-5'-UTR, LPP-5'-UTR, SPARC-5'-UTR, SCAND1-5'-UTR, VASN-5'-UTR, SLC26A1-5'-UTR, LCLAT1-5'-UTR, FBXL18-5'-UTR, SLC35F6-5'-UTR, RAB3D-5'-UTR, MAP1B-5'-UTR, VMA21-5'-UTR, CYBA-5'-UTR, SEZ6L2-5'-UTR, PCOLCE-5'-UTR, VTN-5'-UTR, ALDH16A1-5'-UTR, RAVER1-5'-UTR, KPNA6-5'-UTR, SERINC5-5'-UTR, JUP-5'-UTR, CPN2-5'-UTR, CRIP2-5'-UTR, EPT1-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR, (all preferably human) and Dpysl2-5'-UTR, Ccnd1-5'-UTR, Acox2-5'-UTR, Cbx6-5'-UTR, Ubc-5'-UTR, Ldlr-5'-UTR, Nudt22-5'-UTR, Pcyox11-5'-UTR, Ankrd1-5'-UTR, Tmem37-5'-UTR, Tspyl4-5'-UTR, Slc7a3-5'-UTR, Cst6-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Aurkb-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Kif2c-5'-UTR, Tspan10-5'-UTR, Scand1-5'-UTR, Gpr84-5'-UTR, Fads3-5'-UTR, Cers6-5'-UTR, Cxcr4-5'-UTR, Gprc5c-5'-UTR, Fen1-5'-UTR, Cspg4-5'-UTR, Mrp134-5'-UTR, Comtd1-5'-UTR, Armc6-5'-UTR, Emr4-5'-UTR, Atp5d-5'-UTR, 1110001J03Rik-5'-UTR, Csf2ra-5'-UTR, Aarsd1-5'-UTR, Kif22-5'-UTR, Cth-5'-UTR, Tpgs1-5'-UTR, Ccl17-5'-UTR, Alkbh7-5'-UTR, Ms4a8a-5'-UTR (all preferably mouse).

Preferably, the at least one 3'-UTR element comprises or consists of a nucleic acid sequence which is derived from the 3'-UTR of a transcript of a gene selected from the group consisting of NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, CD9-3'-UTR, CDK9-3'-UTR, PSMB3-3'-UTR, PSMB6-3'-UTR, PRSS56-3'-UTR, SCAND1-3'-UTR, AMN-3'-UTR, CYBA-3'-UTR, PCOLCE-3'-UTR, MAP1 S-3'-UTR, VTN-3'-UTR, ALDH16A1-3'-UTR (all preferably human) and Acox2-3'-UTR, Ubc-3'-UTR, Slpi-3'-UTR, Pcyox11-3'-UTR, Igf2bp1-3'-UTR, Tmem37-3'-UTR, Slc7a3-3'-UTR, Cst6-3'-UTR, Ebp-3'-UTR, Sf3b5-3'-UTR, Plk1-3'-UTR, Cdca8-3'-UTR, Kif22-3'-UTR, Cad-3'-UTR, Cth-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrpl34-3'-UTR, Comtd1-3'-UTR, Armc6-3'-UTR, Atp5d-3'-UTR, 1110001J03Rik-3'-UTR, Nudt22-3'-UTR, Aarsd1-3'-UTR (all preferably mouse).

It is also preferred that the artificial nucleic acid of the invention comprises both (i) at least one preferred 5'-UTR and (i) at least one preferred 3'-UTR.

In a particularly preferred embodiment, the at least one 5'-UTR element comprises a nucleic acid sequence which is derived from the 5'-UTR of a transcript of a gene selected from the group consisting of ZNF460-5'-UTR, TGM2-5'-UTR, IL7R-5'-UTR, COL8A1-5'-UTR, NDUFS7-5'-UTR, PLK2-5'-UTR, FBXO32-5'-UTR, ATP5D-5'-UTR, TUBB4B-5'-UTR, ORMDL2-5'-UTR, FSCN1-5'-UTR, CD9-5'-UTR, PYSL2-5'-UTR, PSMB3-5'-UTR, PSMB6-5'-UTR, KPNA6-5'-UTR, SFT2D2-5'-UTR, LCLAT1-5'-UTR, FBXL18-5'-UTR, SLC35F6-5'-UTR, VMA21-5'-UTR, SEZ6L2-5'-UTR, PCOLCE-5'-UTR, VTN-5'-UTR, ALDH16A1-5'-UTR, KPNA6-5'-UTR, JUP-5'-UTR, CPN2-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR (all human), Dpysl2-5'-UTR, Acox2-5'-UTR, Ubc-5'-UTR, Nudt22-5'-UTR, Pcyox11-5'-UTR, Ankrd1-5'-UTR, Tspyl4-5'-UTR, Slc7a3-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Tspan10-5'-UTR, Scand1-5'-UTR, Gpr84-5'-UTR, Cers6-5'-UTR, Cxcr4-5'-UTR, Gprc5c-5'-UTR, Fen1-5'-UTR, Cspg4-5'-UTR, Mrp134-5'-UTR, Comtd1-5'-UTR, Armc6-5'-UTR, Emr4-5'-UTR, Atp5d-5'-UTR, Csf2ra-5'-UTR, Aarsd1-5'-UTR, Cth-5'-UTR, Tpgs1-5'-UTR, Ccl17-5'-UTR, Alkbh7-5'-UTR, Ms4a8a-5'-UTR (all mouse). Such UTR elements were shown to contribute to high translation efficiency.

In a particularly preferred embodiment, the at least one 3'-UTR element comprises a nucleic acid sequence which is derived from the 3'-UTR of a transcript of a gene selected from the group consisting of NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, CD9-3'-UTR, CDK9-3'-UTR, PSMB3-3'-UTR, PSMB6-3'-UTR, PRSS56-3'-UTR, SCAND1-3'-UTR, AMN-3'-UTR, CYBA-3'-UTR, PCOLCE-3'-UTR, MAP1S-3'-UTR, VTN-3'-UTR, ALDH16A1-3'-UTR (all preferably human) and Acox2-3'-UTR, Ubc-3'-UTR, Slpi-3'-UTR, Pcyox1l-3'-UTR, Igf2bp1-3'-UTR, Tmem37-3'-UTR, Slc7a3-3'-UTR, Cst6-3'-UTR, Ebp-3'-UTR, Sf3b5-3'-UTR, Plk1-3'-UTR, Cdca8-3'-UTR, Kif22-3'-UTR, Cad-3'-UTR, Cth-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrp134-3'-UTR, Comtd1-3'-UTR, Armc6-3'-UTR, Atp5d-3'-UTR, 1110001 J03Rik-3'-UTR, Nudt22-3'-UTR, Aarsd1-3'-UTR, (all preferably mouse). Such UTR elements were shown to contribute to high translation efficiency.

These particularly preferred embodiments are combinable so that that the artificial nucleic acid of the invention comprises both (i) at least one particularly preferred 5'-UTR and (i) at least one particularly preferred 3'-UTR.

The phrase "nucleic acid sequence which is derived from the 3'-UTR and/or the 5'-UTR of a of a transcript of a gene" preferably refers to a nucleic acid sequence which is based on the 3'-UTR sequence and/or on the 5'-UTR sequence of a transcript of a gene or a fragment or part thereof, preferably a naturally occurring gene or a fragment or part thereof. In this context, the term naturally occurring is used synonymously with the term wild-type. This phrase includes sequences corresponding to the entire 3'-UTR sequence and/or the entire 5'-UTR sequence, i.e. the full length 3'-UTR and/or 5'-UTR sequence of a transcript of a gene, and sequences corresponding to a fragment of the 3'-UTR sequence and/or the 5'-UTR sequence of a transcript of a gene. Preferably, a fragment of a 3'-UTR and/or a 5'-UTR of a transcript of a gene consists of a continuous stretch of nucleotides corresponding to a continuous stretch of nucleotides in the full-length 3'-UTR and/or 5'-UTR of a transcript of a gene, which represents at least 5%, 10%, 20%, preferably at least 30%, more preferably at least 40%, more preferably at least 50%, even more preferably at least 60%, even more preferably at least 70%, even more preferably at least 80%, and most preferably at least 90% of the full-length 3'-UTR and/or 5'-UTR of a transcript of a gene. Such a fragment, in the sense of the present invention, is preferably a functional fragment as described herein. Preferably, the fragment retains a regulatory function for the translation of the ORF linked to the 3'-UTR and/or 5'-UTR or fragment thereof.

The terms "variant of the 3'-UTR and/or variant of the 5'-UTR of a of a transcript of a gene" and "variant thereof" in the context of a 3'-UTR and/or a 5'-UTR of a transcript of a gene refers to a variant of the 3'-UTR and/or 5'-UTR of a transcript of a naturally occurring gene, preferably to a variant of the 3'-UTR and/or 5'-UTR of a transcript of a vertebrate gene, more preferably to a variant of the 3'-UTR and/or 5'-UTR of a transcript of a mammalian gene, even more preferably to a variant of the 3'-UTR and/or 5'-UTR of a transcript of a primate gene, in particular a human gene as described above. Such variant may be a modified 3'-UTR and/or 5'-UTR of a transcript of a gene. For example, a variant 3'-UTR and/or a variant of the 5'-UTR may exhibit one or more nucleotide deletions, insertions, additions and/or substitutions compared to the naturally occurring 3'-UTR and/or 5'-UTR from which the variant is derived. Preferably, a variant of a 3'-UTR and/or variant of the 5'-UTR of a of a transcript of a gene is at least 40%, preferably at least 50%, more preferably at least 60%, more preferably at least 70%, even more preferably at least 80%, even more preferably at least 90%, most preferably at least 95% identical to the naturally occurring 3'-UTR and/or 5'-UTR the variant is derived from. Preferably, the variant is a functional variant as described herein.

The phrase "a nucleic acid sequence which is derived from a variant of the 3'-UTR and/or from a variant of the 5'-UTR of a of a transcript of a gene" preferably refers to a nucleic acid sequence which is based on a variant of the 3'-UTR sequence and/or the 5'-UTR of a transcript of a gene or on a fragment or part thereof as described above. This phrase includes sequences corresponding to the entire sequence of the variant of the 3'-UTR and/or the 5'-UTR of a transcript of a gene, i.e. the full length variant 3'-UTR sequence and/or the full length variant 5'-UTR sequence of a transcript of a gene, and sequences corresponding to a fragment of the variant 3'-UTR sequence and/or a fragment of the variant 5'-UTR sequence of a transcript of a gene. Preferably, a fragment of a variant of the 3'-UTR and/or the 5'-UTR of a transcript of a gene consists of a continuous stretch of nucleotides corresponding to a continuous stretch of nucleotides in the full-length variant of the 3'-UTR and/or the 5'-UTR of a transcript of a gene, which represents at least 20%, preferably at least 30%, more preferably at least 40%, more preferably at least 50%, even more preferably at least 60%, even more preferably at least 70%, even more preferably at least 80%, and most preferably at least 90% of the full-length variant of the 3'-UTR and/or the 5'-UTR of a transcript of a gene. Such a fragment of a variant, in the sense of the present invention, is preferably a functional fragment of a variant as described herein.

The terms "functional variant", "functional fragment", and "functional fragment of a variant" (also termed "functional variant fragment") in the context of the present invention, mean that the fragment of the 3'-UTR and/or the 5'-UTR, the variant of the 3'-UTR and/or the 5'-UTR, or the fragment of a variant of the 3'-UTR and/or the 5'-UTR of a transcript of a gene fulfils at least one, preferably more than one function of the naturally occurring 3'-UTR and/or 5'-UTR of a transcript of a gene of which the variant, the fragment, or the fragment of a variant is derived. Such function may be, for example, stabilizing mRNA and/or enhancing, stabilizing and/or prolonging protein production from an mRNA and/or increasing protein expression or total protein production from an mRNA, preferably in a mammalian cell, such as in a human cell. Preferably, the function of the 3'-UTR and/or the 5'-UTR concerns the translation of the protein encoded by the ORF. More preferably, the function comprises enhancing translation efficiency of the ORF linked to the 3'-UTR and/or the 5'-UTR or fragment or variant thereof. It is particularly preferred that the variant, the fragment, and the variant fragment in the context of the present invention fulfil the function of stabilizing an mRNA, preferably in a mammalian cell, such as a human cell, compared to an mRNA comprising a reference 3'-UTR and/or a reference 5'-UTR or lacking a 3'-UTR and/or a 5'-UTR, and/or the function of enhancing, stabilizing and/or prolonging protein production from an mRNA, preferably in a mammalian cell, such as in a human cell, compared to an mRNA comprising a reference 3'-UTR and/or a reference 5'-UTR or lacking a 3'-UTR and/or a 5'-UTR, and/or the function of increasing protein production from an mRNA, preferably in a mammalian cell, such as in a human cell, compared to an mRNA comprising a reference 3'-UTR and/or a reference 5'-UTR or lacking a 3'-UTR and/or a 5'-UTR. A reference 3'-UTR and/or a reference 5'-UTR may be, for example, a 3'-UTR and/or a 5'-UTR naturally occurring in combination with the ORF. Furthermore, a functional variant, a functional fragment, or a functional variant fragment of a 3'-UTR and/or a 5'-UTR of a transcript of a gene preferably does not have a substantially diminishing effect on the efficiency of translation of the mRNA which comprises such variant, fragment, or variant fragment of a 3'-UTR and/or a 5'-UTR compared to the wild-type 3'-UTR and/or the wild-type 5'-UTR from which the variant, the fragment, or the variant fragment is derived. A particularly preferred function of a "functional fragment", a "functional variant" or a "functional fragment of a variant" of the 3'-UTR and/or the 5'-UTR of a transcript of a gene in the context of the present invention is the enhancement, stabilization and/or prolongation of protein production by expression of an mRNA carrying the functional fragment, functional variant or functional fragment of a variant as described above.

Preferably, the efficiency of the one or more functions exerted by the functional variant, the functional fragment, or the functional variant fragment, such as providing translation efficiency, is increased by at least 5%, more preferably by at least 10%, more preferably by at least 20%, more preferably by at least 30%, more preferably by at least 40%, more preferably by at least 50%, more preferably by at least 60%, even more preferably by at least 70%, even more preferably by at least 80%, most preferably by at least 90% with respect to the translation efficiency exhibited by the naturally occurring 3'-UTR and/or 5'-UTR of a transcript of a gene from which the variant, the fragment or the variant fragment is derived.

In the context of the present invention, a fragment of the 3'-UTR and/or of the 5'-UTR of a transcript of a gene or of a variant of the 3'-UTR and/or of the 5'-UTR of a transcript of a gene preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. Preferably, such fragment of the 3'-UTR and/or of the 5'-UTR of a transcript of a gene or of a variant of the 3'-UTR and/or of the 5'-UTR of a transcript of a gene is a functional fragment as described above. In a preferred embodiment, the 3'-UTR and/or the 5'-UTR of a transcript of a gene or a fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70. Typically, the 5'-UTR element and/or the 3'-UTR element is characterized by less than 500, 400, 300, 200, 150 or less than 100 nucleotides.

5'-UTR Elements

Preferably, the at least one 5'-UTR element comprises or consists of a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence selected from the group consisting of SEQ ID NO: 1 to 151 or the corresponding RNA sequence, respectively, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence selected from the group consisting of SEQ ID NO: 1 to 151 or the corresponding RNA sequence, respectively.

Among the sequences detailed in the following, SEQ ID NO: 1 to 136 can be considered as wild-type 5'-UTR sequences, and SEQ ID NO: 136 to 151 can be considered as artificial 5'-UTR sequences.

```
SEQ ID NO: 1 - Homo sapiens ZNF460 5'-UTR
NM_006635.3
GAAACAGTGTGGGGCCTAGAGCGCTGGGTGGGCGCGTTCTGCGGCCTGAGCAGGGACGGGTAGTGA

AGCGGTTACGCCCCTTCTTCGCGTCTTGGCGGGAGCCTGACGCCCCGCTTCTCCCCTAACGAGGTG

TCCCACCGGCGCCCGCCGAGGCCTAGGCCTCCGCAGCCGCCCTCCGTCTCCTCAGCCCCGACGCTG

CGCCTTGGGCCTTGTGCGCATTTTTTTCGGGGGAAAACTGAGGCTCGGAGTGCGAAAGTCAGCCGA

GGTCGCCCCGCCCAGGACAGAGAAGGGCTGTGGTCGGCTGATCCGCGGCATTCCCGGG

SEQ ID NO: 2 - Homo sapiens TGM2 5'-UTR
NM_004613.2
ATAAGTTAGCGCCGCTCTCCGCCTCGGCAGTGCCAGCCGCCAGTGGTCGCACTTGGAGGGTCTCGC

CGCCAGTGGAAGGAGCCACCGCCCCCGCCCGACC

SEQ ID NO: 3 - Homo sapiens IL7R 5'-UTR
NM_002185.3
ATCTAAGCTTCTCTGTCTTCCTCCCTCCCTCCCTTCCTCTTACTCTCATTCATTTCATACACACTG

GCTCACACATCTACTCTCTCTCTATCTCTCAGA

SEQ ID NO: 4 - Homo sapiens BGN 5'-UTR
NM_001711.4
CCTTTCCTCCCTCCCCGCCCTCTCCCCGCTGTCCCCTCCCCGTCGGCCCGCCTGCCCAGCCTTTAG

CCTCCCGCCCGCCGCCTCTGTCTCCCTCTCTCCACAAACTGCCCAGGAGTGAGTAGCTGCTTTCGG

TCCGCCGGACACACCGGACAGATAGACGTGCGGACGGCCCACCACCCCAGCCCGCCAACTAGTCAG

CCTGCGCCTGGCGCCTCCCCTCTCCAGGTCCATCCGCC
```

-continued

SEQ ID NO: 5 - Homo sapiens TK1 5'-UTR
NM_003258.4
GCGCACGTCCCGGATTCCTCCCACGAGGGGGCGGGCTGCGGCCAAATCTCCCGCCAGGTCAGCGGC

CGGGCGCTGATTGGCCCCATGGCGGCGGGGCCGGCTCGTGATTGGCCAGCACGCCGTGGTTTAAAG

CGGTCGGCGCGGGAACCAGGGGCTTACTGCGGGACGGCCTTGGAGAGTACTCGGGTTCGTGAACTT

CCCGGAGGCGCA

SEQ ID NO: 6 - Homo sapiens RAB3B 5'-UTR
NM_002867.3
AGACTCCGCCCTTGGGCGGGGCCTGGATGCGGCCGGAGCGGAGCAGTGCTGGAGCGGGAGCCTCAG

CCCTCAGGCGCCACTGTGAGGACCTGACCGGACCAGACCATCCCGCAGCGCCCCGCCCCGGCCCCC

TCCGCGCCCTCCCGACGCCAGGTCCTGCCGTCCCGCCGACCGTCCGGGAGCGAACCCGTCGTCCCG

CACTCGGAGTCCGCG

SEQ ID NO: 7 - Homo sapiens CBX6 5'-UTR
NM_014292.3
GAGCGGTGCCGCACCGGCCGCGGGCGCAGGGAGTATTATGGGCTGTGGGTGCCGCTGAGCAAG SEQ ID NO: 8 - Homo sapiens FZD2 5'-UTR
NM_001466.3
GAGGAGAGAGGGCAGCAGCGCGCGGTGTCTCCGGCTGCTCAGTCCGACCGCGGCAAGCAAGCGGGC

AGGCGCACCGCCCCCTCCCCCGCCCGGCCTCCCCAACTCTGCGGCCGCGAGTAAAGTTTGCAAAGA

GGCGCGGGAGGCGGCAGCCGCAGCGAGGAGGCGGCGGGGAAGAAGCGCAGTCTCCGGGTTGGGGGC

GGGGGCGGGGGGGCGCCAAGGAGCCGGGTGGGGGGCGGCGGCCAGC

SEQ ID NO: 9 - Homo sapiens COL8A1 5'-UTR
NM_001850.4
ATCACAGCCCTTCCCCGATCCTCTCCGTGGGAGCCAGCGAGCCTCTCTCCCTGATCTTACGTGCTC

AAGGGAGCTCACACGTTCACCAACTCACCCTTGAAGTCATCTCAAGAACAAAAGACAACTGAAAGA

AGCTGTTGTGAAGGCAGAGCAGCATCTGCTGAAGAGACAGAAACCAGCCCCAGAGGTGTCACAGGA

AGGCACCAGCAAGGACATTGGTCTTTGATTTGATTCAGCAGTCCTGTCAAGTATAAATGTG

SEQ ID NO: 10 - Homo sapiens NDUFS7 5'-UTR
NM_024407.4
AAGGAGAACGGACCTCAGAGGTTGTCTGAAGGCCGAGGCCAAG SEQ ID NO: 11 - Homo sapiens PHGDH 5'-UTR
NM_006623.3
GCAGGGATTTGGCAACCTCAGAGCCGCGAGGAGGAGGCGGAGTCGCGGAGAGTTTGAGTATTCCG

TCCAATCAAAAGGAGACTGTAAGAGGAGGAGGAGGAGGAGATGACTGGGGAGCGGGAGCTGGAGAA

TACTGCCCAGTTACTCTAGCGCGCCAGGCCGAACCGCAGCTTCTTGGCTTAGGTACTTCTACTCAC

AGCGGCCGATTCCGAGGCCAACTCCAGCA

SEQ ID NO: 12 - Homo sapiens PLK2 5'-UTR
NM_006622.3
TCCGCCCCCTTCCCGCCTCCCCGTATATAAGACTTCGCCGAGCGCTCTCACTCGCACAAGTGGACC

GGGGTGTTGGGTGCTAGTCGGCACCAGAGGCAAGGGTGCGAGGACCACGGCCGGCTCGGACGTGTG

ACCGCGCCTAGGGGGTGGCAGCGGGCAGTGCGGGGCGGCAAGGCGACC

SEQ ID NO: 13 - Homo sapiens TSPO 5'-UTR
NM_000714.5
GGCGGCTGGGAGGGGCGGGGCGGATGCGGGGACAGCGGCCTGGCTAACTCCTGCCAGGCAGTGCCC

TTCCCGGAGCGTGCCCTCGCCGCTGAGCTCCCCTGAACAGCAGCTGCAGCAGCC

SEQ ID NO: 14 - Homo sapiens PTGS1 5'-UTR
NM_000962.3
ATGGGCTGGAGCTCCGGGCAGTGTGCGAGGCGCACGCACAGGAGCCTGCACTCTGCGTCCCGCACC

CCAGCAGCCGCGCC

```
SEQ ID NO: 15 - Homo sapiens FBXO32 5'-UTR
NM_058229.3
GCTGCGGCCGGCTGCGGGGATAAATACTGCGGCAGCTACTGCCGCGCAGCACTCCCGGAGCCTGCA

ACGCTTGAGATCCTCTCCGCGCCCGCCACCCCGCAGGGTGCCCCGCGCCGTTCCCGCCGCCCCGCC

GCCCCCGTCGCGGGCCCCTGCACCCCGAGCATCCGCCCCGGGTGGCACGTCCCCGAGCCCACCAGG

CCGGCCCCGTCTCCCCATCCGTCTAGTCCGCTCGCGGTGCC

SEQ ID NO: 16 - Homo sapiens NID2 5'-UTR
NM_007361.3
GCCTTAGAAAAGTTAACGAGAACCAGATGTGGTGGCCACTGCCGAACTTTCTCAGAGCCGGTGATT

GGTCCCCAGCCGAGGGCCTCAGCCAATTAGCTTGCTGGGTGGGCCTGGAGTCCCGCCCCGCCCAGG

CGCCCGCGGAGATCCAGGTTCGAGGCTGGCGCGGCGCGGAGAGTGGGCTGGAGGCCGGGGCGGGAC

GCGTTGTGCAGCGGGTAAGCGCACGGCCGAGCGAGC

SEQ ID NO: 17 - Homo sapiens ATP5D 5'-UTR
NM_001687.4
CAGACGTCCCTGCGCGTCGTCCTCCTCGCCCTCCAGGCCGCCCGCGCCGCGCCGGAGTCCGCTGTC

CGCCAGCTACCCGCTTCCTGCCGCCCGCCGCTGCC

SEQ ID NO: 18 - Homo sapiens EXOSC4 5'-UTR
NM_019037.2
ATGGCGGACCTCCGGAAACCGTAGATTCCGGGCGGTCGGAGCCGCCGGGAGCTGTAGTTCTCCCGC

GGCTCAGAGAAGTAGGCAGAGAGCGGACCTGGCGGCCGGGCAGC

SEQ ID NO: 19 - Homo sapiens NOL9 5'-UTR
NM_024654.4
GGCTCGGAGGCCCCTCTTTTCGGCAGCTGGGAGGGCAGCGGGGCGGACCGACGGGATCTCGCGAGA

TTCTCGCGCGGTAGGCCCTGAGGACCCAGC

SEQ ID NO: 20 - Homo sapiens TUBB4B 5'-UTR
NM_006088.5
ATATAAGCGTTGGCGGAGCGTCGGTTGTAGCACTCTGCGCGCCCGCTCTTCTGCTGCTGTTTGTCT

ACTTCCTCCTGCTTCCCCGCCGCCGCCGCCGCCATC

SEQ ID NO: 21 - Homo sapiens VPS18 5'-UTR
NM_020857.2
GCCCGCGTCACGGGGGCGGGAGTCAGCTGAGCTGCCGGGGCGAGGTTGGGATCACCTGGCACCGGC

TGAAGGGAGCCTGTGATTTTTTTGTAGCGGGGGCGGGAGTAAGGTGCAAGACTGCGCCAGATTCA

AGGACGAGGGCTGCCCGATTATCTCGCTGCATAAGGCAAGAGCAAGAGGATCCTCAGGATTTTAAA

GAGGAGGCGACGGCTGCAGGTTCCCAGGATCTGTCAGAGGCTGGGGAGTTACAGCTTCCATTCTGG

GGCGACGGGACCCCGGGGGGGTAGCCCTTTTGTAATCCCCAGGCCCCGGACAAAGAGCCCAGAGG

CCGGGCACC

SEQ ID NO: 22 - Homo sapiens ORMDL2 5'-UTR
NM_014182
AAGGGGCAGAAGGAGAGGCGTTACTTCCTGGAGACTTCAGGTGTGGTAGCCGGCGCCGCGCCCATA

GCCGGACGGGATCTGAGCTGGCAGG

SEQ ID NO: 23 - Homo sapiens FSCN1 5'-UTR
NM_003088.3
AGCTGGGCTTTGTGGAGCGCTGCGGAGGGTGCGTGCGGGCCGCGGCAGCCGAACAAAGGAGCAGGG

GCGCCGCCGCAGGGACCCGCCACCCACCTCCCGGGGCCGCGCAGCGGCCTCTCGTCTACTGCCACC

SEQ ID NO: 24 - Homo sapiens TMEM33 5'-UTR
NM_018126.2
ACGGAAATGAAAGGAGCACTTCCGGGTTCGGCAATAACCTGGAGCCGGCGGCGTAGGTTGGCTCTT

TAGGGCTTCACCCCGAAGCTCCACCTTCGCTCCCGTCTTTCTGGAAACACCGCTTTGATCTCGGCG

GTGCGGGACAGGTACCTCCCGGCTGCTGCGGGTGCCCTGGATCCAGTCGGCTGCACCAGGCGAGCG
```

```
AGACCCTTCCCTGGTGGAGGCTCAGAGTTCCGGCAGGGTGCATCCGGCCTGTGTGTGGCGCGAGGC

AGGGAAGCCGGTACCCGGGTCCTGGCCCCAGCGCTGACGTTTTCTCTCCCCTTTCTTCTCTCTTCG

CGGTTGCGGCGTCGCAGACGCTAGTGTGAGCCCCC

SEQ ID NO: 25 - Homo sapiens TUBA4A 5'-UTR
NM_006000.2
ATAAGGGCGGTGCGGCACTGCAGCTAGCGCAGTTCTCACTGAGACCTGTCACCCCGACTCAACGTG

AGACGCACCGCCCGGACTCACC

SEQ ID NO: 26 - Homo sapiens EMP3 5'-UTR
NM_001425.2
CGGGAGCAAGAGAGAAGGAGGCCCAGACAGTGAGGGCAGGAGGGAGAGAAGAGACGCAGAAGGAGA

GCGAGCGAGAGAGAAAGGGTTCTGGATTGGAGGGGAGAGCAAGGGAGGGAGGAAGGCGGTGAGAGA

GGCGGGGGCCTCGGGAGGGTGAAAGGAGGGAGGAGAAGGGCGGGGCACGGAGGCCCGAGCGAGGGA

CAAGACTCCGACTCCAGCTCTGACTTTTTTCGCGGCTCTCGGCTTCCACTGCAGCC

SEQ ID NO: 27 - Homo sapiens TMEM201 5'-UTR
NM_001010866.3
CTACCCGCCTACCCGCCTACCCCCTGCCGGCCTGCCGTCCTTCCACGCGGAGAGCC SEQ ID NO: 28 - Homo sapiens CRIP2 5'-UTR
NM_001312.3
GGACAGCCGGGCAGGCGGGGCTGGGCGCGGGCGGCGGCGGCCCGGAGGAGAACGGGCGGAGGGCGC

GGGCCGACCGGGCGCACCGACC

SEQ ID NO: 29 - Homo sapiens BRAT1 5'-UTR
NM_152743.3
ACCGGATGCTCGGCATGAACCACTAGGCGCCTGGCGGGGGTGATCTGTCGGAGCGACCGGCTTGGC

GCCTGCCTGTCCCCAGCCCCTCTCAGCTTGAACTCCTTCCTTCAAGTCTGGGCCCTCGAGGCTTCC

AGAGCGGCCTCCAGGGGTGCAGTCTCAGTTCCCCACGCCAGCCGTCTCCGTCCTCCGCCTCCTCCG

GGCCTGGCAGGTGGCACTGTCCGGAGGCGGAGCCTTGGGCGAGGGGTGGTTGCGGCGGAGGACGCA

ACCGAGCGGGCCTGCGGCCTCACC

SEQ ID NO: 30 - Homo sapiens SERPINH1 5'-UTR
NM_001235.3
AGTAGGACCCAGGGGCCGGGAGGCGCCGGCAGAGGGAGGGGCCGGGGGCCGGGGAGGTTTTGAGGG

AGGTCTTTGGCTTTTTTTGGCGGAGCTGGGGCGCCCTCCGGAAGCGTTTCCAACTTTCCAGAAGTT

TCTCGGGACGGGCAGGAGGGGGTGGGGACTGCCATATATAGATCCCGGGAGCAGGGGAGCGGGCTA

AGAGTAGAATCGTGTCGCGGCTCGAGAGCGAGAGTCACGTCCCGGCGCTAGCCCAGCCCGACCCAG

GCCCACCGTGGTGCACGCAAACCACTTCCTGGCC

SEQ ID NO: 31 - Homo sapiens CD9 5'-UTR
NM_001769.3
CTTTTCCCGGCACATGCGCACCGCAGCGGGTCGCGCGCCCTAAGGAGTGGCACTTTTTAAAAGTGC

AGCCGGAGACCAGCCTACAGCCGCCTGCATCTGTATCCAGCGCCAGGTCCCGCCAGTCCCAGCTGC

GCGCGCCCCCAGTCCCGCACCCGTTCGGCCCAGGCTAAGTTAGCCCTCACC

SEQ ID NO: 32 - Homo sapiens DPYSL2 5'-UTR
NM_001386.5
ATATCCCAGGATCGCGGCCAATCGCTGCTCGTCTCTCTCGAAGCGGATGGCTTTTGCCTGAGAGGA

AAGGGAGTGGCTGGCGGCGCATGCGCCACGGTGGCCGACTTGAACCGAGGCTTTTATTGCTGTAGT

TTATTTCCACCCCCTTCCCTCCTGTTTCTCTCTCTCCTTCTCTCTCTCTCTCTCTCTCTCTTTT

TTTTCCGCCCTAGCTGGGGCTGTGTTGGAGGAGAGGAAGAAAGAGAGACAGAGGATTGCATTCATC

CGTTACGTTCTTGAAATTTCCTAATAGCAAGACCAGCGAAGCGGTTGCACCCTTTTCAATCTTGCA

AAGGAAAAAACAAAACAAAACAAAAAAAACCCAAGTCCCCTTCCCGGCAGTTTTTGCCTTAAAGC

TGCCCTCTTGAAATTAATTTTTTCCCAGGAGAGAG
```

-continued

SEQ ID NO: 33 - Homo sapiens CDK9 5'-UTR
NM_001261.3
AAGTGGCCGTGGAGGCGGAAGTGGCGCGGCCGCGGAGGGGCCTGGAGTGCGGCGGCGGCGGGACCC

GGAGCAGGAGCGGCGGCAGCAGCGACTGGGGGCGGCGGCGGCGCGTTGGAGGCGGCC

SEQ ID NO: 34 - Homo sapiens SSSCA1 5'-UTR
NM_006396.1
CCGGCGGTGACAACGGCAAC

SEQ ID NO: 35 - Homo sapiens POLR2L 5'-UTR
NM_021128.4
AGTCTGGGACGCGCCGCCGCC

SEQ ID NO: 36 - Homo sapiens LIN7C 5'-UTR
NM_018362
CTGTGGGTCTGTAGGTTAAGGGAGAAG

SEQ ID NO: 37 - Homo sapiens UQCR10 5'-UTR
NM_001003684.1
GCGGTGGCGCGAGTTGGACTGTGAAGAAAC SEQ ID NO: 38 - Homo sapiens TFRC 5'-UTR
NM_001128148.1
ACGCACAGCCCCCCTGGGGGCCGGGGGCGGGGCCAGGCTATAAACCGCCGGTTAGGGGCCGCCATC

CCCTCAGAGCGTCGGGATATCGGGTGGCGGCTCGGGACGGAGGACGCGCTAGTGTTCTTCTGTGTG

GCAGTTCAGA

SEQ ID NO: 39 - Homo sapiens PSMB3 5'-UTR
NM_002795.2
GAGCGGTTGCGCAGTGAAGGCTAGACCCGGTTTACTGGAATTGCTCTGGCGATCGAGGGGTCCTAG

TACACCGCAATC

SEQ ID NO: 40 - Homo sapiens FASN 5'-UTR
NM_004104.4
GAGAGACGGCAGCGGCCCCGGCCTCCCTCTCCGCCGCGCTTCAGCCTCCCGCTCCGCCGCGCTCCA

GCCTCGCTCTCCGCCGCCCGCACCGCCGCCCGCGCCCTCACCAGAGCAGCC

SEQ ID NO: 41 - Homo sapiens PSMB6 5'-UTR
NM_002798.2
GTGACAGAGCGCTTTACGACAGTTGCTTTGAGGCAGTACCGGAGGAGAAAG SEQ ID NO: 42 - Homo sapiens PYCRL 5'-UTR
NM_023078.3
CTAGATCTGTGGGCGGGGCGCGGCCTGTGG SEQ ID NO: 43 - Homo sapiens PRSS56 5'-UTR
NM_001195129.1
GATGATTTGAGGGACAAGAATTCAGTGCCCGGGGGCCGAAAGGCAGCAGAAGGCGGGCACCAAAGG

ATAGGCACCCGGAAGGTGGACTCCGAGGAGGAGAGAGGACAGGGGTCTCTCACCCCAGCTCCTGGT

CACC

SEQ ID NO: 44 - Homo sapiens KPNA6 5'-UTR
NM_012316.4
CTACAGATCCGCCATATTGTCTACTGAAAGCTGCCGCTGAAGCTGCCGCCGTTGCCTCCGCCGCCA

AGAGTGAGCGAGCGGACCCGCG

SEQ ID NO: 45 - Homo sapiens SFT2D2 5'-UTR
NM_199344.2
CCGTCAACTTAGCGAGCGCAACAGGCTGCCGCTGAGGAGCTGGAGCTGGTGGGGACTGGGCCGCA SEQ ID NO: 46 - Homo sapiens PARD6B 5'-UTR
NM_032521.2
GAGGGAGGGAGCTGCTTCCCCGCCTGCCGCGCCACCAGTCCGACCCTCGGTCCCGCCGTGTGAGCA

GCTGGTGGAGTGGAGCTCAGCGCGGACGCCGGAGCTGCGGCCGCCCCCTCTGCAGGTGCCTGTGAG

GAGGCGCCCGGGCCGCAACCGCTTTCCGAGATCCCCAGTCGCGCACTCGCTCCCCGCGCTCCTGAG

GGGCCGCCCGGCCGGAGGAGGCCGTCGCGGGGCTCGGCGTTCAGC

-continued

SEQ ID NO: 47 - *Homo sapiens* LPP 5'-UTR
GAGGAAGGAGGGGGAAAGGCACCAACCAGCAGCCGCTCCAGCCCTGCCGAAGTTTCACTTTTTGTC

TGTGGGTTCGTTCCCGGGTCCCGCGCGAGCTTTCCCGGGATAAGTAGCTTTAGCGATCGGGAGACA

GCCGGGCGCTGCAAGTGGGAACTTTGAGGCTCAGAGACAGAGCAGAAGACAGAACCTGGTCTTCTG

ATTCCCTGTGTTCTGCTTTTTTCATTGTTCCACTGGACGCTCATCAGAGGGAAGATCTTTTTCCTC

AATTGCATTGCAGTTGGCTGAACCTTGTGTCAACCATCCATTCCAGGAGCCAGCTATCTGAGATTC

CAACA

SEQ ID NO: 48 - *Homo sapiens* SPARC 5'-UTR
NM_003118.3
GGGAGAAGGAGGAGGCCGGGGGAAGGAGGAGACAGGAGGAGGAGGGACCACGGGGTGGAGGGGAGA

TAGACCCAGCCCAGAGCTCTGAGTGGTTTCCTGTTGCCTGTCTCTAAACCCCTCCACATTCCCGCG

GTCCTTCAGACTGCCCGGAGAGCGCGCTCTGCCTGCCGCCTGCCTGCCTGCCACTGAGGGTTCCCA

GCACC

SEQ ID NO: 49 - *Homo sapiens* SCAND1 5'-UTR
CTTCCGGGAGCCCGCAAGCGGCTTCCGGGTGCTCGCGCGCCGACCTGGACGCAGAGAAGCCAGAGA

CTTTCGCTTCCGGCTGCCGCAGGCGCTTCGCTGGTGCAGGTAAGCTCCGCACACTCTCGGCCGGTC

CCGAGTCCGACTCCCTCAAGGGTGACGCGAGCTCTGCCCTTTAACCGGAAACGTCTCCCTGCTCAC

CCCACCCCCGCGCAGACGCAGTGCTGAGCACACAGCTACCGGACAAAGAGTGACGCCCGGAGCTGG

AGTT

SEQ ID NO: 50 - *Homo sapiens* VASN 5'-UTR
NM_138440.2
GACTCCGGAGCCCGAGCCCGGGGCGGGTGGACGCGGACTCGAACGCAGTTGCTTCGGGACCCAGGA

CCCCCTCGGGCCCGACCCGCCAGGAAAGACTGAGGCCGCGGCCTGCCCCGCCCGGCTCCCTGCGCC

GCCGCCGCCTCCCGGGACAGAAG

SEQ ID NO: 51 - *Homo sapiens* SLC26A1 5'-UTR
NM_022042.3
ACAGACCACTGCCTGCAGGTTGGCGCCACCACCCCCACTCTCCCCGCTGCTCGCGGGAGCCAGAGG

GCCCTGCGGTCCTCGGTGGTCTTGCCAGCCCCTCGTCATCCCAGGGCCCTCCGCGCCTGTGAGGAC

TCCCTCAGGTCGGCCACGGGACCTGACGCAACAGG

SEQ ID NO: 52 - *Homo sapiens* LCLAT1 5'-UTR
NM_182551.3
GGCCGGACGCCTCCGCGTTACGGGATGAATTAACGGCGGGTTCCGCACGGAGGTTGTGACCCCTAC

GGAGCCCCAGCTTGCCCACGCACCCCACTCGGCGTCGCGCGGCGTGCCCTGCTTGTCACAGGTGGG

AGGCTGGAACTATCAGGCTGAAAAACAGAGTGGGTACTCTCTTCTGGGAAGCTGGCAACAAATGGA

TGATGTGATAT

SEQ ID NO: 53 - *Homo sapiens* FBXL18 5'-UTR
NM_024963.4
GCGGTGGACGCGCCGGCTTCGAGCATCCCTAGCCGGGCAGGTGGGAGGCACGGGGTTGCGGATCCC

GCGGCCGCGGTTCGGACCCGCCGGCGAC

SEQ ID NO: 54 - *Homo sapiens* SLC35F6 5'-UTR
NM_017877.3
GGAAGCGCTCGCGCAGGAGACCCCGGGTGACGGGGCCCGGCGCCGCTAACTGGAGCGAACCCCAGC

GTCCGCCGAC

SEQ ID NO: 55 - *Homo sapiens* RAB3D 5'-UTR
NM_004283.3
CCTTCCTCCGCCTTCTGGGCGGAGCCCGCGCGGGATCCGGGTGGCTGCAGGCTGCTGGCTTCTGCG

GCTGCGGGGTCGGGGTCGCGGCCAGGGCCAAGCCGCAGCGAGTTCACAGGCGGAACCCCTGCAGGC

-continued

GGCGCCCCCTACGCGAGGTCACCCCTGGGAAGGAGCGCAGCCCACCCGGCCCCTCCGCATCCGAGC

AGGACGCCCGTCTCCTCTCCCTGAGGATTTCAGGTCTCCCTGTCCCAGGAGGCTTGTGCCAAG

SEQ ID NO: 56 - Homo sapiens MAP1B 5'-UTR
NM_005909.3
GCCTAGTCTCCATATAAAAGCGGCGCCGCCTCCCCGCCCTCTCTCACTCCCCGCTCCTCTCCGCCG

CGCACTCTCCGCGGCGCTGGGAGAGGGCGGAGGGGGAGGCGGCGCGCGGCGCCAGAGGAGGGGGA

CGCAGGGGGCGGAGCGGAGACAGTACCTTCGGAGATAATCCTTTCTCCTGCCGCAGTGGAGAGGAG

CGGCCGGAGCGAGACACTTCGCCGAGGCACAGCAGCCGGCAGG

SEQ ID NO: 57 - Homo sapiens VMA21 5'-UTR
NM_001017980.3
GCACTTCCGGCGCGAACCGCTACTTCCGGTGCGAACCGCCTCGGCCGTTCCCTCGCGGAGCTTACT

GAGCGCGGCCGCCGAGCCCAGCTCCGCCGCCGAGCGCCTGTGCCGGCACGGCTACACC

SEQ ID NO: 58 - Homo sapiens AMN 5'-UTR
NM_030943.3
GTCTCCTGGTGGGGTGCAAGGAGCCGAGGCGAG SEQ ID NO: 59 - Homo sapiens CYBA 5'-UTR
NM_000101.3
GGCGGGGTTCGGCCGGGAGCGCAGGGGCGGCAGTGCGCGCCTAGCAGTGTCCCAGCCGGGTTCGTG

TCGCC

SEQ ID NO: 60 - Homo sapiens SEZ6L2 5'-UTR
NM_012410.3
ACCACAGAGCCGCGAGAAGAGGACAGAGGAGACTGAGCAAAGGGGGTGGGCTCCAGGCGACCCCT

AGCCCAATTCTGCCCCTCCATCCCAAGGGGCAGAGAAATTGTCTTTCTTTGCTGACTCCTACGAGG

AAAAAAAAAAAAAAAAAAAAACAATTAAAGGGAAAGATAAACGGAGACGGAGGAAAGGTGGCAGC

CAGATTACTTAGAGAGGCACAGAGGAGAGAGATCGGGGTGAGTCGCC

SEQ ID NO: 61 - Homo sapiens PCOLCE 5'-UTR
NM_002593.3
GACCTAGAGAGGTCCCAGGACACGCCACTGTCCCGCCTTCCCCATTGCCCGCCCCACTGGCCAGTC

CCCACGCCCACACACCCAAGGCTGCCCCATCTGGCGCTGATTATCCTGCTGCTGCCGCCACCGCTG

CTGCTGCTCTGCAAAATTCAGCTGCTGCCTCTGTCTTGAGGACCCCAGCGCCTTTCCCCCGGGGCC

SEQ ID NO: 62 - Homo sapiens MAP1S 5'-UTR
NM_018174.4
GGCCCGAAG

SEQ ID NO: 63 - Homo sapiens VTN 5'-UTR
NM_000638.3
GAGCAAACAGAGCAGCAGAAAAGGCAGTTCCTCTTCTCCAGTGCCCTCCTTCCCTGTCTCTGCCTC

TCCCTCCCTTCCTCAGGCATCAGAGCGGAGACTTCAGGGAGACCAGAGCCCAGCTTGCCAGGCACT

GAGCTAGAAGCCCTGCC

SEQ ID NO: 64 - Homo sapiens ALDH16A1 5'-UTR
NM_001145396.1
ATTCCCATTAGCCCCGCCCCTTTGGGCTGGAACCGGAGGTGTCGCTCTTCGGACCTCAAGGTTCCC

CTTAACACAGAGCGCCCCGCAGTCTTCGCGGAAAGCGTTCGGGGTAGGCG

SEQ ID NO: 65 - Homo sapiens RAVER1 5'-UTR
NM_133452.2
TTAGCCAACGGGGCAAGGGGGGCGGGAAGGAGGTGGGGTTTCTCCCAGCCAATCGACGGGCGCGCC

CTCGTTGCCGCTCT

SEQ ID NO: 66 - Homo sapiens KPNA6 5'-UTR (identical to SEQ ID NO: 44)
NM_012316.4
CTACAGATCCGCCATATTGTCTACTGAAAGCTGCCGCTGAAGCTGCCGCCGTTGCCTCCGCCGCCA

AGAGTGAGCGAGCGGACCCGCG

-continued

SEQ ID NO: 67 - Homo sapiens SERINC5 5'-UTR
NM_178276.5
GTTTTTACCCAGGCCTCGGCGCCTAGGCGCTTCGCCGAGGCTGATCTTCGTTCAAGTGTGAGCTGC

GGCTGAGCCCAGCGCTCGAGGCGCGAGGCAGCCAGGAGGGCCCGTGCGGCGCGGGGAGCCAGCGAG

CGCGCCTTCGGCATTGGCCGCCGCG

SEQ ID NO: 68 - Homo sapiens JUP 5'-UTR
NM_002230.2
TGAGTTGCTGCCTTGGCCAGAGTCCGGAGCAGCCGCCGCCCGACCACGCCGAGCTCAGTTCGCTGT

CCGCGCCGGCTCCCACCCCGGCCCGACCCCGACCCGGCCCGGTCAGGCCCCATACTCAGTAGCCAC

G

SEQ ID NO: 69 - Homo sapiens CPN2 5'-UTR
NM_001080513.2
GGATTGAGCTGACCACAGGCCACACCAGACTCCTCTCTGCTCCTGAGGAAGACAGGGCAGCCCGGC

GCCACCCGCTCGGCCCTCACGAAG

SEQ ID NO: 70 - Homo sapiens CRIP2 5'-UTR
NM_001312.3
GGACAGCCGGGCAGGCGGGGCTGGGCGCGGGCGGCGGCGGCCCGGAGGAGAACGGGCGGAGGGCGC

GGGCCGACCGGGCGCACCGACC

SEQ ID NO: 71 - Homo sapiens EPT1 5'-UTR
NM_033505.2
ACGCGTGCGCGGTGGGCGGAGCGCGGCTCTCCTACCTTCTCGGGCAGCCCAGTCTTTGCCATCCTT

GCCCAGCCGGTGTGGTGCTTGTGTGTCACAGCCTTGTAGCCGGGAGTCGCTGCCGAGTGGGCGCTC

AGTTTTCGGGTCGTC

SEQ ID NO: 72 - Homo sapiens PNPO 5'-UTR
NM_018129.3
CATTGGCTCCGAGGACTTAGGACCTGTTAGCTTGGTTGGGCGACTGGCAAATCCTTCCTTCCCCGG

GGTAGAAGTCCAGGGTGAGAAATTGGTTCCGAACTCAAAGGAACCCAGTGCCGGGCCACAGCCGGG

TCACGTGGCCGGCGGCCCCCC

SEQ ID NO: 73 - Mus musculus Dpys12 5'-UTR
NM_009955.3
CTCTCTCCCTCTTTCTTTTTTCCGCCCTAGCTGGATCTGTGTTGGAGGAGAGGAAAAGAGACAGAG

GATTGCATCTGTTTTGAAATCTCCTAATAGCAAGACCAGTTAAGGGATTGTACCTTTTTCCTACAA

ATATAAATATATATATATTTTAAACCAAGTCTTTTTTTTTCCGGCTATCTTTGCTTTAAAGCTGTC

CTCTTGAGATTACTTCCTCCCGCCCCCCGGAGAG

SEQ ID NO: 74 - Mus musculus Ccnd1 5'-UTR
NM_007631.2
TTTTCTCTGCCCGGCTTTGATCTCTGCTTAACAACAGTAACGTCACACGGACTACAGGGGAGTTTT

GTTGAAGTTGCAAAGTCCTGCAGCCTCCAGAGGGCTGTCGGCGCAGTAGCAGAGAGCTACAGACTC

CGCGCGCTCCGGAGACCGGCAGTACAGCGCGAGGCAGCGCGCGTCAGCAGCCGCCACCGGAGCCCA

ACCGAGACCACAGCCCTCCCCAGACGGCCGCGCC

SEQ ID NO: 75 - Mus musculus Acox2 5'-UTR
NM_001161667.1
CGCTGTCCCAGGACAGAGGTGAGTCAAGAGTTTAGTCCCAGGCCAGCCAGAGAACTGACAGAACAT

ACCAAAGGTTCTTGGTACCTCCCGGTGCTCAGAGCAGACCCTAAAGGAAGCCAAGTCCTTCCTGAG

ACAGGCAGATCCAGG

SEQ ID NO: 76 - Mus musculus Cbx6 (Npcd) 5'-UTR
NM_001013360.2
GAGCGCGCGCCCCGCCGAGCGCCCGCCCGCCGGGGGCCTGAGCGCTGGGGCGCGTGCGCGAGCGGT

GCAGCACCGGCCGCGGGAGCAGGGAGTATTATGGGCTGTGGGTGCCGCTGAGCAAG

SEQ ID NO: 77 - Mus musculus Ubc 5'-UTR
AGTTCCGTGGAGACTGCGAGTTCCGTCTGCTGTGTGAGGACTGCCGCCACCACCGCTGACG -continued SEQ ID NO: 78 - *Mus musculus* Ldlr 5'-UTR
NM_001252659.1
GCAGACTCCTCCCCCGCCTGGAAACCTCGCCCCTAGTACTGGGAATGACTCTGGGCGTGCGGCGTA

GTTTGCAGCCGGGACACCGTGAGGCTTGCGAGCCCAGATTCGCAGCCGAGACACCGTGGGGCCCGC

GATCCAGTGTTTGCAGCGGGAACATTTCGGGGTCTGTGATCCGAGTGAGGACGCAACGCAGAAGCT

AAGG

SEQ ID NO: 79 - *Mus musculus* Nudt22 5'-UTR
GGCCGGGCCAGCCGCTAAATTCCGAGATCAAGCTTCCAGATCCTGGGAGTAGATCAAGCGTGTCCA

GGTTGGAGAGCTGCCCTGTCAGACT

SEQ ID NO: 80 - *Mus musculus* Pcyox1l 5'-UTR
NM_172832.4
GAGCGCCAACCGCTAGAGGCCGATCCGGAGCGTGCTGCCCGGTCACCACCCGCC SEQ ID NO: 81 - *Mus musculus* Ankrd1 5'-UTR
NM_013468.3
CCACAGGGCCAGTTCCAGGGGTTCATCCACAAGAGAGAAAAACATAGACTCACGGCTGCCAAC SEQ ID NO: 82 - *Mus musculus* Tmem37 5'-UTR
NM_019432.2
GAGTGCGACAGCTAGGCCAGGCGACAGCGCTGCCTACCAGAGCGCAGC SEQ ID NO: 83 - *Mus musculus* Tspy14 5'-UTR
NM_030203.2
AGAAGGAAAAGGGGTGGAGCTAAGCACTCACTGCGGTTTTGCGCTGCGTCTGCAGAGGACAAGGAA

AGCTCTGCAGGGCTGTCAGCTGCCAAA

SEQ ID NO: 84 - *Mus musculus* Slc7a3 5'-UTR
GGGCGCTTGGCTTGCAAGGACCCTGAGCTGCGGCATTGAAGCACACCCAACCCAACTCGACTGAAG

TCAGCCTCACTGAACCGGATCTGAGAATCTTCTCTCTCTGGGCTTGCCAGGGCTCTCCGAACCTAG

CTAGCATCCTCTTCAATTCCAACTAGA

SEQ ID NO: 85 - *Mus musculus* Cst6 5'-UTR
CGCGAAGGCTGTAAAAGCCGCGCAGGATGGAAGTCCAGACACTGAATCCGCGGCT SEQ ID NO: 86 - *Mus musculus* Aacs 5'-UTR
NM_030210.1
GAGTCTCGCGCTGTGGTTCGTCGGCGCACCGCTGATCCGCTCCACGCCTTGCGCTCTCCGCTCTCA

GCCAAAGCCCGGCAGCCCCGGCCACGCAGCTCCGCAACC

SEQ ID NO: 87 - *Mus musculus* Nosip 5'-UTR
NM_001163684.1
CTCCTGTCGGGCGGAAGTAGGAGGAGTAGAGTTTAAAAACAGTACTCTTTTTCCGGTTCGGGACGT

AGTTGAAGCAACGACAAGCCGGATAACCGCTCTTGAGACAGG

SEQ ID NO: 88 - *Mus musculus* Itga7 5'-UTR
NM_008398.2
GTACTTAGCTGGTCCTGGGGCAGCAGCGGGAAGGGACTGAAGAGGGGTGCTGAGGTGAAAGATTGG

AAGACCCGGAAAGATCAGCTAGATTTCGGAAACCAGAAACACCCTCGGGGAGACCTGGGGCTCCCG

GCGCGCGACGATTTCCTCGCACTAGCTGGGAGAGCGTTGATCCC

SEQ ID NO: 89 - *Mus musculus* Ccnd2 5'-UTR
NM_009829.3
TGCCTGAGCGAGAGAGGAGAGCGAGCTGAGGAGAGCCGGGCAGTTCGGAGGGAAGGACCGGTGCGA

GTCAGGCGGCCCTTGAGGCTCCGCTCGCCCACCTTCCACTCTTCTCTCTCTCTCCCTCTCTCTC

TTTGCCATTTCTTTCCTCTCCCAAATCTCCCATTCAGCCAAAGGAAGGAGGTAAGGGAAGCACTCC

CCGACCCCCCGCACCTCCAAAAAATAATAATAATAAAAAAAATTTACAGTCGGGACCGAGTGGTG

GCCGGCTGGCT

SEQ ID NO: 90 - *Mus musculus* Ebp 5'-UTR
CGGAACTGGGGCTATTAGGGAGCCTGCAGGTCTTCCTGGAAAGTCGCAAGCCTGTGTTAGGAAGTC

GCCCTGCGATCGCGCCGCCTGGGGTTTTTCTGTCCCTTTGTCCTCGTTTATGTACGAAGCTGCCAG

CGGGCCATAGAAAC

-continued

SEQ ID NO: 91 - Mus musculus Sf3b5 5'-UTR
NM_009829.3
GAAAAGACTGTCTACTCCTGCGTCTCGGTGGCGTCTTTCTCCCGCGCCTGCACGAACTGAGGTTTT

GCGTGGCGGCGGCGGCACCGGCAGCGGCAGCGTCTCTCACTTGAACGCCGCGAGCGGCAGCTTCTC

GTCTGTGTCCTGACCTCGGAGCCTACGAGCAGAGCGGCGCG

SEQ ID NO: 92 - Mus musculus Fasn 5'-UTR
GCAGCGGCGTCCCGTCCAGTTCGCCTGCCGCGCTCCTCGCTTGTCGTCTGCCTCCAGAGCCCAGAC

AGAGAAGAGCC

SEQ ID NO: 93 - Mus musculus Hmgcs1 5'-UTR
CCCGGCGCTGCCCGAGTCGGGTGGGTCGGTGGCTATAAAGCTGCGGAGGGCGGGAGGCACAGTCTG

CGGTCTCCTTGCTTTGCTCGTTCTTCTTCCAGGGTCTGATCCCCTTTGGTGGCTGAAGGAGGAACC

GGTGACCGACCTGGAGACCACAGTTCTCTGTCCTTCACACAGCTCTTTCACC

SEQ ID NO: 94 - Mus musculus Osr1 5'-UTR
NM_011859.3
TAGGCGGCTCGGTGCTAAGGGATGAGTGAGACGTAGCTCGGCCTCTCCCCAGCAAGTTCTCGCCGG

CACTGGTTCAGATTCAGAAAGGGAGCCAGGAGCGAGGCTCAGCAGACCCCGGCGGGTAGAACTCCG

GGGCTGTGAAGCGCTCCCGCGTGTCCGACTCTTGGAGTCACCGCAGCTACAGAAGCGTCAGAAGTC

TAGTTCGCCAGGGGTGCCAGTCGGCTCCAGAGTCTCTGGTCACTCAAGTCCAGCGCAGCGACCCTC

ACAGACGCGCTCTGCCCTGGGACCGCGGCGGAACAAGATATTTGAAATCATTGCGGTTCCCAGCGA

CAGAA

SEQ ID NO: 95 - Mus musculus Lmnb1 5'-UTR
NM_011121.3
GCCCGCCTCTCGCCGCCCTCCTCCTCGGCCCGCCCGCCGCTCTGAGCAGCCCGAGAGGAAACAAAG

TGCTGCGGGCGGGAGACTCGCGTCCGCCGCGCACAGCCGTCTGCGTCTCCCGGCTGCCCTGGCCTC

TTCCCGCGCGCGTCTGCGAGTGTGCGTGTACACTCACAAAGGGCGTCTGGCGGGCGATCGCGGCCC

TCCCGCTTCGCTCTTTGTGCGGTAGCCCCGCCGCCACCGCCAGCCCAGGTCCGCTCGATCCTCACC

GGCCTGTGGTTTGTACCTTCGGTCCCGCCGCCCGCC

SEQ ID NO: 96 - Mus musculus Aarsd1 5'-UTR
NM_144829.1
CCGGCTTTTCTGCGCGCGCGGGTCTCTCCGGCCTAGGAGACCGCG SEQ ID NO: 97 - Mus musculus Vma21 5'-UTR
NM_001081356.2
GCTTCGGCAGGGGCACTTCCGGCGCGACCGGCCTAGACTGTCACCCTGTTAGCCGCCGCTGAGCCT

CCGCTAACTACCCGGCGCCTGCTGCTGCCCTCCCGGCCACGCC

SEQ ID NO: 98 - Mus musculus Kif20a 5'-UTR
AACAAAGCTGTTCCTCGTGGGCGGAGTTGTGCTCTCCAGCCGCAGGAGTCTTGCTGCGCGGGTGGG

TAGAAGCTGGGATCAGAGAAGCGGCGAGGCAGACAGTCTTCGGACATAGACTGACTCTGCTTGTC

SEQ ID NO: 99 - Mus musculus Cdca8 5'-UTR
NM_026560.4
TGTGCCCGTTGAGTTTGAATTGGGTGGCGGTTAACCGAGGAGCCGCCCGTCCCTTAGTTGGAGCTG

TGAGGGTTCCTCAGACTGTGTTTGGGACCTGCAGGTAGGTTTCGGCAGAGTTCTGGAAACCTAGA

CTCCAACGACTGAACTTTCTCAGCTCTCCGACCGCTCACACCCTCTCCCCGTCTCAGTCGCGGAGC

CGGCTGCTTGGCCCCTCGCTCGACGCAGCCAGGCGCC

SEQ ID NO: 100 - Mus musculus Slc7a1 5'-UTR
NM_007513.4
GGTGCCCTGGAAGCTGACGCGCAGCACTGGCCGTGGCCGTGGGCCCGCGGAGGGCGGCGCGCGGC

TGATGAAACCGGCTCGGATTCCGCCCGCGTGCGCCATCCCCTCAGCTAGCAGGTGTGAGAGGCTTT

-continued

CTACCCGCGGTCTCCACACAGCTCAACATCTTGCCGCCTCCTCCGAGCCTGAAGCTACCGTGGACT

CTGCTGTGGCGTCTTGGCCCCCAGGTGCGGATCCTCCCCAGTGAGAAGTCCCACGAGTCTTACAGC

AGATTCGCTCAGCACA

SEQ ID NO: 101 - Mus musculus Ubqln2 5'-UTR
NM_018798.2
CGGAGACGGCCTGCAGGACCTGCTCTCTCAGCCCTCAGCCGAGGCCTACGCCGAGCCGAGTGCGCA

GCCGACGACCGGGAGGAGCCGCAGCCTTCAACTCTGAGGTACTGTGATCCGCGCTGCCCGCCGGGC

CGCCCCAGTCCGCTGCTGCGGCACCTCCTTCCCTCGCGCCCTCTTCGCTCGCCAGCGCCTTCCCTG

TGAGCCTGCGTCACCGCGGCCGCC

SEQ ID NO: 102 - Mus musculus Prps2 5'-UTR
NM_026662.4
AGCCCAGGCCACCGCAGCAGCAGCAGCAACAGCCGCAGCAACGGTAGCAGTAGTCTGCATCGCAGT

CCCTTTCTCCTTCTCCAGCGCGCTCCTCAGTCCCCGGTCACC

SEQ ID NO: 103 - Mus musculus Shmt2 5'-UTR
NM_026662.4
CTCTTTCACTCGAACTTCACGGGGGCAATTTTCTCGCGCACGCGTTCTAAGAGCAGCTGGTTTTCG

ACCCCGGTACTACACCGATACAGAGTTAGTGGCTAGTCCTCCTGTGCCTCCTGTAGCG

SEQ ID NO: 104 - Mus musculus Kif22 5'-UTR
NM_145588.1
GGCCGAAGAAGGGAAGGCT

SEQ ID NO: 105 - Mus musculus Aurkb 5'-UTR
NM_011496.1
GGAGATTCGAAAGCGTCCGGGTCGCGGGGTAAACCGGTTCTCCGTGTGCGAGCGCCTAGTGGCGTA

GGCTGCGGCTTTGCGGGGAACTGCGGGGGCTGCAGTGGTCCACGGGGCTGATCGGGTTCCGTTGGG

CGGATCCACGTGCCCGCTATCCGCCTGGAAGGAGAGGTGCAGGAGTACCCCCGACCTTGGCTGCGT

GCTGACTCGCTTCCTTCTGCCCGCCCAGGCTTGCACTCCCCGGGGATCTGCCTCTGCATCTCTTGC

CTTCGCTGTTGTTTCCCTCTCTGTCCAGCTCCCCTCCCGCTCTCGCCCTGGAGA

SEQ ID NO: 106 - Mus musculus Fignl1 5'-UTR
GTCACTTCGCGCAGGCGCACTTCGAAAGGCGCGCTTTTCGGTGGCTGCGGTCCCGGCAGGGAGCAC

AGCTCATCCTGTGCTGATAACATCGAGAAGTGTTCAGTGCCTGGTAAAGTACATAGACCTTGCTTC

ACTTGGAACTCGGCCTTGATTTCTGCCGTTGGTCATAATCAGCAGAGTTCTCTCTAAACCTTTGAC

SEQ ID NO: 107 - Mus musculus Cad 5'-UTR
NM_023525.2
AGTCGTGCTTCAGCTCACTACGCTTAGGGCTCTGGCTTGCCGCTCCCGCCTGCTCTCCAGCGCCCC

GCGCAGCGAGCCACGTGGACCAACTCCGGCGCGCGGTGTTCGCTTGGTTCCAGTGGGGCTCGCCGC

GCCTCCCGCGTCTGCGTGCTTGCCCTGTCTCAGCTCCGACCCG

SEQ ID NO: 108 - Mus musculus Anln 5'-UTR
NM_028390.3
GTGTCGTCCGGGGCGCTGAAATTCAAATTTTGAACGGCCGTGGTAGCCTACCGACTCCGTGGGTGC

GGAGGGCAGAGCCGACTGGGTGTGAGAGCGCCCGCCGCCTCGACTGCAGTCCTCCTCCAGGAGCTG

CGCCGAGCCTGCACTCACTTCTTTCCTCTTCCTGAGTTTGAACCGTCGGACCCACCGTCTAGCCGT

CCACTGGTGAGGCCTGGGGCG

SEQ ID NO: 109 - Mus musculus Slfn9 5'-UTR
GGGAATTCCACGCCACCTCCGCGCGCTCTGCGCTCTGGGATCCGGAGCGACCAGGACCTGGTGAGA

CCCTCAGCTCCCCTCCACCTTCCCCGAGGTCCAGCACACCAGAACTGGAACCTGAGCAGCCCAGAA

GCCAGGGTGGCACCACTGTGTCTCTCCTGTCTGAAGACCCGGATATTTTCTCAGACTTGGCGACAC

GTTCCTTTAAAAGATCAGC

SEQ ID NO: 110 - *Mus musculus* Ncaph 5'-UTR
NM_144818.3
AAAGACCACGCCCCAGTGACGTCACGCGGCGGTTACCGCGCTTGGCGCTCGCGATTTAAAACTTAC

TCCGGAGACGTGGAGAGCAAG

SEQ ID NO: 111 - *Mus musculus* Cth 5'-UTR
NM_145953.2
AGCCAAAGCAACACCTCGCACTCCTGCCCCAGC SEQ ID NO: 112 - *Mus musculus* Pole 5'-UTR
NM_011132.2
GCCTCGCGAGAGCACGTGGAGAGCGCGCCAAATTCTCCCCGGAGCCTGAGGGAGCTTTGGAGCGTC

GCA

SEQ ID NO: 113 - *Mus musculus* Uhrf1 5'-UTR
NM_001111079.1
AATTGGGGTGGAAGTCTCCCGCAGCAGCCTGTGCACACTAATAAAAACGCCCTGAGTTTTCGCGGG

AAAAAAAGTCCTAGCAGCTGGAAGGAACCCGCGCTCTAGTGCTCACTTGGGTCTTCAGCCACTCAC

GCGGCTCCCTTCTGGGTCACCCAGCCGCAGAGCCCTAGCCTAGAACCAGGCGTTCCAAGGGAGAGG

AGAGTGCGGATCGCCGCCGTGAGAGAGTACATCGGCATC

SEQ ID NO: 114 - *Mus musculus* Gja1 5'-UTR
NM_010288.3
TTTTAAAAGCTCTGTGCTCCAAGTTAAAAAACGCTTTTACGAGGTATCAGCACTTTTCTTTCATTG

GGGGAAAGGCGTGAGGGAAGTACCCAACAGCAGCAGACTTTGAAACTTTAAACAGACAGGTCTGAG

AGCCCGAACTCTCCTTTTCCTTTGACTTCAGCCTCCAAGGAGTTCCACCACTTTGGCGTGCCGGCT

TCACTTTCATTAAGTGAAAGAGAGGTGCCCAGAC

SEQ ID NO: 115 - *Mus musculus* Fam64a 5'-UTR
CGGTGGGCTAGGAGAGGGTGTTGATCTTCGGGTCCGGGTATCGAGCAGGGAGGATCTAGCGGGCAG

CGGAAACTGGACCAAGCAC

SEQ ID NO: 116 - *Mus musculus* Kif2c 5'-UTR
NM_134471.4
TGACGTTGTAGGGAGGCTGGCGCGCGGGATTTAAACTGCAGCGGTTTAGGCGTTGTTAACACAGCG

CAGTATTAGCAGAGTCGTGGTTTCCAAGCTTCTTTCATTTGTGTTGCCTGTTGTTGTTCCTGAGTC

C

SEQ ID NO: 117 - *Mus musculus* Tspan10 5'-UTR
NM_145363.2
CACTGGAGGAGGAGCTTGCAGCTCTCCAGCTCTGGCTTATACAGTTCACAGAGAAGCCAAGGGACA

CCGGGACACCGTTATTTTAGGACTGTAACCTGTTCAGAGAGACCCTGGCCACTGCTCTCCGTGGTT

TTCTCCAATTGTGTGG

SEQ ID NO: 118 - *Mus musculus* Scand1 5'-UTR
TTCATTTCCGGCCACCGAGGAGCTTCGCGGGTCGAGACGCAGGCGAGGCGCCGGACTGCGAAACAA

AGGGGGACGCCAACAGCCGTAGTC

SEQ ID NO: 119 - *Mus musculus* Gpr84 5'-UTR
NM_030720.1
TTATATGTCCAGCTGGAAGCCTGGCTGTCCCTAGAAAAGCTGGAAGCCTGACTGCCCCTCAAAAGA

CCTGCTCTTTAGGAGAGCTAGATATTGTTTACTGAAGACAAGTGTGAAAACTGGGAACCTCAGTCT

CCATC

SEQ ID NO: 120 - *Mus musculus* Tpgs1 5'-UTR
BC138516.1
AAATGGTCGTCGAGGGAAGGCGCCTCATCGCGCCGTGAATT SEQ ID NO: 121 - *Mus musculus* Ccl17 5'-UTR
NM_011332.3
AAGACAGGCAGAAGGACCC -continued SEQ ID NO: 122 - *Mus musculus* Fads3 5'-UTR
NM_021890.3
AAGGGAGGGAAAAGTTCCCTGCGCGGAGAGCCGGGCAGGCGCACGCTCTTACGGCGGCCGCAGCGG

CAGGGCGGGGCCGGTGGGGCGGGCGGAGGAAGACCCCTGATTGCCACCTCGCCTCCCTCAGTGTCT

CTCTTAGACCTTGGTCACGTACCGGGGTCCGGAGGACTTGTGTACAGCGGCA

SEQ ID NO: 123 - *Mus musculus* Cers6 5'-UTR
NM_172856.3
AGCGCGCATCCCCAGTGCCCTGAGCTGCAGAGAGCTCGGAGGAGCGCGGGAGCAGCGACACCGGAG

TGGACAAAGCAAG

SEQ ID NO: 124 - *Mus musculus* Alkbh7 5'-UTR
NM_027372.1
AGCCTGCTGTGGTCAATCCCTGAAG SEQ ID NO: 125 - *Mus musculus* Ms4a8a 5'-UTR
GTAGAGAGGACTTTGGATCATTCTAA SEQ ID NO: 126 - *Mus musculus* Cxcr4 5'-UTR
NM_009911.3
AATTTTGTTGCCTGGTGCAGCAGGTAGCAGTGAAACCTCTGAGGCGTTTGGTGCTCCGGTAACCAC

CACGGCTGTAGAGCGAGTGTTGCC

SEQ ID NO: 127 - *Mus musculus* Gprc5c 5'-UTR
CAGAAACTCCGATCGCCTTTCCCAACCCGAAAGTGCGCGTCGGCCGAGCCTGGAGGGACCCAGCTG

AAGCCTGGCCTGGGAGCCAGG

SEQ ID NO: 128 - *Mus musculus* Fen1 5'-UTR
NM_007999.4
AGATCACGTGACGAGAGCGCGGGCTTTGGAAGGCGGCGAAGCTGGGAACGATACTGAAAGAACGGG

CTCGGGACTGTCCAGAGAACGCTGTGGACTCCAAACCACTGCTAGCTGCTTAAGGCTCGTGCACTC

GAGACGGGGTGAGGTCTCGCGGAAGCGTCTCTGAAAGCGGCAGAGCCGCGGGAACAGCACCGGGCA

GCCCGGGCTTGGGCCATTCGCTCTGCTCCGAACATTCCTCTTCGCCGGTAGGAAGAAGCCATTGCT

CCTGTGCTACC

SEQ ID NO: 129 - *Mus musculus* Cspg4 5'-UTR
NM_139001.2
GACTTGCGACTTGCGACTCGGTGCTGTCCAGATTCAGCACGCTCTGTTCCTTCGCCTTACAAGTCC

AGGCACCCAGCCCCGCCGCG

SEQ ID NO: 130 - *Mus musculus* Mrpl34 5'-UTR
NM_053162.2
GAAGGCATTGTCAAGGAGCCCAGAGTGTAGGAACTGGCATTGACCCGGACGACCGGACCATTGACC

CGCCGCTGGAT

SEQ ID NO: 131 - *Mus musculus* Comtd1 5'-UTR
CGGCTCTGTGGGCAGGGCCCGGACAAGGTGGAGCCCTGTCGGCTTACTGGTCCCAGTCCCATCCTC

GCTACTCCAGCACACGTGACCTCCGCCGCCGCTGCTAACCTGCACC

SEQ ID NO: 132 - *Mus musculus* Armc6 5'-UTR
NM_133972.2
CGCTGCTCACTTCTCAGGGCCGAGTCTACCTAGGTGAAAACTATCTCTTTTGAGGGGAAGCGACAC

CTAGGAGTAGCATTGAGAGTACTGCAAGAGTCTCAGGCCCACGCGTATTCTGTGGCTCCCTTCGCT

TTACCTGTGCTCGCGGTCGCCCTCGTTGCCCCGGAAAGGAGCCTCTCGGCTGAAGGAGGGACGCCG

AGGCGAGGCGGCGCCTCTGCGCTTGCGCTTATATGGTGGCTCGAAGGAGCCAAAGGCAAAGTCTCG

GGTGACAGCTGCGAGCCCCACCCTTTCCCCACGTGGCTGCGTAGACCCGGCAGTG

SEQ ID NO: 133 - *Mus musculus* Emr4 5'-UTR
NM_139138.3
AACATTCCTTGAGAAAGAGAGAACAAGATAAGCAGTGGTGCACTTCCTCCTTCATTGCTGCTGAGA

ATGTTCCAGGCTGAGTGAGAAGTAAAAATTCATCATCTCTGAAGAACTCTTACCCAGCCCTGTTGA

AGAAATTCCCAGA

-continued

SEQ ID NO: 134 - *Mus musculus* Atp5d 5'-UTR
NM_025313.2
CCTTCGGAGAATCCTGTGCGCGTGCGTTCTTGTGGGAACTGCGCCTCCCAGAAGGCACCGCGCGTC

GTCCTTCTCCCTCCCTGAAGGCCGCCTCGCTTGCCCAGTGTGTCGGCCGCCCGCGAAGCTAGAGTC

CACTGACTTTTCCGCCACC

SEQ ID NO: 135 - *Mus musculus* 1110001J03Rik 5'-UTR
GCGGAGTGGGCGGGGAACACCTCGCCCGAGGCAGTGAGGGACCAGGCTCTCCAAGGACAGAAAA SEQ ID NO: 136 - *Mus musculus* Csf2ra 5'-UTR
CCCAACCTGCAGATGAGGAAGAGGAAGCGGGAGACAGACGGACAGACGGACGGACACAGACGCTGC

GCCCAGGCCTCACCATCCATCGCAGGAAGCCCCCTGTCTCAG

Some of these wild-type 5'-UTR elements differ from publically available 5'-UTR sequences identified by Gen-Bank at NCBI, see the Table 1 (Example 1). This table reflects sequencing results of the present inventors.

Thus, 5'-UTR elements selected from the group consisting of SEQ ID NO: 45, SEQ ID NO: 47, SEQ ID NO: 49, SEQ ID NO: 77, SEQ ID NO: 79, SEQ ID NO: 84, SEQ ID NO: 85, SEQ ID NO: 90, SEQ ID NO: 92, SEQ ID NO: 93, SEQ ID NO: 98, SEQ ID NO: 106, SEQ ID NO: 109, SEQ ID NO: 115, SEQ ID NO: 118, SEQ ID NO: 125, SEQ ID NO: 127, SEQ ID NO: 131, SEQ ID NO: 135 are contributed by the present invention and may be employed in any aspect of the present invention.

Examples of Artificial 5'-UTR Elements Useful in the Present Invention

In some embodiments, the 5'-UTR element according to the present invention differs from a wild-type 5'-UTR element. Such 5'-UTR elements are designated "artificial 5'-UTR elements".

It is preferred that an artificial 5'-UTR element shows a degree of sequence identity to a wild-type 5'-UTR element which is (a) less than 100%, and at the same time (B) more than 10%, more than 20%, more than 30%, more than 40%, more than 50%, more than 60%, more than 70%, more than 80%, more than 90%, more than 95%, such wild-type 5'-UTR element being selected from the group consisting of SEQ ID NOs: 1 to 136. Typically the artificial 5'-UTR element differs from the wild-type 5'-UTR element it is based on in that at least one nucleotide, such as two nucleotides, three nucleotides, four nucleotides, five nucleotides, six nucleotides, seven nucleotides, eight nucleotides, nine nucleotides, ten nucleotides, or more than ten nucleotides, is/are exchanged. For example, such a nucleotide exchange may be recommendable in case the wild-type 5'-UTR element comprises a nucleotide element which is considered disadvantageous. For example, in some embodiments a nucleotide element which is considered disadvantageous is selected from (i) an internal ATG triplet (i.e. an ATG triplet other than the start codon of the open reading frame of the nucleic acid of the invention) or (ii) a restriction enzyme recognition site (cleavage site), particularly the restriction enzyme recognition site (cleavage site) which is recognized (cleavable) by a restriction enzyme used in the process of making (cloning) the artificial nucleic acid of the present invention. Hence, it is possible to specifically introduce certain base(s) (in exchange, preferably substitution, for the respective wild-type base(s)), so that the artificial 5'-UTR element does not contain a nucleotide element which is considered disadvantageous. In specific embodiments, the artificial 5'-UTR elements is selected from the group consisting of SEQ ID NOs: 137 to 151:

SEQ ID NO: 137 - Artificial Sequence (based on SEQ ID NO: 3)
ATCT<u>TAGCTT</u>CTCTGTCTTCCTCCCTCCCTCCCTTCCTCTTACTCTCATT

CATTTCATACACACTGGCTCACACATCTACTCTCTCTCTCTATCTCTCTC

AGA

[This sequence corresponds to the wild-type sequence it is based on, except that AAGCTT is replaced by TAGCTT underlined above for emphasis]

SEQ ID NO: 138 - Artificial Sequence (based on SEQ ID NO: 9)
ATCACAGCCCTTCCCCGATCCTCTCCGTGGGAGCCAGCGAGCCTCTCTCCCTGATCTTACGTGCTC

AAGGGAGCTCACACGTTCACCAACTCACCCTTGAAGTCATCTCAAGAACAAAAGACAACTGAAAGA

AGCTGTTGTGAAGGCAGAGCAGCATCTGCTGAAGAGACAGAAACCAGCCCCAGAGGTGTCACAGGA

AGGCACCAGCAAGGACATTGGTCTTTGATTTGATTCAGCAGTCCTGTCAAGTATAA<u>TAG</u>TG

[This sequence corresponds to the wild-type sequence it is based on, except that ATG is replaced by TAG, underlined above for emphasis]

SEQ ID NO: 139 - Artificial Sequence (based on SEQ ID NO: 14)
<u>TAG</u>GGCTGGAGCTCCGGGCAGTGTGCGAGGCGCACGCACAGGAGCCTGCACTCTGCGTCCCGCACC

CCAGCAGCCGCGCC

-continued

[This sequence corresponds to the wild-type sequence it is based on,
except that ATG is replaced by TAG, underlined above for emphasis]

SEQ ID NO: 140 - Artificial Sequence (based on SEQ ID NO: 17)
CAGTCGTCCCTGCGCGTCGTCCTCCTCGCCCTCCAGGCCGCCCGCGCCGCGCCGGAGTCCGCTGTC

CGCCAGCTACCCGCTTCCTGCCGCCCGCCGCTGCC

[This sequence corresponds to the wild-type sequence it is based on,
except that GACGTC is replaced by GTCGTC, underlined above for emphasis]

SEQ ID NO: 141 - Artificial Sequence (based on SEQ ID NO: 18)
TAGGCGACCTCCGGAAACCGTAGATTCCGGGCGGTCGGAGCCGCCGGGAGCTGTAGTTCTCCCGC

GGCTCAGAGAAGTAGGCAGAGAGCGGACCTGGCGGCCGGGCAGC

[This sequence corresponds to the wild-type sequence it is based on,
except that ATG is replaced by TAG, underlined above for emphasis]

SEQ ID NO: 142 - Artificial Sequence (based on SEQ ID NO: 29)
ACCGGTAGTAGCTCGGCTAGAACCACTAGGCGCCTGGCGGGGGTGATCTGTCGGAGCGACCGGCTT

GGCGCCTGCCTGTCCCCAGCCCCTCTCAGCTTGAACTCCTTCCTTCAAGTCTGGGCCCTCGAGGCT

TCCAGAGCGGCCTCCAGGGGTGCAGTCTCAGTTCCCCACGCCAGCCGTCTCCGTCCTCCGCCTCCT

CCGGGCCTGGCAGGTGGCACTGTCCGGAGGCGGAGCCTTGGGCGAGGGGTGGTTGCGGCGGAGGAC

GCAACCGAGCGGGCCTGCGGCCTCACC

[This sequence corresponds to the wild-type sequence it is based on,
except that two ATG have each been replaced by TAG, both underlined
above for emphasis]

SEQ ID NO: 143 - Artificial Sequence (based on SEQ ID NO: 31)
CTTTTCCCGGCACTAGCGCACCGCAGCGGGTCGCGCGCCCTAAGGAGTGGCACTTTTTAAAAGTGC

AGCCGGAGACCAGCCTACAGCCGCCTGCATCTGTATCCAGCGCCAGGTCCCGCCAGTCCCAGCTGC

GCGCGCCCCCAGTCCCGCACCCGTTCGGCCCAGGCTAAGTTAGCCCTCACC

[This sequence corresponds to the wild-type sequence it is based on,
except that ATG is replaced by TAG, underlined above for emphasis]

SEQ ID NO: 144 - Artificial Sequence (based on SEQ ID NO: 42)
CTTGATCTGTGGGCGGGGCGCGGCCTGTGG

[This sequence corresponds to the wild-type sequence it is based on,
except that AGATCT is replaced by TGATCT, underlined above for emphasis]

SEQ ID NO: 145 - Artificial Sequence (based on SEQ ID NO: 43)
GTAGATTTGAGGGACAACAATTCAGTGCCCGGGGGCCGAAAGGCAGCAGAAGGCGGGCACCAAAGG

ATAGGCACCCGGAAGGTGGACTCCGAGGAGGAGAGAGGACAGGGGTCTCTCACCCCAGCTCCTGGT

CACC

[This sequence corresponds to the wild-type sequence it is based on,
except (i) that ATG is replaced by TAG, and (ii) that GAATTC is replaced by
CAATTC, each underlined above for emphasis]

SEQ ID NO: 146 - Artificial Sequence (based on SEQ ID NO: 52)
GGCCGGACGCCTCCGCGTTACGGGATGAATTAACGGCGGGTTCCGCACGGAGGTTGTGACCCCTAC

GGAGCCCCAGCTTGCCCACGCACCCCACTCGGCGTCGCGCGGCGTGCCCTGCTTGTCACAGGTGGG

AGGCTGGAACTATCAGGCTGAAAAACAGAGTGGGTACTCTCTTCTGGGAAGCTGGCAACAATAGGT

AGTAGTGATAT

[This sequence corresponds to the wild-type sequence it is based on,
except that three ATG have each been replaced by TAG, each underlined
above for emphasis]

SEQ ID NO: 147 - Artificial Sequence (based on SEQ ID NO: 109)
GGCAATTCCACGCCACCTCCGCGCGCTCTGCGCTCTGGGATCCGGAGCGACCAGGACCTGGTGAGA

CCCTCAGCTCCCCTCCACCTTCCCCGAGGTCCAGCACACCAGAACTGGAACCTGAGCAGCCCAGAA

-continued

```
GCCAGGGTGGCACCACTGTGTCTCTCCTGTCTGAAGACCCGGATATTTTCTCAGACTTGGCGACAC

GTTCCTTTAAAAGATCAGC
```

[This sequence corresponds to the wild-type sequence it is based on,
except that GAATTC is replaced by CAATTC, underlined above for emphasis]

SEQ ID NO: 148 - Artificial Sequence (based on SEQ ID NO: 110)
```
AAAGACCACGCCCCAGTCACGTCACGCGGCGGTTACCGCGCTTGGCGCTCGCGATTTAAAACTTAC

TCCGGAGACGTGGAGAGCAAG
```

[This sequence corresponds to the wild-type sequence it is based on,
except that GACGTC is replaced by CACGTC, underlined above for emphasis]

SEQ ID NO: 149 - Artificial Sequence (based on SEQ ID NO: 119)
```
TTATTAGTCCAGCTGGAAGCCTGGCTGTCCCTAGAAAAGCTGGAAGCCTGACTGCCCCTCAAAAGA

CCTGCTCTTTAGGAGAGCTAGATATTGTTTACTGAAGACAAGTGTGAAAACTGGGAACCTCAGTCT

CCATC
```

[This sequence corresponds to the wild-type sequence it is based on,
except that ATG is replaced by TAG, underlined above for emphasis]

SEQ ID NO: 150 - Artificial Sequence (based on SEQ ID NO: 120)
```
AATAGGTCGTCGAGGGAAGGCGCCTCATCGCGCCGTGAATT
```

[This sequence corresponds to the wild-type sequence it is based on,
except that ATG is replaced by TAG, underlined above for emphasis]

SEQ ID NO: 151 - Artificial Sequence (based on SEQ ID NO: 136)
```
CCCAACCTGCAGTAGAGGAAGAGGAAGCGGGAGACAGACGGACAGACGGACGGACACAGACGCTGC

GCCCAGGCCTCACCATCCATCGCAGGAAGCCCCCTGTCTCAG
```

[This sequence corresponds to the wild-type sequence it is based on,
except that ATG is replaced by TAG, underlined above for emphasis]

3'-UTR Elements

Preferably, the at least one 3'-UTR element comprises or consists of a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence selected from the group consisting of SEQ ID NO: 152 to 204 or the corresponding DNA or RNA sequence, respectively, or wherein the at least one 3'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence selected from the group consisting of SEQ ID NO: 152 to 204 or the corresponding DNA or RNA sequence, respectively.

Among the sequences detailed in the following, SEQ ID NO: 152 to 203 can be considered as wild-type 3'-UTR sequences, and SEQ ID NO: 204 can be considered as artificial 5'-UTR sequence.

SEQ ID NO: 152 - Homo sapiens NDUFS7 3'-UTR
NM_024407.4
```
CGCCGCCGCCGCCGCCGCCGGAGCCTGTCGCCGTCCTGTCCCCAGCCTGCTTGTGTCCCGTGAGGT

TGTCAATAAACCTGCCCTCGGGCTGCCGCCTCCC
```

SEQ ID NO: 153 - Homo sapiens PHGDH 3'-UTR
NM_006623.3
```
CCTTGGAGCTCACTGGTCCCTGCCTCTGGGGCTTTTCTGAAGAAACCCACCCACTGTGATCAATAG

GGAGAGAAAATCCACATTCTTGGGCTGAACGCGGGCCTCTGACACTGCTTACACTGCACTCTGACC

CTGTAGTACAGCAATAACCGTCTAATAAAGAGCCTACCCCCAACTCCTTCTGC
```

SEQ ID NO: 154 - Homo sapiens TSPO 3'-UTR
NM_000714.5
```
GTGCCCGGCCCACCAGGGACTGCAGCTGCACCAGCAGGTGCCATCACGCTTGTGATGTGGTGGCCG

TCACGCTTTCATGACCACTGGGCCTGCTAGTCTGTCAGGGCCTTGGCCCAGGGGTCAGCAGAGCTT

CAGAGGTGGCCCCACCTGAGCCCCCACCCGGGAGCAGTGTCCTGTGCTTTCTGCATGCTTAGAGCA

TGTTCTTGGAACATGGAATTTTATAAGCTGAATAAAGTTTTTGACTTCCTTT
```

SEQ ID NO: 155 - Homo sapiens ATP5D 3'-UTR
NM_001687.4
GCGGTGCGTACCCGGTGTCCCGAGGCCCGGCCAGGGGCTGGGCAGGGATGCCAGGTGGGCCCAGCC

AGCTCCTGGGGTCCCGGCCACCTGGGGAAGCCGCGCCTGCCAAGGAGGCCACCAGAGGGCAGTGCA

GGCTTCTGCCTGGGCCCCAGGCCCTGCCTGTGTTGAAAGCTCTGGGGACTGGGCAGGGAAGCTCC

TCCTCAGCTTTGAGCTGTGGCTGCCACCCATGGGGCTCTCCTTCCGCCTCTCAAGATCCCCCCAGC

CTGACGGGCCGCTTACCATCCCCTCTGCCCTGCAGAGCCAGCCGCCAAGGTTGACCTCAGCTTCGG

AGCCACCTCTGGATGAACTGCCCCAGCCCCGCCCCATTAAAGACCCGGAAGCCTG

SEQ ID NO: 156 - Homo sapiens EXOSC4 3'-UTR
NM_019037.2
CCACCCAGCCACCCATGTCCAGAATAAAACCCTCCTCTGCCCACAC SEQ ID NO: 157 - Homo sapiens TUBB4B 3'-UTR
NM_006088.5
AGCCTTCAGTCACTGGGGAAAGCAGGGAAGCAGTGTGAACTCTTTATTCACTCCCAGCCTGTCCTG

TGGCCTGTCCCACTGTGTGCACTTGCTGTTTTCCCTGTCCACATCCATGCTGTACAGACACCACCA

TTAAAGCATTTTCATAGTG

SEQ ID NO: 158 - Homo sapiens TUBA4A 3'-UTR
NM_006000.1
AGCAGCTGCCTGGAGCCTATTCACTATGTTTATTGCAAAATCCTTTCGAAATAAACAGTTTCCTTG

CACGGTT

SEQ ID NO: 159 - Homo sapiens EMP3 3'-UTR
GCGCCCCGCCTCGCTCGGCTGCCCCCGCCCCTTCCCGGCCCCCCTCGCCGCGCGTCCTCCAAAAAA

TAAAACCTTAACCGCGG

SEQ ID NO: 160 - Homo sapiens CRIP2 3'-UTR
NM_001312.3
GCTACAGCGGCTCTCATGATGTGGGCTCACCTGCGCCCCAGACCCTGCAGGGGCCCCCCTGCTTGG

CTCTGCTGGGAGAGTGCTCAGCCGCCCAGTCCTGCCTGCAAGCCCAGGGCGAGTATTGGAGGAGGG

GCAGCCACGGGCAGAGCACCATGCCCATCCCCGAGTCTCTGGTGTGTCTGCCCCCTCTGGCATCCT

CTGGGCGTCCCATGATCCCTTCTGTGTCTGCGTGTCCGAATCCCCGTGTGACCCTGTCCCAGCATT

TTCCCGCCGACCCTGCGTGTCCCCGTGGCGCTGTCCGCTCTCCCTCTCCTGCTGCCCACCCACCTG

CCAGTGTTATTTATGCTCCCTTCGTGGGTGATGGCCACGCCCTCACCATGTCCCTGGCAGAGGGCT

TCCCTCCGGGATCCCCTGCCTGGTGCCCACACTGCCTCGCAAGCGCTCGCCACCCTCACGTGGCTC

ACCTGCTGTTGAGCCTTGTGCTGTCAATAAACGGTTTGAGGATTGCAGGATTGTC

SEQ ID NO: 161 - Homo sapiens BRAT1 3'-UTR
NM_152743.3
GCAGAACCAGAGTCTGCCACTGGGGCTCAGGACCAAGGGAGGCAGCACCATGTCCTTCTGTGGGAC

ACTGCCAGCCCCAGGGCTCCAGCCCAGCCCGGTGGATCCTCTGGGGAAGCCAGGACCAGGAGAGAA

GCAAGGTCAAGAAATCCCACAGTTTGATGTATTAAAGAAATGACTTATTTCTACTCAAAATAAATG

GCATTGAAGTCTTTCTTTAACCCTTTTTGAGTTAATTTAATAATAATGATCTGAGACAAGG

SEQ ID NO: 162 - Homo sapiens CD9 3'-UTR
NM_001769.3
AGTCAGCTTACATCCCTGAGCAGGAAAGTTTACCCATGAAGATTGGTGGGATTTTTTGTTTGTTTG

TTTTGTTTTGTTTGTTGTTTGTTGTTTGTTTTTTTGCCACTAATTTTAGTATTCATTCTGCATTGC

TAGATAAAAGCTGAAGTTACTTTATGTTTGTCTTTTAATGCTTCATTCAATATTGACATTTGTAGT

TGAGCGGGGGTTTGGTTTGCTTTGGTTTATATTTTTTCAGTTGTTTGTTTTTGCTTGTTATATTA

AGCAGAAATCCTGCAATGAAAGGTACTATATTTGCTAGACTCTAGACAAGATATTGTACATAAAAG

AATTTTTTTGTCTTTAAATAGATACAAATGTCTATCAACTTTAATCAAGTTGTAACTTATATTGAA

GACAATTTGATACATAATAAAAAATTATGACAATGTCCTGGACTGGT

-continued

SEQ ID NO: 163 - Homo sapiens CDK9 3'-UTR
NM_001261.3
GGGCCGGCGCTTGCCACTAGGGCTCTTGTGTTTTTTTCTTCTGCTATGTGACTTGCATCGTGGAG

ACAGGGCATTTGAGTTTATATCTCTCATGCATATTTTATTTAATCCCCACCCTGGGCTCTGGGAGC

AGCCCGCTGAGTGGACTGGAGTGGAGCATTGGCTGAGAGACCAGGAGGGCACTGGAGCTGTCTTGT

CCTTGCTGGTTTTCTGGATGGTTCCCAGAGGGTTTCCATGGGGTAGGAGGATGGGCTCGCCCACCA

GTGACTTTTTCTAAGAGCTCCCGGCGTGGTGGAAGAGGGGACAGGTCCCTCACCCACCCACAATCC

TATTCTCGGGCTGAGAACCCTGCGTGGGGACAGGGCTCGCCTCAGGAATGGGCTGTTTTTGGCCTA

ACCCTCAGAAACACTGGGGCTGGCACAAACTCTTGGTTTCTTCAACAGGAGAATTTTACTGTGTTT

CTTTTGGTTCCATTGTTTGGAGACATTCCTGGGCACAGTTTGGTCCGTTAGAATTAAAAGTTGAA

SEQ ID NO: 164 - Homo sapiens PSMB3 3'-UTR
NM_002795.2
CCCTGTTCCCAGAGCCCACTTTTTTTTCTTTTTTTGAAATAAAATAGCCTGTCTTTC SEQ ID NO: 165 - Homo sapiens PSMB6 3'-UTR
NM_002798.2
ATCCTGGGATTCTAGTATGCAATAAGAGATGCCCTGTACTGATGCAAAATTTAATAAAGTTTGTCA

CAGAGAATCTTTGTA

SEQ ID NO: 166 - Homo sapiens PRSS56 3'-UTR
NM_001195129.1
GCCATGTCTGGGCCCCCAGCCCCTGGGGAGGACCTACTGCTCCCAGGGGCTGAGAGGGGTTCGGGA

GCATAATGACAAACTGTCGCTGCCCCAGTGGCTGGGTGTGTGGGTGGGATGGGGTGGGGGTCCT

GGGCCCCCCGTGTCTTCCCAGGTTTACAATCAGAGAATCACAGCTGCTTTAATAAATGTTATTTAT

AATACACGGAA

SEQ ID NO: 167 - Homo sapiens SCAND1 3'-UTR
NM_016558
GCGGTGGAGCTGCGGGCGGCCAGGGCCGGGCGCTCTGTGCGGACTGGGGCCATGATCGGGCCCGGG

GGCCTGAGCCTGGGACCCCACCCCGTGTTAATGAAAAATGAGTTTTGGCAGCGCCTGTGGTC

SEQ ID NO: 168 - Homo sapiens AMN 3'-UTR
NM_030943.3
GCGGCCGCCTGACCGTCGACCTTGGGGCTCTCCACCCGCTCTGGCCCCAGTCGAACTGGGGGCTAG

CCACCTCCTCGTCCAGCCCCCAAACCTCCCCTTCCTTTCCCCCTCCTCCGGGGGCCAAGGACAGGG

TGGCCTTACTCAGTAAAGGTGTTTCCTGC

SEQ ID NO: 169 - Homo sapiens CYBA 3'-UTR
NM_000101.3
CCTCGCCCCGGACCTGCCCTCCCGCCAGGTGCACCCACCTGCAATAAATGCAGCGAAGCCGGG SEQ ID NO: 170 - Homo sapiens PCOLCE 3'-UTR
NM_002593.3
GACGCAGGCCAGCCCCGGCCCCTAGCCCTCAGGCCTTCTTTCTTATCCAAATAAATGTTTCTTAAT

GAGG

SEQ ID NO: 171 - Homo sapiens MAP1S 3'-UTR
NM_018174.4
CCCCATCGCCGACACGCCCCCCACTCAGCCCAGCCCGCCTGTCCCTAGATTCAGCCACATCAGAAA

TAAACTGTGACTACACTTGGCAA

SEQ ID NO: 172 - Homo sapiens VTN 3'-UTR
NM_000638.3
GAGTCAGAGCCCACATGGCCGGGCCCTCTGTAGCTCCCTCCTCCCATCTCCTTCCCCCAGCCCAAT

AAAGGTCCCTTAGCCCCGAGTTTAAA

SEQ ID NO: 173 - Homo sapiens ALDH16A1 3'-UTR
NM_001145396.1
TGCCTGAGCGCCACCTACTGCATTTTGGACACCTCACACCAAGGGGAGATGCACCCCACAGACACC

TGGGACTTTCCCCTTCTGGTTCCTGTGTCTCCCAATAAACTCTCTGACCAACCCTAGCTGTGCTTC

```
TGCGAGAAGAAAGGGTGTAGCAACTTCTGGCAGATATGAGGCTTTTTCTTTTTTTTTTTTTT

TGAGACAACGTCTGGCTCTGTCACCCAGGCTGGAGCGCAGTGGCACAATCTCGGCCCACTGCAGCC

TCGACCTCTGGGGCTCAAGGGATCCTCATGCCTCAGCCTCATATGTAGCTGGGGCCACAGACATGC

ACCACCACACCTGGCTCGAGGCCATTTTAGTTCTGAGGTTGAGCAGCTCAGGAGCCGGCTCCAGCA

CGGTGCTGTGTTTGTGAAACAGAGAAAGGGGACCCCCGAGGACCCCAGACAGGGCCTTAGGACTCT

CATATCTTCTTGTCTTCTCCATCTGGTGGCTCTTGCTCTCTGGTTTTCTCTACCTTTTCATGGCCC

CAGAATCCATATGCAGTAAAGGAACTCTCTGGAATAAAATTAAAGTCCTCCT

SEQ ID NO: 174 - Mus musculus Acox2 3'-UTR
NM_001161667.1
AAAGCCAAAGGATTCAGGACCAAGCAGCACCATGGCCTTCCTATGGCACATATGCATATAAAGAAT

TTAAAGCACGGGGTGGCGTGCGGCTTGTTCAGATCAGCGAGTAAACTGGTACATGAAAGGATGTTC

ATCATATTATTCTGCTACTGAGTACATCTGAAACTTTCCCTTGTCTGTTTGTAGTACGTATTTGGC

TAAATGCTAGAATTTTGCTTTAAATACAGCAAAAGCTAATAAACTTGTTAGTAACTA

SEQ ID NO: 175 - Mus musculus Ubc 3'-UTR
BC006680.1
TGGGGGAGGTGTCTTAGTTTTCCCTATCTTTTAAGCTGTTAACAAGTTTCATTGCACTTTGAATAA

AGTTCTTGCATTCC

SEQ ID NO: 176 - Mus musculus Slpi 3'-UTR
NM_011414.3
GCCTGATCCCTGACATTGGCGCCGGCTCTGGACTCGTGCTCGGTGTGCTCTGGAAACTACTTCCCT

GCTCCCAGGCGTCCCTGCTCCGGGTTCCATGGCTCCCGGCTCCCTGTATCCCAGGCTTGGATCCTG

TGGACCAGGGTTACTGTTTTACCACTAACATCTCCTTTTGGCTCAGCATTCACCGATCTTTAGGGA

AATGCTGTTGGAGAGCAAATAAATAAACGCATTCATTTCTCTATGCA

SEQ ID NO: 177 - Mus musculus Nudt22 3'-UTR
NM_026675.2
AGACAATAAAGGACTTTATTCTTGT SEQ ID NO: 178 - Mus musculus Pcyox1l 3'-UTR
NM_172832.4
GGGCTCCCAGGAGAGCCCAGGGACTCTGCGCCACACTGAAGATAACTGAGATGGAGCGCACTCCAG

CCGCGCAGGACTGACGAGGCCACACCCATGGGCTCTGTGGCTTTCTCTGCTCTCATGGATTGAACA

GGGTCCCCCATGTGGGCCCGGGCGATCTGCTGTCTGCTTATCTAAGGATCCTCTTAGAGGCTGCCT

TTTTTTTTTTTTTTTAAGGAGCGATTAAGAAAAGGGAAGGAAATTCAAGTCAGTGTTTTGGCTG

TTTTTGTTTTTTGTTTGTTTGTTTTTGTTTGTTTTTGTGGTGTTGGGTTTTGAGGTTTTTTGTTT

GGTTGGTTTGGTTTTGGGATCGTGTGTTTATTTTATTGTTTTTGTTTTGGGGGGTTGGTCGTTTGT

TGTTTTGGGGGGTTGTTTTGTTTTGTTTGTTGGTTACTGTTTTTCAAGAAGAAATATAAATT

CATCCTCCAAGCT

SEQ ID NO: 179 - Mus musculus Igf2bp1 3'-UTR
CCCCGCCCCCTCCTGTCCCATTGGCTCCAAGATCAGCAGGAGGAACACAGAACTGGAGGGGCGGGT

GGAGGGCCGGTGTGCTCTTCCCAGCAGGCCTGAGAATGAGTGGGAATCAGGGCATTTGGGCCTGGC

TGGAGATCAGGTTTGCACACTGTCTTGAGAACAATGTTCCAGTGAGGAATCCTGATCTCTCGCCCC

CAATTGAGCCAGCTGGCCACAGCCCACCCCTTGGAATATCACCATTGCAATCATAGCTTGGGTTGC

TTTTAAACGTGGATTGTCTTGAAGTTCTCCAGCCTCCATGGAAGGATGGGTCAGATCCCAG

SEQ ID NO: 180 - Mus musculus Tmem37 3'-UTR
GACCTCTGGCTGAGATTGAATAGGACAACCAATGACCTTGACACTGCCTCTTAGGCACTTAGCTCT

AGCAATGCCCTGGAAGTCTCTTCAGCTGAGCTCCAGGGCAAAGGCAGAAGGGTGCCTCTGTACGAC

GGCACAGTGAGCTGGATAGGTTAGTCATGC
```

SEQ ID NO: 181 - *Mus musculus* Slc7a3 3'-UTR (240)
NM_007515
CCTAACCATACCTAATTGTTGTCTTGTTCTCCTATACAATAATGGAGAGTACTCTTGACCCCACGA

AGAGCTGGGCCTCTCATGTGGTGTTAGTGACGGATATGAAATAATGCTCTGTATTTCTTGTGAAAT

GATGGCTATGTCTTTGCTGTTTCTCATTTGTTTTTAACTTGTATACTTTGAAATAGTCTCTGTAGT

TGTTTCCTGGCTTTGAAAAAAATGTTATTAAAGGAAAATTGT

SEQ ID NO: 182 - *Mus musculus* Cst6 3'-UTR
CCGGCCCCAGGGTGACAGAGTCAGGGCCCCATGGGAACAAGCATGGTGGAGGCGCCTCAGGGCCAC

GGGCCACGTCTGTTGCAATAAATCTGCAGCTCTGCTTCTTGC

SEQ ID NO: 183 - *Mus musculus* Ebp 3'-UTR
AGAGCCGGAGAGTGGGCTGAGTCCCTGCTGATGAGGCGCTCTCCTCACTTCCCAGAAGACTCAAAT

CTTCTTCCTCCTCGCACAGGTTGGGGGGGTCAGAACTATCGGACTTGTCCCACTCAAACATGATGA

GTGAGCACACAAAGGGCCAGAGTCAGAAAAGGAAGGGAACAAGTTGAGCTACTGCTAGGAACCTGA

GGGAAAAGATGGATGAGAAGGTGGCAAGTCCGTGACGGTGGCAACTTCCCAAACCAGGAAATAAAA

TGTCTTTTACTATAA

SEQ ID NO: 184 - *Mus musculus* Sf3b5 3'-UTR
NM_009829.3
GGTGAGCGCTGCCCAGTCTTCCCCGTGTGCCGGCTGCGAGCCTCCTTGCTCCTGCATCTCGACCAT

TCCGTGTTGGCTGTGTCGCCTGACCTGCGTACCTGTGGAGGATTCGGAACAAGTCATGGAGAGACT

GTCCGGGTCCGCTCCTTGTGAACTGTGCAGAAGGAGTGATCCCAGCATCGGCAAGCGAGGGAGAAG

ACTGCACGAGAGTGATGCGCATTTCGAGTCTGCTTTTCGATAGTTGATGTCTTCTTGCCT

SEQ ID NO: 185 - *Mus musculus* Plk1 3'-UTR
NM_011121.3
GTCTCTCTCCTTCGGACTGGTGCCCCTTCACTCTGCTAGCTCTGAGCCTGCACTGTAGGCTCCTGG

GGGCTGCTGTTCAGTGCCCCTGGCCCTGGGGGCTGGGCAGGAGCAGGGCCCCCTTTGAAGGGGTTG

CTGTGTGTAAGTTATTTTGTACATGTCTGGGTGTGGGTTTACATCTGCTTCCCTGCCCTCGCTCAG

CCCACTGTATGAATTGTATAAATGTTTCTATTAAATTGGGACTGCTCTTTCCTTAGCTTTATATAT

ATTAAAATGTGTACATCTCTC

SEQ ID NO: 186 - *Mus musculus* Aarsd1 3'-UTR
NM_144829.1
GGGGCCAGGACGTCGTCCCTGTGACCAACAGTAAAATATTGTGACTC SEQ ID NO: 187 - *Mus musculus* Cdca8 3'-UTR
NM_026560.4
GAGGACAACAGGACACACAGTGGCAGCAGGGACTGTGGTAGCAGAGTGCACACATCTGTCCTTCTT

CTGTGGGGTCCTTCACTGCCAACACCTGCAACGGTGCTTTGTCTCTCTGACAGCTATGGTGTCTTG

CTGCACACTTCTAGTTAGTGGGAATTTTAGACGGGGAACACAGGGCTAGTCAGGGCCTTTGTGTGC

TTGGTGTGGAGTGACTGAGAACCGTCTATGGTTCAAGGTCCCACTGGGGATAAACTGCTTAGAGCA

CTGTCCTAGAGGGCAAGTGTAGCCTTCGCCTCCGGGCCCAGGCAGGCTATGCAGTCAGCAGTAGGG

TCTGTGCTCCATGCGGGTCCAGGCGCACGGCTCTCCTATTCTGTTGTCATTTGTGCCCTCTATGGG

CAGGTGTGTTTCAAGTTGGTTTTCTGTTGCTGAGGCTTTCATACACATCAGTTACCATCTCAGCTG

ATTTGTCTACTGAAAGCTTGCTGTTTTCAATAAATCTTAGTTTGCCATGGTTTTAAGTC

SEQ ID NO: 188 - *Mus musculus* Kif22 3'-UTR
NM_145588.1
GACACTACCTTCTTTTAAAAATCCTTGTATAGTGACGTGTTGTGTAAATACAGTTTTTATTCC SEQ ID NO: 189 - *Mus musculus* Cad 3'-UTR
NM_023525.2
GTCCCAGCTTCCTTTCTTGTCTCTTCAGGCCCAGCTGCTGGGCAAGGAATCCCGATGCCCCCCCCA

CGGGGGCAGCACACTTAGCAGACAATCCTGGAGCATACAGATAGCCCAAGCACATAGATGTACTAA

ACTGGGACCATGCTTTAGGCTCCAGACGAGAGTCTTTTCTAACTTGGGGATGCAGTCTCAGATACT

GGGGGCCCCTCTGCCTCATCTCCATTCTTACACCTCAAATCTGTACAGTTACTTTTGTACTGACTG

TAATAAACAGCCAAACAGTT

SEQ ID NO: 190 - *Mus musculus* Cth 3'-UTR
NM_145953.2
AAGTTCGAGTCAAAGCTGTCATTCCAGTGCTGCCATCAGGAGCAGCATCCAAGGGGCCAAATCTTC

GGAATAACTGGACAGATCATTACGGAGCATACGCAGAACTGCACTGAATATTTTAAGGCCCTAATG

AGTTTACAGCTGTAACCTTCCATGGATCTTCCCTTAAGAACTGTCTTCTGTTTATCTTCTAACTAA

CAGGTTGTTCTGTTAGTATCATTTCGGTAATTTTGCTATATTTGTGTCCAAGGAAGTAAGAGTTGT

TCTGTTTTGGGATCATGTTGTCTTTTTTCTTTCTTCAGTAGCTTATGATATATTTTAATCATGTTT

ACAATGTTACAATTTAGTATTGATGTTTTATGAAGTTAAATTATTAAATGAATGGTCTTAAATCCA

CTGTGGTGGTTTTTTTTTGAAAAATTATATAATTACCATAAGCCAAAAATCAAATATTTGGAATAC

CTACTGTGAAATTCAAGAGATTAAAGGTTGTACTTGATACTTGTTATTTTTCTTAAATAAATCTAG

TTATCAAGTTATTTTTCTTAAATAAATCTAGTTATCAAATGT

SEQ ID NO: 191 - *Mus musculus* Pole 3'-UTR
NM_011132.2
CAAGCCTAGGCTAAAGACACTTTGGTATCCCACACCTACTGCCTGCTCCAAAAGGCAGAACCACTG

ACCACCTTGCTTTTCCAAACTCATGAGCACAGCCCAGAAGGAACAGAAGACTTCTGCTAACGTCAT

CATGCCATAAACAGACAGAAGCAGGGAATGGCTCTATCCCTAGCTGCCTGCTAAGTAAACACGGTT

TTGAAGCGTC

SEQ ID NO: 192 - *Mus musculus* Kif2c 3'-UTR
NM_134471.4
TGACTTCAAATAAAGATCTGTTTGATATCACACTAGCCTCTTCCCCTCCCCAGAAAACTTTGGGCA

CCTTCTGGCTTTGGTTAGGAACTGAGTTGGACAGGTTGGGTAAATTTCAACCTCAGGGCATCATGC

CCAGGAAAGCTGGGGAGAGGCGATGTTCTTTTCCTCAGTTTGGAGCGGGAAGAAGGAGTTTTAATG

ACTGTGCTTCCTCTTCTCCTCCCCATGGAAGGGGGGGGGGATCCCTGGCTCAGCATCCACTGCTGG

TGGAAACCTCGCTGCGAGGTGCCGCTGTGAGGTGTGCCGCTGTGAGGTGCGTGCTCTGGAAGAGAG

GCGGAGCTTGTCCGCTTCCTGCTGCCTCTGCCTGCAGTACCACCCTCGGTCTAAGCACTCATGATT

TTATACTTTCAGAAAAAAGTTTTAAGACTTCTTTGGGTTTTTTGTTTTTGTTTTGAAGCCTAAGAA

AGTCACTAGTTCTTGCCTTTATGTATTTATATGCTGTACCTAACAATAAAGAAAGAAGAAAAAAAA

CAAA

SEQ ID NO: 193 - *Mus musculus* Scand1 3'-UTR
NM_020255.3
GCGGCGGAGCCTGGGGCTCCCTGGACTGACACCCTACCCCTGAGTTAATAAAAGTTGAATTTTGAC

AGCTCCCA

SEQ ID NO: 194 - *Mus musculus* Gpr84 3'-UTR
NM_030720.1
AGCTATTTAAAGCTAGTAGTCCATTCACCAGGACAGGCCAAACATCCGGAACCAGAGTGGCCTGCA

GAGGACAGGACAGGAGCCCTTCAGTCCTTGGGTATTTCACAGACAACCTCAGTGGTATAGAGGTAC

ACCACTTTCCCATTCAGGAATCAGTGCGTCAACCCTGTGTGACCCAAGGAGTGTGGTTAATTATTA

ATAAAGACATTGCATCCCCCCCTC

SEQ ID NO: 195 - *Mus musculus* Tpgs1 3'-UTR
NM_148934.2
GACCACGATGCACCCACATCCCGCCACCTGCCCAGGACTTGGGACCTGCAAACTGATGTCCCGGCA

TTCTGCACAGGGTCATCACCCAGGAAGGGGTACCCGCTTGGACTTTGCAGGACCAGCACCTGCAGC

TCAATCCCCTCTGTACTGGCCTGCCTACCCCACTCACAGAAATAAAATCTAAAACGAC

SEQ ID NO: 196 - *Mus musculus* Cc117 3'-UTR
NM_011332.3
CCTTCCCGCTGAGGCATTTGGAGACGCCAGGGCTGCTGTCCATGGTTTCAACATAAAACGGCCTGT

GACCAGCAGAGCCCAAGAGCAGCCACAGAGCAGAAGTCCCTGTTCCCTTTTTTATGGACTCTTATG

CACTACAGGCGAACACAAAAAAAAGCAACGGAATAAAGCCTTCCTCCCTC

SEQ ID NO: 197 - *Mus musculus* Alkbh7 3'-UTR
CCTCCCACATATCCTCCATATTTGTGAATAAAGTAGGGAAAATGCTGTCAT SEQ ID NO: 198 - *Mus musculus* Ms4a8a 3'-UTR
NM_022430.2
GTGAACCTGAAGATTCTAGAGACCAAGTGACATCCTCTCCTACCTAGACTCCTATAAACCAAGTTC

TTCCTTTCCTGACGAAGGGTAAATATCTTTCTTGTGGCCTAAATTATAGACTCTTGCTTCAACTCA

CCCTGGAAAAATCTCTATTAAAACGAGATGGGAGATTGAAATGGATTCAAATAAAGATGCTCTAGC

AGGA

SEQ ID NO: 199 - *Mus musculus* Mrp134 3'-UTR
NM_053162.2
GGAGCGCAACGTCGCAGGGAATAGACTCAGACGCCGGTAGAGTTGCCCGAGGGCGAGAAGTTGGGG

CAAGCTGAAAGTGGGGGTCTGTCCCTTCGTAGGTTTTTAGACGCATCCCCCGTCGACGGCTGCTTA

CCAACCACCAGCACCTGCGATACCTCATCCATTTCTGTGAATATATTTGAAGGCATCTTTGCAAGA

CGGGGTCATTAAAACACAGACACCACCCCTACGTTTCCAGCCATTCCAAAGTATTACCGACTTAAT

AAATATTCACGTTTCTTGAACCACT

SEQ ID NO: 200 - *Mus musculus* Comtd1 3'-UTR
GGTTAACACGAAGCTTAGGGCCTGGGTGTGAGAACCTAAGACCCCCAGCCAGTGACCTGACTTTTA

AACCTGACAATAAAGGTACTGGACACGCG

SEQ ID NO: 201 - *Mus musculus* Armc6 3'-UTR
NM_133972.2
CCTTAGCTCAGAGAACTCTGACTCCAGAACGTGGGTGGCTATGGGGCCCTGCCTCTCTGTCCTCCT

TCCCATGCTACCCAGAGCACAAGTGTGCTAGCAGGGCAGGGGGTGGGAGGGCAGAAGCAGTGATG

ACCTGGTGGCCCACCACTGCCAGTGTCCCTTCTACCACAGCTGCTCTCTGCAGCTTTGGGACAAAG

GGCACATGGAACTGCAGTGTTCTGTCTGGAGTTTGAGGCCTCCACAAGCTGGTGTCCCAGCAGGGC

CAGCCTGCAATCCGGGCACCACTCCAAGCAGTTGATAACCCTGCTCCTTGGGCAGGCCCCCTGGGT

AGAGGTGCTTCAGCCAAGGCTGATTCCCCAAGATCCGCATGATGGGAGGAGGGAGGTGTCTCCTCC

AAATTGTCCTCTGAACTCTGTATGTGTGCTGTGGTGCACACATACATGCTAGCTAAATAAACAAAC

AAACAAATAA

SEQ ID NO: 202 - *Mus musculus* Atp5d 3'-UTR
NM_025313.2
GTGGTACCTACTGTCTGACACCCACGGGGAAACTGAGCCAGGTCCAGGCCGATGAGAAGTTCCCAG

TGGGCTGAAGTGGCCACCAGGGGTCAGCAGTGCTCCAGTTGCTGGGCTTAAAGCTTCCTGGTGCCT

GTCTGCCAGGTCATGGAGGATTCCCCAATCTGGCATCCCCACGATGCCTCTGGAGAGATGGCCTTG

ATTGCCCCTCAAAGCCACCTGAACCGTCGTCAACTTACCCAGCCTGTCTCCATTAAACACCAGGAA

CCAACTGAG

SEQ ID NO: 203 - *Mus musculus* 1110001J03Rik 3'-UTR
NM_025363.3
TGCAGAGAGTCCTCAGATGTTCCTTCATTCAAGAGTTTAACCATTTCTAACAATATGTAGTTATCA

TTAAATCTTTTTTAAAGTGTG

Some of these wild-type 3'-UTR elements differ from publically available 3'-UTR sequences identified by GenBank at NCBI, see the Table 2 (Example 1). This table reflects sequencing results of the present inventors.

Thus, 3'-UTR elements selected from the group consisting of SEQ ID NO: 179, SEQ ID NO: 180, SEQ ID NO: 182, SEQ ID NO: 183, SEQ ID NO: 197, SEQ ID NO: 200 are contributed by the present invention and may be employed in any aspect of the present invention.

Example of Artificial 3'-UTR Elements Useful in the Present Invention

In some embodiments, the 3'-UTR element according to the present invention differs from a wild-type 3'-UTR element. Such 3'-UTR elements are designated "artificial 3'-UTR elements".

It is preferred that an artificial 3'-UTR element shows a degree of sequence identity to a wild-type 3'-UTR element which is (a) less than 100%, and at the same time (B) more than 10%, more than 20%, more than 30%, more than 40%, more than 50%, more than 60%, more than 70%, more than 80%, more than 90%, more than 95%, such wild-type 3'-UTR element being selected from the group consisting of SEQ ID NOs: 152 to 203. Typically the artificial 3'-UTR element differs from the wild-type 3'-UTR element it is based on in that at least one nucleotide, such as two nucleotides, three nucleotides, four nucleotides, five nucleotides, six nucleotides, seven nucleotides, eight nucleotides, nine nucleotides, ten nucleotides, or more than ten nucleotides, is/are exchanged. For example, such a nucleotide exchange may be recommendable in case the wild-type 3'-UTR element comprises a nucleotide element which is considered disadvantageous. For example, in some embodiments a nucleotide element which is considered disadvantageous is a restriction enzyme recognition site (cleavage site), particularly the restriction enzyme recognition site (cleavage site) which is recognized (cleavable) by a restriction enzyme used in the process of making (cloning) the artificial nucleic acid of the present invention. Hence, it is possible to specifically introduce certain base(s) (in exchange, preferably substitution, for the respective wild-type base(s)), so that the artificial 3'-UTR element does not contain a nucleotide element which is considered disadvantageous. In a specific embodiment, the artificial 3'-UTR elements is SEQ ID NO: 204:

```
SEQ ID NO: 204 - Artificial Sequence (based on
SEQ ID NO: 192)
TGACTTCAAATAATGATCTGTTTGATATCACACTAGCCTCTTCCCCTCC

CCAGAAAACTTTGGGCACCTTCTGGCTTTGGTTAGGAACTGAGTTGGAC

AGGTTGGGTAAATTTCAACCTCAGGGCATCATGCCCAGGAAAGCTGGGG

AGAGGCGATGTTCTTTTCCTCAGTTTGGAGCGGGAAGAAGGAGTTTTAA

TGACTGTGCTTCCTCTTCTCCTCCCCATGGAAGGGGGGGGGATCCCTG

GCTCAGCATCCACTGCTGGTGGAAACCTCGCTGCGAGGTGCCGCTGTGA

GGTGTGCCGCTGTGAGGTGCGTGCTCTGGAAGAGAGGCGGAGCTTGTCC

GCTTCCTGCTGCCTCTGCCTGCAGTACCACCCTCGGTCTAAGCACTCAT

GATTTTATACTTTCAGAAAAAGTTTTAAGACTTCTTTGGGTTTTTTGT

TTTTGTTTTGAAGCCTAAGAAAGTCACTAGTTCTTGCCTTTATGTATTT

ATATGCTGTACCTAACAATAAAGAAAGAAGAAAAAAAACAAA
```

[This sequence corresponds to the wild-type sequence it is based on, except that AGATCT is replaced by TGATCT underlined above for emphasis]

Novel 5'-UTR Elements and Novel 3'-UTR Elements

The present invention also provides novel 5'-UTR elements and novel 3'-UTR elements, i.e. 5'-UTR elements and 3'-UTR elements which the present inventors found to be expressed in human cells and mouse cells, respectively, but which are not known from public databases (see Example 1). Any 5'-UTR selected from the group consisting of SEQ ID NO: 45, SEQ ID NO: 47, SEQ ID NO: 49 can be preferred in some embodiments of this invention. Any 5'-UTR selected from the group consisting of SEQ ID NO: 77, SEQ ID NO: 79, SEQ ID NO: 84, SEQ ID NO: 85, SEQ ID NO: 90, SEQ ID NO: 92, SEQ ID NO: 93, SEQ ID NO: 98, SEQ ID NO: 106, SEQ ID NO: 109, SEQ ID NO: 115, SEQ ID NO: 118, SEQ ID NO: 125, SEQ ID NO: 127, SEQ ID NO: 131, SEQ ID NO: 135 can be preferred in some embodiments of this invention. Any 3'-UTR selected from the group consisting of SEQ ID NO: 179, SEQ ID NO: 180, SEQ ID NO: 182, SEQ ID NO: 183, SEQ ID NO: 197, SEQ ID NO: 200 can be preferred in some embodiments of this invention.

Description of 5'-UTR Elements and Preferred 3'-UTR Elements

Preferably, the at least one 3'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the 3'-UTR sequence of a transcript of a gene selected from the group consisting of NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, PSMB3-3'-UTR, PSMB6-3'-UTR, SCAND1-3'-UTR, AMN-3'-UTR, CYBA-3'-UTR, PCOLCE-3'-UTR, MAP1S-3'-UTR, VTN-3'-UTR, ALDH16A1-3'-UTR (all human), Acox2-3'-UTR, Ubc-3'-UTR, Slpi-3'-UTR, Igf2bp1-3'-UTR, Tmem37-3'-UTR, Slc7a3-3'-UTR, Cst6-3'-UTR, Ebp-3'-UTR, Sf3b5-3'-UTR, Cdca8-3'-UTR, Kif22-3'-UTR, Cad-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrp134-3'-UTR, Comtd1-3'-UTR, Armc6-3'-UTR, Atp5d-3'-UTR, 1110001J03Rik-3'-UTR, Nudt22-3'-UTR (all mouse). Most preferably, the at least one 3'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to a sequence selected from the group consisting of SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (alternatively SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177, or the corresponding RNA sequences, respectively.

Preferably, the at least one 5'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the 5'-UTR sequence of a transcript of ZNF460-5'-UTR, TGM2-5'-UTR, IL7R-5'-UTR, COL8A1-5'-UTR, NDUFS7-5'-UTR, PLK2-5'-UTR, FBXO32-5'-UTR, ATP5D-5'-UTR, TUBB4B-5'-UTR, ORMDL2-5'-UTR, FSCN1-5'-UTR, CD9-5'-UTR, PYSL2-5'-UTR, PSMB3-5'-UTR, PSMB6-5'-UTR, KPNA6-5'-UTR, SFT2D2-5'-UTR, LCLAT1-5'-UTR, FBXL18-5'-UTR, SLC35F6-5'-UTR, VMA21-5'-UTR, SEZ6L2-5'-UTR, PCOLCE-5'-UTR, VTN-5'-UTR, ALDH16A1-5'-UTR, KPNA6-5'-UTR, JUP-5'-UTR, CPN2-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR (all human), Dpysl2-5'-UTR, Acox2-5'-UTR, Ubc-5'-UTR, Nudt22-5'-UTR, Pcyox1l-5'-UTR, Ankrd1-5'-UTR, Tspyl4-5'-UTR, Slc7a3-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Tspan10-5'-UTR, Scand1-5'-UTR, Gpr84-5'-UTR, Cers6-5'-UTR, Cxcr4-5'-UTR, Gprc5c-5'-UTR, Fen1-5'-UTR, Cspg4-5'-UTR, Mrpl34-5'-UTR, Comtd1-5'-UTR, Armc6-5'-UTR, Emr4-5'-UTR, Atp5d-5'-UTR, Csf2ra-5'-UTR, Aarsd1-5'-UTR, Cth-5'-UTR, Tpgs1-5'-UTR, Ccl17-5'-UTR, Alkbh7-5'-UTR, Ms4a8a-5'-UTR (all mouse). Most preferably, the at least one 5'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to a sequence according to SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125, or the corresponding RNA sequence, respectively.

The at least one 3'-UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of the 3'-UTR of a transcript of a gene, such as to the 3'-UTR of a sequence according to SEQ ID NOs: 152 to 204, wherein the fragment is preferably a functional fragment or a functional variant fragment as described above. Such fragment preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. In a preferred embodiment, the fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70. Preferably, said variants, fragments or variant fragments are functional variants, functional fragments, or functional variant fragments of the 3'-UTR, prolong protein production from the artificial nucleic acid molecule according to the invention with an efficiency of at least 30%, preferably with an efficiency of at least 40%, more preferably of at least 50%, more preferably of at least 60%, even more preferably of at least 70%, even more preferably of at least 80%, most preferably of at least 90% of the protein production prolonging efficiency exhibited by an artificial nucleic acid molecule comprising the nucleic acid sequence selected from the group consisting of SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (alternatively SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177.

The at least one 5'-UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of the 5'-UTR of a transcript of a gene, such as to the 5'-UTR of a sequence according to SEQ ID NO: 1 to 151, wherein the fragment is preferably a functional fragment or a functional variant fragment as described above. Such fragment preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. In a preferred embodiment, the fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70. Preferably, said variants, fragments or variant fragments are functional variants, functional fragments, or functional variant fragments of the 5'-UTR, increase protein production from the artificial nucleic acid molecule according to the invention with an efficiency of at least 30%, preferably with an efficiency of at least 40%, more preferably of at least 50%, more preferably of at least 60%, even more preferably of at least 70%, even more preferably of at least 80%, most preferably of at least 90% of the protein production increasing efficiency exhibited by an artificial nucleic acid molecule comprising the nucleic acid sequence selected from the group consisting of SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125.

Further Preferred Embodiments

Preferably, the at least one 3'-UTR element and/or the at least one 5'-UTR element of the artificial nucleic acid molecule according to the present invention exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. The upper limit for the length of the at least one 3'-UTR element and/or the at least one 5'-UTR element may be 500 nucleotides or less, e.g. 400, 300, 200, 150 or 100 nucleotides. For other embodiments the upper limit may be chosen within the range of 50 to 100 nucleotides. For example, the fragment or variant thereof may exhibit a length of between 3 and about 500 nucleotides, preferably of between 5 and about 150 nucleotides, more preferably of between 10 and 100 nucleotides, even more preferably of between 15 and 90, most preferably of between 20 and 70.

It may also be preferable that the UTR element comprised in the artificial nucleic acid molecule comprises (or consists of) a continuous sequence which is shorter than any sequence selected from SEQ ID NOs: 1 to 204 provided herein, but still shares a degree of identity of 70% or more, 80% or more, 90% or more or 95% or more with the respective sequence any sequence selected from SEQ ID NOs: 1 to 204. In such case, preferably, the replacing UTR element comprises of a continuous sequence which is over its entire length identical to any sequence selected from SEQ ID NOs: 1 to 204; however, the replacing UTR element is shorter, e.g has a length of 70% or more, 80% or more, 90% or more or 95% or more with respect to the total length of the sequence it is otherwise identical to, and which is selected from SEQ ID NOs: 1 to 204.

Furthermore, the artificial nucleic acid molecule according to the present invention may comprise more than one 3'-UTR elements and/or more than one 5'-UTR elements as described above. For example, the artificial nucleic acid molecule according to the present invention may comprise one, two, three, four or more 3'-UTR elements, and/or one, two, three, four or more 5'-UTR elements, wherein the individual 3'-UTR elements may be the same or they may be different, and similarly, the individual 5'-UTR elements may be the same or they may be different. For example, the artificial nucleic acid molecule according to the present invention may comprise two essentially identical 3'-UTR elements as described above, e.g. two 3'-UTR elements comprising or consisting of a nucleic acid sequence, which is derived from the 3'-UTR of a transcript of a gene, such as from a sequence according to SEQ ID NO: 152 to 204, or from a fragment or variant of the 3'-UTR of a transcript of a gene, functional variants thereof, functional fragments thereof, or functional variant fragments thereof as described above. Accordingly, for example, the artificial nucleic acid molecule according to the present invention may comprise two essentially identical 5'-UTR elements as described above, e.g. two 5'-UTR elements comprising or consisting of a nucleic acid sequence, which is derived from the 5'-UTR of a transcript of a gene, such as from a sequence according to SEQ ID NO: 1 to 151, or from a fragment or variant of the 5'-UTR of a transcript of a gene, functional variants thereof, functional fragments thereof, or functional variant fragments thereof as described above.

Surprisingly, the inventors found that an artificial nucleic acid molecule comprising a 3'-UTR element as described above and/or a 5'-UTR element as described above may represent or may provide an mRNA molecule, which provides high translation efficiency. Thus, a 3'-UTR element as described herein and/or a 5'-UTR element as described herein may improve translation efficiency of an mRNA molecule.

In particular, the artificial nucleic acid molecule according to the invention may comprise (i) at least one 3'-UTR element and at least one 5'-UTR element, which provides high translation efficiency; (ii) at least one 3'-UTR element, which provides high translation efficiency, but no 5'-UTR element, which provides high translation efficiency; or (iii) at least one 5'-UTR element, which provides high translation efficiency, but no 3'-UTR element, provides high translation efficiency.

However, in particular in case (ii) and (iii), but possibly also in case (i), the artificial nucleic acid molecule according to the present invention may further comprise one or more "further 3'-UTR elements and/or 5'-UTR elements", i.e. 3'-UTR elements and/or 5'-UTR elements which do not fulfil the requirements as described above. For example, an artificial nucleic acid molecule according to the invention, which comprises a 3'-UTR element according to the present invention, i.e. a 3'-UTR element which provides high translation efficiency to said artificial nucleic acid molecule, may additionally comprise any further 3'-UTR and/or any further 5'-UTR, in particular a further 5'-UTR, e.g. a 5'-TOP UTR, or any other 5'-UTR or 5'-UTR element. Similarly for example, an artificial nucleic acid molecule according to the invention, which comprises a 5'-UTR element according to the present invention, i.e. a 5'-UTR element which provides high translation efficiency to said artificial nucleic acid molecule, may additionally comprise any further 3'-UTR and/or any further 5'-UTR, in particular a further 3'-UTR, e.g. a 3'-UTR derived from a 3'-UTR of an albumin gene, particularly preferably a 3'-UTR comprising a sequence according to SEQ ID NO: 206 or 207, in particular to SEQ ID NO: 207, or any other 3'-UTR or 3'-UTR element.

If additionally to the inventive at least one 5'-UTR element and/or to the inventive at least one 3'-UTR element, which provides high translation efficiency, a further 3'-UTR (element) and/or a further 5'-UTR (element) are present in the artificial nucleic acid molecule according to the invention, the further 5'-UTR (element) and/or the further 3'-UTR (element) may interact with the inventive 3'-UTR element and/or inventive 5'-UTR element and, thus, support the translation efficiency effect of the inventive 3'-UTR element and/or of the inventive 5'-UTR element, respectively. Such further 3'-UTR and/or 5'-UTR (elements) may further support stability and translational efficiency. Moreover, if both, an inventive 3'-UTR element and an inventive 5'-UTR element are present in the artificial nucleic acid molecule according to the invention, a translation efficiency effect of the inventive 5'-UTR element and the inventive 3'-UTR element results preferably in the provision of high translation efficiency in a synergistic way.

Preferably, the further 3'-UTR comprises or consists of a nucleic acid sequence which is derived from a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(1) gene, or from a variant of a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(1) gene according to SEQ ID No. 1369-1390 of the patent application WO2013/143700 whose disclosure is incorporated herein by reference. In a particularly preferred embodiment, the further 3'-UTR comprises or consists of a nucleic acid sequence which is derived from a 3'-UTR of an albumin gene, preferably a vertebrate albumin gene, more preferably a mammalian albumin gene, most preferably a human albumin gene according to SEQ ID NO: 206:

```
SEQ ID NO: 206:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT
(Human albumin 3'-UTR; corresponding to
SEQ ID No: 1369 of the patent application WO
2013/143700).
```

In another particularly preferred embodiment, the further 3'-UTR comprises or consists of a nucleic acid sequence which is derived from a 3'-UTR of an α-globin gene, preferably a vertebrate α- or β-globin gene, more preferably a mammalian α- or β-globin gene, most preferably a human α- or β-globin gene according to SEQ ID No. 1370 of the patent application WO 2013/143700 (3'-UTR of *Homo sapiens* hemoglobin, alpha 1 (HBA1)), or according to SEQ ID No. 1371 of the patent application WO 2013/143700 (3'-UTR of *Homo sapiens* hemoglobin, alpha 2 (HBA2)), and/or according to SEQ ID No. 1372 of the patent application WO 2013/143700 (3'-UTR of *Homo sapiens* hemoglobin, beta (HBB)).

For example, the further 3'-UTR may comprise or consist of the center, α-complex-binding portion of the 3'-UTR of an α-globin gene, according to SEQ ID No. 1393 of the patent application WO 2013/143700.

In this context it is particularly preferred that the inventive nucleic acid molecule comprises a further 3'-UTR element derived from the nucleic acids according to SEQ ID No. 1369-1390 of the patent application WO 2013/143700 or a fragment, homolog or variant thereof.

Most preferably the further 3'-UTR comprises the nucleic acid sequence derived from a fragment of the human albumin gene according to SEQ ID NO: 207:

```
SEQ ID NO: 207:
CATCACATTTAAAAGCATCTCAGCCTACCATGAGAATAAGAGAAAGAAA

ATGAAGATCAATAGCTTATTCATCTCTTTTTCTTTTTCGTTGGTGTAAA

GCCAACACCCTGTCTAAAAAACATAAATTTCTTTAATCATTTTGCCTCT

TTTCTCTGTGCTTCAATTAATAAAAAATGGAAAGAACCT
(albumin7 3'-UTR; corresponding to SEQ ID No:
1376 of the patent application WO 2013/143700)
```

In this context it is particularly preferred that the further 3'-UTR of the inventive artificial nucleic acid molecule comprises or consists of the nucleic acid sequence according to SEQ ID NO: 207, or a corresponding RNA sequence.

In some embodiments, the further 3'-UTR comprises or consists of a nucleic acid sequence derived from a ribosomal protein coding gene, preferably as described in the international patent applications WO 2015/101414 or WO 2015/101415, the disclosure of which is herewith incorporated by reference.

The further 3'-UTR may also comprise or consist of a nucleic acid sequence derived from a ribosomal protein coding gene, whereby ribosomal protein coding genes from which a further 3'-UTR may be derived include, but are not limited to, ribosomal protein L9 (RPL9), ribosomal protein L3 (RPL3), ribosomal protein L4 (RPL4), ribosomal protein L5 (RPL5), ribosomal protein L6 (RPL6), ribosomal protein L7 (RPL7), ribosomal protein L7a (RPL7A), ribosomal protein L11 (RPL11), ribosomal protein L12 (RPL12), ribosomal protein L13 (RPL13), ribosomal protein L23 (RPL23), ribosomal protein L18 (RPL18), ribosomal protein L18a (RPL18A), ribosomal protein L19 (RPL19), ribosomal protein L21 (RPL21), ribosomal protein L22 (RPL22), ribosomal protein L23a (RPL23A), ribosomal protein L17 (RPL17), ribosomal protein L24 (RPL24), ribosomal protein L26 (RPL26), ribosomal protein L27 (RPL27), ribosomal protein L30 (RPL30), ribosomal protein L27a (RPL27A), ribosomal protein L28 (RPL28), ribosomal protein L29 (RPL29), ribosomal protein L31 (RPL31), ribosomal protein L32 (RPL32), ribosomal protein L35a (RPL35A), ribosomal protein L37 (RPL37), ribosomal protein L37a (RPL37A), ribosomal protein L38 (RPL38), ribosomal protein L39 (RPL39), ribosomal protein, large, P0 (RPLP0), ribosomal protein, large, P1 (RPLP1), ribosomal protein, large, P2 (RPLP2), ribosomal protein S3 (RPS3), ribosomal protein S3A (RPS3A), ribosomal protein S4, X-linked (RPS4X), ribosomal protein S4, Y-linked 1 (RPS4Y1), ribosomal protein S5 (RPS5), ribosomal protein S6 (RPS6), ribosomal protein S7 (RPS7), ribosomal protein S8 (RPS8), ribosomal protein S9 (RPS9), ribosomal protein S10 (RPS10), ribosomal protein S11 (RPS11), ribosomal protein S12 (RPS12), ribosomal protein S13 (RPS13), ribosomal protein S15 (RPS15), ribosomal protein S15a (RPS15A), ribosomal protein S16 (RPS16), ribosomal protein S19 (RPS19), ribosomal protein S20 (RPS20), ribosomal protein S21 (RPS21), ribosomal protein S23 (RPS23), ribosomal protein S25 (RPS25), ribosomal protein S26 (RPS26), ribosomal protein S27 (RPS27), ribosomal protein S27a (RPS27a), ribosomal protein S28 (RPS28), ribosomal protein S29 (RPS29), ribosomal protein L15 (RPL15), ribosomal protein S2 (RPS2), ribosomal protein L14 (RPL14), ribosomal protein S14 (RPS14), ribosomal protein L10 (RPL10), ribosomal protein L10a (RPL10A), ribosomal protein L35 (RPL35), ribosomal protein L13a (RPL13A), ribosomal protein L36 (RPL36), ribosomal protein L36a (RPL36A), ribosomal protein L41 (RPL41), ribosomal protein S18 (RPS18), ribosomal protein S24 (RPS24), ribosomal protein L8 (RPL8), ribosomal protein L34 (RPL34), ribosomal protein S17 (RPS17), ribosomal protein SA (RPSA), ubiquitin A-52 residue ribosomal protein fusion product 1 (UBA52), Finkel-Biskis-Reilly murine sarcoma virus (FBR-MuSV) ubiquitously expressed (FAU), ribosomal protein L22-like 1 (RPL22L1), ribosomal protein S17 (RPS17), ribosomal protein L39-like (RPL39L), ribosomal protein L10-like (RPL10L), ribosomal protein L36a-like (RPL36AL), ribosomal protein L3-like (RPL3L), ribosomal protein S27-like (RPS27L), ribosomal protein L26-like 1 (RPL26L1), ribosomal protein L7-like 1 (RPL7L1), ribosomal protein L13a pseudogene (RPL13AP), ribosomal protein L37a pseudogene 8 (RPL37AP8), ribosomal protein S10 pseudogene 5 (RPS10P5), ribosomal protein S26 pseudogene 11 (RPS26P11), ribosomal protein L39 pseudogene 5 (RPL39P5), ribosomal protein, large, P0 pseudogene 6 (RPLP0P6) and ribosomal protein L36 pseudogene 14 (RPL36P14).

Preferably, the further 5'-UTR comprises or consists of a nucleic acid sequence which is derived from the 5'-UTR of a TOP gene or which is derived from a fragment, homolog or variant of the 5'-UTR of a TOP gene.

It is particularly preferred that the 5'-UTR element does not comprise a TOP-motif or a 5'TOP, as defined above. In particular, it is preferred that a 5'-UTR of a TOP gene is a 5'-UTR of a TOP gene lacking the TOP motif.

The nucleic acid sequence which is derived from the 5'-UTR of a TOP gene is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the further 5'-UTR is preferably selected from 5'-UTR elements comprising or consisting of a nucleic acid sequence which is derived from a nucleic acid sequence selected from the group consisting of SEQ ID NOs. 1-1363, SEQ ID NO. 1395, SEQ ID NO. 1421 and SEQ ID NO. 1422 of the patent application WO2013/143700 whose disclosure is incorporated herein by reference, from the homologs of SEQ ID NOs. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID NOs. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID NOs. 1-1363, SEQ ID NO. 1395, SEQ ID NO. 1421 and SEQ ID NO. 1422 of the patent application WO2013/143700.

In a preferred embodiment, the further 5'-UTR comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the further 5'-UTR is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the further 5'-UTR comprises or consists of a nucleic acid sequence which is derived from a 5'-UTR of a TOP gene encoding a ribosomal protein or from a variant of a 5'-UTR of a TOP gene encoding a ribosomal protein. For example, the 5'-UTR element comprises or consists of a nucleic acid sequence which is derived from a 5'-UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360 of the patent application WO2013/143700, a corresponding RNA sequence, a homolog thereof, or a variant thereof as described herein, preferably lacking the 5'-TOP motif. As described above, the sequence extending from position 5 to the nucleotide immediately 5' to the ATG (which is located at the 3'end of the sequences) corresponds to the 5'-UTR of said sequences.

Preferably, the further 5'-UTR comprises or consists of a nucleic acid sequence which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR element comprises or consists of a nucleic acid sequence which is derived from a 5'-UTR of a nucleic acid sequence according to any of SEQ ID NOs: SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'-UTR element comprises or consists of a nucleic acid sequence which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the further 5'-UTR does not comprise the 5'TOP of said gene.

Accordingly, in a particularly preferred embodiment, the further 5'-UTR comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 208 (5'-UTR of human ribosomal protein Large 32 lacking the 5' terminal oligopyrimidine tract: GGCGCTGCCTACGGAGGTGGCAGCCATCTCC-TTCTCGGCATC (SEQ ID NO: 208); corresponding to SEQ ID NO. 1368 of the patent application WO2013/143700) or preferably to a corresponding RNA sequence, or wherein the further 5'-UTR comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 208 or more preferably to a corresponding RNA sequence, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the artificial nucleic acid molecule comprises a further 5'-UTR which comprises or consists of a nucleic acid sequence which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB or from a homolog or variant thereof, wherein preferably the further 5'-UTR does not comprise a TOP-motif or the 5'TOP of said genes, and wherein optionally the further 5'-UTR starts at its 5'-end with a nucleotide located at position 1, 2, 3, 4, 5, 6, 7, 8, 9 or 10 downstream of the 5' terminal oligopyrimidine tract (TOP) and wherein further optionally the further 5'-UTR which is derived from a 5'-UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In certain embodiments, a further 5'-UTR comprises or consists of a nucleic acid sequence, which is derived from a 5'-UTR as described in the international patent application WO 2016/107877, the disclosure of which is herewith incorporated by reference.

The artificial nucleic acid molecule according to the present invention may be RNA, such as mRNA or viral RNA or a replicon, DNA, such as a DNA plasmid or viral DNA, or may be a modified RNA or DNA molecule. It may be provided as a double-stranded molecule having a sense strand and an anti-sense strand, for example, as a DNA molecule having a sense strand and an anti-sense strand.

The artificial nucleic acid molecule according to the present invention may further comprise optionally a 5'-cap. The optional 5'-cap is preferably located 5' to the ORF, more preferably 5' to the at least one 5'-UTR or to any further 5'-UTR within the artificial nucleic acid molecule according to the present invention.

Preferably, the artificial nucleic acid molecule according to the present invention further comprises a poly(A) sequence and/or a polyadenylation signal. Preferably, the optional poly(A) sequence is located 3' to the at least one 3'-UTR element or to any further 3'-UTR, more preferably the optional poly(A) sequence is connected to the 3'-end of an 3'-UTR element. The connection may be direct or indirect, for example, via a stretch of 2, 4, 6, 8, 10, 20 etc. nucleotides, such as via a linker of 1-50, preferably of 1-20 nucleotides, e.g. comprising or consisting of one or more restriction sites. However, even if the artificial nucleic acid molecule according to the present invention does not comprise a 3'-UTR, for example if it only comprises at least one 5'-UTR element, it preferably still comprises a poly(A) sequence and/or a polyadenylation signal.

In one embodiment, the optional polyadenylation signal is located downstream of the 3' of the 3'-UTR element. Preferably, the polyadenylation signal comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. Preferably, the polyadenylation signal, preferably the consensus sequence NNUANA, is located less than about 50 nucleotides, more preferably less than about 30 bases, most preferably less than about 25 bases, for example 21 bases, downstream of the 3'-end of the 3'-UTR element or of the ORF, if no 3'-UTR element is present.

Transcription of an artificial nucleic acid molecule according to the present invention, e.g. of an artificial DNA molecule, comprising a polyadenylation signal downstream of the 3'-UTR element (or of the ORF) will result in a premature-RNA containing the polyadenylation signal downstream of its 3'-UTR element (or of the ORF).

Using an appropriate transcription system will then lead to attachment of a poly(A) sequence to the premature-RNA. For example, the inventive artificial nucleic acid molecule may be a DNA molecule comprising a 3'-UTR element as described above and a polyadenylation signal, which may result in polyadenylation of an RNA upon transcription of this DNA molecule. Accordingly, a resulting RNA may comprise a combination of the inventive 3'-UTR element followed by a poly(A) sequence.

Potential transcription systems are in vitro transcription systems or cellular transcription systems etc. Accordingly, transcription of an artificial nucleic acid molecule according to the invention, e.g. transcription of an artificial nucleic acid molecule comprising an open reading frame, a 3'-UTR element and/or a 5'-UTR element and optionally a polyadenylation-signal, may result in an mRNA molecule comprising an open reading frame, a 3'-UTR element and optionally a poly(A) sequence.

Accordingly, the invention also provides an artificial nucleic acid molecule, which is an mRNA molecule comprising an open reading frame, a 3'-UTR element as described above and/or a 5'-UTR element as described above and optionally a poly(A) sequence.

In another embodiment, the 3'-UTR of the artificial nucleic acid molecule according to the invention does not comprise a polyadenylation signal or a poly(A) sequence. Further preferably, the artificial nucleic acid molecule according to the invention does not comprise a polyadenylation signal or a poly(A) sequence. More preferably, the 3'-UTR of the artificial nucleic acid molecule, or the inventive artificial nucleic acid molecule as such, does not comprise a polyadenylation signal, in particular it does not comprise the polyadenylation signal AAU/TAAA.

In a preferred embodiment, the invention provides an artificial nucleic acid molecule which is an artificial RNA molecule comprising an open reading frame and an RNA sequence corresponding to a DNA sequence selected from the group consisting of sequences according to SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125 or a fragment thereof as described above. Moreover, a corresponding artificial DNA molecule is also provided.

In another preferred embodiment, the invention provides an artificial nucleic acid molecule which is an artificial DNA molecule comprising an open reading frame and a sequence selected from the group consisting of sequences according to SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125.

Accordingly, the invention provides an artificial nucleic acid molecule which may serve as a template for an RNA molecule, preferably for an mRNA molecule, which is characterized by high translation efficiency. In other words, the artificial nucleic acid molecule may be a DNA which may be used as a template for production of an mRNA. The obtainable mRNA, may, in turn, be translated for production of a desired peptide or protein encoded by the open reading frame. If the artificial nucleic acid molecule is a DNA, it may, for example, be used as a double-stranded storage form for continued and repetitive in vitro or in vivo production of mRNA. Thereby, in vitro refers in particular to ("living") cells and/or tissue, including tissue of a living subject. Cells include in particular cell lines, primary cells, cells in tissue or subjects. In specific embodiments cell types allowing cell culture may be suitable for the present invention. Particularly preferred are mammalian cells, e.g. human cells and mouse cells. In particularly preferred embodiments the human cell lines HeLa, HEPG2 and U-937 and the mouse cell lines NIH3T3, JAWSII and L929 are used. Furthermore primary cells are particularly preferred, in particular preferred embodiments human dermal fibroblasts (HDF) may be used. A preferred group of cell lines comprises Alternatively also a tissue of a subject may be used.

In one embodiment, the artificial nucleic acid molecule according to the present invention further comprises a poly(A) sequence. For example, a DNA molecule comprising an ORF, optionally followed by a 3' UTR, may contain a stretch of thymidine nucleotides which can be transcribed into a poly(A) sequence in the resulting mRNA. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides. Most preferably, the inventive nucleic acid comprises a poly(A) sequence of about 60 to about 70 nucleotides, most preferably 64 adenine nucleotides.

Artificial RNA-molecules may also be obtainable in vitro by common methods of chemical-synthesis without being necessarily transcribed from a DNA-progenitor.

In a particularly preferred embodiment, the artificial nucleic acid molecule according to the present invention is an RNA molecule, preferably an mRNA molecule comprising in 5'-to-3'-direction an open reading frame, a 3'-UTR element as described above and a poly(A) sequence or comprising in 5'-to-3'-direction a 5'-UTR element as described above, an open reading frame and a poly(A) sequence.

In a preferred embodiment, the open reading frame is derived from a gene, which is distinct from the gene from which the 3'-UTR element and/or the 5'-UTR element of the inventive artificial nucleic acid is derived. In some further preferred embodiments, the open reading frame does not code for a gene selected from the group consisting of ZNF460, TGM2, IL7R, BGN, TK1, RAB3B, CBX6, FZD2, COL8A1, NDUFS7, PHGDH, PLK2, TSPO, PTGS1, FBXO32, NID2, ATP5D, EXOSC4, NOL9, UBB4B, VPS18, ORMDL2, FSCN1, TMEM33, TUBA4A, EMP3, TMEM201, CRIP2, BRAT1, SERPINH1, CD9, DPYSL2, CDK9, TFRC, PSMB3, FASN, PSMB6, PRSS56, KPNA6, SFT2D2, PARD6B, LPP, SPARC, SCAND1, VASN, SLC26A1, LCLAT1, FBXL18, SLC35F6, RAB3D, MAP1B, VMA21, CYBA, SEZ6L2, PCOLCE, VTN, ALDH16A1, RAVER1, KPNA6, SERINC5, JUP, CPN2, CRIP2, EPT1, PNPO, SSSCA1, POLR2L, LIN7C, UQCR10, PYCRL, AMN, MAP1S, NDUFS7, PHGDH, TSPO, ATP5D, EXOSC4, TUBB4B, TUBA4A, EMP3, CRIP2, BRAT1, CD9, CDK9, PSMB3, PSMB6, PRSS56, SCAND1, AMN, CYBA, PCOLCE, MAP1S, VTN, ALDH16A1 (all preferably human) and Dpysl2, Ccnd1, Acox2, Cbx6, Ubc, Ldlr, Nudt22, Pcyox11, Ankrd1, Tmem37, Tspyl4, Slc7a3, Cst6, Aacs, Nosip, Itga7, Ccnd2, Ebp, Sf3b5, Fasn, Hmgcsl, Osr1, Lmnb1, Vma21, Kif20a, Cdca8, Slc7a1, Ubqln2, Prps2, Shmt2, Aurkb, Fignl1, Cad, Anln, Slfn9, Ncaph, Pole, Uhrf1, Gja1, Fam64a, Kif2c, Tspan10, Scand1, Gpr84, Fads3, Cers6, Cxcr4, Gprc5c, Fen1, Cspg4, Mrp134, Comtd1, Armc6, Emr4, Atp5d, 1110001J03Rik, Csf2ra, Aarsd1, Kif22, Cth, Tpgs1, Ccl17, Alkbh7, Ms4a8a, Acox2, Ubc, Slpi, Pcyox11, Igf2bp1, Tmem37, Slc7a3, Cst6, Ebp, Sf3b5, Plk1, Cdca8, Kif22, Cad, Cth, Pole, Kif2c, Scand1, Gpr84, Tpgs1, Ccl17, Alkbh7, Ms4a8a, Mrp134, Comtd1, Armc6, Atp5d, 1110001J03Rik, Nudt22, Aarsd1 (all preferably mouse), or variants thereof, provided that the 3'-UTR element and/or the 5'-UTR element is a sequence which is selected from the group consisting of sequences according to SEQ ID NO: 1 to 204.

In a preferred embodiment, the ORF does not encode human or plant, in particular Arabidopsis, ribosomal proteins, in particular does not encode human ribosomal protein S6 (RPS6), human ribosomal protein L36a-like (RPL36AL) or Arabidopsis ribosomal protein 516 (RPS16). In a further preferred embodiment, the open reading frame (ORF) does not encode ribosomal protein S6 (RPS6), ribosomal protein L36a-like (RPL36AL) or ribosomal protein S16 (RPS16) of whatever origin.

In one embodiment, the invention provides an artificial DNA molecule comprising an open reading frame, preferably an open reading frame derived from a gene, which is distinct from the gene from which the 3'-UTR element and/or the 5'-UTR element is derived; a 3'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to a DNA sequence selected from the group consisting of sequences according to SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (alternatively SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177, and/or a 5'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to a DNA sequence selected from the group consisting of sequences according to SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125; and a polyadenylation signal and/or a poly(A) sequence.

Furthermore, the invention provides an artificial RNA molecule, preferably an artificial mRNA molecule or an artificial viral RNA molecule, comprising an open reading frame, preferably an open reading frame is derived from a gene, which is distinct from the gene from which the 3'-UTR element and/or the 5'-UTR element is derived; a 3'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to an RNA sequence corresponding to a DNA sequence selected from the group consisting of sequences according to SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (alternatively SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177, and/or a 5'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to an RNA sequence corresponding to a DNA sequence selected from the group consisting of sequences according to SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125; and a polyadenylation signal and/or a poly(A) sequence.

The invention provides an artificial nucleic acid molecule, preferably an artificial mRNA, which may be characterized by high translation efficiency. Without being bound by any theory, high translation efficiency may result from reduction in degradation of the artificial nucleic acid molecule, such as an artificial mRNA molecule according to the present invention. Accordingly, the inventive 3'-UTR element and/or the inventive 5'-UTR element may prevent the artificial nucleic acid from degradation and decay.

Preferably, the artificial nucleic acid molecule may additionally comprise a histone stem-loop. Thus, an artificial nucleic acid molecule according to the present invention may, for example, comprise in 5'-to-3'-direction an ORF, a 3'-UTR element, an optional histone stem-loop sequence, an optional poly(A) sequence or polyadenylation signal and an optional poly(C) sequence or in 5'-to-3'-direction an 5'-UTR element, an ORF, an optional histone stem-loop sequence, an optional poly(A) sequence or polyadenylation signal and an optional poly(C) sequence or in 5'-to-3'-direction an 5'-UTR element, an ORF, a 3'-UTR element, an optional histone stem-loop sequence, an optional poly(A) sequence or polyadenylation signal and an optional poly(C) sequence. It may also comprise in 5'-to-3'-direction an ORF, an 3'-UTR element, an optional poly(A) sequence, an optional poly (C) sequence and an optional histone stem-loop sequence, or in 5'-to-3'-direction an 5'-UTR element, an ORF, an optional poly(A) sequence, an optional poly(C) sequence and an optional histone stem-loop sequence, or in 5'-to-3'-direction an 5'-UTR element, an ORF, a 3'-UTR element, an optional poly(A) sequence, an optional poly(C) sequence and an optional histone stem-loop sequence.

In a preferred embodiment, the artificial nucleic acid molecule according to the invention further comprises at least one histone stem-loop sequence.

Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

formula (I) (stem-loop sequence without stem bordering elements):

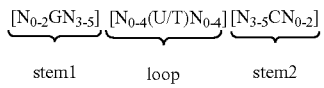

formula (II) (stem-loop sequence with stem bordering elements):

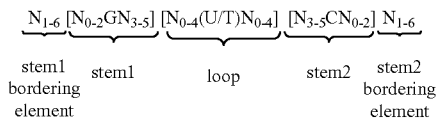

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

According to a further preferred embodiment the histone stem-loop sequence may be selected according to at least one of the following specific formulae (Ia) or (IIa):

formula (Ia) (stem-loop sequence without stem bordering elements):

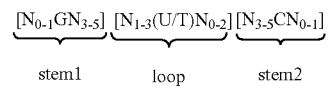

formula (IIa) (stem-loop sequence with stem bordering elements):

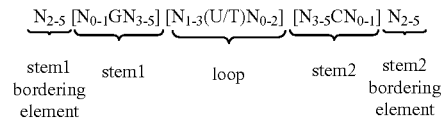

wherein:

N, C, G, T and U are as defined above.

According to a further more particularly preferred embodiment of the first aspect, the artificial nucleic acid molecule sequence may comprise at least one histone stem-loop sequence according to at least one of the following specific formulae (Ib) or (Ib):

formula (Ib) (stem-loop sequence without stem bordering elements):

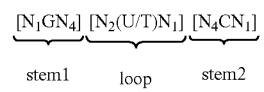

formula (IIb) (stem-loop sequence with stem bordering elements):

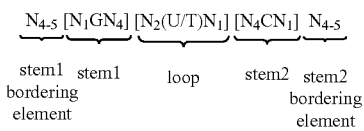

wherein:

N, C, G, T and U are as defined above.

A particular preferred histone stem-loop sequence is the sequence according to SEQ ID NO: 209: CAAAGGCTCTTTTCAGAGCCACCA or more preferably the corresponding RNA sequence of the nucleic acid sequence according to SEQ ID NO: 209.

As an example, the single elements may be present in the artificial nucleic acid molecule in the following order:

5'-cap-5'-UTR (element)-ORF-3'-UTR (element)-histone stem-loop-poly(A)/(C) sequence;

5'-cap-5'-UTR (element)-ORF-3'-UTR (element)-poly(A)/(C) sequence-histone stem-loop;

5'-cap-5'-UTR (element)-ORF-IRES-ORF-3'-UTR (element)-histone stem-loop-poly(A)/(C) sequence;

5'-cap-5'-UTR (element)-ORF-IRES-ORF-3'-UTR (element)-histone stem-loop-poly(A)/(C) sequence-poly(A)/(C) sequence;

5'-cap-5'-UTR (element)-ORF-IRES-ORF-3'-UTR (element)-poly(A)/(C) sequence-histone stem-loop;

5'-cap-5'-UTR (element)-ORF-IRES-ORF-3'-UTR (element)-poly(A)/(C) sequence-poly(A)/(C) sequence-histone stem-loop;

5'-cap-5'-UTR (element)-ORF-3'-UTR (element)-poly(A)/(C) sequence-poly(A)/(C) sequence;

5'-cap-5'-UTR (element)-ORF-3'-UTR (element)-poly(A)/(C) sequence-poly(A)/(C) sequence-histone stem loop;

etc.

In some embodiments, the artificial nucleic acid molecule comprises further elements such as a 5'-cap, a poly(C) sequence and/or an IRES-motif. A 5'-cap may be added during transcription or post-transcriptionally to the 5'end of an RNA. Furthermore, the inventive artificial nucleic acid molecule, particularly if the nucleic acid is in the form of an mRNA or codes for an mRNA, may be modified by a sequence of at least 10 cytidines, preferably at least 20 cytidines, more preferably at least 30 cytidines (so-called "poly(C) sequence"). In particular, the inventive artificial nucleic acid molecule may contain, especially if the nucleic acid is in the form of an (m)RNA or codes for an mRNA, a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. Most preferably, the inventive nucleic acid comprises a poly(C) sequence of 30 cytidine residues. Thus, preferably the artificial nucleic acid molecule according to the present invention comprises, preferably in 5'-to-3' direction, at least one 5'-UTR element as described above, an ORF, at least one 3'-UTR element as described above, a poly(A) sequence or a polyadenylation signal, and a poly(C) sequence or, in 5'-to-3' direction, optionally a further 5'-UTR, an ORF, at least one 3'-UTR element as described above, a poly(A) sequence or a polyadenylation signal, and a poly(C) sequence, or, in 5'-to-3' direction, at least one 5'-UTR element as described above, an ORF, optionally a further 3'-UTR, a poly(A) sequence or a polyadenylation signal, and a poly(C) sequence.

An internal ribosome entry site (IRES) sequence or IRES-motif may separate several open reading frames, for example if the artificial nucleic acid molecule encodes for two or more peptides or proteins. An IRES-sequence may be particularly helpful if the artificial nucleic acid molecule is a bi- or multicistronic nucleic acid molecule.

Furthermore, the artificial nucleic acid molecule may comprise additional 5'-elements, preferably a promoter or a promoter containing-sequence. The promoter may drive and or regulate transcription of the artificial nucleic acid molecule according to the present invention, for example of an artificial DNA-molecule according to the present invention.

Preferably, the artificial nucleic acid molecule according to the present invention, preferably the open reading frame, is at least partially G/C modified. Thus, the inventive artificial nucleic acid molecule may be thermodynamically stabilized by modifying the G (guanosine)/C (cytidine) content of the molecule. The G/C content of the open reading frame of an artificial nucleic acid molecule according to the present invention may be increased compared to the G/C content of the open reading frame of a corresponding wild-type sequence, preferably by using the degeneration of the genetic code. Thus, the encoded amino acid sequence of the artificial nucleic acid molecule is preferably not modified by the G/C modification compared to the coded amino acid sequence of the particular wild-type sequence. The codons of the coding sequence or the whole artificial nucleic acid molecule, e.g. an mRNA, may therefore be varied compared to the wild-type coding sequence, such that they include an increased amount of G/C nucleotides while the translated amino acid sequence is maintained. Due to the fact that several codons code for one and the same amino acid (so-called degeneration of the genetic code), it is feasible to alter codons while not altering the encoded peptide/protein sequence (so-called alternative codon usage). Hence, it is possible to specifically introduce certain codons (in exchange for the respective wild-type codons encoding the same amino acid), which are more favourable with respect to stability of RNA and/or with respect to codon usage in a subject (so-called codon optimization).

Depending on the amino acid to be encoded by the coding region of the inventive artificial nucleic acid molecule as defined herein, there are various possibilities for modification of the nucleic acid sequence, e.g. the open reading frame, compared to its wild-type coding region. In the case of amino acids, which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons which contain A and/or U/T nucleotides may be modified by substitution of other codons which code for the same amino acids but contain no A and/or U/T. For example the codons for Pro can be modified from CC(U/T) or CCA to CCC or CCG;

the codons for Arg can be modified from CG(U/T) or CGA or AGA or AGG to CGC or CGG;

the codons for Ala can be modified from GC(U/T) or GCA to GCC or GCG;

the codons for Gly can be modified from GG(U/T) or GGA to GGC or GGG.

In other cases, although A or (U/T) nucleotides cannot be eliminated from the codons, it is however possible to decrease the A and (U/T) content by using codons which contain a lower content of A and/or (U/T) nucleotides. Examples of these are:

The codons for Phe can be modified from (U/T)(U/T)(U/T) to (U/T) (U/T)C;
the codons for Leu can be modified from (U/T) (U/T)A, (U/T) (U/T)G, C(U/T) (U/T) or C(U/T)A to C(U/T)C or C(U/T)G;
the codons for Ser can be modified from (U/T)C(U/T) or (U/T)CA or AG(U/T) to (U/T)CC, (U/T)CG or AGC;
the codon for Tyr can be modified from (U/T)A(U/T) to (U/T)AC;
the codon for Cys can be modified from (U/T)G(U/T) to (U/T)GC;
the codon for His can be modified from CA(U/T) to CAC;
the codon for Gin can be modified from CAA to CAG;
the codons for lie can be modified from A(U/T)(U/T) or A(U/T)A to A(U/T)C;
the codons for Thr can be modified from AC(U/T) or ACA to ACC or ACG;
the codon for Asn can be modified from AA(U/T) to AAC;
the codon for Lys can be modified from AAA to AAG;
the codons for Val can be modified from G(U/T)(U/T) or G(U/T)A to G(U/T)C or G(U/T)G;
the codon for Asp can be modified from GA(U/T) to GAC;
the codon for Glu can be modified from GAA to GAG;
the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive artificial nucleic acid molecule as defined herein, compared to its particular wild-type open reading frame (i.e. the original sequence). Thus, for example, all codons for Thr occurring in the wild-type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild-type coding region without altering the encoded amino acid sequence, i.e. using the degeneracy of the genetic code. According to a specific embodiment at least 5%, 10%, 20%, 30%, 40%, 50%, 60%, more preferably at least 70%, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive artificial nucleic acid molecule as defined herein, to the maximum (i.e. 100% of the substitutable codons), compared to the wild-type open reading frame, without altering the encoded amino acid sequence.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case where codons coding for relatively "frequent" tRNAs are present.

Thus, the open reading frame of the inventive artificial nucleic acid molecule is preferably modified compared to the corresponding wild-type coding region such that at least one codon of the wild-type sequence which codes for a tRNA which is relatively rare in the cell is exchanged for a codon which codes for a tRNA which is comparably frequent in the cell and carries the same amino acid as the relatively rare tRNA. By this modification, the open reading frame of the inventive artificial nucleic acid molecule as defined herein, is modified such that codons for which frequently occurring tRNAs are available may replace codons which correspond to rare tRNAs. In other words, according to the invention, by such a modification all codons of the wild-type open reading frame which code for a rare tRNA may be exchanged for a codon which codes for a tRNA which is more frequent in the cell and which carries the same amino acid as the rare tRNA. Which tRNAs occur relatively frequently in the cell and which, in contrast, occur relatively rarely is known to a person skilled in the art; cf. e.g.: Akashi, Curr. Opin. Genet. Dev. 2001, 11(6): 660-666. Accordingly, preferably, the open reading frame is codon-optimized, preferably with respect to the system in which the artificial nucleic acid molecule according to the present invention is to be expressed, preferably with respect to the system in which the artificial nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo (or in vitro as defined above) degradation by an exo- or endonuclease, and/or for further improving stability of protein expression from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Generally, the artificial nucleic acid molecule of the present invention may comprise any native (=naturally occurring) nucleotide, e.g. guanosine, uracil, adenosine, and/or cytosine or an analogue thereof. In this respect, nucleotide analogues are defined as natively and non-natively occurring variants of the naturally occurring nucleotides adenosine, cytosine, thymidine, guanosine and uridine. Accordingly, analogues are e.g. chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the RNA sequence. Analogues of guanosine, uridine, adenosine, thymidine and cytosine include, without implying any limitation, any natively occurring or non-natively occurring guanosine, uridine, adenosine, thymidine or cytosine that has been altered e.g. chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-amino-2'-deoxyadenosine, 2'-amino-2'-deoxycytidine, 2'-amino-2'-deoxyguanosine, 2'-amino-2'-deoxyuridine, 2-amino-6-chloropurineriboside, 2-aminopurine-riboside, 2'-araadenosine, 2'-aracytidine, 2'-arauridine, 2'-azido-2'-deoxyadenosine, 2'-azido-2'-deoxycytidine, 2'-azido-2'-deoxyguanosine, 2'-azido-2'-deoxyuridine, 2-chloroadenosine, 2'-fluoro-2'-deoxyadenosine, 2'-fluoro-2'-deoxycytidine, 2'-fluoro-2'-deoxyguanosine, 2'-fluoro-2'-deoxyuridine, 2'-fluorothymidine, 2-methyl-adenosine, 2-methyl-guanosine, 2-methyl-thio-N6-isopenenyl-adenosine, 2'-O-methyl-2-aminoadenosine, 2'-O-methyl-2'-deoxyadenosine, 2'-O-methyl-2'-deoxycytidine, 2'-O-methyl-2'-deoxyguanosine, 2'-O-methyl-2'-deoxyuridine, 2'-O-methyl-5-methyluridine, 2'-O-methylinosine, 2'-O-methylpseudouridine, 2-thiocytidine, 2-thio-cytosine, 3-methyl-cytosine, 4-acetyl-cytosine, 4-thiouridine, 5-(carboxyhydroxymethyl)-uracil, 5,6-dihydrouridine, 5-aminoallylcytidine, 5-aminoallyl-deoxy-uridine, 5-bromouridine, 5-carboxymehtylaminomethyl-2-thio-uracil, 5-carboxymethylamonomethyl-uracil, 5-chloro-ara-cytosine, 5-fluoro-uridine, 5-iodouridine, 5-methoxycarbonylmethyl-uridine, 5-methoxy-uridine, 5-methyl-2-thio-uridine, 6-azacytidine, 6-azauridine, 6-chloro-7-deaza-guanosine, 6-chloropurineriboside, 6-mercapto-guanosine, 6-methyl-mercaptopurine-riboside, 7-deaza-2'-deoxy-guanosine, 7-deazaadenosine, 7-methyl-guanosine, 8-azaadenosine, 8-bromo-adenosine, 8-bromo-guanosine, 8-mercapto-guanosine, 8-oxoguanosine, benzimidazole-riboside, beta-D-mannosyl-queosine, dihydrouracil, Inosine, $N^6$-Methyladenosine, $N^6$-([6-aminohexyl]carbamoylmethyl)-adenosine, $N^6$-isopentenyl-adenosine, $N^6$-methyl-adenosine, N7-Methyl-xanthosine, N-uracil-5-oxyacetic acid methyl ester, puromycin, queosine, uracil-5-oxyacetic acid, uracil-5-oxyacetic acid methyl ester, wybutoxosine, xanthosine, and xylo-adenosine. The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference may be given according to certain embodiments of the invention to those analogues that increase the protein expression of the encoded peptide or protein or that increase the immunogenicity of the artificial nucleic acid molecule of the invention and/or do not interfere with a further modification of the artificial nucleic acid molecule that has been introduced.

According to a particular embodiment, the artificial nucleic acid molecule of the present invention can contain a lipid modification.

In a preferred embodiment, the artificial nucleic acid molecule comprises, preferably from 5' to 3' direction, the following elements:
a 5'-UTR element which provides high translation efficiency to said artificial nucleic acid molecule, preferably a nucleic acid sequence according to any of SEQ ID NO: 1 to 151; or a further 5'-UTR, preferably a 5'-TOP UTR;
at least one open reading frame (ORF), wherein the ORF preferably comprises at least one modification with respect to the wild-type sequence;
a 3'-UTR element which provides high translation efficiency to said artificial nucleic acid molecule, preferably a nucleic acid sequence according to any of SEQ ID NO: 152 to 204; or a further 3'-UTR, preferably an albumin7 3'-UTR;
a poly(A) sequence, preferably comprising 64 adenylates;
a poly(C) sequence, preferably comprising 30 cytidylates;
a histone stem-loop sequence.

In a particularly preferred embodiment, the artificial nucleic acid molecule according to the invention may further comprise one or more of the modifications described in the following:
Chemical Modifications:
The term "modification" as used herein with regard to the artificial nucleic acid molecule may refer to chemical modifications comprising backbone modifications as well as sugar modifications or base modifications.

In this context, the artificial nucleic acid molecule, preferably an RNA molecule, as defined herein may contain nucleotide analogues/modifications, e.g. backbone modifications, sugar modifications or base modifications. A backbone modification in connection with the present invention is a modification, in which phosphates of the backbone of the nucleotides contained in a nucleic acid molecule as defined herein are chemically modified. A sugar modification in connection with the present invention is a chemical modification of the sugar of the nucleotides of the nucleic acid molecule as defined herein. Furthermore, a base modification in connection with the present invention is a chemical modification of the base moiety of the nucleotides of the nucleic acid molecule of the nucleic acid molecule. In this context, nucleotide analogues or modifications are preferably selected from nucleotide analogues which are applicable for transcription and/or translation.
Sugar Modifications:
The modified nucleosides and nucleotides, which may be incorporated into the artificial nucleic acid molecule, preferably an RNA, as described herein, can be modified in the sugar moiety. Examples of "oxy"-2'-hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O($CH_2CH_2O$) $nCH_2CH_2OR$; "locked" nucleic acids (LNA) in which the 2' hydroxyl is connected, e.g., by a methylene bridge, to the 4' carbon of the same ribose sugar; and amino groups (—O-amino), wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleic acid molecule can include nucleotides containing, for instance, arabinose as the sugar.
Backbone Modifications:
The phosphate backbone may further be modified in the modified nucleosides and nucleotides, which may be incorporated into the artificial nucleic acid molecule, preferably an RNA, as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into the artificial nucleic acid molecule, preferably an RNA molecule, as described herein, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-aminopurine-riboside-5'-triphosphate; 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methylinosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments the artificial nucleic acid molecule, preferably an RNA molecule, may comprise nucleoside modifications selected from 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, α-thio-adenosine, 8-azido-adenosine, 7-deaza-adenosine.

Lipid Modification:

According to a further embodiment, the artificial nucleic acid molecule, preferably an RNA, as defined herein can contain a lipid modification. Such a lipid-modified RNA typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an artificial nucleic acid molecule, preferably an RNA molecule, as defined herein, at least one linker covalently linked with that RNA molecule, and at least one lipid covalently linked with the respective linker, and also at least one (bifunctional) lipid covalently linked (without a linker)

with that RNA molecule. In this context, it is particularly preferred that the lipid modification is present at the terminal ends of a linear RNA sequence.

Modification of the 5'-End of the Modified RNA:

According to another preferred embodiment of the invention, the artificial nucleic acid molecule, preferably an RNA molecule, as defined herein, can be modified by the addition of a so-called "5' CAP" structure.

A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in the modified RNA according to the invention. This means the artificial nucleic acid molecule, preferably an RNA molecule, according to the present invention may comprise a m7GpppN as 5'-CAP, but additionally the artificial nucleic acid molecule, preferably an RNA molecule, comprises at least one further modification as defined herein.

Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety. These modified 5'-CAP structures are regarded as at least one modification comprised in the artificial nucleic acid molecule, preferably in an RNA molecule, according to the present invention.

Particularly preferred modified 5'-CAP structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In a preferred embodiment, the at least one open reading frame encodes a therapeutic protein or peptide. In another embodiment, an antigen is encoded by the at least one open reading frame, such as a pathogenic antigen, a tumour antigen, an allergenic antigen or an autoimmune antigen. Therein, the administration of the artificial nucleic acid molecule encoding the antigen is used in a genetic vaccination approach against a disease involving said antigen.

In an alternative embodiment, an antibody or an antigen-specific T cell receptor or a fragment thereof is encoded by the at least one open reading frame of the artificial nucleic acid molecule according to the invention.

Antigens:
Pathogenic Antigens:

The artificial nucleic acid molecule according to the present invention may encode a protein or a peptide, which comprises a pathogenic antigen or a fragment, variant or derivative thereof. Such pathogenic antigens are derived from pathogenic organisms, in particular bacterial, viral or protozoological (multicellular) pathogenic organisms, which evoke an immunological reaction in a subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii, Anaplasma genus, Anaplasma phagocytophilum, Ancylostoma braziliense, Ancylostoma duodenale, Arcanobacterium haemolyticum, Ascaris lumbricoides, Aspergillus genus,* Astroviridae, *Babesia genus, Bacillus anthracis, Bacillus cereus, Bartonella henselae,* BK virus, *Blastocystis hominis, Blastomyces dermatitidis, Bordetella pertussis, Borrelia burgdorferi, Borrelia genus, Borrelia spp, Brucella genus, Brugia malayi,* Bunyaviridae family, *Burkholderia cepacia* and other *Burkholderia* species, *Burkholderia mallei, Burkholderia pseudomallei,* Caliciviridae family, *Campylobacter genus, Candida albicans, Candida* spp, *Chlamydia trachomatis, Chlamydophila pneumoniae, Chlamydophila psittaci,* CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii,* Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis,* Ebolavirus (EBOV), *Echinococcus* genus, *Ehrlichia chaffeensis, Ehrlichia ewingii, Ehrlichia* genus, *Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica,* FFI prion, Filarioidea superfamily, Flaviviruses, *Francisella tularensis, Fusobacterium* genus, *Geotrichum candidum, Giardia intestinalis, Gnathostoma* spp, GSS prion, Guanarito virus, *Haemophilus ducreyi, Haemophilus influenzae, Helicobacter pylori,* Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum,* HIV (Human immunodeficiency virus), *Hortaea werneckii,* Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis,* Kuru prion, Lassa virus, *Legionella pneumophila, Leishmania* genus, *Leptospira* genus, *Listeria monocytogenes,* Lymphocytic choriomeningitis virus (LCMV), Machupo virus, *Malassezia* spp, Marburg virus, Measles virus, *Metagonimus yokagawai,* Microsporidia phylum, Molluscum contagiosum virus (MCV), Mumps virus, *Mycobacterium leprae* and *Mycobacterium* lepromatosis, *Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides,* Nocardia spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In this context particularly preferred are antigens from the pathogens selected from Influenza virus, respiratory syncytial virus (RSV), Herpes simplex virus (HSV), human Papilloma virus (HPV), Human immunodeficiency virus (HIV), *Plasmodium*, *Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus.

Tumour Antigens:

In a further embodiment the artificial nucleic acid molecule according to the present invention may encode a protein or a peptide, which comprises a peptide or protein comprising a tumour antigen, a fragment, variant or derivative of said tumour antigen, preferably, wherein the tumour antigen is a melanocyte-specific antigen, a cancer-testis antigen or a tumour-specific antigen, preferably a CT-X antigen, a non-X CT-antigen, a binding partner for a CT-X antigen or a binding partner for a non-X CT-antigen or a tumour-specific antigen, more preferably a CT-X antigen, a binding partner for a non-X CT-antigen or a tumour-specific antigen or a fragment, variant or derivative of said tumour antigen; and wherein each of the nucleic acid sequences encodes a different peptide or protein; and wherein at least one of the nucleic acid sequences encodes for 5T4, 707-AP, 9D7, AFP, AIbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/ SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, $p^1$90 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, WT1 and a immunoglobulin idiotype of a lymphoid blood cell or a T cell receptor idiotype of a lymphoid blood cell, or a fragment, variant or derivative of said tumour antigen; preferably survivin or a homologue thereof, an antigen from the MAGE-family or a binding partner thereof or a fragment, variant or derivative of said tumour antigen. Particularly preferred in this context are the tumour antigens NY-ESO-1, 5T4, MAGE-C1, MAGE-C2, Survivin, Muc-1, PSA, PSMA, PSCA, STEAP and PAP.

In a preferred embodiment, the artificial nucleic acid molecule encodes a protein or a peptide, which comprises a therapeutic protein or a fragment, variant or derivative thereof.

Therapeutic proteins as defined herein are peptides or proteins, which are beneficial for the treatment of any inherited or acquired disease or which improves the condition of an individual. Particularly, therapeutic proteins play an important role in the creation of therapeutic agents that could modify and repair genetic errors, destroy cancer cells or pathogen infected cells, treat immune system disorders, treat metabolic or endocrine disorders, among other functions. For instance, Erythropoietin (EPO), a protein hormone can be utilized in treating patients with erythrocyte deficiency, which is a common cause of kidney complications. Furthermore adjuvant proteins, therapeutic antibodies are encompassed by therapeutic proteins and also hormone replacement therapy which is e.g. used in the therapy of women in menopause. In more recent approaches, somatic cells of a patient are used to reprogram them into pluripotent stem cells, which replace the disputed stem cell therapy. Also these proteins used for reprogramming of somatic cells or used for differentiating of stem cells are defined herein as therapeutic proteins. Furthermore, therapeutic proteins may be used for other purposes, e.g. wound healing, tissue regeneration, angiogenesis, etc. Furthermore, antigen-specific B cell receptors and fragments and variants thereof are defined herein as therapeutic proteins.

Therefore therapeutic proteins can be used for various purposes including treatment of various diseases like e.g. infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired.

In this context, particularly preferred therapeutic proteins which can be used inter alia in the treatment of metabolic or endocrine disorders are selected from (in brackets the particular disease for which the therapeutic protein is used in the treatment): Acid sphingomyelinase (Niemann-Pick disease), Adipotide (obesity), Agalsidase-beta (human galactosidase A) (Fabry disease; prevents accumulation of lipids that could lead to renal and cardiovascular complications), Alglucosidase (Pompe disease (glycogen storage disease type II)), alpha-galactosidase A (alpha-GAL A, Agalsidase alpha) (Fabry disease), alpha-glucosidase (Glycogen storage disease (GSD), Morbus Pompe), alpha-L-iduronidase (mucopolysaccharidoses (MPS), Hurler syndrome, Scheie syndrome), alpha-N-acetylglucosaminidase (Sanfilippo syndrome), Amphiregulin (cancer, metabolic disorder), Angiopoietin ((Ang1, Ang2, Ang3, Ang4, ANGPTL2, ANGPTL3, ANGPTL4, ANGPTL5, ANGPTL6, ANGPTL7) (angiogenesis, stabilize vessels), Betacellulin (metabolic disorder), Beta-glucuronidase (Sly syndrome), Bone morphogenetic protein BMPs (BMP1, BMP2, BMP3, BMP4, BMP5, BMP6, BMP7, BMP8a, BMP8b, BMP10, BMP15) (regenerative effect, bone-related conditions, chronic kidney disease (CKD)), CLN6 protein (CLN6 disease—Atypical Late Infantile, Late Onset variant, Early Juvenile, Neuronal Ceroid Lipofuscinoses (NCL)), Epidermal growth factor (EGF) (wound healing, regulation of cell growth, proliferation, and differentiation), Epigen (metabolic disorder), Epiregulin (metabolic disorder), Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23) (wound healing, angiogenesis, endocrine disorders, tissue regeneration), Galsulphase (Mucopolysaccharidosis VI), Ghrelin (irritable bowel syndrome (IBS), obesity, Prader-Willi syndrome, type II diabetes mellitus), Glucocerebrosidase (Gaucher's disease), GM-CSF (regenerative effect, production of white blood cells, cancer), Heparin-binding EGF-like growth factor (HB-EGF) (wound healing, cardiac hypertrophy and heart development and function), Hepatocyte growth factor HGF (regenerative effect, wound healing), Hepcidin (iron metabolism disorders, Beta-thalassemia), Human albumin (Decreased production of albumin (hypoproteinaemia), increased loss of albumin (nephrotic syndrome), hypovolaemia, hyperbilirubinaemia), Idursulphase (Iduronate-2-sulphatase) (Mucopolysaccharidosis II (Hunter syndrome)), Integrins αVβ3, αVβ5 and α5β1 (Bind matrix macromolecules and proteinases, angiogenesis), Iuduronate sulfatase (Hunter syndrome), Laronidase (Hurler and Hurler-Scheie forms of mucopolysaccharidosis I), N-acetylgalactosamine-4-sulfatase (rhASB; galsulfase, Arylsulfatase A (ARSA), Arylsulfatase B (ARSB)) (arylsulfatase B deficiency, Maroteaux-Lamy syndrome, mucopolysaccharidosis VI), N-acetylglucosamine-6-sulfatase (Sanfilippo syndrome), Nerve growth factor (NGF, Brain-Derived Neurotrophic Factor (BDNF), Neurotrophin-3 (NT-3), and Neurotrophin 4/5 (NT-4/5) (regenerative effect, cardiovascular diseases, coronary atherosclerosis, obesity, type 2 diabetes, metabolic syndrome, acute coronary syndromes, dementia, depression, schizophrenia, autism, Rett syndrome, anorexia nervosa, bulimia nervosa, wound healing, skin ulcers, corneal ulcers, Alzheimer's disease), Neuregulin (NRG1, NRG2, NRG3, NRG4) (metabolic disorder, schizophrenia), Neuropilin (NRP-1, NRP-2) (angiogenesis, axon guidance, cell survival, migration), Obestatin (irritable bowel syndrome (IBS), obesity, Prader-Willi syndrome, type II diabetes mellitus), Platelet Derived Growth factor (PDGF (PDFF-A, PDGF-B, PDGF-C, PDGF-D) (regenerative effect, wound healing, disorder in angiogenesis, Arteriosclerosis, Fibrosis, cancer), TGF beta receptors (endoglin, TGF-beta 1 receptor, TGF-beta 2 receptor, TGF-beta 3 receptor) (renal fibrosis, kidney disease, diabetes, ultimately end-stage renal disease (ESRD), angiogenesis), Thrombopoietin (THPO) (Megakaryocyte growth and development factor (MGDF)) (platelets disorders, platelets for donation, recovery of platelet counts after myelosuppressive chemotherapy), Transforming Growth factor (TGF (TGF-alpha, TGF-beta (TGFbeta1, TGFbeta2, and TGFbeta3))) (regenerative effect, wound healing, immunity, cancer, heart disease, diabetes, Marfan syndrome, Loeys-Dietz syndrome), VEGF (VEGF-A, VEGF-B, VEGF-C, VEGF-D, VEGF-E, VEGF-F and PlGF) (regenerative effect, angiogenesis, wound healing, cancer, permeability), Nesiritide (Acute decompensated congestive heart failure), Trypsin (Decubitus ulcer, varicose ulcer, debridement of eschar, dehiscent wound, sunburn, meconium ileus), adrenocorticotrophic hormone (ACTH) ("Addison's disease, Small cell carcinoma, Adrenoleukodystrophy, Congenital adrenal hyperplasia, Cushing's syndrome, Nelson's syndrome, Infantile spasms), Atrial-natriuretic peptide (ANP) (endocrine disorders), Cholecystokinin (diverse), Gastrin (hypogastrinemia), Leptin (Diabetes, hypertriglyceridemia, obesity), Oxytocin (stimulate breastfeeding, non-progression of parturition), Somatostatin (symptomatic treatment of carcinoid syndrome, acute variceal bleeding, and acromegaly, polycystic diseases of the liver and kidney, acromegaly and symptoms caused by neuroendocrine tumors), Vasopressin (antidiuretic hormone) (diabetes insipidus), Calcitonin (Postmenopausal osteoporosis, Hypercalcaemia, Paget's disease, Bone metastases, Phantom limb pain, Spinal Stenosis), Exenatide (Type 2 diabetes resistant to treatment with metformin and a sulphonylurea), Growth hormone (GH), somatotropin (Growth failure due to GH deficiency or chronic renal insufficiency, Prader-Willi syndrome, Turner syndrome, AIDS wasting or cachexia with antiviral therapy), Insulin (Diabetes mellitus, diabetic ketoacidosis, hyperkalaemia), Insulin-like growth factor 1 IGF-1 (Growth failure in children with GH gene deletion or severe primary IGF1 deficiency, neurodegenerative disease, cardiovascular diseases, heart failure), Mecasermin rinfabate, IGF-1 analog (Growth failure in children with GH gene deletion or severe primary IGF1 deficiency, neurodegenerative disease, cardiovascular diseases, heart failure), Mecasermin, IGF-1 analog (Growth failure in children with GH gene deletion or severe primary IGF1 deficiency, neurodegenerative disease, cardiovascular diseases, heart failure), Pegvisomant (Acromegaly), Pramlintide (Diabetes mellitus, in combination with insulin), Teriparatide (human parathyroid hormone residues 1-34) (Severe osteoporosis), Becaplermin (Debridement adjunct for diabetic ulcers), Dibotermin-alpha (Bone morphogenetic protein 2) (Spinal fusion surgery, bone injury repair), Histrelin acetate (gonadotropin releasing hormone; GnRH) (Precocious puberty), Octreotide (Acromegaly, symptomatic relief of VIP-secreting adenoma and metastatic carcinoid tumours), and Palifermin (keratinocyte growth factor; KGF) (Severe oral mucositis in patients undergoing chemotherapy, wound healing).

These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunedeficiencies following therapeutic proteins may be used: Alteplase (tissue plasminogen activator; tPA) (Pulmonary embolism, myocardial infarction, acute ischaemic stroke, occlusion of central venous access devices), Anistreplase (Thrombolysis), Antithrombin III (AT-III) (Hereditary AT-III deficiency, Thromboembolism), Bivalirudin (Reduce blood-clotting risk in coronary angioplasty and heparin-induced thrombocytopaenia), Darbepoetin-alpha (Treatment of anaemia in patients with chronic renal insufficiency and chronic renal failure (+/−dialysis)), Drotrecogin-alpha (activated protein C) (Severe sepsis with a high risk of death), Erythropoietin, Epoetin-alpha, erythropoetin, erthropoyetin (Anaemia of chronic disease, myleodysplasia, anaemia due to renal failure or chemotherapy, preoperative preparation), Factor IX (Haemophilia B), Factor Vila (Haemorrhage in patients with haemophilia A or B and inhibitors to factor VIII or factor IX), Factor VIII (Haemophilia A), Lepirudin (Heparin-induced thrombocytopaenia), Protein C concentrate (Venous thrombosis, Purpura fulminans), Reteplase (deletion mutein of tPA) (Management of acute myocardial infarction, improvement of ventricular function), Streptokinase (Acute evolving transmural myocardial infarction, pulmonary embolism, deep vein thrombosis, arterial thrombosis or embolism, occlusion of arteriovenous cannula), Tenecteplase (Acute myocardial infarction), Urokinase (Pulmonary embolism), Angiostatin (Cancer), Anti-CD22 immunotoxin (Relapsed CD33+ acute myeloid leukaemia), Denileukin diftitox (Cutaneous T-cell lymphoma (CTCL)), Immunocyanin (bladder and prostate cancer), MPS (Metallopanstimulin) (Cancer), Aflibercept (Non-small cell lung cancer (NSCLC), metastatic colorectal cancer (mCRC), hormone-refractory metastatic prostate cancer, wet macular degeneration), Endostatin (Cancer, inflammatory diseases like rheumatoid arthritis as well as Crohn's disease, diabetic retinopathy, psoriasis, and endometriosis), Collagenase (Debridement of chronic dermal ulcers and severely burned areas, Dupuytren's contracture, Peyronie's disease), Human deoxy-ribonuclease I, dornase (Cystic fibrosis; decreases respiratory tract infections in selected patients with FVC greater than 40% of predicted), Hyaluronidase (Used as an adjuvant to increase the absorption and dispersion of injected drugs, particularly anaesthetics in ophthalmic surgery and certain imaging agents), Papain (Debridement of necrotic tissue or liquefication of slough in acute and chronic lesions, such as pressure ulcers, varicose and diabetic ulcers, burns, postoperative wounds, pilonidal cyst wounds, carbuncles, and other wounds), L-Asparaginase (Acute lymphocytic leukaemia, which requires exogenous asparagine for proliferation), Peg-asparaginase (Acute lymphocytic leukaemia, which requires exogenous asparagine for proliferation), Rasburicase (Paediatric patients with leukaemia, lymphoma, and solid tumours who are undergoing anticancer therapy that may cause tumour lysis syndrome), Human chorionic gonadotropin (HCG) (Assisted reproduction), Human follicle-stimulating hormone (FSH) (Assisted reproduction), Lutropin-alpha (Infertility with luteinizing hormone deficiency), Prolactin (Hypoprolactinemia, serum prolactin deficiency, ovarian dysfunction in women, anxiety, arteriogenic erectile dysfunction, premature ejaculation, oligozoospermia, asthenospermia, hypofunction of seminal vesicles, hypoandrogenism in men), alpha-1-Proteinase inhibitor (Congenital antitrypsin deficiency), Lactase (Gas, bloating, cramps and diarrhoea due to inability to digest lactose), Pancreatic enzymes (lipase, amylase, protease) (Cystic fibrosis, chronic pancreatitis, pancreatic insufficiency, post-Billroth II gastric bypass surgery, pancreatic duct obstruction, steatorrhoea, poor digestion, gas, bloating), Adenosine deaminase (pegademase bovine, PEG-ADA) (Severe combined immunodeficiency disease due to adenosine deaminase deficiency), Abatacept (Rheumatoid arthritis (especially when refractory to TNFalpha inhibition)), Alefacept (Plaque Psoriasis), Anakinra (Rheumatoid arthritis), Etanercept (Rheumatoid arthritis, polyarticular-course juvenile rheumatoid arthritis, psoriatic arthritis, ankylosing spondylitis, plaque psoriasis, ankylosing spondylitis), Interleukin-1 (IL-1) receptor antagonist, Anakinra (inflammation and cartilage degradation associated with rheumatoid arthritis), Thymulin (neurodegenerative diseases, rheumatism, anorexia nervosa), TNF-alpha antagonist (autoimmune disorders such as rheumatoid arthritis, ankylosing spondylitis, Crohn's disease, psoriasis, hidradenitis suppurativa, refractory asthma), Enfuvirtide (HIV-1 infection), and Thymosin α1 (Hepatitis B and C). (in brackets is the particular disease for which the therapeutic protein is used in the treatment)

In a further aspect, the present invention provides a vector comprising
a. an open reading frame (ORF) and/or a cloning site, e.g. for insertion of an open reading frame or a sequence comprising an open reading frame; and
b. at least one 3'-untranslated region element (3'-UTR element) and/or at least one 5'-untranslated region element (5'-UTR element), wherein said artificial nucleic acid molecule is characterized by high translation efficiency.

In general, the vector according to the present invention may comprise an artificial nucleic acid molecule according to the present invention as described above. In particular, the preferred embodiments described above for an artificial nucleic acid molecule according to the present invention also apply for an artificial nucleic acid molecule according to the present invention, which is comprised by a vector according to the present invention. For example, in the inventive vector the at least one 3'-UTR element and/or the at least one 5'-UTR element and the ORF are as described above for the artificial nucleic acid molecule according to the present invention, including the preferred embodiments. For example, in the vector according to the present invention, the stable mRNA from which the at least one 3'-UTR element and/or the at least one 5'-UTR element is derived may be preferably characterized by an mRNA decay wherein the ratio of the amount of said mRNA at a second point in time to the amount of said mRNA at a first point in time is at least 0.5 (50%), at least 0.6 (60%), at least 0.7 (70%), at least 0.75 (75%), at least 0.8 (80%), at least 0.85 (85%), at least 0.9 (90%), or at least 0.95 (95%).

The cloning site may be any sequence that is suitable for introducing an open reading frame or a sequence comprising an open reading frame, such as one or more restriction sites. Thus, the vector comprising a cloning site is preferably suitable for inserting an open reading frame into the vector, preferably for inserting an open reading frame 3' to the 5'-UTR element and/or 5' to the 3'-UTR element. Preferably the cloning site or the ORF is located 3' to the 5'-UTR element and/or 5' to the 3'-UTR element, preferably in close proximity to the 3'-end of the 5'-UTR element and/or to the 5'-end of the 3'-UTR element. For example, the cloning site or the ORF may be directly connected to the 3'-end of the 5'-UTR element and/or to the 5'-end of the 3'-UTR element or they may be connected via a stretch of nucleotides, such as by a stretch of 2, 4, 6, 8, 10, 20 etc. nucleotides as described above for the artificial nucleic acid molecule according to the present invention.

Preferably, the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognized by a polymerase, such as by an RNA polymerase, e.g. by a eukaryotic, prokaryotic, viral, or phage RNA polymerase. In a preferred embodiment, the vector comprises a phage RNA polymerase promoter such as an SP6, T3 or T7, preferably a T7 promoter. Preferably, the vector is suitable for in vitro transcription using a phage based in vitro transcription system, such as a T7 RNA polymerase based in vitro transcription system.

In another preferred embodiment, the vector may be used directly for expression of the encoded peptide or protein in cells or tissue. For this purpose, the vector comprises particular elements, which are necessary for expression in those cells/tissue e.g. particular promoter sequences, such as a CMV promoter.

The vector may further comprise a poly(A) sequence and/or a polyadenylation signal as described above for the artificial nucleic acid molecule according to the present invention.

The vector may be an RNA vector or a DNA vector. Preferably, the vector is a DNA vector. The vector may be any vector known to the skilled person, such as a viral vector or a plasmid vector. Preferably, the vector is a plasmid vector, preferably a DNA plasmid vector.

In a preferred embodiment, the vector according to the present invention comprises the artificial nucleic acid molecule according to the present invention.

Preferably, a DNA vector according to the invention comprises a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'-UTR of a transcript of a gene, such as to the nucleic acid sequences according to SEQ ID NOs: 152 to 204.

Preferably, a DNA vector according to the invention comprises a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 5'-UTR element of a transcript of a gene, such as to the nucleic acid sequences according to SEQ ID NOs: 1 to 151.

Preferably, a DNA vector according to the present invention comprises a sequence selected from the group consisting of DNA sequences according to 5'-UTR elements represented by SEQ ID NO: 1, SEQ ID NO: 2, SEQ ID NO: 137 (alternatively SEQ ID NO: 3), SEQ ID NO: 138 (alternatively SEQ ID NO: 9), SEQ ID NO: 10, SEQ ID NO: 12, SEQ ID NO: 15, SEQ ID NO: 140 (alternatively SEQ ID NO: 17), SEQ ID NO: 20, SEQ ID NO: 22, SEQ ID NO: 23, SEQ ID NO: 143 (alternatively SEQ ID NO: 31), SEQ ID NO: 32, SEQ ID NO: 39, SEQ ID NO: 41, SEQ ID NO: 44, SEQ ID NO: 45, SEQ ID NO: 146 (alternatively SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (alternatively SEQ ID NO: 42), SEQ ID NO: 58, SEQ ID NO: 62; SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (alternatively SEQ ID NO: 109), SEQ ID NO: 148 (alternatively SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (alternatively SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (alternatively SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125 and 3'-UTR elements represented by SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173; SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (alternatively SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% sequence identity to any of said sequences, or a fragment thereof as described above, preferably a functional fragment thereof.

Preferably, an RNA vector according to the present invention comprises a sequence selected from the group consisting of the sequences according to RNA sequences corresponding to DNA sequences described above in relation to the DNA vector according to the present invention.

Preferably, the vector is a circular molecule. Preferably, the vector is a double-stranded molecule, such as a double-stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the ORF, or—if present—located immediately 3' to the 3'-UTR element, or—if present—located 3' to the poly(A) sequence or polyadenylation signal, or—if present—located 3' to the poly(C) sequence, or—if present—located 3' to the histone stem-loop. Thus, preferably, the product obtained by linearizing the vector terminates at the 3' end with the 3'-end of the ORF, or—if present—with the 3'-end of the 3'-UTR element, or—if present—with the 3'-end of the poly(A) sequence or polyadenylation signal, or—if present—with the 3'-end of the poly(C) sequence. In the embodiment, wherein the vector according to the present invention comprises the artificial nucleic acid molecule according to the present invention, a restriction site, preferably a unique restriction site, is preferably located immediately 3' to the 3'-end of the artificial nucleic acid molecule.

In a further aspect, the present invention relates to a cell comprising the artificial nucleic acid molecule according to the present invention or the vector according to present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection, transduction or transformation methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of human subject, a domestic animal, a laboratory animal, such as a mouse or rat cell. Preferably the cell is a human cell. The cell may be a cell of an established cell line, such as a CHO, BHK, 293T, COS-7, HeLa, HEPG2 and HEK, etc. or the cell may be a primary cell, such as a human dermal fibroblast (HDF) cell etc., preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable vehicles, diluents and/or excipients and/or one or more adjuvants. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g phosphate, citrate etc. buffered solutions. The buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive artificial nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component which may be suitable for depot and delivery of an artificial nucleic acid molecule or vector according to the invention. Such components may be, for example, cationic or polycationic carriers or compounds which may serve as transfection or complexation agent.

In a preferred embodiment according to the invention, the artificial nucleic acid molecule or the vector is complexed with one or more cationic or polycationic compounds, preferably with cationic or polycationic polymers, cationic or polycationic peptides or proteins, e.g. protamine, cationic or polycationic polysaccharides and/or cationic or polycationic lipids.

According to a preferred embodiment, the artificial nucleic acid molecule or the vector may be complexed with lipids to form one or more liposomes, lipoplexes, or lipid nanoparticles. Therefore, in one embodiment, the inventive pharmaceutical composition comprises liposomes, lipoplexes, and/or lipid nanoparticles comprising the artificial nucleic acid molecule or the vector, preferably RNA, more preferably mRNA.

Lipid-based formulations have been increasingly recognized as one of the most promising delivery systems for nucleic acids, particularly for RNA, due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are typically colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin RNA-shRNA). Cationic lipids, such as DOTAP (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.).

Therefore, in one embodiment the artificial nucleic acid molecule or the vector, preferably the RNA of the pharmaceutical composition according to the present invention, is complexed with cationic lipids and/or neutral lipids and thereby forms liposomes, lipid nanoparticles, lipoplexes or neutral lipid-based nanoliposomes.

In further embodiments particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\}; \qquad \text{formula (I)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Preferred cationic peptides and proteins are also described in the international patent application WO 2009/030481, the disclosure of which is herewith incorporated by reference.

Further, the cationic or polycationic peptide or protein, when defined according to formula $\{(Arg)_l; (Lys)_m; (His)_n; (Orn)_o; (Xaa)_x\}$ (formula (I)) as shown above and which comprise or are additionally modified to comprise at least one —SH moeity, may be, without being restricted thereto, selected from subformula (Ia):

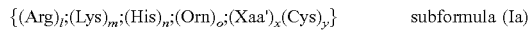
{(Arg)$_l$;(Lys)$_m$;(His)$_n$;(Orn)$_o$;(Xaa')$_x$(Cys)$_y$}   subformula (Ia)

wherein (Arg)$_l$; (Lys)$_m$; (His)$_n$; (Orn)$_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. In this context, the disclosure of WO 2012/013326 is incorporated herewith by reference. Further, the cationic or polycationic peptide may be selected from subformula (Ib):

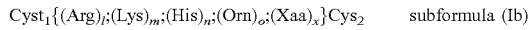
Cys$_1${(Arg)$_l$;(Lys)$_m$;(His)$_n$;(Orn)$_o$;(Xaa)$_x$}Cys$_2$   subformula (Ib)

wherein empirical formula {(Arg)$_l$; (Lys)$_m$; (His); (Orn)$_o$; (Xaa)} (formula (III)) is as defined herein and forms a core of an amino acid sequence according to (semiempirical) formula (III) and wherein Cys, and Cys$_2$ are Cysteines proximal to, or terminal to (Arg)$_l$; (Lys)$_m$; (His)$_n$; (Orn)$_o$; (Xaa)$_x$. In this context the disclosure of WO 2011/026641 is incorporated herewith by reference Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C$_{14}$-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyamino acids, such as β-amino acid-polymers or reversed polyamides, etc., modified polyethylenes, such as PVP (poly (N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly (ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycol); etc.

According to another embodiment, the pharmaceutical composition according to the invention may comprise an adjuvant in order to enhance the immunostimulatory properties of the pharmaceutical composition. In this context, an adjuvant may be understood as any compound, which is suitable to support administration and delivery of the components such as the artificial nucleic acid molecule or vector comprised in the pharmaceutical composition according to the invention. Furthermore, such an adjuvant may, without being bound thereto, initiate or increase an immune response of the innate immune system, i.e. a non-specific immune response. With other words, when administered, the pharmaceutical composition according to the invention typically initiates an adaptive immune response directed to the antigen encoded by the artificial nucleic acid molecule. Additionally, the pharmaceutical composition according to the invention may generate an (supportive) innate immune response due to addition of an adjuvant as defined herein to the pharmaceutical composition according to the invention.

Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i)N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-lbeta; interleukin-2; interleukin-7; interleukin-12; ISCOMS™; ISCOPREP 7.0.3.™; liposomes; LOXOR-IBINE™ (7-allyl-8-oxoguanosine); LT oral adjuvant (E. coli labile enterotoxin-protoxin); microspheres and microparticles of any composition; MF59™; (squalene-water emulsion); MONTANIDE ISA 51™ (purified incomplete Freund's adjuvant); MONTANIDE ISA$_{720}$™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5 c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robanee (2,6,10,15,19,23-hexamethyltetracosan and 2,6,10,15,19,23-hexamethyl-2,6,10,14,18,22-tetracosahexane); stearyltyrosi ne (octadecyltyrosine hydrochloride); Theramid (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNF-PIIV/Lewis X, antimicrobial peptides, UC-1V150, RSV fusion protein, cdiGMP; and adjuvants suitable as antagonists including CGRP neuropeptide.

Suitable adjuvants may also be selected from cationic or polycationic compounds wherein the adjuvant is preferably prepared upon complexing the artificial nucleic acid molecule or the vector of the pharmaceutical composition with the cationic or polycationic compound.

Association or complexing the artificial nucleic acid molecule or the vector of the pharmaceutical composition with cationic or polycationic compounds as defined herein preferably provides adjuvant properties and confers a stabilizing effect to the artificial nucleic acid molecule or the vector of the pharmaceutical composition. Particularly such preferred, such cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, protamine, spermine, spermidine, or histones. Further preferred cationic or polycationic compounds may include cationic polysaccharides, for example chitosan, polybrene, cationic polymers, e.g. polyethyleneimine (PEI), cationic lipids, e.g. DOTMA: 1-(2,3-sioleyloxy)propyl)-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]-trimethylammonium, CLIP9: rac-[2(2,3-dihexadecyloxypropyl-oxysuccinyloxy)ethyl]-tri methylammonium, oligofectamine, or cationic or polycationic polymers, e.g. modified polyamino acids, such as -amino acid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the artificial nucleic acid molecule or the vector, preferably an RNA, of the composition, may be selected from following proteins or peptides having the following total formula (I): $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred oligoargines in this context are e.g. $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc.

The ratio of the artificial nucleic acid or the vector to the cationic or polycationic compound may be calculated on the basis of the nitrogen/phosphate ratio (N/P-ratio) of the entire nucleic acid complex. For example, 1 μg RNA typically contains about 3 nmol phosphate residues, provided the RNA exhibits a statistical distribution of bases. Additionally, 1 μg peptide typically contains about x nmol nitrogen residues, dependent on the molecular weight and the number of basic amino acids. When exemplarily calculated for (Arg)9 (molecular weight 1424 g/mol, 9 nitrogen atoms), 1 μg $(Arg)_9$ contains about 700 pmol $(Arg)_9$ and thus 700× 9=6300 pmol basic amino acids=6.3 nmol nitrogen atoms.

For a mass ratio of about 1:1 RNA/(Arg)$_9$ an N/P ratio of about 2 can be calculated. When exemplarily calculated for protamine (molecular weight about 4250 g/mol, 21 nitrogen atoms, when protamine from salmon is used) with a mass ratio of about 2:1 with 2 µg RNA, 6 nmol phosphate are to be calculated for the RNA; 1 µg protamine contains about 235 pmol protamine molecules and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of nucleic acid:peptide in the complex, and most preferably in the range of about 0.7-1.5.

Patent application WO2010/037539, the disclosure of which is incorporated herein by reference, describes an immunostimulatory composition and methods for the preparation of an immunostimulatory composition. Accordingly, in a preferred embodiment of the invention, the composition is obtained in two separate steps in order to obtain both, an efficient immunostimulatory effect and efficient translation of the artificial nucleic acid molecule according to the invention. Therein, a so called "adjuvant component" is prepared by complexing—in a first step—the artificial nucleic acid molecule or vector, preferably an RNA, of the adjuvant component with a cationic or polycationic compound in a specific ratio to form a stable complex. In this context, it is important, that no free cationic or polycationic compound or only a negligibly small amount remains in the adjuvant component after complexing the nucleic acid. Accordingly, the ratio of the nucleic acid and the cationic or polycationic compound in the adjuvant component is typically selected in a range that the nucleic acid is entirely complexed and no free cationic or polycationic compound or only a neglectably small amount remains in the composition. Preferably the ratio of the adjuvant component, i.e. the ratio of the nucleic acid to the cationic or polycationic compound is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

According to a preferred embodiment, the artificial nucleic acid molecule or vector, preferably an RNA molecule, according to the invention is added in a second step to the complexed nucleic acid molecule, preferably an RNA, of the adjuvant component in order to form the (immunostimulatory) composition of the invention. Therein, the artificial acid molecule or vector, preferably an RNA, of the invention is added as free nucleic acid, i.e. nucleic acid, which is not complexed by other compounds. Prior to addition, the free artificial nucleic acid molecule or vector is not complexed and will preferably not undergo any detectable or significant complexation reaction upon the addition of the adjuvant component.

Suitable adjuvants may furthermore be selected from nucleic acids having the formula (II): GlXmGn, wherein: G is guanosine (guanine), uridine (uracil) or an analogue of guanosine (guanine) or uridine (uracil); X is guanosine (guanine), uridine (uracil), adenosine (adenine), thymidine (thymine), cytidine (cytosine) or an analogue of the above-mentioned nucleotides (nucleosides); l is an integer from 1 to 40, wherein when l=1 G is guanosine (guanine) or an analogue thereof, when l>1 at least 50% of the nucleotides (nucleosides) are guanosine (guanine) or an analogue thereof; m is an integer and is at least 3; wherein when m=3 X is uridine (uracil) or an analogue thereof, when m>3 at least 3 successive uridines (uracils) or analogues of uridine (uracil) occur; n is an integer from 1 to 40, wherein when n=1 G is guanosine (guanine) or an analogue thereof, when n>1 at least 50% of the nucleotides (nucleosides) are guanosine (guanine) or an analogue thereof.

Other suitable adjuvants may furthermore be selected from nucleic acids having the formula (III): ClXmCn, wherein: C is cytidine (cytosine), uridine (uracil) or an analogue of cytidine (cytosine) or uridine (uracil); X is guanosine (guanine), uridine (uracil), adenosine (adenine), thymidine (thymine), cytidine (cytosine) or an analogue of the above-mentioned nucleotides (nucleosides); l is an integer from 1 to 40, wherein when l=1 C is cytidine (cytosine) or an analogue thereof, when l>1 at least 50% of the nucleotides (nucleosides) are cytidine (cytosine) or an analogue thereof; m is an integer and is at least 3; wherein when m=3 X is uridine (uracil) or an analogue thereof, when m>3 at least 3 successive uridines (uracils) or analogues of uridine (uracil) occur; n is an integer from 1 to 40, wherein when n=1 C is cytidine (cytosine) or an analogue thereof, when n>1 at least 50% of the nucleotides (nucleosides) are cytidine (cytosine) or an analogue thereof.

The pharmaceutical composition according to the present invention preferably comprises a "safe and effective amount" of the components of the pharmaceutical composition, particularly of the inventive artificial nucleic acid molecule, the vector and/or the cells as defined herein. As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments which benefit from an increased and prolonged presence of therapeutic peptides, polypeptides or proteins in a subject to be treated are especially suitable as medical application in the context of the present invention, since the inventive 3'-UTR element provides for a stable and prolonged expression of the encoded peptide or protein of the inventive artificial nucleic acid molecule or vector and/or the inventive 5'-UTR element provides for an increased expression of the encoded peptide or protein of the inventive artificial nucleic acid molecule or vector. Thus, a particularly suitable medical application for the artificial nucleic acid molecule according to the present invention, the vector according to the present invention, the cell according to the present invention, or the pharmaceutical composition according to the present invention is vaccination. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may code for a protein that has to be supplied to a patient suffering from total lack or at least partial loss of function of a protein, such as a patient suffering from a genetic disease. Additionally the open reading frame may be chosen from an ORF coding for a peptide or protein which beneficially influences a disease or the condition of a subject. Furthermore, the open reading frame may code for a peptide or protein which effects down-regulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may code for an antigen or immunogen, e.g. for an epitope of a pathogen or for a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, a 3'-UTR element as described above and/or a 5'-UTR element as described above, and optional further components, such as a poly(A) sequence etc.

In the context of medical application, in particular, in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention may be administered orally, parenterally, by inhalation spray, topically, rectally, nasally, buccally, vaginally, via an implanted reservoir or via jet injection. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. In a preferred embodiment, the artificial nucleic acid molecule according to the present invention, the vector according to the present invention, the cell according to the present invention, or the pharmaceutical composition according to the present invention is administered via needle-free injection (e.g. jet injection).

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intradermal and intramuscular injection. Sterile injectable forms of the inventive pharmaceutical composition may be aqueous or oleaginous suspension. These suspensions may be formulated according to techniques known in the art using suitable dispersing or wetting agents and suspending agents. Preferably, the solutions or suspensions are administered via needle-free injection (e.g. jet injection).

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro or ex vivo transfection of mammalian cells, more preferably in vitro transfection of isolated cells of a subject to be treated by the medicament. If the use comprises the in vitro transfection of isolated cells, the use as a medicament may further comprise the readministration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof.

Furthermore, the present invention provides a method for treating or preventing a disease or disorder comprising transfection of a cell with an artificial nucleic acid molecule according to the present invention or with the vector according to the present invention. Said transfection may be performed in vitro, ex vivo or in vivo. In a preferred embodiment, transfection of a cell is performed in vitro and the transfected cell is administered to a subject in need thereof, preferably to a human patient. Preferably, the cell which is to be transfected in vitro is an isolated cell of the subject, preferably of the human patient. Thus, the present invention provides a method of treatment comprising the steps of isolating a cell from a subject, preferably from a human patient, transfecting the isolated cell with the artificial nucleic acid according to the present invention or the vector according to the present invention, and administering the transfected cell to the subject, preferably the human patient.

The method of treating or preventing a disorder according to the present invention is preferably a vaccination method or a gene therapy method as described above.

As described above, the inventive 3'-UTR element and/or the inventive 5'-UTR element are capable of prolonging and/or increasing the protein production from an mRNA. Thus, in a further aspect, the present invention relates to a method for increasing and/or prolonging protein production from an artificial nucleic acid molecule, preferably from an mRNA molecule or a vector, the method comprising the step of associating an open reading frame with a 3'-UTR element and/or a 5'-UTR element, wherein the 3'-UTR element and/or the 5'-UTR element provides high translation efficiency to a resulting artificial nucleic acid molecule, to obtain an artificial nucleic acid molecule, preferably an mRNA molecule, according to the present invention as described above or a vector according to the present invention as described above.

Preferably, in the method for increasing and/or prolonging protein production from an artificial nucleic acid molecule, preferably from an mRNA molecule or a vector, according to the present invention the 3'-UTR element and/or the 5'-UTR element comprises or consists of a nucleic acid sequence which is derived from the 3'-UTR and/or the 5'-UTR of a transcript of a gene selected from the group consisting of ZNF460, TGM2, IL7R, BGN, TK1, RAB3B, CBX6, FZD2, COL8A1, NDUFS7, PHGDH, PLK2, TSPO, PTGS1, FBXO32, NID2, ATP5D, EXOSC4, NOL9, UBB4B, VPS18, ORMDL2, FSCN1, TMEM33, TUBA4A, EMP3, TMEM201, CRIP2, BRAT1, SERPINH1, CD9, DPYSL2, CDK9, TFRC, PSMB3, FASN, PSMB6, PRSS56, KPNA6, SFT2D2, PARD6B, LPP, SPARC, SCAND1, VASN, SLC26A1, LCLAT1, FBXL18, SLC35F6, RAB3D, MAP1B, VMA21, CYBA, SEZ6L2, PCOLCE, VTN, ALDH16A1, RAVER1, KPNA6, SERINC5, JUP, CPN2, CRIP2, EPT1, PNPO, SSSCA1, POLR2L, LIN7C, UQCR10, PYCRL, AMN, MAP1S, NDUFS7, PHGDH, TSPO, ATP5D, EXOSC4, TUBB4B, TUBA4A, EMP3, CRIP2, BRAT1, CD9, CDK9, PSMB3, PSMB6, PRSS56, SCAND1, AMN, CYBA, PCOLCE, MAP1S, VTN, ALDH16A1 (all preferably human) and Dpysl2, Ccnd1, Acox2, Cbx6, Ubc, Ldlr, Nudt22, Pcyox1l, Ankrd1, Tmem37, Tspyl4, Slc7a3, Cst6, Aacs, Nosip, Itga7, Ccnd2, Ebp, Sf3b5, Fasn, Hmgcsl, Osr1, Lmnb1, Vma21, Kif20a, Cdca8, Slc7a1, Ubqln2, Prps2, Shmt2, Aurkb, Fignl1, Cad, Anln, Slfn9, Ncaph, Pole, Uhrf1, Gja1, Fam64a, Kif2c, Tspan10, Scand1, Gpr84, Fads3, Cers6, Cxcr4, Gprc5c, Fen1, Cspg4, Mrp134, Comtd1, Armc6, Emr4, Atp5d, 1110001J03Rik, Csf2ra, Aarsd1, Kif22, Cth, Tpgs1, Ccl17, Alkbh7, Ms4a8a, Acox2, Ubc, Slpi, Pcyox1l, Igf2bp1, Tmem37, Slc7a3, Cst6, Ebp, Sf3b5, Plk1, Cdca8, Kif22, Cad, Cth, Pole, Kif2c, Scand1, Gpr84, Tpgs1, Ccl17, Alkbh7, Ms4a8a, Mrp134, Comtd1, Armc6, Atp5d, 1110001J03Rik, Nudt22, Aarsd1 (all preferably mouse); preferably from the group consisting of ZNF460-5'-UTR, TGM2-5'-UTR, IL7R-5'-UTR, BGN-5'-UTR, TK1-5'-UTR, RAB3B-5'-UTR, CBX6-5'-UTR, FZD2-5'-UTR, COL8A1-5'-UTR, NDUFS7-5'-UTR, PHGDH-5'-UTR, PLK2-5'-UTR, TSPO-5'-UTR, PTGS1-5'-UTR, FBXO32-5'-UTR, NID2-5'-UTR, ATP5D-5'-UTR, EXOSC4-5'-UTR, NOL9-5'-UTR, UBB4B-5'-UTR, VPS18-5'-UTR, ORMDL2-5'-UTR, FSCN1-5'-UTR, TMEM33-5'-UTR, TUBA4A-5'-UTR, EMP3-5'-UTR, TMEM201-5'-UTR, CRIP2-5'-UTR, BRAT1-5'-UTR, SERPINH1-5'-UTR, CD9-5'-UTR, DPYSL2-5'-UTR, CDK9-5'-UTR, TFRC-5'-UTR, PSMB3 5'-UTR, FASN-5'-UTR, PSMB6-5'-UTR, PRSS56-5'-UTR, KPNA6-5'-UTR, SFT2D2-5'-UTR, PARD6B-5'-UTR, LPP-5'-UTR, SPARC-5'-UTR, SCAND1-5'-UTR, VASN-5'-UTR, SLC26A1-5'-UTR, LCLAT1-5'-UTR, FBXL18-5'-UTR, SLC35F6-5'-UTR, RAB3D-5'-UTR, MAP1B-5'-UTR, VMA21-5'-UTR, CYBA-5'-UTR, SEZ6L2-5'-UTR, PCOLCE-5'-UTR, VTN-5'-UTR, ALDH16A1-5'-UTR, RAVER1-5'-UTR, KPNA6-5'-UTR, SERINC5-5'-UTR, JUP-5'-UTR, CPN2-5'-UTR, CRIP2-5'-UTR, EPT1-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR, (all preferably human) and Dpysl2-5'-UTR, Ccnd1-5'-UTR, Acox2-5'-UTR, Cbx6-5'-UTR, Ubc-5'-UTR, Ldlr-5'-UTR, Nudt22-5'-UTR, Pcyox1l-5'-UTR, Ankrd1-5'-UTR, Tmem37-5'-UTR, Tspyl4-5'-UTR, Slc7a3-5'-UTR, Cst6-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Aurkb-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Kif2c-5'-UTR, Tspan10-5'-UTR, Scand1-5'-UTR, Gpr84-5'-UTR, Fads3-5'-UTR, Cers6-5'-UTR, Cxcr4-5'-UTR, Gprc5c-5'-UTR, Fen1-5'-UTR, Cspg4-5'-UTR, Mrpl34-5'-UTR, Comtd1-5'-UTR, Armc6-5'-UTR, Emr4-5'-UTR, Atp5d-5'-UTR, 1110001J03Rik-5'-UTR, Csf2ra-5'-UTR, Aarsd1-5'-UTR, Kif22-5'-UTR, Cth-5'-UTR, Tpgs1-5'-UTR, Ccl17-5'-UTR, Alkbh7-5'-UTR, Ms4a8a-5'-UTR (all preferably mouse); and NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, CD9-3'-UTR, CDK9-3'-UTR, PSMB3-3'-UTR, PSMB6-3'-UTR, PRSS56-3'-UTR, SCAND1-3'-UTR, AMN-3'-UTR, CYBA-3'-UTR, PCOLCE-3'-UTR, MAP1S-3'-UTR, VTN-3'-UTR, ALDH16A1-3'-UTR (all preferably human) and Acox2-3'-UTR, Ubc-3'-UTR, Slpi-3'-UTR, Pcyox1l-3'-UTR, Igf2bp1-3'-UTR, Tmem37-3'-UTR, Slc7a3-3'-UTR, Cst6-3'-UTR, Ebp-3'-UTR, Sf3b5-3'-UTR, Plk1-3'-UTR, Cdca8-3'-UTR, Kif22-3'-UTR, Cad-3'-UTR, Cth-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrpl34-3'-UTR, Comtd1-3'-UTR, Armc6-3'-UTR, Atp5d-3'-UTR, 1110001J03Rik-3'-UTR, Nudt22-3'-UTR, Aarsd1-3'-UTR, (all preferably mouse).

The term "associating the artificial nucleic acid molecule or the vector with a 3'-UTR element and/or a 5'-UTR element" in the context of the present invention preferably means functionally associating or functionally combining the artificial nucleic acid molecule or the vector with the 3'-UTR element and/or with the 5'-UTR element. This means that the artificial nucleic acid molecule or the vector and the 3'-UTR element and/or the 5'-UTR element, preferably the 3'-UTR element and/or the 5'-UTR element as described above, are associated or coupled such that the function of the 3'-UTR element and/or of the 5'-UTR element, e.g., the RNA and/or protein production prolonging and/or increasing function, is exerted. Typically, this means that the 3'-UTR element and/or the 5'-UTR element is integrated into the artificial nucleic acid molecule or the vector, preferably the mRNA molecule, 3' and/or 5', respectively, to an open reading frame, preferably immediately 3' to an open reading frame and/or immediately 5' to an open reading frame, the 3'-UTR element preferably between the open reading frame and a poly(A) sequence or a polyadenylation signal. Preferably, the 3'-UTR element and/or the 5'-UTR element is integrated into the artificial nucleic acid molecule or the vector, preferably the mRNA, as 3'-UTR and/or as 5'-UTR respectively, i.e. such that the 3'-UTR element and/or the 5'-UTR element is the 3'-UTR and/or the 5'-UTR, respectively, of the artificial nucleic acid molecule or the vector, preferably the mRNA, i.e., such that the 5'-UTR ends immediately before the 5'-end of the ORF and the 3'-UTR extends from the 3'-side of the open reading frame to the 5'-side of a poly(A) sequence or a polyadenylation signal, optionally connected via a short linker, such as a sequence comprising or consisting of one or more restriction sites. Thus, preferably, the term "associating the artificial nucleic acid molecule or the vector with a 3'-UTR element and/or a 5'-UTR element" means functionally associating the 3'-UTR element and/or the 5'-UTR element with an open reading frame located within the artificial nucleic acid molecule or the vector, preferably within the mRNA molecule. The 3'-UTR and/or the 5'-UTR and the ORF are as described above for the artificial nucleic acid molecule according to the present invention, for example, preferably the ORF and the 3'-UTR are heterologous and/or the ORF and the 5'-UTR are heterologous, respectively, e.g. derived from different genes, as described above. The association with a 3'-UTR element and/or a 5'-UTR element can either be achieved by de novo association of individual elements, or by modifying a pre-existing nucleic acid (template). In the latter case, for example and for purposes of illustration, a nucleic acid molecule according to the present invention may be obtained by (i) using a nucleic acid corresponding to the sequence shown in FIG. 1A as template, (ii) modifying said template by replacing at least one of (a) the underlined 5'-UTR element (underlined in FIG. 1A) or (b) the 3'-UTR element (double underlined in FIG. 1A) by a (a) a different 5'-UTR element or (b) a different 3'-UTR element, thereby associating the artificial nucleic acid molecule with said 5'-UTR element or 3'-UTR element.

In a further aspect, the present invention provides the use of a 3'-UTR element and/or of a 5'-UTR element, preferably the 3'-UTR element as described above and/or the 5'-UTR element as described above, for increasing and/or prolonging protein production from an artificial nucleic acid molecule, preferably from an mRNA molecule or a vector, wherein the 3'-UTR element and/or the 5'-UTR element comprises or consists of a nucleic acid sequence which is derived from the 3'-UTR and/or the 5'-UTR of a transcript of a gene selected from the group consisting of ZNF460, TGM2, IL7R, BGN, TK1, RAB3B, CBX6, FZD2, COL8A1, NDUFS7, PHGDH, PLK2, TSPO, PTGS1, FBXO32, NID2, ATP5D, EXOSC4, NOL9, UBB4B, VPS18, ORMDL2, FSCN1, TMEM33, TUBA4A, EMP3, TMEM201, CRIP2, BRAT1, SERPINH1, CD9, DPYSL2, CDK9, TFRC, PSMB3 5'-UTR, FASN, PSMB6, PRSS56, KPNA6, SFT2D2, PARD6B, LPP, SPARC, SCAND1, VASN, SLC26A1, LCLAT1, FBXL18, SLC35F6, RAB3D, MAP1B, VMA21, CYBA, SEZ6L2, PCOLCE, VTN, ALDH16A1, RAVER1, KPNA6, SERINC5, JUP, CPN2, CRIP2, EPT1, PNPO, SSSCA1, POLR2L, LIN7C, UQCR10, PYCRL, AMN, MAP1S, NDUFS7, PHGDH, TSPO, ATP5D, EXOSC4, TUBB4B, TUBA4A, EMP3, CRIP2, BRAT1, CD9, CDK9, PSMB3, PSMB6, PRSS56, SCAND1, AMN, CYBA, PCOLCE, MAP1S, VTN, ALDH16A1 (all preferably human and Dpysl2, Ccnd1, Acox2, Cbx6, Ubc, Ldlr, Nudt22, Pcyox1l, Ankrd1, Tmem37, Tspyl4, Slc7a3, Cst6, Aacs, Nosip, Itga7, Ccnd2, Ebp, Sf3b5, Fasn, Hmgcsl, Osr1, Lmnb1, Vma21, Kif20a, Cdca8, Slc7a1, Ubqln2, Prps2, Shmt2, Aurkb, Fignl1, Cad, Anln, Slfn9, Ncaph, Pole, Uhrf1, Gja1, Fam64a, Kif2c, Tspan10, Scand1, Gpr84, Fads3, Cers6, Cxcr4, Gprc5c, Fen1, Cspg4, Mrpl34, Comtd1, Armc6, Emr4, Atp5d, 1110001J03Rik, Csf2ra, Aarsd1, Kif22, Cth, Tpgs1, Ccl17, Alkbh7, Ms4a8a, Acox2, Ubc, Slpi, Pcyox1l, Igf2bp1, Tmem37, Slc7a3, Cst6, Ebp, Sf3b5, Plk1, Cdca8, Kif22, Cad, Cth, Pole, Kif2c, Scand1, Gpr84, Tpgs1, Ccl17, Alkbh7, Ms4a8a, Mrpl34, Comtd1, Armc6, Atp5d, 1110001J03Rik, Nudt22, Aarsd1 (all preferably mouse); preferably from the group consisting of ZNF460-5'-UTR, TGM2-5'-UTR, IL7R-5'-UTR, BGN-5'-UTR, TK1-5'-UTR, RAB3B-5'-UTR, CBX6-5'-UTR, FZD2-5'-UTR, COL8A1-5'-UTR, NDUFS7-5'-UTR, PHGDH-5'-UTR, PLK2-5'-UTR, TSPO-5'-UTR, PTGS1-5'-UTR, FBXO32-5'-UTR, NID2-5'-UTR, ATP5D-5'-UTR, EXOSC4-5'-UTR, NOL9-5'-UTR, UBB4B-5'-UTR, VPS18-5'-UTR, ORMDL2-5'-UTR, FSCN1-5'-UTR, TMEM33-5'-UTR, TUBA4A-5'-UTR, EMP3-5'-UTR, TMEM201-5'-UTR, CRIP2-5'-UTR, BRAT1-5'-UTR, SERPINH1-5'-UTR, CD9-5'-UTR, DPYSL2-5'-UTR, CDK9-5'-UTR, TFRC-5'-UTR, PSMB3 5'-UTR, FASN-5'-UTR, PSMB6-5'-UTR, PRSS56-5'-UTR, KPNA6-5'-UTR, SFT2D2-5'-UTR, PARD6B-5'-UTR, LPP-5'-UTR, SPARC-5'-UTR, SCAND1-5'-UTR, VASN-5'-UTR, SLC26A1-5'-UTR, LCLAT1-5'-UTR, FBXL18-5'-UTR, SLC35F6-5'-UTR, RAB3D-5'-UTR, MAP1B-5'-UTR, VMA21-5'-UTR, CYBA-5'-UTR, SEZ6L2-5'-UTR, PCOLCE-5'-UTR, VTN-5'-UTR, ALDH16A1-5'-UTR, RAVER1-5'-UTR, KPNA6-5'-UTR, SERINC5-5'-UTR, JUP-5'-UTR, CPN2-5'-UTR, CRIP2-5'-UTR, EPT1-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR, (all preferably human) and Dpysl2-5'-UTR, Ccnd1-5'-UTR, Acox2-5'-UTR, Cbx6-5'-UTR, Ubc-5'-UTR, Ldlr-5'-UTR, Nudt22-5'-UTR, Pcyox1l-5'-UTR, Ankrd1-5'-UTR, Tmem37-5'-UTR, Tspyl4-5'-UTR, Slc7a3-5'-UTR, Cst6-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Aurkb-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Kif2c-5'-UTR, Tspan10-5'-UTR, Scand1-5'-UTR, Gpr84-5'-UTR, Fads3-5'-UTR, Cers6-5'-UTR, Cxcr4-5'-UTR, Gprc5c-5'-UTR, Fen1-5'-UTR, Cspg4-5'-UTR, Mrpl34-5'-UTR, Comtd1-5'-UTR, Armc6-5'-UTR, Emr4-5'-UTR, Atp5d-5'-UTR, 1110001J03Rik-5'-UTR, Csf2ra-5'-UTR, Aarsd1-5'-UTR, Kif22-5'-UTR, Cth-5'-UTR, Tpgs1-5'-UTR, Ccl17-5'-UTR, Alkbh7-5'-UTR, Ms4a8a-5'-UTR (all preferably mouse); and NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, CD9-3'-UTR, CDK9-3'-UTR, PSMB3-3'-UTR, PSMB6-3'-UTR, PRSS56-3'-UTR, SCAND1-3'-UTR, AMN-3'-UTR, CYBA-3'-UTR, PCOLCE-3'-UTR, MAP1S-3'-UTR, VTN-3'-UTR, ALDH16A1-3'-UTR (all preferably human) and Acox2-3'-UTR, Ubc-3'-UTR, Slpi-3'-UTR, Pcyox11-3'-UTR, Igf2bp1-3'-UTR, Tmem37-3'-UTR, Slc7a3-3'-UTR, Cst6-3'-UTR, Ebp-3'-UTR, Sf3b5-3'-UTR, Plk1-3'-UTR, Cdca8-3'-UTR, Kif22-3'-UTR, Cad-3'-UTR, Cth-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrp134-3'-UTR, Comtd1-3'-UTR, Armc6-3'-UTR, Atp5d-3'-UTR, 1110001 J03Rik-3'-UTR, Nudt22-3'-UTR, Aarsd1-3'-UTR, (all preferably mouse).

The uses according to the present invention preferably comprise associating the artificial nucleic acid molecule, the vector, or the RNA with the 3'-UTR element as described above and/or with the 5'-UTR element as described above.

The compounds and ingredients of the inventive pharmaceutical composition may also be manufactured and traded separately of each other. Thus, the invention relates further to a kit or kit of parts comprising an artificial nucleic acid molecule according to the invention, a vector according to the invention, a cell according to the invention, and/or a pharmaceutical composition according to the invention. Preferably, such kit or kits of parts may, additionally, comprise instructions for use, cells for transfection, an adjuvant, a means for administration of the pharmaceutical composition, a pharmaceutically acceptable carrier and/or a pharmaceutically acceptable solution for dissolution or dilution of the artificial nucleic acid molecule, the vector, the cells or the pharmaceutical composition.

Method for Identifying a 3'-Untranslated Region Element (3'-UTR Element) and/or a 5'-Untranslated Region Element (5'-UTR Element)

In a further aspect the present description provides a method for identifying a 3'-untranslated region element (3'-UTR element) and/or a 5'-untranslated region element (5'-UTR element) comprising the following steps:
  a) Analyzing the stability of an mRNA comprising the following sub-steps:
    i. Determining the amount of said mRNA at a first point in time during a decay process of said mRNA,
    ii. Determining the amount of said mRNA at a second point in time during a decay process of said mRNA, and
    iii. Calculating the ratio of the amount of said mRNA determined in step (i) to the amount of said mRNA determined in step (ii);
  b) Selecting a stable mRNA having a ratio calculated in sub-step (iii) of at least 0.5 (50%), at least 0.6 (60%), at least 0.7 (70%), at least 0.75 (75%), at least 0.8 (80%), at least 0.85 (85%), at least 0.9 (90%), or at least 0.95 (95%); and
  c) Determining the nucleotide sequence of a 3'- and/or 5'-UTR element of said stable mRNA.

Thereby, the stability of the mRNA is preferably assessed under standard conditions, for example standard conditions (standard medium, incubation, etc.) for a certain cell line or cell type used.

In order to analyze the stability of an mRNA, the decay process of this mRNA is assessed by determining the amount or concentration of said mRNA at a first and at a second point in time during the decay process of said mRNA (cf. steps a) i. and a) ii.).

To determine the amount or concentration of mRNA during the RNA decay process in vivo or in vitro as defined above (i.e. in vitro referring in particular to ("living") cells and/or tissue, including tissue of a living subject; cells include in particular cell lines, primary cells, cells in tissue or subjects, preferred are mammalian cells, e.g. human cells and mouse cells and particularly preferred are the human cell lines HeLa, HEPG2 and U-937 and the mouse cell lines NIH3T3, JAWSII and L929 are used; furthermore primary cells are particularly preferred, in particular preferred embodiments human dermal fibroblasts (HDF)), various methods may be used, which are known to the skilled person. Non-limiting examples of such methods include general inhibition of transcription, e.g. with a transcription inhibitor such as Actinomycin D, use of inducible promoters to specifically promote transient transcription, e.g. c-fos serum-inducible promoter system and Tet-off regulatory promoter system, and kinetic labelling techniques, e.g. pulse labelling.

For example, if transcriptional inhibitor-mediated transcriptional arrest is used in step a) to determine the amount or concentration of mRNA during the RNA decay process in vivo or in vitro as defined above, transcriptional inhibitors such as Actinomycin D (ActD), 5,6-dichloro-1-D-ribofuranosyl-benzimidazole (DRB) or -amanitin (α-Am) may be used. Hereby, to assess mRNA decay, the transcriptional inhibitors are usually added to the cells and, thereby the transcription is generally inhibited and RNA decay can be observed without interferences of ongoing transcription.

Alternatively, inducible promoters to specifically promote transient transcription may be used in step a), whereby the rationale is to provide a stimulus that activates transcription and leads to a burst of mRNA synthesis, then remove the stimulus to shut off transcription and monitor the decay of mRNA. Thereby, the inducible promoter enables a stringent control, so that induction and silencing of transcription is accomplished within a narrow window of time. In mammalian cells, the cfos promoter is known to be valuable for this purpose, because it can be induced in response to serum addition quickly and transiently, thereby providing a reliable and simple way of achieving a transient burst in transcription. The Tet-off promoter system offers another option that further broadens the application of a transcriptional pulsing approach to study mRNA turnover in mammalian cells.

However, in the present invention kinetic labelling techniques are preferred in step a) for determining the amount of mRNA during the RNA decay process in vivo or in vitro as defined above. In kinetic labelling RNA is usually labelled, whereby labels include in particular labelled nucleotides and labelled nucleosides and labelled uridine and labelled uracil are particularly preferred. Examples of preferred labels include 4-thiouridine (4sU), 2-thiouridine, 6-thioguanosine, 5-ethynyluridine (EU), 5-bromo-uridine (BrU), Biotin-16-

Aminoallyluridine, 5-Aminoallyluridine, 5-Aminoallylcytidine, etc., whereby 4-Thiouridine (4sU), 5-ethynyluridine (EU) or 5'-bromo-uridine (BrU) are more preferred. Particularly preferred is 4-thiouridine (4sU). 4-thiouridine (4sU) is preferably used in a concentration of 100-500 µM. Moreover, also radioactively labelled nucleotides may be used, e.g. with Uridine-$^3$H. Also combinations of the above mentioned labelled nucleotides may be used, whereby a combination of 4-thiouridine and 6-thioguanosine is particularly preferred.

In kinetic labelling, usually the emerging RNA is labelled, e.g. by incorporation of labelled uridine or uracil during transcription. After a while, the provision of label is stopped and RNA decay may then be observed by assessing specifically labelled RNA without generally inhibiting transcription.

For determining the amount of mRNA during the RNA decay process in step a), pulse labelling is preferred, and a pulse-chase methodology is particularly preferred. As used herein, the term "pulse labelling refers to a technique in which a label, e.g. the labels described above, is used for the measurement of the rates of synthesis and/or decay of compounds within living cells. Typically, cells are exposed to a small quantity of a label for a brief period, hence the term 'pulse'. In the pulse-chase methodology, after pulse-labelling usually a much larger quantity of an unlabeled compound corresponding to the "pulse" (e.g. unlabelled uridine, if labelled uridine is used as pulse) is added following the required period of exposure to the label. The effect of competition between the labelled and the unlabeled compound is to reduce to a negligible level the further uptake of the labelled compound, hence the term "chase".

To determine the amount or concentration of mRNA usually the mRNA has to be isolated. Different techniques for RNA isolation are known to the skilled person, e.g. by Guanidinium thiocyanate-phenol-chloroform extraction or by silica-column based extraction. Also commercially available kits may be used, e.g. RNeasy Kit from Qiagen.

Furthermore, an extraction step may be required, in particular if kinetic labelling is used (in contrast to a transcription inhibitor, wherein the total RNA represents "decaying" RNA since transcription is generally inhibited). In the extraction step, labelled RNA (i.e. representing "decaying" RNA) is extracted from total isolated RNA. Thus, the means of extraction may be selected depending on the label used. For example, immunopurification with antibodies to the label may be used.

Furthermore, for example, for extraction of thio-labelled, e.g. 4-thiouridine (4sU)-labelled, RNA, HPDP-Biotin (pyridyldithiol-activated, sulfhydryl-reactive biotinylation reagent that conjugates via a cleavable (reversible) disulfide bond) may be incubated with the isolated "total RNA". This reagent specifically reacts with the reduced thiols (—SH) in the 4-thiouridine (4sU)-labelled RNA to form reversible disulfide bonds. The biotinylation allows for binding of the thio-labelled e.g. 4-thiouridine (4sU)-labelled RNA to streptavidin and therefore can be extracted from the total RNA by reduction of the disulfide bond with dithiothreitol or beta-mercaptoethanol (or any other reduction agent).

In case biotin-labelled nucleotides, e.g. Biotin-16-Aminoallyluridine, streptavidin can directly be used to extract the labelled RNA from total RNA.

For example, for extraction of newly transcribed 5-ethynyluridine (EU)-labelled cellular RNAs from total RNA, biotinylation of EU in a copper-catalyzed cycloaddition reaction (often referred to as click chemistry) may be used, which is followed by purification by streptavidin affinity. This method is commercially available as the Click-iT Nascent RNA Capture Kit (Catalog no. C10365, Invitrogen). The manufacturer's instruction of this kit recommends that the pulse labeling time is 30 to 60 min for a 0.5 mM EU dose, or 1 to 24 h for a 0.1 or 0.2 mM EU dose.

For example, BrU-labeled RNA molecules may be extracted by immunopurification with an anti-Bromodeoxyuridine antibody (e.g. Clone. 2B1, Catalog no. MI-11-3, MBL), and Protein G Sepharose.

The amount or concentration of mRNA, i.e. the transcript level, may then be measured by various methods known to the person skilled in the art. Non-limiting examples for such methods include micro array analysis, Northern Blot analysis, quantitative PCR or by next generation sequencing (high throughput sequencing). Particularly preferred are micro array analysis and next generation sequencing. Moreover, whole-genome approaches/whole transcriptome approaches are particularly preferred, e.g. in micro array analysis whole genome micro array analysis, e.g. Affymetrix Human Gene 1.0 ST or 2.0 ST or Affymetrix Mouse Gene 1.0 ST or 2.0 ST or whole transcriptome analysis by next generation sequencing.

In substeps i. and ii. of step a), the amount of mRNA is determined at a first and at a second point in time during a decay process of the mRNA. Typically, this means that mRNA is in particular isolated at a first and at a second point in time during a decay process of the mRNA to determine the respective amounts. Therefore, "the first point in time" and "the second point in time" are in particular points in time during the RNA decay process, at which RNA is isolated to determine the RNA amount. In general, "the second point in time" is later in the RNA decay process than the "the first point in time".

Preferably, the first point in time is selected such, that only mRNA undergoing a decay process is considered, i.e. emerging mRNA—e.g. in ongoing transcription—is avoided. For example, if kinetic labelling techniques, e.g. pulse labelling, are used, the first point in time is preferably selected such that the incorporation of the label into mRNA is completed, i.e. no ongoing incorporation of the label into mRNA occurs. Thus, if kinetic labelling is used, the first point in time may be at least 10 min, at least 20 min, at least 30 min, at least 40 min, at least 50 min, at least 60 min, at least 70 min, at least 80 min, or at least 90 min after the end of the experimental labelling procedure, e.g. after the end of the incubation of cells with the label.

For example, the first point in time may be preferably from 0 to 6 h after the stop of transcription (e.g. by a transcriptional inhibitor), stop of promoter induction in case of inducible promoters or after stop of pulse or label supply, e.g. after end of labelling. More preferably, the first point in time may be from 30 min to 5 h, even more preferably from 1 h to 4 h and particularly preferably about 3 h after the stop of transcription (e.g. by a transcriptional inhibitor), stop of promoter induction in case of inducible promoters or after stop of pulse or label supply, e.g. after end of labelling.

Preferably, the second point in time is selected as late as possible during the mRNA decay process. However, if a plurality of mRNA species is considered, the second point in time is preferably selected such that still a considerable amount of the plurality of mRNA species, preferably at least 10% of the mRNA species, is present in a detectable amount, i.e. in an amount higher than 0. Preferably, the second point in time is at least 5 h, at least 6 h, at least 7 h, at least 8 h, at least 9 h, at least 10 h, at least 11 h, at least 12 h, at least 13 h, at least 14 h, or at least 15 h after the stop of transcription (e.g. by a transcriptional inhibitor), stop of promoter induction in case of inducible promoters or after stop of pulse or label supply, e.g. after end of labelling.

For example, the second point in time may be preferably from 3 to 48 h after the stop of transcription (e.g. by a transcriptional inhibitor), stop of promoter induction in case of inducible promoters or after stop of pulse or label supply, e.g. after end of labelling. More preferably, the second point in time may be from 6 min to 36 h, even more preferably from 10 h to 24 h and particularly preferably about 15 h after the stop of transcription (e.g. by a transcriptional inhibitor), stop of promoter induction in case of inducible promoters or after stop of pulse or label supply, e.g. after end of labelling.

Thus, the time span between the first point in time and the second point in time is preferably as large as possible within the above described limits. Therefore, the time span between the first point in time and the second point in time is preferably at least 4 h, at least 5 h, at least 6 h, at least 7 h, at least 8 h, at least 9 h, at least 10 h, at least 11 h, or at least 12 h, whereby a time span of about 12 h is particularly preferred. In general, the second later point in time is at least 10 minutes later than the first point in time.

In sub-step iii. of step a) the ratio of the amount of the mRNA determined in step (i) to the the amount of the mRNA determined in step (ii) is calculated. To this end, the amount of the mRNA (transcript level) determined as described above at the second point in time is divided by the amount of the mRNA (transcript level) determined as described above at the first point in time. This ratio prevents that stable mRNAs, which are already at the first point in time present only in very low amounts, are disregarded in respect to mRNAs, which are present in high amounts.

In step b), such an mRNA is selected, which has a ratio calculated in sub-step (iii) of step a) of at least 0.5 (50%), at least 0.6 (60%), at least 0.7 (70%), at least 0.75 (75%), at least 0.8 (80%), at least 0.85 (85%), at least 0.9 (90%), or at least 0.95 (95%). Such mRNA is in the present invention considered as a particular stable mRNA.

In step c), the nucleotide sequence of a 3'- and/or 5'-UTR element of said mRNA, i.e. the mRNA selected in step b), is determined. To this end, different methods known to the skilled person may be applied, e.g. sequencing or selection from a publicly available database, such as e.g. NCBI (National Center for Biotechnology Information). For example, the mRNA sequence of the mRNA selected in step b) may be searched in a database and the 3'- and/or 5'-UTR may then be extracted from the mRNA sequence present in the database.

In particular, in the above described method for identifying a 3'-untranslated region element (3'-UTR element) and/or a 5'-untranslated region element (5'-UTR element) the term "mRNA" and/or "stable mRNA", respectively, may also refer to an mRNA species as defined herein and/or to a stable mRNA species, respectively.

Furthermore, it is preferred herein that a "stable mRNA" may have a slower mRNA decay compared to average mRNA decay, preferably assessed in vivo or in vitro as defined above. Thereby, "average mRNA decay" may be assessed by investigating mRNA decay of a plurality of mRNA species.

Accordingly, provided herein in a further aspect is a method for identifying a 3'-untranslated region element (3'-UTR element) and/or a 5'-untranslated region element (5'-UTR element) comprising the following steps:

a) Analyzing the stability of a plurality of mRNA species comprising the following sub-steps:

i. Determining the amount of each mRNA species of said plurality of mRNA species at a first point in time during a decay process of said mRNA species, ii. Determining the amount of each mRNA species of said plurality of mRNA species at a second point in time during a decay process of said mRNA species, and iii. Calculating for each mRNA species of said plurality of mRNA species the ratio of the amount of said mRNA species determined in step (i) to the amount of said mRNA species determined in step (ii);

b) Ranking of the mRNA species of the plurality of mRNA species according to the ratio calculated in sub-step (iii) for each mRNA species;

c) Selecting one or more mRNA species having the highest ratio or the highest ratios calculated in sub-step (iii); and d) Determining the nucleotide sequence of a 3'- and/or 5'-UTR element of said mRNA.

An "mRNA species", as used herein, corresponds to a genomic transcription unit, i.e. usually to a gene. Thus, within one "mRNA species" different transcripts may occur, for example, due to mRNA processing. For example, an mRNA species may be represented by a spot on a microarray. Accordingly, a microarray provides an advantageous tool to determine the amount of a plurality of mRNA species, e.g. at a certain point in time during mRNA decay. However, also other techniques known to the skilled person, e.g. RNA-seq (also called Whole Transcriptome Shotgun Sequencing which is a technology that uses the capabilities of next-generation sequencing to reveal a snapshot of RNA presence and quantity from a genome at a given moment in time), quantitative PCR etc. may be used.

Preferably, "a plurality of mRNA species", refers to at least 100, at least 300, at least 500, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, at least 19000, at least 20000, at least 21000, at least 22000, at least 23000, at least 24000, at least 25000, at least 26000, at least 27000, at least 28000, at least 29000, or at least 30000 mRNA species. It is particularly preferred that the whole transcriptome is assessed, or as many mRNA species of the transcriptome as possible. This may be achieved, for example, by using a micro array providing whole transcript coverage.

Step a) of this method with its sub-steps i. to iii. corresponds essentially to step a) with its sub-steps i. to iii. of the previously described inventive method, but differs only in that the amount of each mRNA species of a plurality of mRNA species is determined at a first and at a second point in time and in that the ratio is calculated for each mRNA species. Accordingly, the detailed methods and preferred embodiments outlined above apply here as well and the ratio for a single mRNA species (and each single mRNA species, respectively) may be determined as outlined above for "an mRNA".

However, in contrast to the above method, the stability of the mRNA is not assessed by the absolute value of the ratio, but by a ranking of the mRNA species of the plurality of mRNA species according to the ratio calculated in sub-step (iii) of step a) for each mRNA species. In sub-step c) one or more mRNA species having the highest ratio or the highest ratios calculated in sub-step (iii) of step a) are then selected.

In this context it is particularly preferred to select the 0.1%, 0.2%, 0.3%, 0.4%, 0.5%, 0.6%, 0.7%, 0.8%, 0.9%, 1%, 2%, 3%, 4%, 5%, 10%, 15%, 20% most stable mRNA species in step c). Alternatively or additionally, in step c) such mRNA species may be selected which show a ratio calculated in sub-step iii. of step a) corresponding to a least 100% of the average ratio calculated from all mRNA species analyzed. More preferably such mRNA species are selected showing a ratio of at least 150%, even more preferably of at least 200% and most preferably of at least 300% of the average ratio calculated from all mRNA species analyzed.

In step d) the nucleotide sequence of a 3'- and/or 5'-UTR element of the mRNA selected in step c) is determined as described above, for step c) of the previously described inventive method.

Preferably, in both of the above described methods for identifying a 3'-UTR element and/or a 5'-UTR element according to the present invention, the time period between the first point in time and the second point in time is at least 5 h, preferably at least 6 h, preferably at least 7 h, more preferably at least 8 h, more preferably at least 9 h, even more preferably at least 10 h, even more preferably at least 11 h, and particularly preferably at least 12 h.

Preferably, in both of the above described methods for identifying a 3'-UTR element and/or a 5'-UTR element according to the present invention, the stability of an mRNA is analysed by pulse labelling, preferably using a pulse-chase methodology.

Method for Identifying a 3'-Untranslated Region Element (3'-UTR Element) and/or a 5'-Untranslated Region Element (5'-UTR Element)

In a further aspect, the present invention also provides a method for identifying a 3'-untranslated region element (3'-UTR element) and/or a 5'-untranslated region element (5'-UTR element), which provides high translation efficiency to an artificial nucleic acid molecule comprising the following steps:
  a) identifying a 3'-UTR element and/or a 5'-UTR element which is derived from a stable mRNA by a method for identifying a 3'-UTR element and/or a 5'-UTR element according to any of the methods described above;
  b) synthesizing an artificial nucleic acid molecule comprising at least one open reading frame and at least one 3'-UTR element and/or at least one 5'-UTR element which corresponds to or is comprised by the 3'-UTR element and/or the 5'-UTR element identified in step a);
  c) analyzing the expression of the protein encoded by the at least one open reading frame (ORF) of the artificial nucleic acid molecule synthesized in step b);
  d) analyzing the expression of a protein encoded by at least one open reading frame of a reference artificial nucleic acid molecule lacking a 3'-UTR element and/or a 5'-UTR element;
  e) comparing the protein expression from the artificial nucleic acid molecule analysed in step c) to the protein expression from the reference artificial nucleic acid molecule analysed in step d); and
  f) selecting the 3'-UTR element and/or the 5'-UTR element if the protein expression from the artificial nucleic acid molecule analysed in step c) is prolonged and/or increased in comparison to the protein expression from the reference artificial nucleic acid molecule analysed in step d).

In this method, at first a 3'-UTR element and/or a 5'-UTR element are identified by a method according to the present invention as described above. This enables synthesis of the 3'- and/or the 5'-UTR element by methods known to the skilled person, e.g. by PCR amplification. The primers used for such a PCR may preferably comprise restriction sites for cloning. Alternatively, the 3'- and/or 5'-UTR element may be synthesized e.g. by chemical synthesis or oligo annealing. Accordingly, in step b), an artificial nucleic acid molecule is synthesized comprising at least one open reading frame and at least one 3'-UTR element and/or at least one 5'-UTR element which corresponds to or is comprised by the 3'-UTR element and/or the 5'-UTR element identified in step a). In particular, the at least one 3'-UTR element and/or at least one 5'-UTR element is usually combined with an open reading frame, which results in an artificial nucleic acid comprising a 3'- and/or 5'-UTR element according to the present invention, if the 3'- and/or 5'-UTR element fulfil the respective requirements, i.e. if they prolong and/or increase protein expression. To test this, the 3'- and/or the 5'-UTR element identified in step a), or a PCR fragment or synthesized sequence thereof respectively, may be cloned into a particular vector, preferably in an expression vector, in order to assess protein expression from the respective ORF.

The protein expression from the artificial nucleic acid molecule comprising the at least one 3'-UTR element and/or the at least one 5'-UTR element is then assessed in step c) as described herein and compared to the protein expression assessed in step d) from a respective reference artificial nucleic acid molecule lacking a 3'-UTR element and/or a 5'-UTR element as described herein in step e).

Thereafter, in step f), such a 3'-UTR element and/or 5'-UTR element is selected, which increases the protein expression from the artificial nucleic acid molecule analysed in step c) in comparison to the protein expression from the reference artificial nucleic acid molecule analysed in step d). The comparison of the protein expression of the inventive nucleic acid molecule to the reference nucleic acid molecule is carried out as described herein, in particular in the context of the inventive artificial nucleic acid molecule.

Furthermore, the present invention provides a particularly preferred method for identifying a 3'-untranslated region element (3'-UTR element) and/or a 5'-untranslated region element (5'-UTR element), which provides high translation efficiency to an artificial nucleic acid molecule comprising the following steps:
  a) feeding/incubating cells with a labelled nucleotide for incorporation in newly transcribed RNA molecules (pulse-chase labelling);
  b) isolating total RNA of the cells at a first point in time and at at least one second later point in time;
  c) extracting of the labelled RNA molecules from the total RNA isolated in step b);
  d) measuring of the amount/transcript level of the different mRNA species comprised in the labelled RNA;
  e) calculating the ratio of the amount/transcript level of an mRNA species present at the at least one second later point in time to the amount/transcript level of the mRNA species present at the first point in time;
  f) ranking of the mRNA species according to the ratio determined in step e);
  g) selecting the most stable mRNA species;
  h) determining the nucleotide sequence of the 3'- and/or 5'-UTR of the most stable mRNA species selected in step g);
  i) synthesizing a 3'- and/or a 5'-UTR element comprised in the 3'- and/or 5'-UTR determined in step h);
  j) combination of the 3'- and/or 5'-UTR element synthesized in step i) with an open reading frame to get a nucleic acid according to the invention as described herein; and
  k) optionally comparing the expression of the open reading frame present in the inventive nucleic acid compared to the expression of the open reading frame present in a reference nucleic acid without a 3'- and/or 5'-UTR element as described herein.

Thereby, the details and preferred embodiments described for the inventive methods above also apply herein, within the respective limitation outlined in steps a) to k).

In particular, the following labelled nucleotides are preferred for feeding the cells in step a) of the inventive method: 4-thiouridine (4sU), 2-thiouridine, 6-thioguanosine, 5-ethynyluridine (EU), 5-bromo-uridine (BrU), Biotin-16-Aminoallyluridine, 5-Aminoallyluridine, 5-Aminoallylcytidine, etc. Particularly preferred is 4-thiouridine (4sU). 4-thiouridine is preferably used in a concentration of 100-500 µM. Alternatively, radioactively labelled nucleotides may be used, e.g. Uridine-$^3$H. Combinations of the above mentioned labelled nucleotides may be used. Particularly preferred is the combination of 4-thiouridine and 6-thioguanosine The incubation of the cells with the labelled nucleotide in step a) can be varied. Particularly preferred is an incubation (feeding time) from 10 minutes to 24 hours. Particularly preferred are 2 to 6 hours, more preferably 2 to 3 hours.

Cells, which can be used for the inventive method, include in particular cell lines, primary cells, cells in tissue or subjects. In specific embodiments cell types allowing cell culture may be suitable for the inventive method. Particularly preferred are mammalian cells, e.g. human cells and mouse cells. In particularly preferred embodiments the human cell lines HeLa, HEPG2 and U-937 and the mouse cell lines NIH3T3, JAWSII and L929 are used. Furthermore primary cells are particularly preferred; in particular preferred embodiments particularly human dermal fibroblasts (HDF) can be used. Alternatively the labelled nucleotide may also be applied to a tissue of a subject and after the incubation time the RNA of the tissue is isolated according to step c).

For determination of the most stable mRNAs of a cell (type), total RNA is extracted at a first point in time as described above, e.g. 0 to 6 h after labelling, preferably 3 h after labelling and at a second later point in time as described above, e.g. 3 to 48 h after labelling, preferably 10 to 24 h, most preferably 15 h after labelling. The second later point in time is at least 10 minutes later than the first time.

In step f) the mRNA species are ranked according to the ratio calculated in step e). In this context it is particularly preferred to select the 0.1%, 0.2%, 0.3%, 0.4%, 0.5%, 0.6%, 0.7%, 0.8%, 0.9%, 1%, 2%, 3%, 4%, 5%, 10%, 15%, 20% most stable mRNA species.

In this context it is further preferred to select these mRNA species showing at least 50% (0,5 fold), at least 60% (0,6 fold), at least 70% (0,7 fold), at least 90% (0,9 fold) or at least 95% (0,95 fold) transcript level/amount of the mRNA species at the second later time compared to the first time. This embodiment is particularly preferred if the RNA is isolated at 3 hours (first point in time) and at 15 hours (second point in time) after labelling.

Alternatively or additionally, these mRNA species are selected showing a ratio calculated in step e) corresponding to a least 100% of the average ratio calculated from all mRNA species analyzed. More preferably these mRNA species are selected showing a ratio of at least 150% and more preferably of at least 200% and most preferably of at least 300% of the average ratio calculated from all mRNA species analyzed.

In a further step of the inventive method the nucleotide sequence of the 3'- and/or 5'-UTR of the most stable mRNA species selected in step g) is determined and in step i) the 3'- and/or 5'-UTR element is synthesized e.g. by PCR amplification. The primers used for the PCR may preferably comprise restriction sites for cloning. Alternatively the 3'- and/or 5'-UTR element may be synthesized (e.g. by chemical synthesis or oligo annealing).

In step j) of the inventive method the resulting PCR fragment or synthesized sequence is combined with an open reading frame resulting in an artificial nucleic acid comprising a 3'- and/or 5'-UTR element according to the invention. Preferably, the PCR fragment or sequence may be cloned into a vector.

In a particularly preferred embodiment the invention provides a method comprising the steps a) to k) for identifying 3'-untranslated region elements (3'-UTR elements) and/or 5'-untranslated region elements (5'-UTR elements), wherein the 3'-UTR elements and/or the 5'-UTR elements prolong protein production from an artificial nucleic acid molecule comprising at least one of the 3'-UTR elements and/or at least one of the 5'-UTR elements.

In a further aspect, the present invention also provides a method for generating an artificial nucleic acid molecule, wherein an artificial nucleic acid molecule comprising at least one open reading frame and at least one 3'-UTR element and/or at least one 5'-UTR element identified by a method for identifying a 3'-UTR element and/or a 5'-UTR element according to the present invention as described above is synthesized. Synthesizing of such an artificial nucleic acid molecule is typically carried out by methods known to the skilled person, e.g. cloning methods for example as generally known or described herein.

Preferably, a vector according to the present invention as described herein is used in such an inventive method for generating an artificial nucleic acid molecule.

Preferably, the artificial nucleic acid molecule generated by such a method for generating an artificial nucleic acid molecule is a nucleic acid molecule according to the present invention as described herein.

In addition, the present invention also provides an artificial nucleic acid molecule obtainable by a method for generating an artificial nucleic acid molecule according to the present invention as described herein.

The following Figures, Sequences and Examples are intended to illustrate the invention further. They are not intended to limit the subject matter of the invention thereto.

FIG. 1 shows sequences encoding mRNA (i.e. artificial nucleic acid molecules) that can be obtained by in vitro transcription.

The following abbreviations are used:
PpLuc (GC GC-enriched mRNA sequence coding for *Photinus pyralis* luciferase.
The PpLuc(GC) ORF is highlighted in italics.
A64: poly(A)-sequence with 64 adenylates
C30: poly(C-sequence with 30 cytidylates
hSL: a histone stem-loop sequence taken from (Cakmakci, Lerner, Wagner, Zheng, & William F Marzluff, 2008. Mol. Cell. Biol. 28(3):1182-94)
32L4: an artificial variant of the 5' untranslated region 5'-UTR of human ribosomal protein Large 32 lacking the 5' terminal oligopyrimidine tract. The 5'-UTR is derived from human ribosomal protein Large 32 mRNA lacking the 5' terminal oligopyrimidine tract.
albumin7: an artificial variant of the 3' untranslated region (3'-UTR) of human albumin with three single point mutations introduced to remove a T7 termination signal as well as a HindIII and XbaI restriction site FIG. 1A: Reference Construct, SEQ ID NO: 205, i.e. the mRNA sequence of 32L4-PpLuc(GC)-albumin7-A64-C30-hSL (R3111).

For UTR elements of human origin that were subject to experimental testing, see Table 3.

For UTR elements of mouse origin that were subject to experimental testing, see Table 4.

FIG. 1B: Artificial nucleic acid (SEQ ID NO: 210), said artificial nucleic acid comprising a tested 5'-UTR corresponding to SEQ ID NO: 1 (single underline). All elements of the sequence shown in this figure, except for the single-underlined element, are identical to SEQ ID NO: 205. SEQ ID NO: 210 thus differs from SEQ ID NO: 205 in that a 5'-UTR element is different.

[5'-UTR corresponding to SEQ ID NO: 1]-PpLuc(GC)-albumin7-A64-C30-hSL

FIG. 1C: Artificial nucleic acid (SEQ ID NO: 211), said artificial nucleic acid comprising a tested 3'-UTR corresponding to SEQ ID NO: 152 (double underline). All elements of the sequence shown in this figure, except for the double-underlined element, are identical to SEQ ID NO: 205. SEQ ID NO: 211 thus differs from SEQ ID NO: 205 in that a 3'-UTR element is different.

32L4-PpLuc(GC)-[3'-UTR corresponding to SEQ ID NO: 152]-A64-C30-hSL

FIGS. 2 to 9 show the mean luciferase expression and SEM of mRNAs that were analyzed in triplicate; i.e. relative PpLuc expression normalized to RrLuc (mean values of three independent experiments and standard error of mean (SEM) are given). The effect of 5'-UTR elements and 3'-UTR elements of human origin (Table 3) and of 5'-UTR elements and 3'-UTR elements of mouse origin (Table 4) on luciferase expression from mRNA was examined, compared to luciferase expression from mRNA shown in FIG. 1 (Reference Construct). For details of the constructs comprising the tested 5'-UTR elements and 3'-UTR elements of Tables 3 and 4, see Example 3, particularly sections 3.3 and 3.4. To this end, the cell lines indicated in the Figures were transfected with different mRNAs by lipofection (FIG. 2: HDF cells transfected with the mRNAs having the 5'-UTR elements and 3'-UTR elements of human origin as shown in Table 3;

FIG. 3: HDF cells transfected with the mRNAs having the 5'-UTR elements and 3'-UTR elements of mouse origin as shown in Table 4;

FIG. 4: L929 cells transfected with the mRNAs having the 5'-UTR elements and 3'-UTR elements of human origin as shown in Table 3;

FIG. 5: L929 cells transfected with the mRNAs having the 5'-UTR elements and 3'-UTR elements of mouse origin as shown in Table 4;

FIG. 6: HEPG2 cells transfected with the mRNAs having the 5'-UTR elements and 3'-UTR elements of human origin as shown in Table 3;

FIG. 7: HEPG2 cells transfected with the mRNAs having the 5'-UTR elements and 3'-UTR elements of mouse origin as shown in Table 4;

FIG. 8: HeLa cells transfected with the mRNAs having the 5'-UTR elements and 3'-UTR elements of human origin as shown in Table 3;

FIG. 9: HeLa cells transfected with the mRNAs having the 5'-UTR elements and 3'-UTR elements of mouse origin as shown in Table 4). For details, see Example 3, particularly section 3.5.

FIGS. 2 to 9 each show 96 bars, corresponding to the 96 wells of the assay of Example 3. In FIGS. 2 to 9, the 96 bars are shown in consecutive order, i.e. A1, B1, C1, D1, [ . . . ], F12, G12, H12.

RLU=relative light units (Luciferase activity measurement)

EXAMPLES

Example 1: Candidate UTR Elements mRNA expression in human and mouse cells was experimentally evaluated. This led to the identification of mRNAs expressed in the respective cells. The nucleotide sequence of the 5'- and/or 3'-UTRs of the mRNA species was determined by data base search, verified by and adjusted according to high-throughput sequencing data of cell transcriptomes, and amplified by PCR or synthesized by oligo annealing.

Since the identified mRNAs originate from their native cell environment, these mRNAs are understood to be wild-type mRNAs:

SEQ ID NO: 1 to 72 represent wild-type human 5'-UTR elements.

SEQ ID NO: 73 to 136 represent wild-type mouse 5'-UTR elements.

SEQ ID NO: 152 to 173 represent wild-type human 3'-UTR elements.

SEQ ID NO: 174 to 203 represent wild-type mouse 3'-UTR elements.

While several of these UTR elements are known (e.g. in their wild-type environment), this approach also led to the identification of novel 5'-UTR elements and novel 3'-UTR elements, i.e. 5'-UTR elements and 3'-UTR elements which the present inventors found to be expressed in human cells and mouse cells, respectively, but which are not known from public databases (NCBI):

In particular, among the group consisting of human 5'-UTR elements of SEQ ID NO: 1 to 72, the following wild-type 5'-UTR elements differ from 5'-UTR elements known from public databases (NCBI): SEQ ID NO: 45, SEQ ID NO: 47, SEQ ID NO: 49.

Among the group consisting of mouse 5'-UTR elements of SEQ ID NO: 73 to 136, the following wild-type 5'-UTR elements differ from 5'-UTR elements known from public databases (NCBI): SEQ ID NO: 77, SEQ ID NO: 79, SEQ ID NO: 84, SEQ ID NO: 85, SEQ ID NO: 90, SEQ ID NO: 92, SEQ ID NO: 93, SEQ ID NO: 98, SEQ ID NO: 106, SEQ ID NO: 109, SEQ ID NO: 115, SEQ ID NO: 118, SEQ ID NO: 125, SEQ ID NO: 127, SEQ ID NO: 131, SEQ ID NO: 135.

Among the group consisting of mouse 3'-UTR element of SEQ ID NO: 174 to 203, the following wild-type 3'-UTR elements differ from 3'-UTR elements known from public databases (NCBI): SEQ ID NO: 179, SEQ ID NO: 180, SEQ ID NO: 182, SEQ ID NO: 183, SEQ ID NO: 197, SEQ ID NO: 200.

The differences of the newly identified 5'-UTR elements and newly identified 3'-UTR elements to known 5'-UTR elements and to known 3'-UTR elements, respectively, are shown in Tables 1 and 2. In particular, these newly identified elements have not previously been described to be 3'-UTR element or 5'-UTR elements, respectively.

TABLE 1

Novel wild-type 5'-UTR elements

| 5'-UTR element of the present invention (SEQ ID NO) | Difference to entry at GenBank at NCBI (ACCESSION or VERSION) |
| --- | --- |
| SEQ ID NO: 45 | The first two nucleotides at the 5'-end (CC) are not part of NM_199344.2 |
| SEQ ID NO: 47 | Comprised of nucleotides of both of NM_001167671.1 and NM_001167672.1 |
| SEQ ID NO: 49 | Not identified as 5'-UTR at NCBI. |
| SEQ ID NO: 77 | Part of SEQ ID NO: 77 corresponds to BC006680.1 |
| SEQ ID NO: 79 | Part of SEQ ID NO: 79 corresponds to NM_026675.2 |
| SEQ ID NO: 84 | Similar to NM_001301840 |
| SEQ ID NO: 85 | Not identified as 5'-UTR at NCBI. |
| SEQ ID NO: 90 | Not identified as 5'-UTR at NCBI. |
| SEQ ID NO: 92 | Not identified as 5'-UTR at NCBI. |
| SEQ ID NO: 93 | Comprises NM_145942.4 plus additional upstream bases |
| SEQ ID NO: 98 | Slightly shorter than NM_009004.4 |
| SEQ ID NO: 106 | Deletion with respect to NM_001163359.1 |
| SEQ ID NO: 109 | Not identified as 5'-UTR at NCBI. |
| SEQ ID NO: 115 | Contains additional bases at 5' end with respect to NM_144526.3 |
| SEQ ID NO: 118 | Not identified as 5'-UTR at NCBI. |
| SEQ ID NO: 125 | Not identified as 5'-UTR at NCBI. |
| SEQ ID NO: 127 | Significantly shorter than NM_001110337.1 |
| SEQ ID NO: 131 | Not identified as 5'-UTR at NCBI. |
| SEQ ID NO: 135 | Not identified as 5'-UTR at NCBI. |
| SEQ ID NO: 136 | Comprises elements of NM_009970.2; and XM_011247136.1 |

TABLE 2

Novel wild-type 3'-UTR elements

| 3'-UTR element of the present invention (SEQ ID NO) | Difference to entry at GenBank at NCBI (ACCESSION or VERSION) |
| --- | --- |
| SEQ ID NO: 179 | Shorter than 3'-UTR of NM_009951.4 |
| SEQ ID NO: 180 | Shorter than 3'-UTR of NM_019432.2 |
| SEQ ID NO: 182 | Not found at NCBI. |
| SEQ ID NO: 183 | Not found at NCBI. |
| SEQ ID NO: 197 | Significantly shorter than 3'-UTR of NM_027372.1 |
| SEQ ID NO: 200 | Corresponds to a large extent to BC049670.1 |

Artificial 5'-UTR Elements and Artificial 3'-UTR Elements

Artificial 5'-UTR elements and artificial 3'-UTR elements were prepared in some cases. This was done by modifying wild-type 5'-UTR elements and 3'-UTR elements, in a PCR-based approach using modified primers, as follows:
(i) some ATG triplets in a 5'-UTR sequences (if present) were converted to the triplet TAG.
(i) Further, the presence of a particular cleavage site for a particular restriction enzyme (if present) was not desired, in case that said particular cleavage site was considered to interfere with subsequent cloning experiments. A cleavage site present in a wild-type sequence was considered to interfere with subsequent cloning experiments if a restriction enzyme used in subsequent cloning experiments (such as described in Examples 2 and 3) would have recognized and cleaved the wild-type 3'-UTR element or 5'-UTR element. Since such internal cleavage of 5'-UTR elements and 3'-UTR elements was undesired, cleavage sites for said specific restriction enzyme were removed by replacing one nucleotide within the cleavage site for said specific restriction enzyme by the complementary nucleotide, thereby removing the cleavage sites for said specific restriction enzyme.

SEQ ID NO: 137 (based on SEQ ID NO: 3), SEQ ID NO: 138, (based on SEQ ID NO: 9), SEQ ID NO: 139 (based on SEQ ID NO: 14), SEQ ID NO: 140—(based on SEQ ID NO: 17), SEQ ID NO: 141 (based on SEQ ID NO: 18), SEQ ID NO: 142 (based on SEQ ID NO: 29),SEQ ID NO: 143 (based on SEQ ID NO: 31), SEQ ID NO: 144 (based on SEQ ID NO: 42), SEQ ID NO: 145 (based on SEQ ID NO: 43), SEQ ID NO: 146 (based on SEQ ID NO: 52), SEQ ID NO: 147 (based on SEQ ID NO: 109), SEQ ID NO: 148 (based on SEQ ID NO: 110), SEQ ID NO: 149 (based on SEQ ID NO: 119), SEQ ID NO: 150 (based on SEQ ID NO: 120), and SEQ ID NO: 151 (based on SEQ ID NO: 136) represent artificial 5'-UTR elements. SEQ ID NO: 204 (based on SEQ ID NO: 192) represents an artificial 3'-UTR element. The exact differences to the respective wild-type sequences are indicated above.

In summary, SEQ ID NO: 1 to 136 can be considered as wild-type 5'-UTR sequences, and SEQ ID NO: 137 to 151 can be considered as artificial 5'-UTR sequences; SEQ ID NO: 152 to 203 can be considered as wild-type 3'-UTR sequences, and SEQ ID NO: 204 can be considered as artificial 3'-UTR sequence.

In summary, this example provides several 5'-UTR elements and 3'-UTR elements (wild-type and artificial) which can each be tested for their relative influence on translation efficiency, with reference to reference UTR elements (as described below in Examples 2 and 3).

Example 2: Reference UTR Elements and Reference Construct Comprising the Same FIG. 1A shows the RNA sequence of a Reference Construct used in the present invention. A vector for in vitro transcription, comprising a DNA sequence corresponding to the RNA sequence of FIG. 1A was also constructed. The vector contains a T7 promoter, an artificial variant of the 5' untranslated region (5'-UTR) of 32L4 (ribosomal protein Large 32), a GC-enriched sequence (open reading frame, ORF) coding for *Photinus pyralis* luciferase (PpLuc(GC)), an artificial variant of the 3' untranslated region (3'-UTR) of human albumin (ALB), albumin7. An A64 poly(A) sequence, followed by C30 and a histone stem-loop sequence, was present 3' of albumin7. The histone stem-loop sequence was followed by a restriction site used for linearization of the vector before in vitro transcription.

PCR fragments corresponding to the sequences shown in Example 1 were cloned individually into a vector containing a DNA sequence corresponding to the RNA sequence of FIG. 1. In cases where the wild-type sequences of Example 1 contained ATG triplets in the 5'-UTR, and/or undesired restriction sites in the 5'-UTR or the 3'-UTR, the respective artificial sequences identified in Example 1 were used (e.g. SEQ ID NO: 137 was used instead of SEQ ID NO: 3).

In detail, in order to generate a construct for testing a candidate 5'-UTR element, the single underlined 5'-UTR element in FIG. 1A was replaced by the candidate (wild-type or artificial) 5'-UTR element (Example 1) to be tested (an example thereof is shown in FIG. 1B); and in order to generate a construct for testing a candidate 3'-UTR element, the double underlined 3'-UTR element in FIG. 1A was replaced by the candidate (wild-type or artificial) 3'-UTR element (Example 1) to be tested (an example thereof is shown in FIG. 1C). The obtained vectors or plasmids (containing DNA corresponding e.g. to an RNA sequence, e.g. to the RNA shown in FIG. 1A to C) can also be termed DNA templates.

The DNA templates were linearized and transcribed in vitro using T7-RNA polymerase (WO2015101416). The DNA templates were then digested by DNase-treatment.

mRNA transcripts contained a 5'-CAP structure obtained by adding an excess of $N^7$-methyl-guanosine-5'-triphosphate-5'-guanosine to the transcription reaction. mRNA thus obtained was purified and resuspended in water. The so-obtained mRNAs for testing UTR elements correspond to the mRNA shown in FIG. 1A (Reference Construct), except that the 5'-UTR element or the 3'-UTR element of the Reference Construct is replaced by the respective UTR element to be tested.

Example 3: Translation Efficiency of Candidate UTR Elements with Reference to the Reference Construct 5'-UTR elements of human origin or mouse origin or 3'-UTR elements of human origin or mouse origin were experimentally tested. Within the context of this Example, "human origin" can mean either a human wild-type sequence (e.g. SEQ ID NO: 1) or an artificial sequence based on a human wild-type sequence by substitution of one or more bases (e.g. SEQ ID NO: 137), and the term "mouse origin" is used accordingly. The details of how artificial sequences of Tables 3 and 4 are based on wild-type sequences are given in Example 1.

It was experimentally tested whether any tested (5'- or 3'-) UTR (Tables 3 and 4, below) has a beneficial effect on translation efficiency. This was done by a method comprising the steps:
(i) transfecting mammalian cells with an artificial nucleic acid molecule and measuring expressed amounts of the protein encoded by the ORF of the artificial nucleic acid molecule at one or two certain points in time after transfection (24 and 48 h),
(ii) transfecting mammalian cells with a reference nucleic acid molecule (FIG. 1A) and measuring expressed amounts of the protein encoded by the ORF of the reference nucleic acid molecule at the same one or two points in time after transfection (24 and 48 h),
(iii) calculating the ratio of the amount of protein expressed from the artificial nucleic acid molecule to the amount of protein expressed from the reference nucleic acid molecule,
wherein the ratio calculated in (iii) is ≥1.

This ratio is associated with high translation efficiency.

All UTR sequences subjected to experimental testing within this example are also referred to as "experimentally tested UTR elements" or "tested UTR elements" or "experimentally tested UTRs" or "tested UTRs".

The artificial nucleic acid molecule of (i) comprised a tested UTR element. In particular, the artificial nucleic acid molecule (mRNA) did not structurally differ from the reference nucleic acid molecule (FIG. 1A), except that either the 5'-UTR element or the 3'-UTR element of the reference nucleic acid molecule was replaced by a tested UTR element (for illustrative examples, see FIGS. 1B and 1C).

3.1 UTR Elements of Human Origin

The details of UTR elements of human origin that were subject to experimental testing are given in below Table 3. Experimental testing was performed with reference to a reference construct as described in detail above and in the section "Construct Details".

TABLE 3

Tested UTR elements of human origin.

| UTR tested | | | | Corresponding | |
| --- | --- | --- | --- | --- | --- |
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 1- H.s. ZNF460 5'-UTR | | | | ZNF460-5'-UTR | A1 |
| SEQ ID NO: 2- H.s. TGM2 5'-UTR | | | | TGM2-5'-UTR | B1 |
| | SEQ ID NO: 137- (based on SEQ ID NO: 3) | | | IL7R-5'-UTR | C1 |
| SEQ ID NO: 4- H.s. BGN 5'-UTR | | | | BGN-5'-UTR | D1 |
| SEQ ID NO: 5- H.s. TK1 5'-UTR | | | | TK1-5'-UTR | E1 |
| SEQ ID NO: 6- H.s. RAB3B 5'-UTR | | | | RAB3B-5'-UTR | F1 |
| SEQ ID NO: 7- H.s. CBX6 5'-UTR | | | | CBX6-5'-UTR | G1 |
| SEQ ID NO: 8- H.s. FZD2 5'-UTR | | | | FZD2-5'-UTR | H1 |
| | | SEQ ID NO: 138- (based on SEQ ID NO: 9 - H.s. COL8A1 5'-UTR) | | COL8A1-5'-UTR | A2 |
| SEQ ID NO: 10 - H.s. NDUFS7 5'-UTR | | | | NDUFS7-5'-UTR | B2 |
| SEQ ID NO: 11 - H.s. PHGDH 5'-UTR | | | | PHGDH-5'-UTR | C2 |

TABLE 3-continued

Tested UTR elements of human origin.

| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | Corresponding wild-type sequence | Position in Assay |
|---|---|---|---|---|---|
| SEQ ID NO: 12 - H.s. PLK2 5'-UTR | | | | PLK2-5'-UTR | D2 |
| SEQ ID NO: 13 - H.s. TSPO 5'-UTR | | | | TSPO-5'-UTR | E2 |
| | SEQ ID NO: 139- (based on SEQ ID NO: 14 - H.s. PTGS1 5'-UTR) | | | PTGS1-5'-UTR | F2 |
| SEQ ID NO: 15 - H.s. FBXO32 5'-UTR | | | | FBXO32-5'-UTR | G2 |
| SEQ ID NO: 16 - H.s. NID2 5'-UTR | | | | NID2-5'-UTR | H2 |
| | SEQ ID NO: 140 (based on SEQ ID NO: 17 - H.s. ATP5D 5'-UTR) | | | ATP5D-5'-UTR | A3 |
| | SEQ ID NO: 141 Sequence (based on SEQ ID NO: 18 - H.s. EXOSC4 5'-UTR) | | | EXOSC4-5'-UTR | B3 |
| SEQ ID NO: 19 - H.s. NOL9 5'-UTR | | | | NOL9-5'-UTR | C3 |
| SEQ ID NO: 20 - H.s. TUBB4B 5'-UTR | | | | TUBB4B-5'-UTR | D3 |
| SEQ ID NO: 21 - H.s. VPS18 5'-UTR | | | | VPS18-5'-UTR | E3 |
| SEQ ID NO: 22 - H.s. ORMDL2 5'-UTR | | | | ORMDL2-5'-UTR | F3 |
| SEQ ID NO: 23 - H.s. FSCN1 5'-UTR | | | | FSCN1-5'-UTR | G3 |
| SEQ ID NO: 24 - H.s. TMEM33 5'-UTR | | | | TMEM33-5'-UTR | H3 |
| SEQ ID NO: 25 - H.s. TUBA4A 5'-UTR | | | | TUBA4A-5'-UTR | A4 |
| SEQ ID NO: 26 - H.s. EMP3 5'-UTR | | | | EMP3-5'-UTR | B4 |
| SEQ ID NO: 27 - H.s. TMEM201 5'-UTR | | | | TMEM201-5'-UTR | C4 |
| SEQ ID NO: 28 - H.s. CRIP2 5'-UTR | | | | CRIP2-5'-UTR | D4 |
| | SEQ ID NO: 142 (based on SEQ ID NO: 29 - H.s. BRAT1 5'-UTR) | | | BRAT1-5'-UTR | E4 |
| SEQ ID NO: 30 - H.s. SERPINH1 5'-UTR | | | | SERPINH1-5'-UTR | F4 |
| | SEQ ID NO: 143 (based on SEQ ID NO: 31 - H.s. CD9 5'-UTR) | | | CD9-5'-UTR | G4 |

TABLE 3-continued

Tested UTR elements of human origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 32 - H.s. DPYSL2 5'-UTR | | | | DPYSL2-5'-UTR | H4 |
| SEQ ID NO: 33 - H.s. CDK9 5'-UTR | | | | CDK9-5'-UTR | A5 |
| SEQ ID NO: 38 - H.s. TFRC 5'-UTR | | | | TFRC-5'-UTR | B5 |
| SEQ ID NO: 39 - H.s. PSMB3 5'-UTR | | | | PSMB3-5'-UTR | C5 |
| SEQ ID NO: 40 - H.s. FASN 5'-UTR | | | | FASN-5'-UTR | D5 |
| SEQ ID NO: 41 - H.s. PSMB6 5'-UTR | | | | PSMB6-5'-UTR | E5 |
| | SEQ ID NO: 145 (based on SEQ ID NO: 43 - H.s. PRSS56 5'-UTR) | | | PRSS56-5'-UTR | F5 |
| SEQ ID NO: 44 - H.s. KPNA6 5'-UTR | | | | KPNA6-5'-UTR | G5 |
| SEQ ID NO: 45 - H.s. SFT2D2 5'-UTR | | | | SFT2D2-5'-UTR | H5 |
| SEQ ID NO: 46 - H.s. PARD6B 5'-UTR | | | | PARD6B-5'-UTR | A6 |
| SEQ ID NO: 47 - H.s. LPP 5'-UTR | | | | LPP-5'-UTR | B6 |
| SEQ ID NO: 48 - H.s. SPARC 5'-UTR | | | | SPARC-5'-UTR | C6 |
| SEQ ID NO: 49 - H.s. SCAND1 5'-UTR | | | | SCAND1-5'-UTR | D6 |
| SEQ ID NO: 50 - H.s. VASN 5'-UTR | | | | VASN-5'-UTR | E6 |
| SEQ ID NO: 51 - H.s. SLC26A1 5'-UTR | | | | SLC26A1-5'-UTR | F6 |
| | SEQ ID NO: 146- (based on SEQ ID NO: 52 - H.s. LCLAT1 5'-UTR) | | | LCLAT1-5'-UTR | G6 |
| SEQ ID NO: 53 - H.s. FBXL18 5'-UTR | | | | FBXL18-5'-UTR | H6 |
| SEQ ID NO: 54 - H.s. SLC35F6 5'-UTR | | | | SLC35F6-5'-UTR | A7 |
| SEQ ID NO: 55 - H.s. RAB3D 5'-UTR | | | | RAB3D-5'-UTR | B7 |
| SEQ ID NO: 56 - H.s. MAP1B 5'- | | | | MAP1B-5'-UTR | C7 |

TABLE 3-continued

Tested UTR elements of human origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 57 - H.s. VMA21 5'-UTR | | | | VMA21-5'-UTR | D7 |
| SEQ ID NO: 59 - H.s. CYBA 5'-UTR | | | | CYBA-5'-UTR | E7 |
| SEQ ID NO: 60 - H.s. SEZ6L2 5'-UTR | | | | SEZ6L2-5'-UTR | F7 |
| SEQ ID NO: 61 - H.s. PCOLCE 5'-UTR | | | | PCOLCE-5'-UTR | G7 |
| SEQ ID NO: 63 - H.s. VTN 5'-UTR | | | | VTN-5'-UTR | H7 |
| SEQ ID NO: 64 - H.s. ALDH16A1 5'-UTR | | | | ALDH16A1-5'-UTR | A8 |
| SEQ ID NO: 65 - H.s. RAVER1 5'-UTR | | | | RAVER1-5'-UTR | B8 |
| SEQ ID NO: 66 - H.s. KPNA6 5'-UTR | | | | KPNA6-5'-UTR | C8 |
| SEQ ID NO: 67 - H.s. SERINC5 5'-UTR | | | | SERINC5-5'-UTR | D8 |
| SEQ ID NO: 68 - H.s. JUP 5'-UTR | | | | JUP-5'-UTR | E8 |
| SEQ ID NO: 69 - H.s. CPN2 5'-UTR | | | | CPN2-5'-UTR | F8 |
| SEQ ID NO: 70 - H.s. CRIP2 5'-UTR | | | | CRIP2-5'-UTR | G8 |
| SEQ ID NO: 71 - H.s. EPT1 5'-UTR | | | | EPT1-5'-UTR | H8 |
| SEQ ID NO: 72 - H.s. PNPO 5'-UTR | | | | PNPO-5'-UTR | A9 |
| | | SEQ ID NO: 152 - *Homo sapiens* NDUFS7 3'-UTR | | NDUFS7-3'-UTR | B9 |
| | | SEQ ID NO: 153 - *Homo sapiens* PHGDH 3'-UTR | | PHGDH-3'-UTR | C9 |
| | | SEQ ID NO: 154 - *Homo sapiens* TSPO 3'-UTR | | TSPO-3'-UTR | D9 |
| | | SEQ ID NO: 155 - H.s. ATP5D 3'-UTR | | ATP5D-3'-UTR | E9 |
| | | SEQ ID NO: 156 - H.s. EXOSC4 3'-UTR | | EXOSC4-3'-UTR | F9 |

TABLE 3-continued

Tested UTR elements of human origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| | | SEQ ID NO: 157 - H.s. TUBB4B 3'-UTR | | TUBB4B-3'-UTR | G9 |
| | | SEQ ID NO: 158 - H.s. TUBA4A 3'-UTR | | TUBA4A-3'-UTR | H9 |
| | | SEQ ID NO: 159 - H.s. EMP3 3'-UTR | | EMP3-3'-UTR | A10 |
| | | SEQ ID NO: 160 - H.s. CRIP2 3'-UTR | | CRIP2-3'-UTR | B10 |
| | | SEQ ID NO: 161 - H.s. BRAT1 3'-UTR | | BRAT1-3'-UTR | C10 |
| | | SEQ ID NO: 162 - H.s. CD9 3'-UTR | | CD9-3'-UTR | D10 |
| | | SEQ ID NO: 163 - H.s. CDK9 3'-UTR | | CDK9-3'-UTR | E10 |
| | | SEQ ID NO: 164 - H.s. PSMB3 3'-UTR | | PSMB3-3'-UTR | F10 |
| | | SEQ ID NO: 165 - H.s. PSMB6 3'-UTR | | PSMB6-3'-UTR | G10 |
| | | SEQ ID NO: 166 - H.s. PRSS56 3'-UTR | | PRSS56-3'-UTR | H10 |
| | | SEQ ID NO: 167 - H.s. SCAND1 3'-UTR | | SCAND1-3'-UTR | A11 |
| | | SEQ ID NO: 168 - H.s. AMN 3'-UTR | | AMN-3'-UTR | B11 |
| | | SEQ ID NO: 169 - H.s. CYBA 3'-UTR | | CYBA-3'-UTR | C11 |
| | | SEQ ID NO: 170 - H.s. PCOLCE 3'-UTR | | PCOLCE-3'-UTR | D11 |
| | | SEQ ID NO: 171 - H.s. MAP1S 3'-UTR | | MAP1S-3'-UTR | E11 |
| | | SEQ ID NO: 172 - H.s. VTN 3'-UTR | | VTN-3'-UTR | F11 |
| | | SEQ ID NO: 173 - H.s. ALDH16A1 3'-UTR | | ALDH16A1-3'-UTR | G11 |
| SEQ ID NO: 34 - H.s. SSSCA1 5'-UTR | | | | SSSCA1-5'-UTR | H11 |
| SEQ ID NO: 35 - H.s. POLR2L 5'-UTR | | | | POLR2L-5'-UTR | A12 |
| SEQ ID NO: 36 - H.s. LIN7C 5'-UTR | | | | LIN7C-5'-UTR | B12 |

TABLE 3-continued

Tested UTR elements of human origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 37 - H.s. UQCR10 5'-UTR | | | | UQCR10-5'-UTR | C12 |
| | SEQ ID NO: 144 (based on SEQ ID NO: 42 - H.s. PYCRL 5'-UTR) | | | PYCRL-5'-UTR | D12 |
| SEQ ID NO: 58 - H.s. AMN 5'-UTR | | | | AMN-5'-UTR | E12 |
| SEQ ID NO: 62 - H.s. MAP1S 5'-UTR | | | | MAP1S-5'-UTR | F12 |
| | | | | Reference Construct (FIG. 1A) | G12 |
| | | | | Reference Construct (FIG. 1A) | H12 |

(H.s. = *Homo sapiens* = human)

3.2 UTR Elements of Mouse Origin

The details of UTR elements of mouse origin that were subject to experimental testing are given in below Table 4. Experimental testing was performed with reference to a reference construct as described in detail above and in the section "Construct Details".

TABLE 4

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 73- M.m. Dpysl2 5'-UTR | | | | Dpysl2-5'-UTR | A1 |
| SEQ ID NO: 74- M.m. Ccnd1 5'-UTR | | | | Ccnd1-5'-UTR | B1 |
| SEQ ID NO: 75- M.m. Acox2 5'-UTR | | | | Acox2-5'-UTR | C1 |
| SEQ ID NO: 76- M.m. Cbx6 (Npcd) 5'-UTR | | | | Cbx6-5'-UTR | D1 |
| SEQ ID NO: 77- M.m. Ubc 5'-UTR | | | | Ubc-5'-UTR | E1 |
| SEQ ID NO: 78- M.m. Ldlr 5'-UTR | | | | Ldlr-5'-UTR | F1 |
| SEQ ID NO: 79- M.m. Nudt22 5'UTR | | | | Nudt22-5'-UTR | G1 |
| SEQ ID NO: 80- M.m. Pcyox1l 5'-UTR | | | | Pcyox1l-5'-UTR | H1 |
| SEQ ID NO: 81- M.m. Ankrd1 5'-UTR | | | | Ankrd1-5'-UTR | A2 |

TABLE 4-continued

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 82- M.m. Tmem37 5'-UTR | | | | Tmem37-5'-UTR | B2 |
| SEQ ID NO: 83- M.m. Tspyl4 5'-UTR | | | | Tspyl4-5'-UTR | C2 |
| SEQ ID NO: 84- M.m. Slc7a3 5'-UTR | | | | Slc7a3-5'-UTR | D2 |
| SEQ ID NO: 85- M.m. Cst6 5'-UTR | | | | Cst6-5'-UTR | E2 |
| SEQ ID NO: 86- M.m. Aacs 5'-UTR | | | | Aacs-5'-UTR | F2 |
| SEQ ID NO: 87- M.m. Nosip 5'-UTR | | | | Nosip-5'-UTR | G2 |
| SEQ ID NO: 88- M.m. Itga7 5'-UTR | | | | Itga7-5'-UTR | H2 |
| SEQ ID NO: 89- M.m. Ccnd2 5'-UTR | | | | Ccnd2-5'-UTR | A3 |
| SEQ ID NO: 90- M.m. Ebp 5'-UTR | | | | Ebp-5'-UTR | B3 |
| SEQ ID NO: 91- M.m. Sf3b5 5'-UTR | | | | Sf3b5-5'-UTR | C3 |
| SEQ ID NO: 92- M.m. Fasn 5'-UTR | | | | Fasn-5'-UTR | D3 |
| SEQ ID NO: 93- M.m. Hmgcs1 5'-UTR | | | | Hmgcs1-5'-UTR | E3 |
| SEQ ID NO: 94- M.m. Osr1 5'-UTR | | | | Osr1-5'-UTR | F3 |
| SEQ ID NO: 95- M.m. Lmnb1 5'-UTR | | | | Lmnb1-5'-UTR | G3 |
| SEQ ID NO: 97- M.m. Vma21 5'-UTR | | | | Vma21-5'-UTR | H3 |
| SEQ ID NO: 98- M.m. Kif20a 5'-UTR | | | | Kif20a-5'-UTR | A4 |
| SEQ ID NO: 99- M.m. Cdca8 5'-UTR | | | | Cdca8-5'-UTR | B4 |
| SEQ ID NO: 100 - M.m. Slc7a1 5'-UTR | | | | Slc7a1-5'-UTR | C4 |
| SEQ ID NO: 101 - M.m. Ubqln2 5'-UTR | | | | Ubqln2-5'-UTR | D4 |
| SEQ ID NO: 102 - M.m. Prps2 5'-UTR | | | | Prps2-5'-UTR | E4 |
| SEQ ID NO: 103 - M.m. Shmt2 5'-UTR | | | | Shmt2-5'-UTR | F4 |
| SEQ ID NO: 105 - M.m. Aurkb 5'-UTR | | | | Aurkb-5'-UTR | G4 |
| SEQ ID NO: 106 - M.m. Fignl1 5'-UTR | | | | Fignl1-5'-UTR | H4 |
| SEQ ID NO: 107 - M.m. | | | | Cad-5'-UTR | A5 |

TABLE 4-continued

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| Cad 5'-UTR SEQ ID NO: 108 - M.m. Anln 5'-UTR | | | | Anln-5'-UTR | B5 |
| | SEQ ID NO: 147 (based on SEQ ID NO: 109 - M.m. Slfn9 5'-UTR) | | | Slfn9-5'-UTR | C5 |
| | SEQ ID NO: 148- (based on SEQ ID NO: 110 - M.m. Ncaph 5'-UTR) | | | Ncaph-5'-UTR | D5 |
| SEQ ID NO: 112 - M.m. Pole 5'-UTR | | | | Pole-5'-UTR | E5 |
| SEQ ID NO: 113 - M.m. Uhrf1 5'-UTR | | | | Uhrf1-5'-UTR | F5 |
| SEQ ID NO: 114 - M.m. Gja1 5'-UTR | | | | Gja1-5'-UTR | G5 |
| SEQ ID NO: 115 - M.m. Fam64a 5'-UTR | | | | Fam64a-5'-UTR | H5 |
| SEQ ID NO: 116 - M.m. Kif2c 5'-UTR | | | | Kif2c-5'-UTR | A6 |
| SEQ ID NO: 117 - M.m. Tspan10 5'-UTR | | | | Tspan10-5'-UTR | B6 |
| SEQ ID NO: 118 - M.m. Scand1 5'-UTR | | | | Scand1-5'-UTR | C6 |
| | SEQ ID NO: 149- Artificial Sequence (based on SEQ ID NO: 119 - M.m. Gpr84 5'-UTR) | | | Gpr84-5'-UTR | D6 |
| SEQ ID NO: 122 - M.m. Fads3 5'-UTR | | | | Fads3-5'-UTR | E6 |
| SEQ ID NO: 123 - M.m. Cers6 5'-UTR | | | | Cers6-5'-UTR | F6 |
| SEQ ID NO: 126 - M.m. Cxcr4 5'-UTR | | | | Cxcr4-5'-UTR | G6 |
| SEQ ID NO: 127 - M.m. Gprc5c 5'-UTR | | | | Gprc5c-5'-UTR | H6 |
| SEQ ID NO: 128 - M.m. Fen1 5'-UTR | | | | Fen1-5'-UTR | A7 |
| SEQ ID NO: 129 - M.m. Cspg4 5'-UTR | | | | Cspg4-5'-UTR | B7 |
| SEQ ID NO: 130 - M.m. Mrpl34 5'-UTR | | | | Mrpl34-5'-UTR | C7 |
| SEQ ID NO: 131 - M.m. Comtd1 5'-UTR | | | | Comtd1-5'-UTR | D7 |
| SEQ ID NO: 132 - M.m. Armc6 5'-UTR | | | | Armc6-5'-UTR | E7 |

TABLE 4-continued

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| SEQ ID NO: 133 - M.m. Emr4 5'-UTR | | | | Emr4-5'-UTR | F7 |
| SEQ ID NO: 134 - M.m. Atp5d 5'-UTR | | | | Atp5d-5'-UTR | G7 |
| SEQ ID NO: 135 - M.m. 1110001J03Rik 5'-UTR | | | | 1110001J03Rik-5'-UTR | H7 |
| | SEQ ID NO: 151- Artificial Sequence (based on SEQ ID NO: 136 - M.m. Csf2ra 5'-UTR) | | | Csf2ra-5'-UTR | A8 |
| | | SEQ ID NO: 174 - M.m. Acox2 3'-UTR | | Acox2-3'-UTR | B8 |
| | | SEQ ID NO: 175 - M.m. Ubc 3'-UTR | | Ubc-3'-UTR | C8 |
| | | SEQ ID NO: 176 - M.m. Slpi 3'-UTR | | Slpi-3'-UTR | D8 |
| | | SEQ ID NO: 178 - M.m. Pcyox1l 3'-UTR | | Pcyox1l-3'-UTR | E8 |
| | | SEQ ID NO: 179 - M.m. Igf2bp1 3'-UTR | | Igf2bp1-3'-UTR | F8 |
| | | SEQ ID NO: 180 - M.m. Tmem37 3'-UTR | | Tmem37-3'-UTR | G8 |
| | | SEQ ID NO: 181 - M.m. Slc7a3 3'-UTR (240) | | Slc7a3-3'-UTR | H8 |
| | | SEQ ID NO: 182 - M.m. Cst6 3'-UTR | | Cst6-3'-UTR | A9 |
| | | SEQ ID NO: 183 - M.m. Ebp 3'-UTR | | Ebp-3'-UTR | B9 |
| | | SEQ ID NO: 184 - M.m. Sf3b5 3'-UTR | | Sf3b5-3'-UTR | C9 |
| | | SEQ ID NO: 185 - M.m. Plk1 3'-UTR | | Plk1-3'-UTR | D9 |
| | | SEQ ID NO: 187 - M.m. Cdca8 3'-UTR | | Cdca8-3'-UTR | E9 |
| | | SEQ ID NO: 188 - M.m. Kif22 3'-UTR | | Kif22-3'-UTR | F9 |
| | | SEQ ID NO: 189 - M.m. Cad 3'-UTR | | Cad-3'-UTR | G9 |
| | | SEQ ID NO: 190 - M.m. Cth 3'-UTR | | Cth-3'-UTR | H9 |
| | | SEQ ID NO: 191 - M.m. Pole 3'-UTR | | Pole-3'-UTR | A10 |

TABLE 4-continued

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| | | | SEQ ID NO: 204 (based on SEQ ID NO: 192 - M.m. Kif2c 3'-UTR) | Kif2c-3'-UTR | B10 |
| | | SEQ ID NO: 193 - M.m. Scand1 3'-UTR | | Scand1-3'-UTR | C10 |
| | | SEQ ID NO: 194 - M.m. Gpr84 3'-UTR | | Gpr84-3'-UTR | D10 |
| | | SEQ ID NO: 195 - M.m. Tpgs1 3'-UTR | | Tpgs1-3'-UTR | E10 |
| | | SEQ ID NO: 196 - M.m. Ccl17 3'-UTR | | Ccl17-3'-UTR | F10 |
| | | SEQ ID NO: 197 - M.m. Alkbh7 3'-UTR | | Alkbh7-3'-UTR | G10 |
| | | SEQ ID NO: 198 - M.m. Ms4a8a 3'-UTR | | Ms4a8a-3'-UTR | H10 |
| | | SEQ ID NO: 199 - M.m. Mrpl34 3'-UTR | | Mrpl34-3'-UTR | A11 |
| | | SEQ ID NO: 200 - M.m. Comtd1 3'-UTR | | Comtd1-3'-UTR | B11 |
| | | SEQ ID NO: 201 - M.m. Armc6 3'-UTR | | Armc6-3'-UTR | C11 |
| | | SEQ ID NO: 202 - M.m. Atp5d 3'-UTR | | Atp5d-3'-UTR | D11 |
| | | SEQ ID NO: 203 - M.m. 1110001J03Rik 3'-UTR | | 1110001J03Rik-3'-UTR | E11 |
| SEQ ID NO: 96 - M.m. Aarsd1 5'-UTR | | | | Aarsd1-5'-UTR | F11 |
| SEQ ID NO: 104 - M.m. Kif22 5'-UTR | | | | Kif22-5'-UTR | G11 |
| SEQ ID NO: 111 - M.m. Cth 5'-UTR | | | | Cth-5'-UTR | H11 |
| | SEQ ID NO: 150 (based on SEQ ID NO: 120 - M.m. Tpgs1 5'-UTR) | | | Tpgs1-5'-UTR | A12 |
| SEQ ID NO: 121 - M.m. Ccl17 5'-UTR | | | | Ccl17-5'-UTR | B12 |
| SEQ ID NO: 124 - M.m. Alkbh7 5'-UTR | | | | Alkbh7-5'-UTR | C12 |
| SEQ ID NO: 125 - M.m. Ms4a8a 5'-UTR | | | | Ms4a8a-5'-UTR | D12 |

TABLE 4-continued

Tested UTR elements of mouse origin.

| UTR tested | | | | Corresponding | |
|---|---|---|---|---|---|
| Wild-type 5'-UTR (SEQ ID NO) | Artificial 5'-UTR (SEQ ID NO) | Wild-type 3'-UTR (SEQ ID NO) | Artificial 3'-UTR (SEQ ID NO) | wild-type sequence | Position in Assay |
| | | SEQ ID NO: 177 - M.m. Nudt22 3'-UTR | | Nudt22-3'-UTR | E12 |
| | | SEQ ID NO: 186 - M.m. Aarsd1 3'-UTR | | Aarsd1-3'-UTR | F12 |
| | | | | Reference Construct (FIG. 1A) | G12 |
| | | | | Reference Construct (FIG. 1A) | H12 |

(M.m. = Mus musculus = mouse)

3.3 Construct Details

When a 5'-UTR was tested, this was done by replacing the 5'-UTR of the Reference Construct (i.e. 32L4-PpLuc(GC)-albumin7-A64-C30-hSL; FIG. 1) by the "tested" 5'-UTR—i.e. either the wild-type 5'-UTR sequence (mRNA sequence corresponding to the DNA sequence referred to in Table 3 or 4, first column) or the artificial 5'-UTR sequence based thereon (mRNA sequence corresponding to the DNA sequence referred to in Table 3 or 4, second column). The other sequence elements of the Reference Construct remained unchanged.

In turn, when a 3'-UTR was tested, this was done by replacing the 3'-UTR of the Reference Construct (i.e. 32L4-PpLuc(GC)-albumin7-A64-C30-hSL; FIG. 1) by the "tested" 3'-UTR—i.e. either the wild-type 3'-UTR sequence (mRNA sequence corresponding to the DNA sequence referred to in Table 3 or 4, third column) or the artificial 3'-UTR sequence based thereon (mRNA sequence corresponding to the DNA sequence referred to in Table 3 or 4, fourth column). The other sequence elements of the Reference Construct remained unchanged.

3.4. Luciferase Assay for Determination of Translation Efficiency

Translation efficiency was tested experimentally in a cell transfection assay using different mammalian (human, mouse) cell lines, i.e. HDF, L929, HepG2 and Hela (see FIGS. 2 to 9).

Human dermal fibroblasts (HDF), L929 cells, HEPG2 cells and HeLa cells were seeded in 96 well plates at a density of $1 \times 10^4$ cells per well. The following day, cells were washed in Opti-MEM and then transfected with 25 ng per well of Lipofectamine2000-complexed PpLuc-encoding mRNA in Opti-MEM. Untransfected cells served as control. mRNA coding for *Renilla reniformis* luciferase (RrLuc) was transfected together with PpLuc mRNA to control for transfection efficiency (1 ng of RrLuc mRNA per well). 90 minutes after start of transfection, Opti-MEM was exchanged for medium. 24 and 48 hours after transfection, medium was aspirated and cells were lysed in 100 µl of Passive Lysis buffer (Promega). Lysates were stored at −80° C. until luciferase activity was measured.

Luciferase activity was measured as relative light units (RLU) in a Hidex Chameleon plate reader. The activities of Ppluc and Rrluc are measured sequentially from a single sample in a dual luciferase assay. The PpLuc activity was measured first at 2 seconds measuring time using 20 µl of lysate and 50 µl of Beetle juice (pjk GmbH). After 1500 ms delay RrLuc activity is measured with 50 µl *Renilla* juice (pjk GmbH).

This was done in 96-well plates, and every tested UTR element (in the framework of the construct in which it was contained, see 3.3) was allocated a position in the 96-well plate. Two 96 well plates were used, one for testing UTR elements of human origin, and one for testing UTR elements of mouse origin. In each plate, the Reference Construct (corresponding to the mRNA sequence shown in FIG. 1A) was at positions G12 and H12. The tested UTR elements were at the positions indicated in the last column in Tables 3 and 4, respectively. For illustration, a construct comprising the 3'-UTR of mouse Aarsd1 (SEQ ID NO: 186) was at position F12 (see Table 4).

Luciferase activity was measured 24 hours (1 d, 24 h) post transfection of the cells, and again 48 hours (2d, 48 h) post transfection of the cells.

The results of this assay are described in 3.5 below.

3.5 Results—Determination of UTR Elements Associated with High Translation Efficiency The expression results of the assay (see 3.4 above), measured after 24 hours (1d, 24 h) and again after 48 hours (2d, 48 h) after transfection into different mammalian cell lines (HDF, L929, HepG2 and Hela) are shown in FIGS. 2 to 9. Note that there are two sets of 96 well plates, one set relating to UTR elements of human origin and one set relating to UTR elements of mouse origin.

While FIGS. 2 to 9 refer to specific positions in the 96 well plate (e.g. A1), Tables 3 and 4 allocate specific tested (5'- or 3'-)UTR elements to specific positions in the 96 well plate. For example, it can be taken from Table 3 that, at position A1 of the 96 well plate of tested human UTR elements, the ZNF460-5'-UTR element (SEQ ID NO: 1) was tested, and so on.

A group of particularly preferred UTR elements (also termed "final selection") was determined. This group comprises 5'-UTR elements and 3'-UTR elements which are characterized by a translation efficiency equal or better, preferably better, than the reference Construct (FIG. 1A) in at least one of the cell lines tested, measured after 1 day (24 h). This group falls into four subgroups: (i) 5'-UTR elements of human origin (see Table 5), (ii) 3'-UTR elements of human origin (see Table 6), (iii) 5'-UTR elements of mouse origin (see Table 7), (ii) 3'-UTR elements of mouse origin (see Table 8).

TABLE 5

Preferred 5'-UTR elements of human origin

| 5'-UTR elements of human origin | | Corresponding | |
|---|---|---|---|
| Wild-type 5'-UTR (SEQ ID NO) | Artificial 5'-UTR (SEQ ID NO) | wild-type sequence | Position in Assay |
| SEQ ID NO: 1 - H.s. ZNF460 5'-UTR | | ZNF460-5'-UTR | A1 |
| SEQ ID NO: 2 - H.s. TGM2 5'-UTR | | TGM2-5'-UTR | B1 |
| | SEQ ID NO: 137 - (based on SEQ ID NO: 3 - H.s. IL7R-5'-UTR) | IL7R-5'-UTR | C1 |
| | SEQ ID NO: 138 - (based on SEQ ID NO: 9 - H.s. COL8A1 5'-UTR) | COL8A1-5'-UTR | A2 |
| SEQ ID NO: 10 - H.s. NDUFS7 5'-UTR | | NDUFS7-5'-UTR | B2 |
| SEQ ID NO: 12 - H.s. PLK2 5'-UTR | | PLK2-5'-UTR | D2 |
| SEQ ID NO: 15 - H.s. FBXO32 5'-UTR | | FBXO32-5'-UTR | G2 |
| | SEQ ID NO: 140 (based on SEQ ID NO: 17 - H.s. ATP5D 5'-UTR) | ATP5D-5'-UTR | A3 |
| SEQ ID NO: 20 - H.s. TUBB4B 5'-UTR | | TUBB4B-5'-UTR | D3 |
| SEQ ID NO: 22 - H.s. ORMDL2 5'-UTR | | ORMDL2-5'-UTR | F3 |
| SEQ ID NO: 23 - H.s. FSCN1 5'-UTR | | FSCN1-5'-UTR | G3 |
| | SEQ ID NO: 143 (based on SEQ ID NO: 31 - H.s. CD9 5'-UTR) | CD9-5'-UTR | G4 |
| SEQ ID NO: 32 - H.s. DPYSL2 5'-UTR | | DPYSL2-5'-UTR | H4 |
| SEQ ID NO: 39 - H.s. PSMB3 5'-UTR | | PSMB3-5'-UTR | C5 |
| SEQ ID NO: 41 - H.s. PSMB6 5'-UTR | | PSMB6-5'-UTR | E5 |
| SEQ ID NO: 44 - H.s. KPNA6 5'-UTR | | KPNA6-5'-UTR | G5 |
| SEQ ID NO: 45 - H.s. SFT2D2 5'-UTR | | SFT2D2-5'-UTR | H5 |
| | SEQ ID NO: 146 - (based on SEQ ID NO: 52 - H.s. LCLAT1 5'-UTR) | LCLAT1-5'-UTR | G6 |
| SEQ ID NO: 53 - H.s. FBXL18 5'-UTR | | FBXL18-5'-UTR | H6 |
| SEQ ID NO: 54 - H.s. SLC35F6 5'-UTR | | SLC35F6-5'-UTR | A7 |
| SEQ ID NO: 57 - H.s. VMA21 5'-UTR | | VMA21-5'-UTR | D7 |
| SEQ ID NO: 60 - H.s. SEZ6L2 5'-UTR | | SEZ6L2-5'-UTR | F7 |
| SEQ ID NO: 61 - H.s. PCOLCE 5'-UTR | | PCOLCE-5'-UTR | G7 |
| SEQ ID NO: 63 - H.s. VTN 5'-UTR | | VTN-5'-UTR | H7 |
| SEQ ID NO: 64 - H.s. ALDH16A1 5'-UTR | | ALDH16A1-5'-UTR | A8 |
| SEQ ID NO: 66 - H.s. KPNA6 5'-UTR | | KPNA6-5'-UTR | C8 |
| SEQ ID NO: 68 - H.s. JUP 5'-UTR | | JUP-5'-UTR | E8 |
| SEQ ID NO: 69 - H.s. CPN2 5'-UTR | | CPN2-5'-UTR | F8 |
| SEQ ID NO: 72 - H.s. PNPO 5'-UTR | | PNPO-5'-UTR | A9 |
| SEQ ID NO: 34 - H.s. SSSCA1 5'-UTR | | SSSCA1-5'-UTR | H11 |
| SEQ ID NO: 35 - H.s. POLR2L 5'-UTR | | POLR2L-5'-UTR | A12 |
| SEQ ID NO: 36 - H.s. LIN7C 5'-UTR | | LIN7C-5'-UTR | B12 |
| SEQ ID NO: 37 - H.s. UQCR10 5'-UTR | | UQCR10-5'-UTR | C12 |

TABLE 5-continued

Preferred 5'-UTR elements of human origin

| 5'-UTR elements of human origin | | Corresponding | |
|---|---|---|---|
| Wild-type 5'-UTR (SEQ ID NO) | Artificial 5'-UTR (SEQ ID NO) | wild-type sequence | Position in Assay |
| | SEQ ID NO: 144 (based on SEQ ID NO: 42 - H.s. PYCRL 5'-UTR) | PYCRL-5'-UTR | D12 |
| SEQ ID NO: 58 - H.s. AMN 5'-UTR | | AMN-5'-UTR | E12 |
| SEQ ID NO: 62 - H.s. MAP1S 5'-UTR | | MAP1S-5'-UTR | F12 |

Thus, 5'-UTRs of the human genes from the group consisting of ZNF460-5'-UTR, TGM2-5'-UTR, IL7R-5'-UTR, COL8A1-5'-UTR, NDUFS7-5'-UTR, PLK2-5'-UTR, FBXO32-5'-UTR, ATP5D-5'-UTR, TUBB4B-5'-UTR, ORMDL2-5'-UTR, FSCN1-5'-UTR, CD9-5'-UTR, PYSL2-5'-UTR, PSMB3-5'-UTR, PSMB6-5'-UTR, KPNA6-5'-UTR, SFT2D2-5'-UTR, LCLAT1-5'-UTR, FBXL18-5'-UTR, SLC35F6-5'-UTR, VMA21-5'-UTR, SEZ6L2-5'-UTR, PCOLCE-5'-UTR, VTN-5'-UTR, ALDH16A1-5'-UTR, KPNA6-5'-UTR, JUP-5'-UTR, CPN2-5'-UTR, PNPO-5'-UTR, SSSCA1-5'-UTR, POLR2L-5'-UTR, LIN7C-5'-UTR, UQCR10-5'-UTR, PYCRL-5'-UTR, AMN-5'-UTR, MAP1S-5'-UTR are considered to contribute high translation efficiency.

Also, 5'-UTRs reflected by SEQ ID NO: 1, SEQ ID NO: 2, SEQ ID NO: 137 (or its wild-type equivalent SEQ ID NO: 3), SEQ ID NO: 138 (or its wild-type equivalent SEQ ID NO: 9), SEQ ID NO: 10, SEQ ID NO: 12, SEQ ID NO: 15, SEQ ID NO: 140 (or its wild-type equivalent SEQ ID NO: 17), SEQ ID NO: 20, SEQ ID NO: 22, SEQ ID NO: 23, SEQ ID NO: 143 (or its wild-type equivalent SEQ ID NO: 31), SEQ ID NO: 32, SEQ ID NO: 39, SEQ ID NO: 41, SEQ ID NO: 44, SEQ ID NO: 45, SEQ ID NO: 146—(or its wild-type equivalent SEQ ID NO: 52), SEQ ID NO: 53, SEQ ID NO: 54, SEQ ID NO: 57, SEQ ID NO: 60, SEQ ID NO: 61, SEQ ID NO: 63, SEQ ID NO: 64, SEQ ID NO: 66, SEQ ID NO: 68, SEQ ID NO: 69, SEQ ID NO: 72, SEQ ID NO: 34, SEQ ID NO: 35, SEQ ID NO: 36, SEQ ID NO: 37, SEQ ID NO: 144 (or its wild-type equivalent SEQ ID NO: 42), SEQ ID NO: 58, SEQ ID NO: 62 are considered to contribute high translation efficiency.

TABLE 6

Preferred 3'-UTR elements of human origin

| Wild-type 3'-UTR element (SEQ ID NO) tested | Corresponding wild-type sequence | Position in Assay |
|---|---|---|
| SEQ ID NO: 152 - H.s. NDUFS7 3'-UTR | NDUFS7-3'-UTR | B9 |
| SEQ ID NO: 153 - H.s. PHGDH 3'-UTR | PHGDH-3'-UTR | C9 |
| SEQ ID NO: 154 - H.s. TSPO 3'-UTR | TSPO-3'-UTR | D9 |
| SEQ ID NO: 155 - H.s. ATP5D 3'-UTR | ATP5D-3'-UTR | E9 |
| SEQ ID NO: 156 - H.s. EXOSC4 3'-UTR | EXOSC4-3'-UTR | F9 |
| SEQ ID NO: 157 - H.s. TUBB4B 3'-UTR | TUBB4B-3'-UTR | G9 |
| SEQ ID NO: 158 - H.s. TUBA4A 3'-UTR | TUBA4A-3'-UTR | H9 |
| SEQ ID NO: 159 - H.s. EMP3 3'-UTR | EMP3-3'-UTR | A10 |
| SEQ ID NO: 160 - H.s. CRIP2 3'-UTR | CRIP2-3'-UTR | B10 |
| SEQ ID NO: 161 - H.s. BRAT1 3'-UTR | BRAT1-3'-UTR | C10 |
| SEQ ID NO: 164 - H.s. PSMB3 3'-UTR | PSMB3-3'-UTR | F10 |
| SEQ ID NO: 165 - H.s. PSMB6 3'-UTR | PSMB6-3'-UTR | G10 |
| SEQ ID NO: 167 - H.s. SCAND1 3'-UTR | SCAND1-3'-UTR | A11 |
| SEQ ID NO: 168 - H.s. AMN 3'-UTR | AMN-3'-UTR | B11 |
| SEQ ID NO: 169 - H.s. CYBA 3'-UTR | CYBA-3'-UTR | C11 |
| SEQ ID NO: 170 - H.s. PCOLCE 3'-UTR | PCOLCE-3'-UTR | D11 |
| SEQ ID NO: 171 - H.s. MAP1S 3'-UTR | MAP1S-3'-UTR | E11 |
| SEQ ID NO: 172 - H.s. VTN 3'-UTR | VTN-3'-UTR | F11 |
| SEQ ID NO: 173 - H.s. ALDH16A1 3'-UTR | ALDH16A1-3'-UTR | G11 |

Thus, 3'-UTRs of the human genes from the group consisting of NDUFS7-3'-UTR, PHGDH-3'-UTR, TSPO-3'-UTR, ATP5D-3'-UTR, EXOSC4-3'-UTR, TUBB4B-3'-UTR, TUBA4A-3'-UTR, EMP3-3'-UTR, CRIP2-3'-UTR, BRAT1-3'-UTR, PSMB3-3'-UTR, PSMB6-3'-UTR, SCAND1-3'-UTR, AMN-3'-UTR, CYBA-3'-UTR, PCOLCE-3'-UTR, MAP1S-3'-UTR, VTN-3'-UTR, ALDH16A1-3'-UTR are considered to contribute high translation efficiency.

Also, the 3'-UTRs reflected by SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 164, SEQ ID NO: 165, SEQ ID NO: 167, SEQ ID NO: 168, SEQ ID NO: 169, SEQ ID NO: 170, SEQ ID NO: 171, SEQ ID NO: 172, SEQ ID NO: 173 are considered to contribute high translation efficiency.

TABLE 7

| Preferred 5'-UTR elements of mouse origin | | | |
|---|---|---|---|
| UTR tested | | Corresponding | |
| Wild-type 5'-UTR element (SEQ ID NO) | Artificial 5'-UTR (SEQ ID NO) | wild-type sequence | Position in Assay |
| SEQ ID NO: 73 - M.m. Dpysl2 5'-UTR | | Dpysl2-5'-UTR | A1 |
| SEQ ID NO: 75 - M.m. Acox2 5'-UTR | | Acox2-5'-UTR | C1 |
| SEQ ID NO: 77 - M.m. Ubc 5'-UTR | | Ubc-5'-UTR | E1 |
| SEQ ID NO: 79 - M.m. Nudt22 5'UTR | | Nudt22-5'-UTR | G1 |
| SEQ ID NO: 80 - M.m. Pcyox1l 5'-UTR | | Pcyox1l-5'-UTR | H1 |
| SEQ ID NO: 81 - M.m. Ankrd1 5'-UTR | | Ankrd1-5'-UTR | A2 |
| SEQ ID NO: 83 - M.m. Tspyl4 5'-UTR | | Tspyl4-5'-UTR | C2 |
| SEQ ID NO: 84 - M.m. Slc7a3 5'-UTR | | Slc7a3-5'-UTR | D2 |
| SEQ ID NO: 86 - M.m. Aacs 5'-UTR | | Aacs-5'-UTR | F2 |
| SEQ ID NO: 87 - M.m. Nosip 5'-UTR | | Nosip-5'-UTR | G2 |
| SEQ ID NO: 88 - M.m. Itga7 5'-UTR | | Itga7-5'-UTR | H2 |
| SEQ ID NO: 89 - M.m. Ccnd2 5'-UTR | | Ccnd2-5'-UTR | A3 |
| SEQ ID NO: 90 - M.m. Ebp 5'-UTR | | Ebp-5'-UTR | B3 |
| SEQ ID NO: 91 - M.m. Sf3b5 5'-UTR | | Sf3b5-5'-UTR | C3 |
| SEQ ID NO: 92 - M.m. Fasn 5'-UTR | | Fasn-5'-UTR | D3 |
| SEQ ID NO: 93 - M.m. Hmgcs1 5'-UTR | | Hmgcs1-5'-UTR | E3 |
| SEQ ID NO: 94 - M.m. Osr1 5'-UTR | | Osr1-5'-UTR | F3 |
| SEQ ID NO: 95 - M.m. Lmnb1 5'-UTR | | Lmnb1-5'-UTR | G3 |
| SEQ ID NO: 97 - M.m. Vma21 5'-UTR | | Vma21-5'-UTR | H3 |
| SEQ ID NO: 98 - M.m. Kif20a 5'-UTR | | Kif20a-5'-UTR | A4 |
| SEQ ID NO: 99 - M.m. Cdca8 5'-UTR | | Cdca8-5'-UTR | B4 |
| SEQ ID NO: 100 - M.m. Slc7a1 5'-UTR | | Slc7a1-5'-UTR | C4 |
| SEQ ID NO: 101 - M.m. Ubqln2 5'-UTR | | Ubqln2-5'-UTR | D4 |
| SEQ ID NO: 102 - M.m. Prps2 5'-UTR | | Prps2-5'-UTR | E4 |
| SEQ ID NO: 103 - M.m. Shmt2 5'-UTR | | Shmt2-5'-UTR | F4 |
| SEQ ID NO: 106 - M.m. Fignl1 5'-UTR | | Fignl1-5'-UTR | H4 |
| SEQ ID NO: 107 - M.m. Cad 5'-UTR | | Cad-5'-UTR | A5 |
| SEQ ID NO: 108 - M.m. Anln 5'-UTR | | Anln-5'-UTR | B5 |
| | SEQ ID NO: 147 (based on SEQ ID NO: 109 - M.m. Slfn9 5'-UTR) | Slfn9-5'-UTR | C5 |
| | SEQ ID NO: 148 - (based on SEQ ID NO: 110 - M.m. Ncaph 5'-UTR) | Ncaph-5'-UTR | D5 |
| SEQ ID NO: 112 - M.m. Pole 5'-UTR | | Pole-5'-UTR | E5 |
| SEQ ID NO: 113 - M.m. Uhrf1 5'-UTR | | Uhrf1-5'-UTR | F5 |
| SEQ ID NO: 114 - M.m. Gja1 5'-UTR | | Gja1-5'-UTR | G5 |
| SEQ ID NO: 115 - M.m. Fam64a 5'-UTR | | Fam64a-5'-UTR | H5 |
| SEQ ID NO: 117 - M.m. Tspan10 5'-UTR | | Tspan10-5'-UTR | B6 |

TABLE 7-continued

Preferred 5'-UTR elements of mouse origin

| UTR tested | | Corresponding | |
|---|---|---|---|
| Wild-type 5'-UTR element (SEQ ID NO) | Artificial 5'-UTR (SEQ ID NO) | wild-type sequence | Position in Assay |
| SEQ ID NO: 118 - M.m. Scand1 5'-UTR | | Scand1-5'-UTR | C6 |
| | SEQ ID NO: 149 (based on SEQ ID NO: 119 - M.m. Gpr84 5'-UTR) | Gpr84-5'-UTR | D6 |
| SEQ ID NO: 123 - M.m. Cers6 5'-UTR | | Cers6-5'-UTR | F6 |
| SEQ ID NO: 126 - M.m. Cxcr4 5'-UTR | | Cxcr4-5'-UTR | G6 |
| SEQ ID NO: 127 - M.m. Gprc5c 5'-UTR | | Gprc5c-5'-UTR | H6 |
| SEQ ID NO: 128 - M.m. Fen1 5'-UTR | | Fen1-5'-UTR | A7 |
| SEQ ID NO: 129 - M.m. Cspg4 5'-UTR | | Cspg4-5'-UTR | B7 |
| SEQ ID NO: 130 - M.m. Mrpl34 5'-UTR | | Mrpl34-5'-UTR | C7 |
| SEQ ID NO: 131 - M.m. Comtd1 5'-UTR | | Comtd1-5'-UTR | D7 |
| SEQ ID NO: 132 - M.m. Armc6 5'-UTR | | Armc6-5'-UTR | E7 |
| SEQ ID NO: 133 - M.m. Emr4 5'-UTR | | Emr4-5'-UTR | F7 |
| SEQ ID NO: 134 - M.m. Atp5d 5'-UTR | | Atp5d-5'-UTR | G7 |
| | SEQ ID NO: 151 (based on SEQ ID NO: 136 - M.m. Csf2ra 5'-UTR) | Csf2ra-5'-UTR | A8 |
| SEQ ID NO: 96 - M.m. Aarsd1 5'-UTR | | Aarsd1-5'-UTR | F11 |
| SEQ ID NO: 111 - M.m. Cth 5'-UTR | | Cth-5'-UTR | H11 |
| | SEQ ID NO: 150 (based on SEQ ID NO: 120 - M.m. Tpgs1 5'-UTR) | Tpgs1-5'-UTR | A12 |
| SEQ ID NO: 121 - M.m. Ccl17 5'-UTR | | Ccl17-5'-UTR | B12 |
| SEQ ID NO: 124 - M.m. Alkbh7 5'-UTR | | Alkbh7-5'-UTR | C12 |
| SEQ ID NO: 125 - M.m. Ms4a8a 5'-UTR | | Ms4a8a-5'-UTR | D12 |

Thus, 5'-UTRs of the mouse genes from the group consisting of Dpysl2-5'-UTR, Acox2-5'-UTR, Ubc-5'-UTR, Nudt22-5'-UTR, Pcyox11-5'-UTR, Ankrd1-5'-UTR, Tspyl4-5'-UTR, Slc7a3-5'-UTR, Aacs-5'-UTR, Nosip-5'-UTR, Itga7-5'-UTR, Ccnd2-5'-UTR, Ebp-5'-UTR, Sf3b5-5'-UTR, Fasn-5'-UTR, Hmgcsl-5'-UTR, Osr1-5'-UTR, Lmnb1-5'-UTR, Vma21-5'-UTR, Kif20a-5'-UTR, Cdca8-5'-UTR, Slc7a1-5'-UTR, Ubqln2-5'-UTR, Prps2-5'-UTR, Shmt2-5'-UTR, Fignl1-5'-UTR, Cad-5'-UTR, Anln-5'-UTR, Slfn9-5'-UTR, Ncaph-5'-UTR, Pole-5'-UTR, Uhrf1-5'-UTR, Gja1-5'-UTR, Fam64a-5'-UTR, Tspan10-5'-UTR, Scand1-5'-UTR, Gpr84-5'-UTR, Cers6-5'-UTR, Cxcr4-5'-UTR, Gprc5c-5'-UTR, Fen 1-5'-UTR, Cspg4-5'-UTR, Mrpl34-5'-UTR, Comtd1-5'-UTR, Armc6-5'-UTR, Emr4-5'-UTR, Atp5d-5'-UTR, Csf2ra-5'-UTR, Aarsd1-5'-UTR, Cth-5'-UTR, Tpgs1-5'-UTR, Ccl17-5'-UTR, Alkbh7-5'-UTR, Ms4a8a-5'-UTR are considered to contribute high translation efficiency.

Also, 5'-UTRs reflected by SEQ ID NO: 73, SEQ ID NO: 75, SEQ ID NO: 77, SEQ ID NO: 79, SEQ ID NO: 80, SEQ ID NO: 81, SEQ ID NO: 83, SEQ ID NO: 84, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 147 (or its wild-type equivalent SEQ ID NO: 109), SEQ ID NO: 148 (or its wild-type equivalent SEQ ID NO: 110), SEQ ID NO: 112, SEQ ID NO: 113, SEQ ID NO: 114, SEQ ID NO: 115, SEQ ID NO: 117, SEQ ID NO: 118, SEQ ID NO: 149 (or its wild-type equivalent SEQ ID NO: 119), SEQ ID NO: 123, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 151 (or its wild-type equivalent SEQ ID NO: 136), SEQ ID NO: 96, SEQ ID NO: 111, SEQ ID NO: 150 (based on SEQ ID NO: 120), SEQ ID NO: 121, SEQ ID NO: 124, SEQ ID NO: 125 are considered to contribute high translation efficiency.

TABLE 8

| Preferred 3'-UTR elements of mouse origin | | | |
|---|---|---|---|
| UTR tested | | Corresponding | |
| Wild-type 3'-UTR (SEQ ID NO) | Artificial 3'-UTR (SEQ ID NO) | wild-type sequence | Position in Assay |
| SEQ ID NO: 174 - M.m. Acox2 3'-UTR | | Acox2-3'-UTR | B8 |
| SEQ ID NO: 175 - M.m. Ubc 3'-UTR | | Ubc-3'-UTR | C8 |
| SEQ ID NO: 176 - M.m. Slpi 3'-UTR | | Slpi-3'-UTR | D8 |
| SEQ ID NO: 179 - M.m. Igf2bp1 3'-UTR | | Igf2bp1-3'-UTR | F8 |
| SEQ ID NO: 180 - M.m. Tmem37 3'-UTR | | Tmem37-3'-UTR | G8 |
| SEQ ID NO: 181 - M.m. Slc7a3 3'-UTR (240) | | Slc7a3-3'-UTR | H8 |
| SEQ ID NO: 182 - M.m. Cst6 3'-UTR | | Cst6-3'-UTR | A9 |
| SEQ ID NO: 183 - M.m. Ebp 3'-UTR | | Ebp-3'-UTR | B9 |
| SEQ ID NO: 184 - M.m. Sf3b5 3'-UTR | | Sf3b5-3'-UTR | C9 |
| SEQ ID NO: 187 - M.m. Cdca8 3'-UTR | | Cdca8-3'-UTR | E9 |
| SEQ ID NO: 188 - M.m. Kif22 3'-UTR | | Kif22-3'-UTR | F9 |
| SEQ ID NO: 189 - M.m. Cad 3'-UTR | | Cad-3'-UTR | G9 |
| SEQ ID NO: 191 - M.m. Pole 3'-UTR | | Pole-3'-UTR | A10 |
| | SEQ ID NO: 204 (based on SEQ ID NO: 192 - M.m. Kif2c 3'-UTR) | Kif2c-3'-UTR | B10 |
| SEQ ID NO: 193 - M.m. Scand1 3'-UTR | | Scand1-3'-UTR | C10 |
| SEQ ID NO: 194 - M.m. Gpr84 3'-UTR | | Gpr84-3'-UTR | D10 |
| SEQ ID NO: 195 - M.m. Tpgs1 3'-UTR | | Tpgs1-3'-UTR | E10 |
| SEQ ID NO: 196 - M.m. Ccl17 3'-UTR | | Ccl17-3'-UTR | F10 |
| SEQ ID NO: 197 - M.m. Alkbh7 3'-UTR | | Alkbh7-3'-UTR | G10 |
| SEQ ID NO: 198 - M.m. Ms4a8a 3'-UTR | | Ms4a8a-3'-UTR | H10 |
| SEQ ID NO: 199 - M.m. Mrpl34 3'-UTR | | Mrpl34-3'-UTR | A11 |
| SEQ ID NO: 200 - M.m. Comtd1 3'-UTR | | Comtd1-3'-UTR | B11 |
| SEQ ID NO: 201 - M.m. Armc6 3'-UTR | | Armc6-3'-UTR | C11 |
| SEQ ID NO: 202 - M.m. Atp5d 3'-UTR | | Atp5d-3'-UTR | D11 |
| SEQ ID NO: 203 - M.m. 1110001J03Rik 3'-UTR | | 1110001J03Rik-3'-UTR | E11 |
| SEQ ID NO: 177 - M.m. Nudt22 3'-UTR | | Nudt22-3'-UTR | E12 |

Thus, 3'-UTRs of the mouse genes from the group consisting of Acox2-3'-UTR, Ubc-3'-UTR, Slpi-3'-UTR, Igf2bp1-3'-UTR, Tmem37-3'-UTR, Slc7a3-3'-UTR, Cst6-3'-UTR, Ebp-3'-UTR, Sf3b5-3'-UTR, Cdca8-3'-UTR, Kif22-3'-UTR, Cad-3'-UTR, Pole-3'-UTR, Kif2c-3'-UTR, Scand1-3'-UTR, Gpr84-3'-UTR, Tpgs1-3'-UTR, Ccl17-3'-UTR, Alkbh7-3'-UTR, Ms4a8a-3'-UTR, Mrpl34-3'-UTR, Comtd1-3'-UTR, Armc6-3'-UTR, Atp5d-3'-UTR, 1110001J03Rik-3'-UTR, Nudt22-3'-UTR are considered to contribute high translation efficiency.

Also, 3'-UTRs reflected by SEQ ID NO: 174, SEQ ID NO: 175, SEQ ID NO: 176, SEQ ID NO: 179, SEQ ID NO: 180, SEQ ID NO: 181, SEQ ID NO: 182, SEQ ID NO: 183, SEQ ID NO: 184, SEQ ID NO: 187, SEQ ID NO: 188, SEQ ID NO: 189, SEQ ID NO: 191, SEQ ID NO: 204 (or its wild-type equivalent SEQ ID NO: 192), SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 177 are considered to contribute high translation efficiency.

The invention claimed is:

1. A purified RNA molecule comprising:
   (a) at least one open reading frame (ORF);
   (b) at least one 3'-untranslated region element (3'-UTR element), which is heterologous relative to the ORF, comprising a sequence at least 90% identical to the RNA sequence encoded by SEQ ID NO: 164; and,
   (c) optionally, at least one 5'-untranslated region element (5'-UTR element).

2. The purified RNA molecule of claim 1, comprising at least one 3'-UTR element and at least one 5'-UTR element.

3. The purified RNA molecule of claim 2, wherein the open reading frame is derived from a gene, which is distinct from a gene from which the at least one 5'-UTR element is derived.

4. The purified RNA molecule according to claim 2, wherein each of the at least one open reading frame, the at least one 3'-UTR element and the at least one 5'-UTR element are heterologous to each other.

5. The purified RNA molecule of claim 1, wherein the purified RNA molecule does not comprise a 3'-UTR or a 5'-UTR of ribosomal protein S6, of RPL36AL, of rps16, or of ribosomal protein L9; and wherein the open reading frame of the purified RNA molecule does not code for a GFP protein.

6. The purified RNA molecule according to claim 1, wherein the open reading frame of the purified RNA molecule does not code for a reporter protein.

7. The purified RNA molecule of claim 1, wherein the at least one 5'-UTR element is derived from a stable mRNA.

8. The purified RNA molecule of claim 1, wherein the at least one 5'-UTR element comprises a nucleic acid sequence which is derived from the 5'-UTR of a eukaryotic protein coding gene.

9. The purified RNA molecule of claim 1, wherein the at least one 3'-UTR element comprises a nucleic acid sequence at least 95% identical to the RNA sequence encoded by SEQ ID NO: 164.

10. The purified RNA molecule of claim 1, wherein the at least one 5'-UTR element comprises a nucleic acid sequence which has an identity of at least about 90% to a nucleic acid sequence selected from the group consisting of the RNA sequences encoded by SEQ ID NOs: 1 to 151.

11. The purified RNA molecule of claim 1, wherein the at least one 5'-UTR element exhibits a length of between 3 and about 500 nucleotides.

12. The purified RNA molecule of claim 1, further comprising a poly (A) sequence.

13. The purified RNA molecule of claim 12, wherein the poly (A) sequence has a length of about 20 to about 300 adenine nucleotides.

14. The purified RNA molecule of claim 1, further comprising a 5'-cap structure, a poly (C) sequence, a histone stem-loop, or an IRES-motif.

15. The purified RNA molecule of claim 1, wherein the nucleic acid comprises a 5'-TOP UTR.

16. The purified RNA molecule of claim 1, wherein the purified RNA molecule is at least partially G/C modified.

17. The purified RNA molecule of claim 1, wherein the open reading frame comprises a codon-optimized region.

18. The purified RNA molecule of claim 9, wherein the at least one 3'-UTR element comprises a nucleic acid sequence identical to the RNA sequence encoded by SEQ ID NO: 164.

* * * * *

SEQUENCE LISTING

<160> NUMBER OF SEQ ID NOS: 211

<210> SEQ ID NO 1
<211> LENGTH: 322
<212> TYPE: DNA
<213> ORGANISM: Homo sapiens

<400> SEQUENCE: 1

| | | | | | |
|---|---|---|---|---|---|
| gaaacagtgt | ggggcctaga | gcgctgggtg | ggcgcgttct | gcggcctgag | cagggacggg | 60 |
| tagtgaagcg | gttacgcccc | ttcttcgcgt | cttggcggga | gcctgacgcc | ccgcttctcc | 120 |
| cctaacgagg | tgtcccaccg | gcgcccgccg | aggcctaggc | ctccgcagcc | gccctccgtc | 180 |
| tcctcagccc | cgacgctgcg | ccttgggcct | tgtgcgcatt | tttttcgggg | gaaaactgag | 240 |
| gctcggagtg | cgaaagtcag | ccgaggtcgc | cccgcccagg | acagagaagg | gctgtggtcg | 300 |
| gctgatccgc | ggcattcccg | gg | | | | 322 |

<210> SEQ ID NO 2
<211> LENGTH: 100
<212> TYPE: DNA
<213> ORGANISM: Homo sapiens

<400> SEQUENCE: 2

| | | | | | |
|---|---|---|---|---|---|
| ataagttagc | gccgctctcc | gcctcggcag | tgccagccgc | cagtggtcgc | acttggaggg | 60 |
| tctcgccgcc | agtggaagga | gccaccgccc | ccgcccgacc | | | 100 |

<210> SEQ ID NO 3
<211> LENGTH: 103
<212> TYPE: DNA
<213> ORGANISM: Homo sapiens

<400> SEQUENCE: 3

| | | | | | |
|---|---|---|---|---|---|
| atctaagctt | ctctgtcttc | ctccctccct | cccttcctct | tactctcatt | catttcatac | 60 |
| acactggctc | acacatctac | tctctctctc | tatctctctc | aga | | 103 |

<210> SEQ ID NO 4
<211> LENGTH: 236
<212> TYPE: DNA
<213> ORGANISM: Homo sapiens

<400> SEQUENCE: 4

| | | | | | |
|---|---|---|---|---|---|
| cctttcctcc | ctccccgccc | tctccccgct | gtccctccc | cgtcggcccg | cctgcccagc | 60 |
| ctttagcctc | ccgcccgccg | cctctgtctc | cctctctcca | caaactgccc | aggagtgagt | 120 |
| agctgctttc | ggtccgccgg | acacaccgga | cagatagacg | tgcggacggc | ccaccacccc | 180 |
| agcccgccaa | ctagtcagcc | tgcgcctggc | gcctcccctc | tccaggtcca | tccgcc | 236 |

<210> SEQ ID NO 5
<211> LENGTH: 210
<212> TYPE: DNA
<213> ORGANISM: Homo sapiens

<400> SEQUENCE: 5

| | | | | | |
|---|---|---|---|---|---|
| gcgcacgtcc | cggattcctc | ccacgagggg | gcgggctgcg | gccaaatctc | ccgccaggtc | 60 |
| agcggccggg | cgctgattgg | ccccatggcg | gcggggccgg | ctcgtgattg | gccagcacgc | 120 |
| cgtggtttaa | agcggtcggc | gcgggaacca | ggggcttact | gcgggacggc | cttggagagt | 180 |
| actcgggttc | gtgaacttcc | cggaggcgca | | | | 210 |

```
<210> SEQ ID NO 6
<211> LENGTH: 213
<212> TYPE: DNA
<213> ORGANISM: Homo sapiens

<400> SEQUENCE: 6
agactccgcc cttgggcggg gcctggatgc ggccggagcg gagcagtgct ggagcgggag      60
cctcagccct caggcgccac tgtgaggacc tgaccggacc agaccatccc gcagcgcccc    120
gccccggccc cctccgcgcc ctcccgacgc caggtcctgc cgtcccgccg accgtccggg    180
agcgaacccg tcgtcccgca ctcggagtcc gcg                                 213

<210> SEQ ID NO 7
<211> LENGTH: 63
<212> TYPE: DNA
<213> ORGANISM: Homo sapiens

<400> SEQUENCE: 7
gagcggtgcc gcaccggccg cgggcgcagg gagtattatg ggctgtgggt gccgctgagc     60
aag                                                                  63

<210> SEQ ID NO 8
<211> LENGTH: 245
<212> TYPE: DNA
<213> ORGANISM: Homo sapiens

<400> SEQUENCE: 8
gaggagagag ggcagcagcg cgcggtgtct ccggctgctc agtccgaccg cggcaagcaa     60
gcgggcaggc gcaccgcccc ctcccccgcc cggcctcccc aactctgcgg ccgcgagtaa   120
agtttgcaaa gaggcgcggg aggcggcagc cgcagcgagg aggcggcggg gaagaagcgc   180
agtctccggg ttgggggcgg gggcggggggg ggcgccaagg agccgggtgg ggggcggcgg   240
ccagc                                                               245

<210> SEQ ID NO 9
<211> LENGTH: 259
<212> TYPE: DNA
<213> ORGANISM: Homo sapiens

<400> SEQUENCE: 9
atcacagccc ttccccgatc ctctccgtgg gagccagcga gcctctctcc ctgatcttac     60
gtgctcaagg gagctcacac gttcaccaac tcacccttga agtcatctca agaacaaaag   120
acaactgaaa gaagctgttg tgaaggcaga gcagcatctg ctgaagagac agaaaccagc   180
cccagaggtg tcacaggaag gcaccagcaa ggacattggt ctttgatttg attcagcagt   240
cctgtcaagt ataaatgtg                                                259

<210> SEQ ID NO 10
<211> LENGTH: 43
<212> TYPE: DNA
<213> ORGANISM: Homo sapiens

<400> SEQUENCE: 10
aaggagaacg gacctcagag gttgtctgaa ggccgaggcc aag                      43

<210> SEQ ID NO 11
<211> LENGTH: 227
<212> TYPE: DNA
<213> ORGANISM: Homo sapiens
```

```
<400> SEQUENCE: 11 gcagggatttt ggcaacctca gagccgcgag gaggaggcgg agtcgcggag agtttgagta      60
tttccgtcca atcaaaagga gactgtaaga ggaggaggag gaggagatga ctggggagcg     120
ggagctggag aatactgccc agttactcta gcgcgccagg ccgaaccgca gcttcttggc     180
ttaggtactt ctactcacag cggccgattc cgaggccaac tccagca                   227

<210> SEQ ID NO 12
<211> LENGTH: 180
<212> TYPE: DNA
<213> ORGANISM: Homo sapiens

<400> SEQUENCE: 12
tccgccccct tcccgcctcc ccgtatataa gacttcgccg agcgctctca ctcgcacaag      60
tggaccgggg tgttgggtgc tagtcggcac cagaggcaag ggtgcgagga ccacggccgg     120
ctcggacgtg tgaccgcgcc tagggggtgg cagcgggcag tgcggggcgg caaggcgacc     180

<210> SEQ ID NO 13
<211> LENGTH: 120
<212> TYPE: DNA
<213> ORGANISM: Homo sapiens

<400> SEQUENCE: 13
ggcggctggg aggggcgggg cggatgcggg gacagcggcc tggctaactc ctgccaggca      60
gtgcccttcc cggagcgtgc cctcgccgct gagctcccct gaacagcagc tgcagcagcc     120

<210> SEQ ID NO 14
<211> LENGTH: 80
<212> TYPE: DNA
<213> ORGANISM: Homo sapiens

<400> SEQUENCE: 14
atgggctgga gctccgggca gtgtgcgagg cgcacgcaca ggagcctgca ctctgcgtcc      60
cgcaccccag cagccgcgcc                                                  80

<210> SEQ ID NO 15
<211> LENGTH: 239
<212> TYPE: DNA
<213> ORGANISM: Homo sapiens

<400> SEQUENCE: 15
gctgcggccg gctgcgggga taaatactgc ggcagctact gccgcgcagc actcccggag      60
cctgcaacgc ttgagatcct ctccgcgccc gccacccgc agggtgcccc gcgccgttcc     120
cgccgccccg ccgcccccgt cgcggggccc tgcaccccga gcatccgccc cgggtggcac     180
gtccccgagc ccaccaggcc ggccccgtct ccccatccgt ctagtccgct cgcggtgcc     239

<210> SEQ ID NO 16
<211> LENGTH: 234
<212> TYPE: DNA
<213> ORGANISM: Homo sapiens

<400> SEQUENCE: 16
gccttagaaa agttaacgag aaccagatgt ggtggccact gccgaacttt ctcagagccg      60
gtgattggtc cccagccgag ggcctcagcc aattagcttg ctgggtgggc ctggagtccc     120
gccccgccca ggcgcccgcg gagatccagg ttcgaggctg gcgcggcgcg gagagtgggc     180
tggaggccgg ggcgggacgc gttgtgcagc gggtaagcgc acggccgagc gagc           234
```

<210> SEQ ID NO 17
<211> LENGTH: 101
<212> TYPE: DNA
<213> ORGANISM: Homo sapiens

<400> SEQUENCE: 17
cagacgtccc tgcgcgtcgt cctcctcgcc ctccaggccg cccgcgccgc gccggagtcc      60
gctgtccgcc agctacccgc ttcctgccgc ccgccgctgc c                        101

<210> SEQ ID NO 18
<211> LENGTH: 110
<212> TYPE: DNA
<213> ORGANISM: Homo sapiens

<400> SEQUENCE: 18
atggcggacc tccggaaacc gtagattccg ggcggtcgga gccgccggga gctgtagttc      60
tcccgcggct cagagaagta ggcagagagc ggacctggcg gccgggcagc                110

<210> SEQ ID NO 19
<211> LENGTH: 96
<212> TYPE: DNA
<213> ORGANISM: Homo sapiens

<400> SEQUENCE: 19
ggctcggagg ccoctctttt cggcagctgg gagggcagcg gggcggaccg acgggatctc      60
gcgagattct cgcgcggtag gccctgagga cccagc                               96

<210> SEQ ID NO 20
<211> LENGTH: 102
<212> TYPE: DNA
<213> ORGANISM: Homo sapiens

<400> SEQUENCE: 20
atataagcgt tggcggagcg tcggttgtag cactctgcgc gcccgctctt ctgctgctgt      60
ttgtctactt cctcctgctt ccccgccgcc gccgccgcca tc                       102

<210> SEQ ID NO 21
<211> LENGTH: 339
<212> TYPE: DNA
<213> ORGANISM: Homo sapiens

<400> SEQUENCE: 21
gcccgcgtca cggggggcggg agtcagctga gctgccgggg cgaggttggg atcacctggc      60
accggctgaa gggagcctgt gatttttttg tagcgggggc ggggagtaag gtgcaagact     120
gcgccagatt caaggacgag ggctgcccga ttatctcgct gcataaggca agagcaagag     180
gatcctcagg attttaaaga ggaggcgacg gctgcaggtt cccaggatct gtcagaggct     240
ggggagttac agcttccatt ctggggcgac ggggaccccg gggggggtagc ccttttgtaa     300 tccccaggcc ccggacaaag agcccagagg ccgggcacc                           339

<210> SEQ ID NO 22
<211> LENGTH: 92
<212> TYPE: DNA
<213> ORGANISM: Homo sapiens

<400> SEQUENCE: 22
aaggggcaga aggagaggcg ttacttcctg gagacttcag gtgtggtagc cggcgccgcg      60

```
cccatagccg acgggatc tgagctggca gg                                    92
```

<210> SEQ ID NO 23
<211> LENGTH: 132
<212> TYPE: DNA
<213> ORGANISM: Homo sapiens

<400> SEQUENCE: 23

```
agctgggctt tgtggagcgc tgcggagggt gcgtgcgggc cgcggcagcc gaacaaagga    60
gcagggcgc cgccgcaggg acccgccacc cacctcccgg ggccgcgcag cggcctctcg   120
tctactgcca cc                                                      132
```

<210> SEQ ID NO 24
<211> LENGTH: 365
<212> TYPE: DNA
<213> ORGANISM: Homo sapiens

<400> SEQUENCE: 24

```
acggaaatga aaggagcact tccgggttcg gcaataacct ggagccggcg gcgtaggttg    60
gctctttagg gcttcacccc gaagctccac cttcgctccc gtctttctgg aaacaccgct   120
ttgatctcgg cggtgcggga caggtacctc ccggctgctg cgggtgccct ggatccagtc   180
ggctgcacca gcgagcgag acccttccct ggtggaggct cagagttccg gcagggtgca   240
tccggcctgt gtgtggcgcg aggcaggaa gccggtaccc gggtcctggc ccagcgctg    300
acgttttctc tccccttct tctctcttcg cggttgcggc gtcgcagacg ctagtgtgag   360
ccccc                                                              365
```

<210> SEQ ID NO 25
<211> LENGTH: 88
<212> TYPE: DNA
<213> ORGANISM: Homo sapiens

<400> SEQUENCE: 25

```
ataagggcgg tgcggcactg cagctagcgc agttctcact gagacctgtc accccgactc    60
aacgtgagac gcaccgcccg gactcacc                                      88
```

<210> SEQ ID NO 26
<211> LENGTH: 254
<212> TYPE: DNA
<213> ORGANISM: Homo sapiens

<400> SEQUENCE: 26

```
cgggagcaag agagaaggag gcccagacag tgagggcagg agggagagaa gagacgcaga    60
aggagagcga gcgagagaga aagggttctg gattggaggg gagagcaagg gagggaggaa   120
ggcggtgaga gaggcggggg cctcgggagg gtgaaaggag ggaggagaag ggcggggcac   180
ggaggcccga gcgagggaca agactccgac tccagctctg acttttttcg cggctctcgg   240
cttccactgc agcc                                                    254
```

<210> SEQ ID NO 27
<211> LENGTH: 57
<212> TYPE: DNA
<213> ORGANISM: Homo sapiens

<400> SEQUENCE: 27

```
ctacccgcct acccgcctac ccccctgccg gcctgccgtc cttccacgcg gagagcc       57
```

-continued

```
<210> SEQ ID NO 28
<211> LENGTH: 88
<212> TYPE: DNA
<213> ORGANISM: Homo sapiens

<400> SEQUENCE: 28
ggacagccgg gcaggcgggg ctgggcgcgg gcggcggcgg cccggaggag aacgggcgga    60
gggcgcgggc cgaccgggcg caccgacc                                      88

<210> SEQ ID NO 29
<211> LENGTH: 288
<212> TYPE: DNA
<213> ORGANISM: Homo sapiens

<400> SEQUENCE: 29
accggatgct cggcatgaac cactaggcgc ctggcggggg tgatctgtcg gagcgaccgg    60
cttggcgcct gcctgtcccc agcccctctc agcttgaact ccttccttca gtctgggcc   120 ctcgaggctt ccagagcggc ctccaggggt gcagtctcag ttccccacgc cagccgtctc   180
cgtcctccgc ctcctccggg cctggcaggt ggcactgtcc ggaggcggag ccttgggcga   240
ggggtggttg cggcggagga cgcaaccgag cgggcctgcg gcctcacc                288

<210> SEQ ID NO 30
<211> LENGTH: 298
<212> TYPE: DNA
<213> ORGANISM: Homo sapiens

<400> SEQUENCE: 30
agtaggaccc aggggccggg aggcgccggc agagggaggg gccgggggcc gggaggttt     60 tgagggaggt cttgggcttt ttttggcgga gctgggcgc cctccggaag cgtttccaac   120
tttccagaag tttctcggga cgggcaggag ggggtgggga ctgccatata tagatcccgg   180
gagcagggga gcgggctaag agtagaatcg tgtcgcggct cgagagcgag agtcacgtcc   240
cggcgctagc ccagcccgac ccaggcccac cgtggtgcac gcaaaccact tcctggcc    298

<210> SEQ ID NO 31
<211> LENGTH: 184
<212> TYPE: DNA
<213> ORGANISM: Homo sapiens

<400> SEQUENCE: 31
cttttcccgg cacatgcgca ccgcagcggg tcgcgcgccc taaggagtgg cactttttaa    60
aagtgcagcc ggagaccagc ctacagccgc ctgcatctgt atccagcgcc aggtcccgcc   120
agtcccagct gcgcgcgccc cccagtcccg cacccgttcg gcccaggcta agttagccct   180
cacc                                                                184

<210> SEQ ID NO 32
<211> LENGTH: 431
<212> TYPE: DNA
<213> ORGANISM: Homo sapiens

<400> SEQUENCE: 32
atatcccagg atcgcggcca atcgctgctc gtctctctcg aagcggatgg cttttgcctg    60
agaggaaagg gagtggctgg cggcgcatgc gccacggtgg ccgacttgaa ccgaggcttt   120
tattgctgta gtttatttcc accccttcc ctctgtttc tctctctcct tctctctctc   180
tctctctctc tctcttttttt ttccgcccta gctggggctg tgttggagga gaggaagaaa   240
```

```
gagagacaga ggattgcatt catccgttac gttcttgaaa tttcctaata gcaagaccag    300
cgaagcggtt gcacccttttt caatcttgca aaggaaaaaa acaaaacaaa acaaaaaaaa    360
cccaagtccc cttcccggca gttttttgcct taaagctgcc ctcttgaaat taatttttttc   420 ccaggagaga g                                                          431
```

```
<210> SEQ ID NO 33
<211> LENGTH: 123
<212> TYPE: DNA
<213> ORGANISM: Homo sapiens

<400> SEQUENCE: 33
aagtggccgt ggaggcggaa gtggcgcggc cgcggagggg cctggagtgc ggcggcggcg    60
ggacccggag caggagcggc ggcagcagcg actgggggcg gcggcggcgc gttggaggcg    120
gcc                                                                   123
```

```
<210> SEQ ID NO 34
<211> LENGTH: 20
<212> TYPE: DNA
<213> ORGANISM: Homo sapiens

<400> SEQUENCE: 34
ccggcggtga caacggcaac                                                 20
```

```
<210> SEQ ID NO 35
<211> LENGTH: 21
<212> TYPE: DNA
<213> ORGANISM: Homo sapiens

<400> SEQUENCE: 35
agtctgggac gcgccgccgc c                                               21
```

```
<210> SEQ ID NO 36
<211> LENGTH: 27
<212> TYPE: DNA
<213> ORGANISM: Homo sapiens

<400> SEQUENCE: 36
ctgtgggtct gtaggttaag ggagaag                                         27
```

```
<210> SEQ ID NO 37
<211> LENGTH: 30
<212> TYPE: DNA
<213> ORGANISM: Homo sapiens

<400> SEQUENCE: 37
gcggtggcgc gagttggact gtgaagaaac                                      30
```

```
<210> SEQ ID NO 38
<211> LENGTH: 142
<212> TYPE: DNA
<213> ORGANISM: Homo sapiens

<400> SEQUENCE: 38
acgcacagcc cccctggggg ccggggggcgg ggccaggcta taaaccgccg gttaggggcc    60
gccatcccct cagagcgtcg ggatatcggg tggcggctcg ggacggagga cgcgctagtg    120
ttcttctgtg tggcagttca ga                                              142
```

```
<210> SEQ ID NO 39
<211> LENGTH: 78
```

```
<212> TYPE: DNA
<213> ORGANISM: Homo sapiens

<400> SEQUENCE: 39
gagcggttgc gcagtgaagg ctagacccgg tttactggaa ttgctctggc gatcgagggg    60
tcctagtaca ccgcaatc                                                  78

<210> SEQ ID NO 40
<211> LENGTH: 117
<212> TYPE: DNA
<213> ORGANISM: Homo sapiens

<400> SEQUENCE: 40
gagagacggc agcggccccg gcctccctct ccgccgcgct tcagcctccc gctccgccgc    60
gctccagcct cgctctccgc cgcccgcacc gccgcccgcg ccctcaccag agcagcc      117

<210> SEQ ID NO 41
<211> LENGTH: 51
<212> TYPE: DNA
<213> ORGANISM: Homo sapiens

<400> SEQUENCE: 41
gtgacagagc gctttacgac agttgctttg aggcagtacc ggaggagaaa g             51

<210> SEQ ID NO 42
<211> LENGTH: 30
<212> TYPE: DNA
<213> ORGANISM: Homo sapiens

<400> SEQUENCE: 42
ctagatctgt gggcggggcg cggcctgtgg                                     30

<210> SEQ ID NO 43
<211> LENGTH: 136
<212> TYPE: DNA
<213> ORGANISM: Homo sapiens

<400> SEQUENCE: 43
gatgatttga gggacaagaa ttcagtgccc gggggccgaa aggcagcaga aggcgggcac    60
caaaggatag gcacccggaa ggtggactcc gaggaggaga gaggacaggg gtctctcacc   120
ccagctcctg gtcacc                                                   136

<210> SEQ ID NO 44
<211> LENGTH: 88
<212> TYPE: DNA
<213> ORGANISM: Homo sapiens

<400> SEQUENCE: 44
ctacagatcc gccatattgt ctactgaaag ctgccgctga agctgccgcc gttgcctccg    60
ccgccaagag tgagcgagcg gacccgcg                                       88

<210> SEQ ID NO 45
<211> LENGTH: 65
<212> TYPE: DNA
<213> ORGANISM: Homo sapiens

<400> SEQUENCE: 45
ccgtcaactt agcgagcgca acaggctgcc gctgaggagc tggagctggt ggggactggg    60
ccgca                                                                65
```

<210> SEQ ID NO 46
<211> LENGTH: 243
<212> TYPE: DNA
<213> ORGANISM: Homo sapiens

<400> SEQUENCE: 46

```
gagggaggga gctgcttccc cgcctgccgc gccaccagtc cgaccctcgg tcccgccgtg      60
tgagcagctg gtggagtgga gctcagcgcg gacgccggag ctgcggccgc cccctctgca     120
ggtgcctgtg aggaggcgcc cgggccgcaa ccgctttccg agatcccag tcgcgcactc      180 gctcccgcg ctcctgaggg gccgcccggc cggaggaggc cgtcgcgggg ctcggcgttc      240
agc                                                                   243
```

<210> SEQ ID NO 47
<211> LENGTH: 335
<212> TYPE: DNA
<213> ORGANISM: Homo sapiens

<400> SEQUENCE: 47

```
gaggaaggag ggggaaaggc accaaccagc agccgctcca gccctgccga agtttcactt      60
tttgtctgtg ggttcgttcc cgggtcccgc gcgagctttc ccgggataag tagctttagc     120
gatcgggaga cagccgggcg ctgcaagtgg aactttgag gctcagagac agagcagaag     180
acagaacctg gtcttctgat tccctgtgtt ctgcttttt cattgttcca ctggacgctc      240
atcagaggga agatcttttt cctcaattgc attgcagttg ctgaacctt gtgtcaacca      300 tccattccag gagccagcta tctgagattc caaca                                335
```

<210> SEQ ID NO 48
<211> LENGTH: 203
<212> TYPE: DNA
<213> ORGANISM: Homo sapiens

<400> SEQUENCE: 48

```
gggagaagga ggaggccggg ggaaggagga gacaggagga ggagggacca cggggtggag      60
gggagataga cccagcccag agctctgagt ggtttcctgt tgcctgtctc taaacccctc     120
cacattcccg cggtccttca gactgcccgg agagcgcgct ctgcctgccg cctgcctgcc     180
tgccactgag ggttcccagc acc                                             203
```

<210> SEQ ID NO 49
<211> LENGTH: 268
<212> TYPE: DNA
<213> ORGANISM: Homo sapiens

<400> SEQUENCE: 49

```
cttccgggag cccgcaagcg gcttccgggt gctcgcgcgc cgacctggac gcagagaagc      60
cagagacttt cgcttccggc tgccgcaggc gcttcgctgg tgcaggtaag ctccgcacac     120
tctcggccgg tcccgagtcc gactccctca agggtgacgc gagctctgcc ctttaaccgg     180
aaacgtctcc ctgctcaccc caccccgcg cagacgcagt gctgagcaca cagctaccgg      240
acaaagagtg acgcccggag ctggagtt                                        268
```

<210> SEQ ID NO 50
<211> LENGTH: 155
<212> TYPE: DNA
<213> ORGANISM: Homo sapiens

<400> SEQUENCE: 50

<210> SEQ ID NO 51
<211> LENGTH: 167
<212> TYPE: DNA
<213> ORGANISM: Homo sapiens

<400> SEQUENCE: 51

```
gactccggag cccgagcccg gggcgggtgg acgcggactc gaacgcagtt gcttcgggac    60
ccaggacccc ctcgggcccg acccgccagg aaagactgag gccgcggcct gccccgcccg   120
gctccctgcg ccgccgccgc ctcccgggac agaag                              155
```

<210> SEQ ID NO 51
<211> LENGTH: 167
<212> TYPE: DNA
<213> ORGANISM: Homo sapiens

<400> SEQUENCE: 51

```
acagaccact gcctgcaggt tggcgccacc accccactc tccccgctgc tcgcgggagc    60
cagagggccc tgcggtcctc ggtggtcttg ccagcccctc gtcatcccag ggccctccgc   120
gcctgtgagg actccctcag gtcggccacg ggacctgacg caacagg                 167
```

<210> SEQ ID NO 52
<211> LENGTH: 209
<212> TYPE: DNA
<213> ORGANISM: Homo sapiens

<400> SEQUENCE: 52

```
ggccggacgc ctccgcgtta cgggatgaat taacggcggg ttccgcacgg aggttgtgac    60
ccctacggag cccagcttg cccacgcacc ccactcggcg tcgcgcggcg tgccctgctt    120
gtcacaggtg ggaggctgga actatcaggc tgaaaaacag agtgggtact ctcttctggg   180
aagctggcaa caaatggatg atgtgatat                                     209
```

<210> SEQ ID NO 53
<211> LENGTH: 94
<212> TYPE: DNA
<213> ORGANISM: Homo sapiens

<400> SEQUENCE: 53

```
gcggtggacg cgccggcttc gagcatccct agccgggcag gtgggaggca cggggttgcg    60
gatcccgcgg ccgcggttcg acccgccgg cgac                                 94
```

<210> SEQ ID NO 54
<211> LENGTH: 76
<212> TYPE: DNA
<213> ORGANISM: Homo sapiens

<400> SEQUENCE: 54

```
ggaagcgctc gcgcaggaga ccccgggtga cggggcccgg cgccgctaac tggagcgaac    60
cccagcgtcc gccgac                                                    76
```

<210> SEQ ID NO 55
<211> LENGTH: 261
<212> TYPE: DNA
<213> ORGANISM: Homo sapiens

<400> SEQUENCE: 55

```
ccttcctccg ccttctgggc ggagcccgcg cgggatccgg gtggctgcag gctgctggct    60
tctgcggctg cggggtcggg gtcgcggcca gggccaagcc gcagcgagtt cacaggcgga   120
accctgcag gcggcgcccc ctacgcgagg tcaccctgg aaggagcgc agcccacccg      180
gcccctccgc atccgagcag gacgcccgtc tcctctccct gaggatttca ggtctccctg   240
tcccaggagg cttgtgccaa g                                             261
```

<210> SEQ ID NO 56
<211> LENGTH: 241
<212> TYPE: DNA
<213> ORGANISM: Homo sapiens

<400> SEQUENCE: 56
gcctagtctc catataaaag cggcgccgcc tccccgccct ctctcactcc ccgctcctct    60
ccgccgcgca ctctccgcgg cgctgggaga gggcggaggg ggaggcggcg cgcggcgcca   120
gaggaggggg gacgcagggg gcggagcgga gacagtacct tcggagataa tcctttctcc   180
tgccgcagtg gagaggagcg gccggagcga gacacttcgc cgaggcacag cagccggcag   240
g                                                                  241

<210> SEQ ID NO 57
<211> LENGTH: 124
<212> TYPE: DNA
<213> ORGANISM: Homo sapiens

<400> SEQUENCE: 57
gcacttccgg cgcgaaccgc tacttccggt gcgaaccgcc tcggccgttc cctcgcggag    60
cttactgagc gcggccgccg agcccagctc cgccgccgag cgcctgtgcc ggcacggcta   120
cacc                                                               124

<210> SEQ ID NO 58
<211> LENGTH: 33
<212> TYPE: DNA
<213> ORGANISM: Homo sapiens

<400> SEQUENCE: 58
gtctcctggt ggggtgcaag gagccgaggc gag                                33

<210> SEQ ID NO 59
<211> LENGTH: 71
<212> TYPE: DNA
<213> ORGANISM: Homo sapiens

<400> SEQUENCE: 59
ggcggggttc ggccgggagc gcaggggcgg cagtgcgcgc ctagcagtgt cccagccggg    60
ttcgtgtcgc c                                                        71

<210> SEQ ID NO 60
<211> LENGTH: 245
<212> TYPE: DNA
<213> ORGANISM: Homo sapiens

<400> SEQUENCE: 60
accacagagc cgcgagaaga ggacagagga gactgagcaa agggggtgg gctccaggcg     60 accctagcc caattctgcc cctccatccc aaggggcaga gaaattgtct ttctttgctg    120
actcctacga ggaaaaaaaa aaaaaaaaa aaaacaatta aagggaaaga taaacgagca    180
cggaggaaag gtggcagcca gattacttag agaggcacag aggagagaga tcggggtgag   240
tcgcc                                                              245

<210> SEQ ID NO 61
<211> LENGTH: 198
<212> TYPE: DNA
<213> ORGANISM: Homo sapiens

<400> SEQUENCE: 61

```
gacctagaga ggtcccagga cacgccactg tcccgccttc ccattgcccg gccccactgg      60
ccagtcccca cgcccacaca cccaaggctg ccccatctgg cgctgattat cctgctgctg     120
ccgccaccgc tgctgctgct ctgcaaaatt cagctgctgc ctctgtcttg aggaccccag     180
cgcctttccc ccggggcc                                                   198

<210> SEQ ID NO 62
<211> LENGTH: 9
<212> TYPE: DNA
<213> ORGANISM: Homo sapiens

<400> SEQUENCE: 62 ggcccgaag                                                               9

<210> SEQ ID NO 63
<211> LENGTH: 149
<212> TYPE: DNA
<213> ORGANISM: Homo sapiens

<400> SEQUENCE: 63
gagcaaacag agcagcagaa aaggcagttc ctcttctcca gtgccctcct tccctgtctc      60
tgcctctccc tcccttcctc aggcatcaga gcggagactt cagggagacc agagcccagc    120
ttgccaggca ctgagctaga agccctgcc                                      149

<210> SEQ ID NO 64
<211> LENGTH: 116
<212> TYPE: DNA
<213> ORGANISM: Homo sapiens

<400> SEQUENCE: 64
attcccatta gccccgcccc tttgggctgg aaccggaggt gtcgctcttc ggacctcaag      60
gttcccctta acacagagcg ccccgcagtc ttcgcggaaa gcgttcgggg taggcg        116

<210> SEQ ID NO 65
<211> LENGTH: 80
<212> TYPE: DNA
<213> ORGANISM: Homo sapiens

<400> SEQUENCE: 65
ttagccaacg gggcaagggg ggcgggaagg aggtggggtt tctcccagcc aatcgacggg      60
cgcgccctcg ttgccgctct                                                 80

<210> SEQ ID NO 66
<211> LENGTH: 88
<212> TYPE: DNA
<213> ORGANISM: Homo sapiens

<400> SEQUENCE: 66
ctacagatcc gccatattgt ctactgaaag ctgccgctga agctgccgcc gttgcctccg      60
ccgccaagag tgagcgagcg gacccgcg                                        88

<210> SEQ ID NO 67
<211> LENGTH: 157
<212> TYPE: DNA
<213> ORGANISM: Homo sapiens

<400> SEQUENCE: 67 gttttttaccc aggcctcggc gcctaggcgc ttcgccgagg ctgatcttcg ttcaagtgtg     60
```

```
agctgcggct gagcccagcg ctcgaggcgc gaggcagcca ggagggcccg tgcggcgcgg    120
ggagccagcg agcgcgcctt cggcattggc cgccgcg                            157

<210> SEQ ID NO 68
<211> LENGTH: 133
<212> TYPE: DNA
<213> ORGANISM: Homo sapiens

<400> SEQUENCE: 68
tgagttgctg ccttggccag agtccggagc agccgccgcc cgaccacgcc gagctcagtt    60
cgctgtccgc gccggctccc accccggccc gaccccgacc cggcccggtc aggccccata   120
ctcagtagcc acg                                                      133

<210> SEQ ID NO 69
<211> LENGTH: 90
<212> TYPE: DNA
<213> ORGANISM: Homo sapiens

<400> SEQUENCE: 69
ggattgagct gaccacaggc cacaccagac tcctctctgc tcctgaggaa gacagggcag    60
cccggcgcca cccgctcggc cctcacgaag                                    90

<210> SEQ ID NO 70
<211> LENGTH: 88
<212> TYPE: DNA
<213> ORGANISM: Homo sapiens

<400> SEQUENCE: 70
ggacagccgg gcaggcgggg ctgggcgcgg gcggcggcgg cccggaggag aacgggcgga    60
gggcgcgggc cgaccgggcg caccgacc                                      88

<210> SEQ ID NO 71
<211> LENGTH: 147
<212> TYPE: DNA
<213> ORGANISM: Homo sapiens

<400> SEQUENCE: 71
acgcgtgcgc ggtgggcgga gcgcggctct cctaccttct cgggcagccc agtctttgcc    60
atccttgccc agccggtgtg gtgcttgtgt gtcacagcct tgtagccggg agtcgctgcc   120
gagtgggcgc tcagttttcg ggtcgtc                                       147

<210> SEQ ID NO 72
<211> LENGTH: 153
<212> TYPE: DNA
<213> ORGANISM: Homo sapiens

<400> SEQUENCE: 72
cattggctcc gaggacttag gacctgttag cttggttggg cgactggcaa atccttcctt    60
ccccggggta gaagtccagg gtgagaaatt ggttccgaac tcaaaggaac ccagtgccgg   120
gccacagccg ggtcacgtgg ccggcggccc ccc                                153

<210> SEQ ID NO 73
<211> LENGTH: 232
<212> TYPE: DNA
<213> ORGANISM: Mus musculus

<400> SEQUENCE: 73
ctctctccct ctttcttttt tccgccctag ctggatctgt gttggaggag aggaaaagag    60
```

```
acagaggatt gcatctgttt tgaaatctcc taatagcaag accagttaag ggattgtacc    120 ttttcctac aaatataaat atatatatat tttaaaccaa gtcttttttt ttccggctat    180
ctttgcttta aagctgtcct cttgagatta cttcctcccg ccccccggag ag           232
```

<210> SEQ ID NO 74
<211> LENGTH: 232
<212> TYPE: DNA
<213> ORGANISM: Mus musculus

<400> SEQUENCE: 74

```
ttttctctgc ccggctttga tctctgctta acaacagtaa cgtcacacgg actacagggg    60
agttttgttg aagttgcaaa gtcctgcagc ctccagaggg ctgtcggcgc agtagcagag   120
agctacagac tccgcgcgct ccggagaccg gcagtacagc gcgaggcagc gcgcgtcagc   180
agccgccacc ggagcccaac cgagaccaca gccctcccca gacggccgcg cc           232
```

<210> SEQ ID NO 75
<211> LENGTH: 147
<212> TYPE: DNA
<213> ORGANISM: Mus musculus

<400> SEQUENCE: 75

```
cgctgtccca ggacagaggt gagtcaagag tttagtccca ggccagccag agaactgaca    60
gaacatacca aaggttcttg gtacctcccg gtgctcagag cagaccctaa aggaagccaa   120
gtccttcctg agacaggcag atccagg                                        147
```

<210> SEQ ID NO 76
<211> LENGTH: 122
<212> TYPE: DNA
<213> ORGANISM: Mus musculus

<400> SEQUENCE: 76

```
gagcgcgcgc cccgccgagc gcccgcccgc cgggggcctg agcgctgggg cgcgtgcgcg    60
agcggtgcag caccggccgc gggagcaggg agtattatgg gctgtgggtg ccgctgagca   120
ag                                                                   122
```

<210> SEQ ID NO 77
<211> LENGTH: 61
<212> TYPE: DNA
<213> ORGANISM: Mus musculus

<400> SEQUENCE: 77

```
agttccgtgg agactgcgag ttccgtctgc tgtgtgagga ctgccgccac caccgctgac    60
g                                                                    61
```

<210> SEQ ID NO 78
<211> LENGTH: 202
<212> TYPE: DNA
<213> ORGANISM: Mus musculus

<400> SEQUENCE: 78

```
gcagactcct cccccgcctg gaaacctcgc ccctagtact gggaatgact ctgggcgtgc    60
ggcgtagttt gcagccggga caccgtgagg cttgcgagcc cagattcgca gccgagacac   120
cgtggggccc gcgatccagt gttttgcagcg ggaacatttc ggggtctgtg atccgagtga   180
ggacgcaacg cagaagctaa gg                                             202
```

<210> SEQ ID NO 79
<211> LENGTH: 91
<212> TYPE: DNA
<213> ORGANISM: Mus musculus

<400> SEQUENCE: 79
ggccgggcca gccgctaaat tccgagatca agcttccaga tcctgggagt agatcaagcg     60
tgtccaggtt ggagagctgc cctgtcagac t                                   91

<210> SEQ ID NO 80
<211> LENGTH: 54
<212> TYPE: DNA
<213> ORGANISM: Mus musculus

<400> SEQUENCE: 80
gagcgccaac cgctagaggc cgatccggag cgtgctgccc ggtcaccacc cgcc           54

<210> SEQ ID NO 81
<211> LENGTH: 63
<212> TYPE: DNA
<213> ORGANISM: Mus musculus

<400> SEQUENCE: 81
ccacagggcc agttccaggg gttcatccac aagagagaaa acatagact cacggctgcc     60 aac                                                                  63

<210> SEQ ID NO 82
<211> LENGTH: 48
<212> TYPE: DNA
<213> ORGANISM: Mus musculus

<400> SEQUENCE: 82
gagtgcgaca gctaggccag gcgacagcgc tgcctaccag agcgcagc                 48

<210> SEQ ID NO 83
<211> LENGTH: 93
<212> TYPE: DNA
<213> ORGANISM: Mus musculus

<400> SEQUENCE: 83
agaaggaaaa ggggtggagc taagcactca ctgcggtttt gcgctgcgtc tgcagaggac     60
aaggaaagct ctgcagggct gtcagctgcc aaa                                 93

<210> SEQ ID NO 84
<211> LENGTH: 159
<212> TYPE: DNA
<213> ORGANISM: Mus musculus

<400> SEQUENCE: 84
gggcgcttgg cttgcaagga ccctgagctg cggcattgaa gcacacccaa cccaactcga     60
ctgaagtcag cctcactgaa ccggatctga gaatcttctc tctctgggct tgccagggct    120
ctccgaacct agctagcatc ctcttcaatt ccaactaga                           159

<210> SEQ ID NO 85
<211> LENGTH: 55
<212> TYPE: DNA
<213> ORGANISM: Mus musculus

<400> SEQUENCE: 85
cgcgaaggct gtaaaagccg cgcaggatgg aagtccagac actgaatccg cggct          55

<210> SEQ ID NO 86
<211> LENGTH: 105
<212> TYPE: DNA
<213> ORGANISM: Mus musculus

<400> SEQUENCE: 86
gagtctcgcg ctgtggttcg tcggcgcacc gctgatccgc tccacgcctt gcgctctccg    60
ctctcagcca aagcccggca gccccggcca cgcagctccg caacc                   105

<210> SEQ ID NO 87
<211> LENGTH: 108
<212> TYPE: DNA
<213> ORGANISM: Mus musculus

<400> SEQUENCE: 87
ctcctgtcgg gcggaagtag gaggagtaga gtttaaaaac agtactcttt ttccggttcg    60
ggacgtagtt gaagcaacga caagccggat aaccgctctt gagacagg               108

<210> SEQ ID NO 88
<211> LENGTH: 176
<212> TYPE: DNA
<213> ORGANISM: Mus musculus

<400> SEQUENCE: 88
gtacttagct ggtcctgggg cagcagcggg aagggactga agaggggtgc tgaggtgaaa    60
gattggaaga cccggaaaga tcagctagat ttcggaaacc agaaacaccc tcggggagac   120
ctggggctcc cggcgcgcga cgatttcctc gcactagctg ggagagcgtt gatccc       176

<210> SEQ ID NO 89
<211> LENGTH: 275
<212> TYPE: DNA
<213> ORGANISM: Mus musculus

<400> SEQUENCE: 89
tgcctgagcg agagaggaga gcgagctgag gagagccggg cagttcggag ggaaggaccg    60
gtgcgagtca ggcggcccct tgaggctccgc tcgcccacct tccactcttc tctctctctc   120
tccctctctc tctttgccat ttctttcctc tcccaaatct cccattcagc caaaggaagg   180
aggtaaggga agcactcccc gaccccccg cacctccaaa aataataat aataaaaaaa     240 atttacagtc gggaccgagt ggtggccggc tggct                             275

<210> SEQ ID NO 90
<211> LENGTH: 146
<212> TYPE: DNA
<213> ORGANISM: Mus musculus

<400> SEQUENCE: 90
cggaactggg gctattaggg agcctgcagg tcttcctgga aagtcgcaag cctgtgttag    60
gaagtcgccc tgcgatcgcg ccgcctgggg tttttctgtc cctttgtcct cgtttatgta   120
cgaagctgcc agcgggccat agaaac                                       146

<210> SEQ ID NO 91
<211> LENGTH: 173
<212> TYPE: DNA
<213> ORGANISM: Mus musculus

<400> SEQUENCE: 91
gaaaagactg tctactcctg cgtctcggtg gcgtctttct cccgcgcctg cacgaactga    60
ggttttgcgt ggcggcggcg gcaccggcag cggcagcgtc tctcacttga acgccgcgag   120
cggcagcttc tcgtctgtgt cctgacctcg gagcctacga gcagagcggc gcg          173

<210> SEQ ID NO 92
<211> LENGTH: 77
<212> TYPE: DNA
<213> ORGANISM: Mus musculus

<400> SEQUENCE: 92
gcagcggcgt cccgtccagt tcgcctgccg cgctcctcgc ttgtcgtctg cctccagagc    60
ccagacagag aagagcc                                                   77

<210> SEQ ID NO 93
<211> LENGTH: 184
<212> TYPE: DNA
<213> ORGANISM: Mus musculus

<400> SEQUENCE: 93
cccggcgctg cccgagtcgg gtgggtcggt ggctataaag ctgcggaggg cgggaggcac    60
agtctgcggt ctccttgctt tgctcgttct tcttccaggg tctgatcccc tttggtggct   120
gaaggaggaa ccggtgaccg acctggagac cacagttctc tgtccttcac acagctcttt   180
cacc                                                                184

<210> SEQ ID NO 94
<211> LENGTH: 335
<212> TYPE: DNA
<213> ORGANISM: Mus musculus

<400> SEQUENCE: 94
taggcggctc ggtgctaagg gatgagtgag acgtagctcg gcctctcccc agcaagttct    60
cgccggcact ggttcagatt cagaaaggga gccaggagcg aggctcagca gaccccggcg   120
ggtagaactc cggggctgtg aagcgctccc gcgtgtccga ctcttggagt caccgcagct   180
acagaagcgt cagaagtcta gttcgccagg ggtgccagtc ggctcagag tctctggtca    240 ctcaagtcca gcgcagcgac cctcacagac gcgctctgcc ctgggaccgc ggcggaacaa   300
gatatttgaa atcattgcgg ttcccagcga cagaa                              335

<210> SEQ ID NO 95
<211> LENGTH: 300
<212> TYPE: DNA
<213> ORGANISM: Mus musculus

<400> SEQUENCE: 95
gcccgcctct cgccgccctc ctcctcggcc cgcccgccgc tctgagcagc ccgagaggaa    60
acaaagtgct gcgggcggga gactcgcgtc cgccgcgcac agccgtctgc gtctcccggc   120
tgccctggcc tcttcccgcg cgcgtctgcg agtgtgcgtg tacactcaca aagggcgtct   180
ggcgggcgat cgcggccctc ccgcttcgct ctttgtgcgg tagccccgcc gccaccgcca   240
gcccaggtcc gctcgatcct caccggcctg tggtttgtac cttcggtccc gccgcccgcc   300

<210> SEQ ID NO 96
<211> LENGTH: 45
<212> TYPE: DNA
<213> ORGANISM: Mus musculus

<400> SEQUENCE: 96

```
ccggcttttc tgcgcgcgcg ggtctctccg gcctaggaga ccgcg                45
```

<210> SEQ ID NO 97
<211> LENGTH: 109
<212> TYPE: DNA
<213> ORGANISM: Mus musculus

<400> SEQUENCE: 97

```
gcttcggcag gggcacttcc ggcgcgaccg gcctagactg tcaccctgtt agccgccgct   60
gagcctccgc taactacccg gcgcctgctg ctgccctccc ggccacgcc              109
```

<210> SEQ ID NO 98
<211> LENGTH: 131
<212> TYPE: DNA
<213> ORGANISM: Mus musculus

<400> SEQUENCE: 98

```
aacaaagctg ttcctcgtgg gcggagttgt gctctccagc cgcaggagtc ttgctgcgcg   60
ggtgggtaga agctgggatc agagaagcgg cgaggcagac agtcttcgga catagactga  120
ctctgcttgt c                                                       131
```

<210> SEQ ID NO 99
<211> LENGTH: 235
<212> TYPE: DNA
<213> ORGANISM: Mus musculus

<400> SEQUENCE: 99

```
tgtgcccgtt gagtttgaat tgggtggcgg ttaaccgagg agccgcccgt cccttagttg   60
gagctgtgag ggttcctcag actgtgtttt gggacctgca ggtaggtttc ggcagagttc  120
tggaaaccta gactccaacg actgaacttt ctcagctctc cgaccgctca caccctctcc  180
ccgtctcagt cgcggagccg gctgcttggc ccctcgctcg acgcagccag gcgcc       235
```

<210> SEQ ID NO 100
<211> LENGTH: 280
<212> TYPE: DNA
<213> ORGANISM: Mus musculus

<400> SEQUENCE: 100

```
ggtgccctgg aagctgacgc gcagcactgg ccgtggccgt ggggcccgcg gagggcggcg   60
cgcggctgat gaaaccggct cggattccgc ccgcgtgcgc catcccctca gctagcaggt  120
gtgagaggct ttctacccgc ggtctccaca cagctcaaca tcttgccgcc tcctccgagc  180
ctgaagctac cgtggactct gctgtggcgt cttggccccc aggtgcggat cctccccagt  240
gagaagtccc acgagtctta cagcagattc gctcagcaca                       280
```

<210> SEQ ID NO 101
<211> LENGTH: 222
<212> TYPE: DNA
<213> ORGANISM: Mus musculus

<400> SEQUENCE: 101

```
cggagacggc ctgcaggacc tgctctctca gccctcagcc gaggcctacg ccgagccgag   60
tgcgcagccg acgaccggga ggagccgcag ccttcaactc tgaggtactg tgatccgcgc  120
tgcccgccgg gccgccccag tccgctgctg cggcacctcc ttccctcgcg ccctcttcgc  180
tcgccagcgc cttccctgtg agcctgcgtc accgcggccg cc                    222
```

```
<210> SEQ ID NO 102
<211> LENGTH: 108
<212> TYPE: DNA
<213> ORGANISM: Mus musculus

<400> SEQUENCE: 102
agcccaggcc accgcagcag cagcagcaac agccgcagca acggtagcag tagtctgcat      60
cgcagtccct ttctccttct ccagcgcgct cctcagtccc cggtcacc                 108

<210> SEQ ID NO 103
<211> LENGTH: 124
<212> TYPE: DNA
<213> ORGANISM: Mus musculus

<400> SEQUENCE: 103
ctctttcact cgaacttcac gggggcaatt ttctcgcgca cgcgttctaa gagcagctgg      60
ttttcgaccc cggtactaca ccgatacaga gttagtggct agtcctcctg tgcctcctgt     120
agcg                                                                  124

<210> SEQ ID NO 104
<211> LENGTH: 19
<212> TYPE: DNA
<213> ORGANISM: Mus musculus

<400> SEQUENCE: 104
ggccgaagaa gggaaggct                                                   19

<210> SEQ ID NO 105
<211> LENGTH: 318
<212> TYPE: DNA
<213> ORGANISM: Mus musculus

<400> SEQUENCE: 105
ggagattcga aagcgtccgg gtcgcggggt aaaccggttc tccgtgtgcg agcgcctagt      60
ggcgtaggct gcggctttgc ggggaactgc gggggctgca gtggtccacg gggctgatcg     120
ggttccgttg ggcggatcca cgtgcccgct atccgcctgg aaggagaggt gcaggagtac     180
ccccgacctt ggctgcgtgc tgactcgctt ccttctgccc gcccaggctt gcactccccg     240
gggatctgcc tctgcatctc ttgccttcgc tgttgtttcc ctctctgtcc agctcccctc     300
ccgctctcgc cctggaga                                                  318

<210> SEQ ID NO 106
<211> LENGTH: 198
<212> TYPE: DNA
<213> ORGANISM: Mus musculus

<400> SEQUENCE: 106
gtcacttcgc gcaggcgcac ttcgaaaggc gcgcttttcg gtggctgcgg tcccggcagg      60
gagcacagct catcctgtgc tgataacatc gagaagtgtt cagtgcctgg taaagtacat     120
agaccttgct tcacttggaa ctcggccttg atttctgccg ttggtcataa tcagcagagt     180
tctctctaaa cctttgac                                                  198

<210> SEQ ID NO 107
<211> LENGTH: 175
<212> TYPE: DNA
<213> ORGANISM: Mus musculus

<400> SEQUENCE: 107
```

```
agtcgtgctt cagctcacta cgcttagggc tctggcttgc cgctcccgcc tgctctccag     60
cgccccgcgc agcgagccac gtggaccaac tccggcgcgc ggtgttcgct tggttccagt    120
ggggctcgcc gcgcctcccg cgtctgcgtg cttgccctgt ctcagctccg acccg         175
```

<210> SEQ ID NO 108
<211> LENGTH: 219
<212> TYPE: DNA
<213> ORGANISM: Mus musculus

<400> SEQUENCE: 108

```
gtgtcgtccg gggcgctgaa attcaaattt tgaacggccg tggtagccta ccgactccgt     60
gggtgcggag ggcagagccg actgggtgtg agagcgcccg ccgcctcgac tgcagtcctc    120
ctccaggagc tgcgccgagc ctgcactcac ttctttcctc ttcctgagtt tgaaccgtcg    180
gacccaccgt ctagccgtcc actggtgagg cctggggcg                           219
```

<210> SEQ ID NO 109
<211> LENGTH: 217
<212> TYPE: DNA
<213> ORGANISM: Mus musculus

<400> SEQUENCE: 109

```
gggaattcca cgccacctcc gcgcgctctg cgctctggga tccggagcga ccaggacctg     60
gtgagaccct cagctcccct ccaccttccc cgaggtccag cacaccagaa ctggaacctg    120
agcagcccag aagccagggt ggcaccactg tgtctctcct gtctgaagac ccggatattt    180
tctcagactt ggcgacacgt tcctttaaaa gatcagc                             217
```

<210> SEQ ID NO 110
<211> LENGTH: 87
<212> TYPE: DNA
<213> ORGANISM: Mus musculus

<400> SEQUENCE: 110

```
aaagaccacg ccccagtgac gtcacgcggc ggttaccgcg cttggcgctc gcgatttaaa     60
acttactccg gagacgtgga gagcaag                                         87
```

<210> SEQ ID NO 111
<211> LENGTH: 33
<212> TYPE: DNA
<213> ORGANISM: Mus musculus

<400> SEQUENCE: 111

```
agccaaagca acacctcgca ctcctgcccc agc                                  33
```

<210> SEQ ID NO 112
<211> LENGTH: 69
<212> TYPE: DNA
<213> ORGANISM: Mus musculus

<400> SEQUENCE: 112

```
gcctcgcgag agcacgtgga gagcgcgcca aattctcccc ggagcctgag ggagctttgg     60
agcgtcgca                                                             69
```

<210> SEQ ID NO 113
<211> LENGTH: 237
<212> TYPE: DNA
<213> ORGANISM: Mus musculus

<400> SEQUENCE: 113

```
aattggggtg gaagtctccc gcagcagcct gtgcacacta ataaaaacgc cctgagtttt    60
cgcgggaaaa aaagtcctag cagctggaag gaacccgcgc tctagtgctc acttgggtct   120
tcagccactc acgcggctcc cttctgggtc acccagccgc agagccctag cctagaacca   180
ggcgttccaa gggagaggag agtgcggatc gccgccgtga gagagtacat cggcatc     237
```

<210> SEQ ID NO 114
<211> LENGTH: 232
<212> TYPE: DNA
<213> ORGANISM: Mus musculus

<400> SEQUENCE: 114

```
ttttaaaagc tctgtgctcc aagttaaaaa acgcttttac gaggtatcag cactttttctt   60
tcattggggg aaaggcgtga gggaagtacc caacagcagc agactttgaa actttaaaca  120
gacaggtctg agagcccgaa ctctcctttt cctttgactt cagcctccaa ggagttccac  180
cactttggcg tgccggcttc actttcatta agtgaaagag aggtgcccag ac          232
```

<210> SEQ ID NO 115
<211> LENGTH: 85
<212> TYPE: DNA
<213> ORGANISM: Mus musculus

<400> SEQUENCE: 115

```
cggtgggcta ggagagggtg ttgatcttcg ggtccgggta tcgagcaggg aggatctagc   60
gggcagcgga aactggacca agcac                                         85
```

<210> SEQ ID NO 116
<211> LENGTH: 133
<212> TYPE: DNA
<213> ORGANISM: Mus musculus

<400> SEQUENCE: 116

```
tgacgttgta gggaggctgg cgcgcgggat ttaaactgca gcggtttagg cgttgttaac   60
acagcgcagt attagcagag tcgtggtttc caagcttctt tcatttgtgt tgcctgttgt  120
tgttcctgag tcc                                                      133
```

<210> SEQ ID NO 117
<211> LENGTH: 148
<212> TYPE: DNA
<213> ORGANISM: Mus musculus

<400> SEQUENCE: 117

```
cactggagga ggagcttgca gctctccagc tctggcttat acagttcaca gagaagccaa   60
gggacaccgg gacaccgtta ttttaggact gtaacctgtt cagagagacc ctggccactg  120
ctctccgtgg ttttctccaa ttgtgtgg                                     148
```

<210> SEQ ID NO 118
<211> LENGTH: 90
<212> TYPE: DNA
<213> ORGANISM: Mus musculus

<400> SEQUENCE: 118

```
ttcatttccg gccaccgagg agcttcgcgg gtcgagacgc aggcgaggcg ccggactgcg   60
aaacaaaggg ggacgccaac agccgtagtc                                    90
```

```
<210> SEQ ID NO 119
<211> LENGTH: 137
<212> TYPE: DNA
<213> ORGANISM: Mus musculus

<400> SEQUENCE: 119
ttatatgtcc agctggaagc ctggctgtcc ctagaaaagc tggaagcctg actgccctc       60 aaaagacctg ctctttagga gagctagata ttgtttactg aagacaagtg tgaaaactgg     120
gaacctcagt ctccatc                                                    137

<210> SEQ ID NO 120
<211> LENGTH: 41
<212> TYPE: DNA
<213> ORGANISM: Mus musculus

<400> SEQUENCE: 120
aaatggtcgt cgagggaagg cgcctcatcg cgccgtgaat t                          41

<210> SEQ ID NO 121
<211> LENGTH: 19
<212> TYPE: DNA
<213> ORGANISM: Mus musculus

<400> SEQUENCE: 121
aagacaggca gaaggaccc                                                   19

<210> SEQ ID NO 122
<211> LENGTH: 184
<212> TYPE: DNA
<213> ORGANISM: Mus musculus

<400> SEQUENCE: 122
aagggaggga aaagttccct gcgcggagag ccgggcaggc gcacgctctt acggcggccg      60
cagcggcagg gcggggccgg tggggcgggc ggaggaagac ccctgattgc cacctcgcct     120
ccctcagtgt ctctcttaga ccttggtcac gtaccggggt ccggaggact tgtgtacagc     180
ggca                                                                  184

<210> SEQ ID NO 123
<211> LENGTH: 79
<212> TYPE: DNA
<213> ORGANISM: Mus musculus

<400> SEQUENCE: 123
agcgcgcatc cccagtgccc tgagctgcag agagctcgga ggagcgcggg agcagcgaca      60
ccggagtgga caaagcaag                                                   79

<210> SEQ ID NO 124
<211> LENGTH: 25
<212> TYPE: DNA
<213> ORGANISM: Mus musculus

<400> SEQUENCE: 124
agcctgctgt ggtcaatccc tgaag                                            25

<210> SEQ ID NO 125
<211> LENGTH: 26
<212> TYPE: DNA
<213> ORGANISM: Mus musculus

<400> SEQUENCE: 125
```

```
gtagagagga ctttggatca ttctaa                                              26

<210> SEQ ID NO 126
<211> LENGTH: 90
<212> TYPE: DNA
<213> ORGANISM: Mus musculus

<400> SEQUENCE: 126
aattttgttg cctggtgcag caggtagcag tgaaacctct gaggcgtttg gtgctccggt        60
aaccaccacg gctgtagagc gagtgttgcc                                         90

<210> SEQ ID NO 127
<211> LENGTH: 87
<212> TYPE: DNA
<213> ORGANISM: Mus musculus

<400> SEQUENCE: 127
cagaaactcc gatcgccttt cccaacccga aagtgcgcgt cggccgagcc tggagggacc        60
cagctgaagc ctggcctggg agccagg                                            87

<210> SEQ ID NO 128
<211> LENGTH: 275
<212> TYPE: DNA
<213> ORGANISM: Mus musculus

<400> SEQUENCE: 128
agatcacgtg acgagagcgc gggctttgga aggcggcgaa gctgggaacg atactgaaag        60
aacgggctcg ggactgtcca gagaacgctg tggactccaa accactgcta gctgcttaag      120
gctcgtgcac tcgagacggg gtgaggtctc gcggaagcgt ctctgaaagc ggcagagccg      180
cgggaacagc accgggcagc ccgggcttgg gccattcgct ctgctccgaa cattcctctt      240
cgccggtagg aagaagccat tgctcctgtg ctacc                                  275

<210> SEQ ID NO 129
<211> LENGTH: 86
<212> TYPE: DNA
<213> ORGANISM: Mus musculus

<400> SEQUENCE: 129
gacttgcgac ttgcgactcg gtgctgtcca gattcagcac gctctgttcc ttcgccttac        60
aagtccaggc acccagcccc gccgcg                                             86

<210> SEQ ID NO 130
<211> LENGTH: 77
<212> TYPE: DNA
<213> ORGANISM: Mus musculus

<400> SEQUENCE: 130
gaaggcattg tcaaggagcc cagagtgtag gaactggcat tgacccggac gaccggacca        60
ttgacccgcc gctggat                                                       77

<210> SEQ ID NO 131
<211> LENGTH: 112
<212> TYPE: DNA
<213> ORGANISM: Mus musculus

<400> SEQUENCE: 131
cggctctgtg gcagggccc ggacaaggtg gagccctgtc ggcttactgg tcccagtccc         60
atcctcgcta ctccagcaca cgtgacctcc gccgccgctg ctaacctgca cc                112
```

```
<210> SEQ ID NO 132
<211> LENGTH: 319
<212> TYPE: DNA
<213> ORGANISM: Mus musculus

<400> SEQUENCE: 132
cgctgctcac ttctcagggc cgagtctacc taggtgaaaa ctatctcttt tgaggggaag      60
cgacacctag gagtagcatt gagagtactg caagagtctc aggcccacgc gtattctgtg     120
gctcccttcg ctttacctgt gctcgcggtc gccctcgttg ccccggaaag gagcctctcg     180
gctgaaggag ggacgccgag gcgaggcggc gcctctgcgc ttgcgcttat atggtggctc     240
gaaggagcca aaggcaaagt ctcgggtgac agctgcgagc cccacccttt ccccacgtgg     300
ctgcgtagac ccggcagtg                                                  319

<210> SEQ ID NO 133
<211> LENGTH: 145
<212> TYPE: DNA
<213> ORGANISM: Mus musculus

<400> SEQUENCE: 133
aacattcctt gagaaagaga gaacaagata agcagtggtg cacttcctcc ttcattgctg      60
ctgagaatgt tccaggctga gtgagaagta aaaattcatc atctctgaag aactcttacc     120
cagccctgtt gaagaaattc ccaga                                           145

<210> SEQ ID NO 134
<211> LENGTH: 151
<212> TYPE: DNA
<213> ORGANISM: Mus musculus

<400> SEQUENCE: 134
ccttcggaga atcctgtgcg cgtgcgttct tgtgggaact gcgcctccca gaaggcaccg      60
cgcgtcgtcc ttctccctcc ctgaaggccg cctcgcttgc ccagtgtgtc ggccgcccgc     120
gaagctagag tccactgact tttccgccac c                                    151

<210> SEQ ID NO 135
<211> LENGTH: 65
<212> TYPE: DNA
<213> ORGANISM: Mus musculus

<400> SEQUENCE: 135
gcggagtggg cgggggaaca cctcgcccga ggcagtgagg gaccaggctc tccaaggaca      60
gaaaa                                                                  65

<210> SEQ ID NO 136
<211> LENGTH: 108
<212> TYPE: DNA
<213> ORGANISM: Mus musculus

<400> SEQUENCE: 136
cccaacctgc agatgaggaa gaggaagcgg gagacagacg gacagacgga cggacacaga      60
cgctgcgccc aggcctcacc atccatcgca ggaagccccc tgtctcag                  108

<210> SEQ ID NO 137
<211> LENGTH: 103
<212> TYPE: DNA
<213> ORGANISM: Artificial Sequence
<220> FEATURE:
```

<223> OTHER INFORMATION: Artificial nucleic acid construct

<400> SEQUENCE: 137

```
atcttagctt ctctgtcttc ctccctccct cccttcctct tactctcatt catttcatac    60
acactggctc acacatctac tctctctctc tatctctctc aga                     103
```

<210> SEQ ID NO 138
<211> LENGTH: 259
<212> TYPE: DNA
<213> ORGANISM: Artificial Sequence
<220> FEATURE:
<223> OTHER INFORMATION: artificial nucleic acid sequence

<400> SEQUENCE: 138

```
atcacagccc ttccccgatc ctctccgtgg gagccagcga gcctctctcc ctgatcttac    60
gtgctcaagg gagctcacac gttcaccaac tcacccttga agtcatctca agaacaaaag  120
acaactgaaa gaagctgttg tgaaggcaga gcagcatctg ctgaagagac agaaaccagc  180
cccagaggtg tcacaggaag gcaccagcaa ggacattggt ctttgatttg attcagcagt  240
cctgtcaagt ataatagtg                                                259
```

<210> SEQ ID NO 139
<211> LENGTH: 80
<212> TYPE: DNA
<213> ORGANISM: Artificial Sequence
<220> FEATURE:
<223> OTHER INFORMATION: artificial nucleic acid sequence

<400> SEQUENCE: 139

```
tagggctgga gctccgggca gtgtgcgagg cgcacgcaca ggagcctgca ctctgcgtcc    60
cgcaccccag cagccgcgcc                                                80
```

<210> SEQ ID NO 140
<211> LENGTH: 101
<212> TYPE: DNA
<213> ORGANISM: Artificial Sequence
<220> FEATURE:
<223> OTHER INFORMATION: artificial nucleic acid sequence

<400> SEQUENCE: 140

```
cagtcgtccc tgcgcgtcgt cctcctcgcc ctccaggccg cccgcgccgc gccggagtcc    60
gctgtccgcc agctacccgc ttcctgccgc ccgccgctgc c                       101
```

<210> SEQ ID NO 141
<211> LENGTH: 110
<212> TYPE: DNA
<213> ORGANISM: Artificial Sequence
<220> FEATURE:
<223> OTHER INFORMATION: artificial nucleic acid sequence

<400> SEQUENCE: 141

```
taggcggacc tccggaaacc gtagattccg ggcggtcgga gccgccggga gctgtagttc    60
tcccgcggct cagagaagta ggcagagagc ggacctggcg gccgggcagc              110
```

<210> SEQ ID NO 142
<211> LENGTH: 291
<212> TYPE: DNA
<213> ORGANISM: Artificial Sequence
<220> FEATURE:
<223> OTHER INFORMATION: artificial nucleic acid sequence

<400> SEQUENCE: 142

```
accggtagta gctcggctag aaccactagg cgcctggcgg gggtgatctg tcggagcgac    60
cggcttggcg cctgcctgtc cccagcccct ctcagcttga actccttcct tcaagtctgg   120
gccctcgagg cttccagagc ggcctccagg ggtgcagtct cagttcccca cgccagccgt   180
ctccgtcctc cgcctcctcc gggctggca gtggcactg tccggaggcg gagccttggg    240
cgaggggtgg ttgcggcgga ggacgcaacc gagcgggcct gcggcctcac c            291
```

<210> SEQ ID NO 143
<211> LENGTH: 184
<212> TYPE: DNA
<213> ORGANISM: Artificial Sequence
<220> FEATURE:
<223> OTHER INFORMATION: artificial nucleic acid sequence

<400> SEQUENCE: 143

```
cttttcccgg cactagcgca ccgcagcggg tcgcgcgccc taaggagtgg cacttttaa    60 aagtgcagcc ggagaccagc ctacagccgc ctgcatctgt atccagcgcc aggtcccgcc   120
agtcccagct gcgcgcgccc cccagtcccg cacccgttcg gcccaggcta agttagccct   180
cacc                                                                184
```

<210> SEQ ID NO 144
<211> LENGTH: 30
<212> TYPE: DNA
<213> ORGANISM: Artificial Sequence
<220> FEATURE:
<223> OTHER INFORMATION: artificial nucleic acid sequence

<400> SEQUENCE: 144

```
cttgatctgt gggcggggcg cggcctgtgg                                    30
```

<210> SEQ ID NO 145
<211> LENGTH: 136
<212> TYPE: DNA
<213> ORGANISM: Artificial Sequence
<220> FEATURE:
<223> OTHER INFORMATION: artificial nucleic acid sequence

<400> SEQUENCE: 145

```
gtagatttga gggacaacaa ttcagtgccc gggggccgaa aggcagcaga aggcgggcac    60
caaaggatag gcacccggaa ggtggactcc gaggaggaga gaggacaggg gtctctcacc   120
ccagctcctg gtcacc                                                   136
```

<210> SEQ ID NO 146
<211> LENGTH: 209
<212> TYPE: DNA
<213> ORGANISM: Artificial Sequence
<220> FEATURE:
<223> OTHER INFORMATION: artificial nucleic acid sequence

<400> SEQUENCE: 146

```
ggccggacgc ctccgcgtta cgggatgaat taacggcggg ttccgcacgg aggttgtgac    60
ccctacggag cccagcttg cccacgcacc ccactcggcg tcgcgcggcg tgccctgctt    120
gtcacaggtg ggaggctgga actatcaggc tgaaaaacag agtgggtact ctcttctggg   180
aagctggcaa caataggtag tagtgatat                                     209
```

<210> SEQ ID NO 147
<211> LENGTH: 217
<212> TYPE: DNA

<213> ORGANISM: Artificial Sequence
<220> FEATURE:
<223> OTHER INFORMATION: artificial nucleic acid sequence

<400> SEQUENCE: 147

```
ggcaattcca cgccacctcc gcgcgctctg cgctctggga tccggagcga ccaggacctg      60
gtgagaccct cagctcccct ccaccttccc cgaggtccag cacaccagaa ctggaacctg     120
agcagcccag aagccagggt ggcaccactg tgtctctcct gtctgaagac ccggatattt     180
tctcagactt ggcgacacgt tcctttaaaa gatcagc                              217
```

<210> SEQ ID NO 148
<211> LENGTH: 87
<212> TYPE: DNA
<213> ORGANISM: Artificial Sequence
<220> FEATURE:
<223> OTHER INFORMATION: artificial nucleic acid sequence

<400> SEQUENCE: 148

```
aaagaccacg ccccagtcac gtcacgcggc ggttaccgcg cttggcgctc gcgatttaaa      60
acttactccg gagacgtgga gagcaag                                          87
```

<210> SEQ ID NO 149
<211> LENGTH: 137
<212> TYPE: DNA
<213> ORGANISM: Artificial Sequence
<220> FEATURE:
<223> OTHER INFORMATION: artificial nucleic acid sequence

<400> SEQUENCE: 149

```
ttattagtcc agctggaagc ctggctgtcc ctagaaaagc tggaagcctg actgcccctc      60
aaaagacctg ctctttagga gagctagata ttgtttactg aagacaagtg tgaaaactgg     120
gaacctcagt ctccatc                                                    137
```

<210> SEQ ID NO 150
<211> LENGTH: 41
<212> TYPE: DNA
<213> ORGANISM: Artificial Sequence
<220> FEATURE:
<223> OTHER INFORMATION: artificial nucleic acid construct

<400> SEQUENCE: 150

```
aataggtcgt cgagggaagg cgcctcatcg cgccgtgaat t                          41
```

<210> SEQ ID NO 151
<211> LENGTH: 108
<212> TYPE: DNA
<213> ORGANISM: Artificial Sequence
<220> FEATURE:
<223> OTHER INFORMATION: artificial nucleic acid sequence

<400> SEQUENCE: 151

```
cccaacctgc agtagaggaa gaggaagcgg gagacagacg gacagacgga cggacacaga      60
cgctgcgccc aggcctcacc atccatcgca ggaagccccc tgtctcag                  108
```

<210> SEQ ID NO 152
<211> LENGTH: 100
<212> TYPE: DNA
<213> ORGANISM: Homo sapiens

<400> SEQUENCE: 152

```
cgccgccgcc gccgccgccg gagcctgtcg ccgtcctgtc cccagcctgc ttgtgtcccg      60
```
tgaggttgtc aataaacctg ccctcgggct gccgcctccc         100

<210> SEQ ID NO 153
<211> LENGTH: 185
<212> TYPE: DNA
<213> ORGANISM: Homo sapiens

<400> SEQUENCE: 153
ccttggagct cactggtccc tgcctctggg gcttttctga agaaacccac ccactgtgat     60
caatagggag agaaaatcca cattcttggg ctgaacgcgg gcctctgaca ctgcttacac    120
tgcactctga ccctgtagta cagcaataac cgtctaataa agagcctacc cccaactcct    180
tctgc                                                                185

<210> SEQ ID NO 154
<211> LENGTH: 250
<212> TYPE: DNA
<213> ORGANISM: Homo sapiens

<400> SEQUENCE: 154
gtgcccggcc caccagggac tgcagctgca ccagcaggtg ccatcacgct tgtgatgtgg     60
tggccgtcac gctttcatga ccactgggcc tgctagtctg tcagggcctt ggcccagggg    120
tcagcagagc ttcagaggtg gccccacctg agccccacc cgggagcagt gtcctgtgct     180
ttctgcatgc ttagagcatg ttcttggaac atggaatttt ataagctgaa taaagttttt    240
gacttccttt                                                           250

<210> SEQ ID NO 155
<211> LENGTH: 387
<212> TYPE: DNA
<213> ORGANISM: Homo sapiens

<400> SEQUENCE: 155
gcggtgcgta cccggtgtcc cgaggcccgg ccaggggctg gcagggatg ccaggtgggc      60 ccagccagct cctggggtcc cggccacctg gggaagccgc gcctgccaag gaggccacca    120
gagggcagtg caggcttctg cctgggcccc aggccctgcc tgtgttgaaa gctctgggga    180
ctgggccagg gaagctcctc ctcagctttg agctgtggct gccacccatg ggctctcct     240 tccgcctctc aagatccccc cagcctgacg ggccgcttac catcccctct gccctgcaga    300
gccagccgcc aaggttgacc tcagcttcgg agccacctct ggatgaactg cccccagccc    360 ccgcccccatt aaagacccgg aagcctg                                      387

<210> SEQ ID NO 156
<211> LENGTH: 46
<212> TYPE: DNA
<213> ORGANISM: Homo sapiens

<400> SEQUENCE: 156
ccacccagcc acccatgtcc agaataaaac cctcctctgc ccacac                    46

<210> SEQ ID NO 157
<211> LENGTH: 151
<212> TYPE: DNA
<213> ORGANISM: Homo sapiens

<400> SEQUENCE: 157
agccttcagt cactggggaa agcagggaag cagtgtgaac tctttattca ctcccagcct     60

```
gtcctgtggc ctgtcccact gtgtgcactt gctgttttcc ctgtccacat ccatgctgta    120
cagacaccac cattaaagca ttttcatagt g                                   151
```

<210> SEQ ID NO 158
<211> LENGTH: 73
<212> TYPE: DNA
<213> ORGANISM: Homo sapiens

<400> SEQUENCE: 158

```
agcagctgcc tggagcctat tcactatgtt tattgcaaaa tcctttcgaa ataaacagtt    60
tccttgcacg gtt                                                        73
```

<210> SEQ ID NO 159
<211> LENGTH: 83
<212> TYPE: DNA
<213> ORGANISM: Homo sapiens

<400> SEQUENCE: 159

```
gcgccccgcc tcgctcggct gccccgccc cttccggcc cccctcgccg cgcgtcctcc      60
aaaaaataaa accttaaccg cgg                                             83
```

<210> SEQ ID NO 160
<211> LENGTH: 517
<212> TYPE: DNA
<213> ORGANISM: Homo sapiens

<400> SEQUENCE: 160

```
gctacagcgg ctctcatgat gtgggctcac ctgcgcccca gaccctgcag gggcccccct    60
gcttggctct gctgggagag tgctcagccg cccagtcctg cctgcaagcc agggcgagt    120 attggaggag gggcagccac gggcagagca ccatgcccat ccccgagtct ctggtgtgtc   180
tgccccctct ggcatcctct gggcgtccca tgatcccttc tgtgtctgcg tgtccgaatc   240
cccgtgtgac cctgtcccag catttttccg ccgaccctgc gtgtccccgt ggcgctgtcc   300 gctctcccctc tcctgctgcc cacccacctg ccagtgttat ttatgctccc ttcgtgggtg   360
atggccacgc cctcaccatg tccctggcag agggcttccc tccgggatcc cctgcctggt   420
gcccacactg cctcgcaagc gctcgccacc ctcacgtggc tcacctgctg ttgagccttg   480
tgctgtcaat aaacggtttg aggattgcag gattgtc                             517
```

<210> SEQ ID NO 161
<211> LENGTH: 259
<212> TYPE: DNA
<213> ORGANISM: Homo sapiens

<400> SEQUENCE: 161

```
gcagaaccag agtctgccac tggggctcag gaccaaggga ggcagcacca tgtccttctg    60
tgggacactg ccagccccag ggctccagcc cagcccggtg gatcctctgg ggaagccagg   120
accaggagag aagcaaggtc aagaaatccc acagtttgat gtattaaaga aatgactat    180 ttctactcaa aataaatggc attgaagtct tcctttaacc ctttttgagt taatttaata   240
ataatgatct gagacaagg                                                  259
```

<210> SEQ ID NO 162
<211> LENGTH: 443
<212> TYPE: DNA
<213> ORGANISM: Homo sapiens

<400> SEQUENCE: 162

```
agtcagctta catccctgag caggaaagtt tacccatgaa gattggtggg attttttgtt      60
tgtttgtttt gttttgtttg ttgtttgttg tttgtttttt tgccactaat tttagtattc     120
attctgcatt gctagataaa agctgaagtt actttatgtt tgtcttttaa tgcttcattc     180
aatattgaca tttgtagttg agcgggggt ttggtttgct ttggtttata ttttttcagt      240
tgtttgtttt tgcttgttat attaagcaga aatcctgcaa tgaaaggtac tatatttgct     300
agactctaga caagatattg tacataaaag aattttttg tctttaaata gatacaaatg      360
tctatcaact ttaatcaagt tgtaacttat attgaagaca atttgataca aataaaaaa     420 ttatgacaat gtcctggact ggt                                             443
```

<210> SEQ ID NO 163
<211> LENGTH: 527
<212> TYPE: DNA
<213> ORGANISM: Homo sapiens

<400> SEQUENCE: 163

```
gggccggcgc ttgccactag ggctcttgtg tttttttct tctgctatgt gacttgcatc      60
gtggagacag ggcatttgag tttatatctc tcatgcatat tttatttaat ccccaccctg    120
ggctctggga gcagcccgct gagtggactg gagtggagca ttggctgaga gaccaggagg    180
gcactggagc tgtcttgtcc ttgctggttt tctggatggt tcccagaggg tttccatggg    240
gtaggaggat gggctcgccc accagtgact ttttctaaga gctcccggcg tggtggaaga    300
ggggacaggt ccctcaccca cccacaatcc tattctcggg ctgagaaccc tgcgtgggga    360
cagggctcgc ctcaggaatg ggctgttttt ggcctaaccc tcagaaacac tggggctggc    420
acaaactctt ggtttcttca acaggagaat tttactgtgt ttcttttggt tccattgttt    480
ggagacattc ctgggcacag tttggtccgt tagaattaaa agttgaa                    527
```

<210> SEQ ID NO 164
<211> LENGTH: 57
<212> TYPE: DNA
<213> ORGANISM: Homo sapiens

<400> SEQUENCE: 164

```
ccctgttccc agagcccact tttttttctt tttttgaaat aaaatagcct gtctttc         57
```

<210> SEQ ID NO 165
<211> LENGTH: 81
<212> TYPE: DNA
<213> ORGANISM: Homo sapiens

<400> SEQUENCE: 165

```
atcctgggat tctagtatgc aataagagat gccctgtact gatgcaaaat ttaataaagt     60
ttgtcacaga gaatctttgt a                                                81
```

<210> SEQ ID NO 166
<211> LENGTH: 209
<212> TYPE: DNA
<213> ORGANISM: Homo sapiens

<400> SEQUENCE: 166

```
gccatgtctg ggcccccagc ccctggggag gacctactgc tcccaggggc tgagaggggt     60
tcgggagcat aatgacaaac tgtcgctgcc ccagtggctg ggtgtgtgtg ggtgggatgg    120
ggtgggggtc ctgggccccc cgtgtcttcc caggtttaca atcagagaat cacagctgct    180
```

```
ttaataaatg ttatttataa tacacggaa                                      209
```

<210> SEQ ID NO 167
<211> LENGTH: 128
<212> TYPE: DNA
<213> ORGANISM: Homo sapiens

<400> SEQUENCE: 167

```
gcggtggagc tgcgggcggc cagggccggg cgctctgtgc ggactggggc catgatcggg    60 cccggggcc tgagcctggg accccacccc gtgttaatga aaatgagtt ttggcagcgc     120 ctgtggtc                                                            128
```

<210> SEQ ID NO 168
<211> LENGTH: 161
<212> TYPE: DNA
<213> ORGANISM: Homo sapiens

<400> SEQUENCE: 168

```
gcggccgcct gaccgtcgac cttggggctc tccacccgct ctggcccag tcgaactggg    60 ggctagccac ctcctcgtcc agccccaaa cctcccttc ctttcccct cctccggggg     120 ccaaggacag ggtggcctta ctcagtaaag gtgtttcctg c                       161
```

<210> SEQ ID NO 169
<211> LENGTH: 63
<212> TYPE: DNA
<213> ORGANISM: Homo sapiens

<400> SEQUENCE: 169

```
cctcgccccg gacctgccct cccgccaggt gcacccacct gcaataaatg cagcgaagcc    60
ggg                                                                 63
```

<210> SEQ ID NO 170
<211> LENGTH: 70
<212> TYPE: DNA
<213> ORGANISM: Homo sapiens

<400> SEQUENCE: 170

```
gacgcaggcc agccccggcc cctagccctc aggccttctt tcttatccaa ataaatgttt    60
cttaatgagg                                                          70
```

<210> SEQ ID NO 171
<211> LENGTH: 89
<212> TYPE: DNA
<213> ORGANISM: Homo sapiens

<400> SEQUENCE: 171

```
ccccatcgcc gacacgcccc ccactcagcc cagcccgcct gtccctagat tcagccacat    60
cagaaataaa ctgtgactac acttggcaa                                     89
```

<210> SEQ ID NO 172
<211> LENGTH: 92
<212> TYPE: DNA
<213> ORGANISM: Homo sapiens

<400> SEQUENCE: 172

```
gagtcagagc ccacatggcc gggccctctg tagctccctc ctcccatctc cttccccag    60 cccaataaag gtcccttagc cccgagttta aa                                 92
```

<210> SEQ ID NO 173
<211> LENGTH: 580
<212> TYPE: DNA
<213> ORGANISM: Homo sapiens

<400> SEQUENCE: 173

```
tgcctgagcg ccacctactg cattttggac acctcacacc aaggggagat gcaccccaca      60
gacacctggg actttcccct tctggttcct gtgtctccca ataaactctc tgaccaaccc     120
tagctgtgct tctgcgagaa gaaagggtgt agcaacttct ggcagatatg aggcttttt      180
cttttttttt ttttttttg  agacaacgtc tggctctgtc acccaggctg gagcgcagtg     240
gcacaatctc ggcccactgc agcctcgacc tctggggctc aagggatcct catgcctcag     300
cctcatatgt agctggggcc acagacatgc accaccacac ctggctcgag gccattttag     360
ttctgaggtt gagcagctca ggagccggct ccagacggt gctgtgtttg tgaaacagag      420
aaagggggacc cccgaggacc ccagacaggg ccttaggact ctcatatctt cttgtcttct    480
ccatctggtg gctcttgctc tctggttttc tctacctttt catggcccca gaatccatat     540
gcagtaaagg aactctctgg aataaaatta aagtcctcct                            580
```

<210> SEQ ID NO 174
<211> LENGTH: 255
<212> TYPE: DNA
<213> ORGANISM: Mus musculus

<400> SEQUENCE: 174

```
aaagccaaag gattcaggac caagcagcac catggccttc ctatggcaca tatgcatata     60
aagaatttaa agcacggggt ggcgtgcggc ttgttcagat cagcgagtaa actggtacat    120
gaaaggatgt tcatcatatt attctgctac tgagtacatc tgaaactttc ccttgtctgt    180
ttgtagtacg tatttggcta aatgctagaa ttttgcttta aatacagcaa aagctaataa    240
acttgttagt aacta                                                      255
```

<210> SEQ ID NO 175
<211> LENGTH: 80
<212> TYPE: DNA
<213> ORGANISM: Mus musculus

<400> SEQUENCE: 175

```
tgggggaggt gtcttagttt tccctatctt ttaagctgtt aacaagtttc attgcacttt     60
gaataaagtt cttgcattcc                                                 80
```

<210> SEQ ID NO 176
<211> LENGTH: 245
<212> TYPE: DNA
<213> ORGANISM: Mus musculus

<400> SEQUENCE: 176

```
gcctgatccc tgacattggc gccggctctg gactcgtgct cggtgtgctc tggaaactac     60
ttccctgctc ccaggcgtcc ctgctccggg ttccatggct cccggctccc tgtatcccag   120
gcttggatcc tgtggaccag ggttactgtt ttaccactaa catctccttt tggctcagca   180
ttcaccgatc tttagggaaa tgctgttgga gagcaaataa ataaacgcat tcatttctct   240
atgca                                                                245
```

<210> SEQ ID NO 177
<211> LENGTH: 25
<212> TYPE: DNA

<213> ORGANISM: Mus musculus

<400> SEQUENCE: 177

| agacaataaa ggactttatt cttgt | 25 |

<210> SEQ ID NO 178
<211> LENGTH: 475
<212> TYPE: DNA
<213> ORGANISM: Mus musculus

<400> SEQUENCE: 178

| gggctcccag gagagcccag ggactctgcg ccacactgaa gataactgag atggagcgca | 60 |
| ctccagccgc gcaggactga cgaggccaca cccatgggct ctgtggcttt ctctgctctc | 120 |
| atggattgaa cagggtcccc catgtgggcc cgggcgatct gctgtctgct tatctaagga | 180 |
| tcctcttaga ggctgccttt tttttttttt tttttaagga gcgattaaga aaagggaagg | 240 |
| aaattcaagt cagtgttttg gctgtttttg tttttgttt gtttgttttt gtttgttttt | 300 |
| tgtggtgttg ggttttgagg ttttttgttt ggttggtttg gttttgggat cgtgtgttta | 360 |
| ttttattgtt tttgttttgg ggggttggtc gtttgttgtt ttgggggggtt gttttgttttt | 420 |
| gtttgtttgt tggttactgt ttttcaagaa gaaatataaa ttcatcctcc aagct | 475 |

<210> SEQ ID NO 179
<211> LENGTH: 325
<212> TYPE: DNA
<213> ORGANISM: Mus musculus

<400> SEQUENCE: 179

| ccccgccccc tcctgtccca ttggctccaa gatcagcagg aggaacacag aactggaggg | 60 |
| gcgggtggag ggccggtgtg ctcttcccag caggcctgag aatgagtggg aatcagggca | 120 |
| tttgggcctg gctggagatc aggtttgcac actgtcttga gaacaatgtt ccagtgagga | 180 |
| atcctgatct ctcgccccca attgagccag ctggccacag cccacccctt ggaatatcac | 240 |
| cattgcaatc atagcttggg ttgcttttaa acgtggattg tcttgaagtt ctccagcctc | 300 |
| catggaagga tgggtcagat cccag | 325 |

<210> SEQ ID NO 180
<211> LENGTH: 162
<212> TYPE: DNA
<213> ORGANISM: Mus musculus

<400> SEQUENCE: 180

| gacctctggc tgagattgaa taggacaacc aatgaccttg acactgcctc ttaggcactt | 60 |
| agctctagca atgccctgga agtctcttca gctgagctcc agggcaaagg cagaagggtg | 120 |
| cctctgtacg acggcacagt gagctggata ggttagtcat gc | 162 |

<210> SEQ ID NO 181
<211> LENGTH: 240
<212> TYPE: DNA
<213> ORGANISM: Mus musculus

<400> SEQUENCE: 181

| cctaaccata cctaattgtt gtcttgttct cctatacaat aatggagagt actcttgacc | 60 |
| ccacgaagag ctgggcctct catgtggtgt tagtgacgga tatgaaataa tgctctgtat | 120 |
| ttcttgtgaa atgatggcta tgtctttgct gtttctcatt tgttttttaac ttgtatactt | 180 |
| tgaaatagtc tctgtagttg tttcctggct ttgaaaaaaa tgttattaaa ggaaaattgt | 240 |

<210> SEQ ID NO 182
<211> LENGTH: 108
<212> TYPE: DNA
<213> ORGANISM: Mus musculus

<400> SEQUENCE: 182

```
ccggccccag ggtgacagag tcagggcccc atgggaacaa gcatggtgga ggcgcctcag      60
ggccacgggc cacgtctgtt gcaataaatc tgcagctctg cttcttgc                  108
```

<210> SEQ ID NO 183
<211> LENGTH: 279
<212> TYPE: DNA
<213> ORGANISM: Mus musculus

<400> SEQUENCE: 183

```
agagccggag agtgggctga gtccctgctg atgaggcgct ctcctcactt cccagaagac      60
tcaaatcttc ttcctcctcg cacaggttgg ggggtcaga actatcggac ttgtcccact      120
caaacatgat gagtgagcac acaaagggcc agagtcagaa aggaaggga acaagttgag      180
ctactgctag gaacctgagg gaaaagatgg atgagaaggt ggcaagtccg tgacggtggc      240
aacttcccaa accaggaaat aaaatgtctt ttactataa                            279
```

<210> SEQ ID NO 184
<211> LENGTH: 258
<212> TYPE: DNA
<213> ORGANISM: Mus musculus

<400> SEQUENCE: 184

```
ggtgagcgct gcccagtctt ccccgtgtgc cggctgcgag cctccttgct cctgcatctc      60
gaccattccg tgttggctgt gtcgcctgac ctgcgtacct gtggaggatt cggaacaagt      120
catggagaga ctgtccgggt ccgctccttg tgaactgtgc agaaggagtg atcccagcat      180
cggcaagcga gggagaagac tgcacgagag tgatgcgcat ttcgagtctg cttttcgata      240
gttgatgtct tcttgcct                                                   258
```

<210> SEQ ID NO 185
<211> LENGTH: 285
<212> TYPE: DNA
<213> ORGANISM: Mus musculus

<400> SEQUENCE: 185

```
gtctctctcc ttcggactgg tgccccttca ctctgctagc tctgagcctg cactgtaggc      60
tcctggggc tgctgttcag tgcccctggc cctgggggct gggcaggagc agggccccct      120
ttgaagggt tgctgtgtgt aagttatttt gtacatgtct gggtgtgggt ttacatctgc      180
ttccctgccc tcgctcagcc cactgtatga attgtataaa tgtttctatt aaattgggac      240
tgctctttcc ttagctttat atatattaaa atgtgtacat ctctc                     285
```

<210> SEQ ID NO 186
<211> LENGTH: 47
<212> TYPE: DNA
<213> ORGANISM: Mus musculus

<400> SEQUENCE: 186

```
ggggccagga cgtcgtccct gtgaccaaca gtaaaatatt gtgactc                   47
```

<210> SEQ ID NO 187

```
<211> LENGTH: 521
<212> TYPE: DNA
<213> ORGANISM: Mus musculus

<400> SEQUENCE: 187
gaggacaaca ggacacacag tggcagcagg gactgtggta gcagagtgca cacatctgtc    60
cttcttctgt ggggtccttc actgccaaca cctgcaacgg tgctttgtct ctctgacagc   120
tatggtgtct tgctgcacac ttctagttag tgggaatttt agacgggaa cacagggcta    180
gtcagggcct ttgtgtgctt ggtgtggagt gactgagaac cgtctatggt tcaaggtccc   240
actggggata aactgcttag agcactgtcc tagagggcaa gtgtagcctt cgcctccggg   300
cccaggcagg ctatgcagtc agcagtaggg tctgtgctcc atgcgggtcc aggcgcacgg   360
ctctcctatt ctgttgtcat ttgtgccctc tatgggcagg tgtgtttcaa gttggttttc   420
tgttgctgag gctttcatac acatcagtta ccatctcagc tgatttgtct actgaaagct   480
tgctgttttc aataaatctt agtttgccat ggttttaagt c                        521

<210> SEQ ID NO 188
<211> LENGTH: 63
<212> TYPE: DNA
<213> ORGANISM: Mus musculus

<400> SEQUENCE: 188
gacactacct tcttttaaaa atccttgtat agtgacgtgt tgtgtaaata cagttttat     60
tcc                                                                   63

<210> SEQ ID NO 189
<211> LENGTH: 284
<212> TYPE: DNA
<213> ORGANISM: Mus musculus

<400> SEQUENCE: 189
gtcccagctt cctttcttgt ctcttcaggc ccagctgctg ggcaaggaat cccgatgccc    60
cccccacggg ggcagcacac ttagcagaca atcctggagc atacagatag cccaagcaca   120
tagatgtact aaactgggac catgctttag gctccagacg agagtctttt ctaacttggg   180
gatgcagtct cagatactgg gggcccctct gcctcatctc cattcttaca cctcaaatct   240
gtacagttac ttttgtactg actgtaataa acagccaaac agtt                     284

<210> SEQ ID NO 190
<211> LENGTH: 570
<212> TYPE: DNA
<213> ORGANISM: Mus musculus

<400> SEQUENCE: 190
aagttcgagt caaagctgtc attccagtgc tgccatcagg agcagcatcc aaggggccaa    60
atcttcggaa taactggaca gatcattacg gagcatacgc agaactgcac tgaatatttt   120
aaggccctaa tgagtttaca gctgtaacct tccatggatc ttcccttaag aactgtcttc   180
tgtttatctt ctaactaaca ggttgttctg ttagtatcat ttcggtaatt ttgctatatt   240
tgtgtccaag gaagtaagag ttgttctgtt tgggatcat gttgtctttt ttctttcttc     300
agtagcttat gatatatttt aatcatgttt acaatgttac aatttagtat tgatgtttta   360
tgaagttaaa ttattaaatg aatggtctta aatccactgt ggtggttttt ttttgaaaaa   420
ttatataatt accataagcc aaaaatcaaa tatttggaat acctactgtg aaattcaaga   480
gattaaaggt tgtacttgat acttgttatt tttcttaaat aaatctagtt atcaagttat   540
```

```
tttcttaaa taaatctagt tatcaaatgt                                      570

<210> SEQ ID NO 191
<211> LENGTH: 208
<212> TYPE: DNA
<213> ORGANISM: Mus musculus

<400> SEQUENCE: 191
caagcctagg ctaaagacac tttggtatcc cacacctact gcctgctcca aaaggcagaa    60
ccactgacca ccttgctttt ccaaactcat gagcacagcc cagaaggaac agaagacttc   120
tgctaacgtc atcatgccat aaacagacag aagcagggaa tggctctatc cctagctgcc   180
tgctaagtaa acacggtttt gaagcgtc                                      208

<210> SEQ ID NO 192
<211> LENGTH: 532
<212> TYPE: DNA
<213> ORGANISM: Mus musculus

<400> SEQUENCE: 192
tgacttcaaa taaagatctg tttgatatca cactagcctc ttcccctccc cagaaaactt    60
tgggcaccct ctggctttgg ttaggaactg agttggacag gttgggtaaa tttcaacctc   120
agggcatcat gcccaggaaa gctggggaga ggcgatgttc ttttcctcag tttggagcgg   180
gaagaaggag ttttaatgac tgtgcttcct cttctcctcc ccatggaagg ggggggggat   240
ccctggctca gcatccactg ctggtggaaa cctcgctgcg aggtgccgct gtgaggtgtg   300
ccgctgtgag gtgcgtgctc tggaagagag gcggagcttg tccgcttcct gctgcctctg   360
cctgcagtac caccctcggt ctaagcactc atgattttat actttcagaa aaaagtttta   420 agacttctttt gggtttttttg tttttgtttt gaagcctaag aaagtcacta gttcttgcct   480 ttatgtatttt atatgctgta cctaacaata aagaagaag aaaaaaaaca aa           532

<210> SEQ ID NO 193
<211> LENGTH: 74
<212> TYPE: DNA
<213> ORGANISM: Mus musculus

<400> SEQUENCE: 193
gcggcggagc ctggggctcc ctggactgac accctacccc tgagttaata aaagttgaat    60
tttgacagct ccca                                                      74

<210> SEQ ID NO 194
<211> LENGTH: 222
<212> TYPE: DNA
<213> ORGANISM: Mus musculus

<400> SEQUENCE: 194
agctatttaa agctagtagt ccattcacca ggacaggcca acatccgga accagagtgg     60 cctgcagagg acaggacagg agcccttcag tccttgggta tttcacagac aacctcagtg   120
gtatagaggt acaccacttt cccattcagg aatcagtgcg tcaaccctgt gtgacccaag   180
gagtgtggtt aattattaat aaagacattg catccccccc tc                      222

<210> SEQ ID NO 195
<211> LENGTH: 190
<212> TYPE: DNA
<213> ORGANISM: Mus musculus
```

```
<400> SEQUENCE: 195
gaccacgatg cacccacatc ccgccacctg cccaggactt gggacctgca aactgatgtc    60
ccggcattct gcacagggtc atacccagg aagggtacc cgcttggact ttgcaggacc     120
agcacctgca gctcaatccc ctctgtactg gcctgcctac cccactcaca gaaataaaat   180
ctaaaacgac                                                          190

<210> SEQ ID NO 196
<211> LENGTH: 182
<212> TYPE: DNA
<213> ORGANISM: Mus musculus

<400> SEQUENCE: 196
ccttcccgct gaggcatttg gagacgccag ggctgctgtc catggtttca acataaaacg    60
gcctgtgacc agcagagccc aagagcagcc acagagcaga agtccctgtt ccctttttta   120
tggactctta tgcactacag gcgaacacaa aaaaagcaa cggaataaag ccttcctccc    180
tc                                                                  182

<210> SEQ ID NO 197
<211> LENGTH: 51
<212> TYPE: DNA
<213> ORGANISM: Mus musculus

<400> SEQUENCE: 197
cctcccacat atcctccata tttgtgaata agtagggaa aatgctgtca t              51

<210> SEQ ID NO 198
<211> LENGTH: 202
<212> TYPE: DNA
<213> ORGANISM: Mus musculus

<400> SEQUENCE: 198
gtgaacctga agattctaga gaccaagtga catcctctcc tacctagact cctataaacc    60
aagttcttcc tttcctgacg aagggtaaat atctttcttg tggcctaaat tatagactct   120
tgcttcaact caccctggaa aaatctctat taaaacgaga tgggagattg aaatggattc   180
aaataaagat gctctagcag ga                                            202

<210> SEQ ID NO 199
<211> LENGTH: 289
<212> TYPE: DNA
<213> ORGANISM: Mus musculus

<400> SEQUENCE: 199
ggagcgcaac gtcgcaggga atagactcag acgccggtag agttgcccga gggcgagaag    60
ttggggcaag ctgaaagtgg gggtctgtcc cttcgtaggt ttttagacgc atccccgtc    120 gacggctgct taccaaccac cagcacctgc gatacctcat ccatttctgt gaatatattt   180
gaaggcatct ttgcaagacg gggtcattaa aacacagaca ccaccctac gtttccagcc    240 attccaaagt attaccgact taataaatat tcacgtttct tgaaccact               289

<210> SEQ ID NO 200
<211> LENGTH: 95
<212> TYPE: DNA
<213> ORGANISM: Mus musculus

<400> SEQUENCE: 200
ggttaacacg aagcttaggg cctgggtgtg agaacctaag accccagcc agtgacctga    60
```

```
cttttaaacc tgacaataaa ggtactggac acgcg                                95
```

<210> SEQ ID NO 201
<211> LENGTH: 472
<212> TYPE: DNA
<213> ORGANISM: Mus musculus

<400> SEQUENCE: 201

```
ccttagctca gagaactctg actccagaac gtgggtggct atggggccct gcctctctgt      60
cctccttccc atgctaccca gagcacaagt gtgctagcag gcagggggt ggggagggca      120 gaagcagtga tgacctggtg gcccaccact gccagtgtcc cttctaccac agctgctctc    180
tgcagctttg ggacaaaggg cacatggaac tgcagtgttc tgtctggagt ttgaggcctc    240
cacaagctgg tgtcccagca gggccagcct gcaatccggg caccactcca agcagttgat    300
aaccctgctc cttgggcagg ccccctgggt agaggtgctt cagccaaggc tgattcccca    360
agatccgcat gatgggagga gggaggtgtc tcctccaaat tgtcctctga actctgtatg    420
tgtgctgtgg tgcacacata catgctagct aaataaacaa acaaacaaat aa             472
```

<210> SEQ ID NO 202
<211> LENGTH: 273
<212> TYPE: DNA
<213> ORGANISM: Mus musculus

<400> SEQUENCE: 202

```
gtggtaccta ctgtctgaca cccacgggga aactgagcca ggtccaggcc gatgagaagt      60
tcccagtggg ctgaagtggc caccagggt cagcagtgct ccagttgctg ggcttaaagc    120
ttcctggtgc ctgtctgcca ggtcatggag gattccccaa tctggcatcc ccacgatgcc    180
tctggagaga tggccttgat tgcccctcaa agccacctga accgtcgtca acttacccag    240
cctgtctcca ttaaacacca ggaaccaact gag                                273
```

<210> SEQ ID NO 203
<211> LENGTH: 87
<212> TYPE: DNA
<213> ORGANISM: Mus musculus

<400> SEQUENCE: 203

```
tgcagagagt ccttcagatgt tccttcattc aagagtttaa ccatttctaa caatatgtag     60
ttatcattaa atctttttta aagtgtg                                          87
```

<210> SEQ ID NO 204
<211> LENGTH: 532
<212> TYPE: DNA
<213> ORGANISM: Artificial Sequence
<220> FEATURE:
<223> OTHER INFORMATION: artificial nucleic acid sequence

<400> SEQUENCE: 204

```
tgacttcaaa taatgatctg tttgatatca cactagcctc ttcccctccc cagaaaactt      60
tgggcacctt ctggctttgg ttaggaactg agttggacag gttgggtaaa tttcaacctc    120
agggcatcat gccaggaaaa gctggggaga ggcgatgttc ttttcctcag tttggagcgg    180
gaagaaggag ttttaatgac tgtgcttcct cttctcctcc ccatggaagg gggggggat    240 ccctggctca gcatccactg ctggtggaaa cctcgctgcg aggtgccgct gtgaggtgtg    300
ccgctgtgag gtgcgtgctc tggaagagag gcggagcttg tccgcttcct gctgcctctg    360
```

| | |
|---|---:|
| cctgcagtac cacccucggt ctaagcactc atgattttat actttcagaa aaaagttttta | 420 |
| agacttcttt gggttttttg tttttgtttt gaagcctaag aaagtcacta gttcttgcct | 480 |
| ttatgtattt atatgctgta cctaacaata aagaagaag aaaaaaaaca aa | 532 |

<210> SEQ ID NO 205
<211> LENGTH: 2035
<212> TYPE: RNA
<213> ORGANISM: Artificial Sequence
<220> FEATURE:
<223> OTHER INFORMATION: artificial nucleic acid sequence

<400> SEQUENCE: 205

| | |
|---|---:|
| ggggcgcugc cuacggaggu ggcagccauc uccuucucgg caucaagcuu gaggauggag | 60 |
| gacgccaaga acaucaagaa gggcccggcg cccuucuacc cgcuggagga cgggaccgcc | 120 |
| ggcgagcagc uccacaaggc caugaagcgg uacgcccugg ugccgggcac gaucgccuuc | 180 |
| accgacgccc acaucgaggu cgacaucacc uacgcggagu acuucgagau gagcgugcgc | 240 |
| cuggccgagg ccaugaagcg guacggccug aacaccaacc accggaucgu ggugugcucg | 300 |
| gagaacagcc ugcaguucuu caugccggug cugggcgccc ucuucaucgg cguggccguc | 360 |
| gccccggcga acgacaucua caacgagcgg gagcugcuga acagcauggg gaucagccag | 420 |
| ccgaccgugg uguucgugag caagaagggc cugcagaaga uccugaacgu gcagaagaag | 480 |
| cugcccauca uccagaagau caucaucaug gacagcaaga ccgacuacca gggcuuccag | 540 |
| ucgauguaca cguucgugac cagccaccuc ccgccgggcu ucaacgagua cgacuucguc | 600 |
| ccggagagcu ucgaccggga caagaccauc gcccugauca ugaacagcag cggcagcacc | 660 |
| ggccugccga aggggguggc ccugccgcac cggaccgccu gcugcgcuu cucgcacgcc | 720 |
| cggaccccca ucuucggcaa ccagaucauc cggacaccg ccauccugag cguggugccg | 780 |
| uuccaccacg gcuucggcau guucacgacc cugggcuacc ucaucugcgg cuuccgggug | 840 |
| guccugaugu accgguucga ggaggagcug uccugcgga gccugcagga cuacaagauc | 900 |
| cagagcgcgc ugcucgugcc gacccuguuc agcuucuucg ccaagagcac ccugaucgac | 960 |
| aaguacgacc ugucgaaccu gcacgagauc gccagcgggg gcgccccgcu gagcaaggag | 1020 |
| gugggcgagg ccguggccaa gcgguuccac cucccgggca uccgccaggg cuacggccug | 1080 |
| accgagacca cgagcgcgau ccugaucacc cccgaggggg acgacaagcc gggcgccgug | 1140 |
| ggcaagguug ucccguucuu cgaggccaag gugguggacc uggacaccgg caagacccug | 1200 |
| ggcgugaacc agcggggcga gcugugcgug cgggggccga ugaucaugag cggcuacgug | 1260 |
| aacaacccgg aggccaccaa cgcccucauc gacaaggacg gcuggcugca cagcggcgac | 1320 |
| aucgccuacu gggacgagga cgagcacuuc uucaucgucg accggcugaa gucgcugauc | 1380 |
| aaguacaagg gcuaccaggu ggcgccggcc gagcuggaga gcauccugcu ccagcaccgc | 1440 |
| aacaucuucg acgccggcgu ggccgggcug ccggacgacg acgccggcga gcugccggcc | 1500 |
| gcggugguug ugcuggagca cggcaagacc augacgaga aggagaucgu cgacuacgug | 1560 |
| gccagccagg ugaccaccgc caagaagcug cggggcggcg ugguguucgu ggacgagguc | 1620 |
| ccgaagggcc ugaccgggaa gcucgacgcc cggaagaucc gcgagauccu gaucaaggcc | 1680 |
| aagaagggcg gcaagaucgc cguguaagac uagugcauca cauuuaaag caucucagcc | 1740 |
| uaccaugaga auaagagaaa gaaaaugaag aucaauagcu auucaucuc uuuuucuuuu | 1800 |
| ucguuggugu aaagccaaca cccugucuaa aaaacauaaa uucuuuaau cauuugccu | 1860 |
| cuuuucucug ugcuucaauu aauaaaaaau ggaaagaacc uagaucuaaa aaaaaaaaaa | 1920 | aaaaaaaaaa aaaaaaaaaa aaaaaaaaaa aaaaaaaaaa aaaaaaaaaa augcaucccc   1980 cccccccccc cccccccccc cccccccaaa ggcucuuuuc agagccacca gaauu         2035

<210> SEQ ID NO 206
<211> LENGTH: 186
<212> TYPE: DNA
<213> ORGANISM: Homo sapiens

<400> SEQUENCE: 206
catcacattt aaaagcatct cagcctacca tgagaataag agaaagaaaa tgaagatcaa     60
aagcttattc atctgttttt cttttttcgtt ggtgtaaagc caacccctg tctaaaaaac   120 ataaatttct ttaatcattt tgcctctttt ctctgtgctt caattaataa aaaatggaaa   180
gaatct                                                              186

<210> SEQ ID NO 207
<211> LENGTH: 186
<212> TYPE: DNA
<213> ORGANISM: Homo sapiens

<400> SEQUENCE: 207
catcacattt aaaagcatct cagcctacca tgagaataag agaaagaaaa tgaagatcaa     60
tagcttattc atctctttttt cttttttcgtt ggtgtaaagc caacccctg tctaaaaaac   120 ataaatttct ttaatcattt tgcctctttt ctctgtgctt caattaataa aaaatggaaa   180
gaacct                                                              186

<210> SEQ ID NO 208
<211> LENGTH: 42
<212> TYPE: DNA
<213> ORGANISM: Homo sapiens

<400> SEQUENCE: 208
ggcgctgcct acggaggtgg cagccatctc cttctcggca tc                       42

<210> SEQ ID NO 209
<211> LENGTH: 24
<212> TYPE: DNA
<213> ORGANISM: Artificial Sequence
<220> FEATURE:
<223> OTHER INFORMATION: artificial nucleic acid sequence

<400> SEQUENCE: 209
caaaggctct tttcagagcc acca                                           24

<210> SEQ ID NO 210
<211> LENGTH: 2316
<212> TYPE: RNA
<213> ORGANISM: Artificial Sequence
<220> FEATURE:
<223> OTHER INFORMATION: artificial nucleic acid sequence

<400> SEQUENCE: 210
ggggaaacag ugugggggccu agagcgcugg gugggcgcgu ucugcggccu gagcagggac     60
ggguagugaa gcgguuacgc cccuucuucg cgucuuggcg ggagccugac gccccgcuuc   120
uccccuaacg agguguccca ccggcgcccg ccgaggccua ggccuccgca gccgcccucc   180
gucuccucag ccccgacgcu gcgccuuggg ccuugugcgc auuuuuuucg ggggaaaacu   240
gaggcucgga gugcgaaagu cagccgaggu cgccccgccc aggacagaga agggcugugg   300

| | |
|---|---|
| ucggcugauc cgcggcauuc ccgggaagcu ugaggaugga ggacgccaag aacaucaaga | 360 |
| agggcccggc gcccuucuac ccgcuggagg acgggaccgc cggcgagcag cuccacaagg | 420 |
| ccaugaagcg guacgcccug gugccgggca cgaucgccuu caccgacgcc cacaucgagg | 480 |
| ucgacaucac cuacgcggag uacuucgaga ugagcgugcg ccuggccgag gccaugaagc | 540 |
| gguacggccu gaacaccaac caccggaucg uggugugcuc ggagaacagc cugcaguucu | 600 |
| ucaugccggu gcugggcgcc cucuucaucg gcguggccgu cgccccggcg aacgacaucu | 660 |
| acaacgagcg ggagcugcug aacagcaugg ggaucagcca gccgaccgug uguucguga | 720 |
| gcaagaaggg ccugcagaag auccugaacg ugcagaagaa gcugcccauc uccagaaga | 780 |
| ucaucaucau ggacagcaag accgacuacc agggcuucca gucgauguac acguucguga | 840 |
| ccagccaccu cccgccgggc uucaacgagu acgacuucgu cccggagagc uucgaccggg | 900 |
| acaagaccau cgcccugauc augaacagca gcggcagcac cggccugccg aaggggugg | 960 |
| cccugccgca ccggaccgcc ugcgugcgcu ucucgcacgc ccgggacccc aucuucggca | 1020 |
| accagaucau cccggacacc gccauccuga gcguggugcc guuccaccac ggcuucggca | 1080 |
| uguucacgac ccugggcuac cucaucugcg gcuuccgggu ggccugaug uaccgguucg | 1140 |
| aggaggagcu guuccugcgg agccugcagg acuacaagau ccagagcgcg cugcucgugc | 1200 |
| cgacccuguu cagcuucuuc gccaagagca cccugaucga caagacgac cugucgaacc | 1260 |
| ugcacgagau cgccagcggg ggcgccccgc ugagcaagga ggugggcgag gccguggcca | 1320 |
| agcgguucca ccucccgggc aucgccagg gcuacggccu gaccgagacc acgagcgcga | 1380 |
| uccugaucac ccccgagggg gacgacaagc cgggcgccgu gggcaaggug gucccguucu | 1440 |
| ucgaggccaa ggugguggac cuggacaccg gcaagacccu gggcgugaac cagcggggcg | 1500 |
| agcugugcgu gcgggggccg augaucauga gcggcuacgu gaacaacccg gaggccacca | 1560 |
| acgcccucau cgacaaggac ggcuggcugc acagcggcga caucgccuac ugggacgagg | 1620 |
| acgagcacuu cuucaucguc gaccggcuga agucgcugau caaguacaag ggcuaccagg | 1680 |
| uggcgccggc cgagcuggag agcauccugc uccagcaccc caacaucuuc gacgccggcg | 1740 |
| uggccgggcu gccggacgac gacgccgcg agcugccggc cgcggugggug ugcuggagc | 1800 |
| acggcaagac caugacggag aaggagaucg ucgacuacgu ggccagccag gugaccaccg | 1860 |
| ccaagaagcu gcggggcggc gugguguucc uggacgaggu cccgaagggc cugaccggga | 1920 |
| agcucgacgc ccggaagauc cgcgagaucc ugaucaaggc caagaagggc ggcaagaucg | 1980 |
| ccguguaaga cuagugcauc acauuuaaaa gcaucucagc cuaccaugag aauaagagaa | 2040 |
| agaaaaugaa gaucaauagc uuauucaucu cuuuuucuuu uucguuggug uaaagccaac | 2100 |
| acccugucua aaaaacauaa auuucuuuaa ucauuugcc ucuuuucucu gugcuucaau | 2160 |
| uaauaaaaaa uggaaagaac cuagaucuaa aaaaaaaaaa aaaaaaaaa aaaaaaaaa | 2220 |
| aaaaaaaaaa aaaaaaaaaa aaaaaaaaaa aaugcauccc cccccccccc ccccccccc | 2280 |
| cccccccaa aggcucuuuu cagagccacc agaauu | 2316 |

<210> SEQ ID NO 211
<211> LENGTH: 1948
<212> TYPE: RNA
<213> ORGANISM: Artificial Sequence
<220> FEATURE:
<223> OTHER INFORMATION: artificial nucleic acid sequence

<400> SEQUENCE: 211

| | |
|---|---|
| ggggcgcugc cuacggaggu ggcagccauc uccuucucgg caucaagcuu gaggauggag | 60 |

```
gacgccaaga acaucaagaa gggcccggcg cccuucuacc cgcuggagga cgggaccgcc    120
ggcgagcagc uccacaaggc caugaagcgg uacgcccugg ugccgggcac gaucgccuuc    180
accgacgccc acaucgaggu cgacaucacc uacgcggagu acuucgagau gagcgugcgc    240
cuggccgagg ccaugaagcg guacggccug aacaccaacc accggaucgu ggugugcucg    300
gagaacagcc ugcaguucuu caugccggug cugggcgccc ucuucaucgg cguggccguc    360
gccccggcga acgacaucua caacgagcgg gagcugcuga acagcauggg gaucagccag    420
ccgaccgugg uguucgugag caagaagggc cugcagaaga uccugaacgu gcagaagaag    480
cugcccauca uccagaagau caucaucaug gacagcaaga ccgacuacca gggcuuccag    540
ucgauguaca cguucgugac cagccaccuc ccgccgggcu ucaacgagua cgacuucguc    600
ccggagagcu ucgaccggga caagaccauc gcccugauca ugaacagcag cggcagcacc    660
ggccugccga aggggguggc ccugccgcac cggaccgccu gcgugcgcuu cucgcacgcc    720
cgggaccccca ucuucggcaa ccagaucauc ccggacaccg ccauccugag cguggugccg    780
uuccaccacg gcuucggcau guucacgacc cugggcuacc ucaucugcgg cuuccggguug    840
guccugaugu accgguucga ggaggagcug uccugcgga gccugcagga cuacaagauc    900
cagagcgcgc ugcucgugcc gacccuguuc agcuucuucg ccaagagcac ccugaucgac    960
aaguacgacc ugucgaaccu gcacgagauc gccagcgggg gcgccccgcu gagcaaggag   1020
gugggcgagg ccgugccaa gcgguuccac cucccgggca uccgccaggg cuacggccug   1080
accgagacca cgagcgcgau ccugaucacc cccgagggggg acgacaagcc gggcgccgug   1140
ggcaaggugg ucccguucuu cgaggccaag gugguggacc uggacaccgg caagacccug   1200
ggcgugaacc agcggggcga gcugugcgug cggggggccga ugaucaugag cggcuacgug   1260
aacaacccgg aggccaccaa cgcccucauc gacaaggacg gcuggcugca cagcggcgac   1320
aucgccuacu gggacgagga cgagcacuuc uucaucgucg accggcugaa gucgcugauc   1380
aaguacaagg gcuaccaggu ggcgccggcc gagcuggaga gcauccugcu ccagcacccc   1440
aacaucuucg acgccggcgu ggccgggcug ccggacgacg acgccggcga gcugccggcc   1500
gcggugugg ugcuggagca cggcaagacc augacggaga aggagaucgu cgacuacgug   1560
gccagccagg ugaccaccgc caagaagcug cggggcggcg uggguucgu ggacgagguc   1620
ccgaagggcc ugaccgggaa gcucgacgcc cggaagaucc gcgagauccu gaucaaggcc   1680
aagaagggcg gcaagaucgc cguguaagac uagucgccgc cgccgccgcc gcggagccu   1740
gucgccgucc uguccccagc cugcuugugu cccgugaggu ugucaauaaa ccugcccucg   1800
ggcugccgcc ucccagaucu aaaaaaaaaa aaaaaaaaaa aaaaaaaaaa aaaaaaaaa    1860
aaaaaaaaaa aaaaaaaaaa aaaaugcauc cccccccccc cccccccccc cccccccccc   1920
aaaggcucuu uucagagcca ccagaauu                                      1948
```